United States Patent
Ewert et al.

(10) Patent No.: US 12,331,104 B2
(45) Date of Patent: Jun. 17, 2025

(54) HEPATITIS B ANTIBODIES

(71) Applicant: Novartis AG, Basel (CH)

(72) Inventors: Stefan Ewert, Geroldswil (CH);
Meghan Marie Holdorf, Oakland, CA (US); Elisabetta Traggiai, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 18/434,265

(22) Filed: Feb. 6, 2024

(65) Prior Publication Data
US 2024/0317840 A1  Sep. 26, 2024

Related U.S. Application Data

(63) Continuation of application No. 17/059,934, filed as application No. PCT/IB2019/054498 on May 30, 2019, now Pat. No. 11,932,681.

(60) Provisional application No. 62/678,756, filed on May 31, 2018.

(51) Int. Cl.
*C07K 16/08* (2006.01)
*A61K 39/00* (2006.01)

(52) U.S. Cl.
CPC ...... *C07K 16/082* (2013.01); *A61K 2039/505* (2013.01); *C07K 2317/21* (2013.01); *C07K 2317/33* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,720,760 A | 3/1973 | Wide et al. |
| 4,522,811 A | 6/1985 | Eppstein et al. |
| 4,526,938 A | 7/1985 | Churchill et al. |
| 4,880,078 A | 11/1989 | Inoue et al. |
| 5,128,326 A | 7/1992 | Balazs et al. |
| 5,290,540 A | 3/1994 | Prince et al. |
| 5,374,548 A | 12/1994 | Caras |
| 5,399,331 A | 3/1995 | Loughrey et al. |
| 5,416,016 A | 5/1995 | Low et al. |
| 5,624,821 A | 4/1997 | Winter et al. |
| 5,641,870 A | 6/1997 | Rinderknecht et al. |
| 5,648,260 A | 7/1997 | Winter et al. |
| 5,667,425 A | 9/1997 | Pineau et al. |
| 5,679,377 A | 10/1997 | Bernstein et al. |
| 5,714,350 A | 2/1998 | Co et al. |
| 5,855,913 A | 1/1999 | Hanes et al. |
| 5,869,046 A | 2/1999 | Presta et al. |
| 5,874,064 A | 2/1999 | Edwards et al. |
| 5,912,015 A | 6/1999 | Bernstein et al. |
| 5,916,597 A | 6/1999 | Lee et al. |
| 5,934,272 A | 8/1999 | Lloyd et al. |
| 5,985,309 A | 11/1999 | Edwards et al. |
| 5,985,320 A | 11/1999 | Edwards et al. |
| 5,989,463 A | 11/1999 | Tracy et al. |
| 6,019,968 A | 2/2000 | Platz et al. |
| 6,121,022 A | 9/2000 | Presta et al. |
| 6,165,745 A | 12/2000 | Ward et al. |
| 6,194,551 B1 | 2/2001 | Idusogie et al. |
| 6,277,375 B1 | 8/2001 | Ward |
| 6,316,024 B1 | 11/2001 | Allen et al. |
| 6,350,466 B1 | 2/2002 | Li et al. |
| 6,350,861 B1 | 2/2002 | Co et al. |
| 6,703,199 B1 | 3/2004 | Koide |
| 6,737,056 B1 | 5/2004 | Presta |
| 7,786,268 B2 * | 8/2010 | Fischer ............... A61P 5/14 424/130.1 |
| 8,008,449 B2 | 8/2011 | Korman et al. |
| 8,354,509 B2 | 1/2013 | Carven et al. |
| 9,284,378 B2 * | 3/2016 | Hu ................ A61P 3/00 |
| 11,932,681 B2 * | 3/2024 | Ewert ............. A61P 31/20 |
| 2003/0153043 A1 | 8/2003 | Carr et al. |
| 2010/0028330 A1 | 2/2010 | Collins et al. |
| 2010/0150918 A1 * | 6/2010 | Kufer ............... C07K 16/28 536/23.53 |
| 2012/0114649 A1 | 5/2012 | Langermann et al. |
| 2016/0326233 A1 | 11/2016 | Mondelli |
| 2019/0389939 A1 | 12/2019 | Luo et al. |

FOREIGN PATENT DOCUMENTS

| | | |
|---|---|---|
| CN | 102786592 A | 11/2012 |
| CN | 103588874 A | 2/2014 |
| CN | 104487090 A | 4/2015 |
| EP | 1176195 B1 | 5/2013 |
| JP | 2002-502222 | 1/2002 |
| JP | 2016-504015 | 2/2016 |
| WO | 91/05548 A1 | 5/1991 |
| WO | 92/19244 A2 | 11/1992 |
| WO | 94/29351 A2 | 12/1994 |
| WO | 96/20698 A2 | 7/1996 |

(Continued)

OTHER PUBLICATIONS

Langer, "Controlled release of macromolecules," Chem. Tech. 12:98-105, 1982.
Langer, "New methods of drug delivery," Science 249:1527-1533, 1990).
Langer, et al., "Chemical and Physical Structure of Polymers as Carriers for Controlled Release of Bioactive Agents: A Review," J. Macromol. Sci. Rev. Macromol. Chem. 23:61, 1983.
Lefranc, M.P., "IMGT, the international ImMunoGeneTics database," Nucleic Acids Res., 29:207-209 (2001).
Levy et al., "Inhibition of calcification of bioprosthetic heart valves by local controlled-release diphosphonate," Science 228:190, 1985.

(Continued)

*Primary Examiner* — Agnieszka Boesen
(74) *Attorney, Agent, or Firm* — K&L Gates LLP

(57) ABSTRACT

The present invention relates to anti-HBsAg antibodies, antibody fragments, and their uses for the prevention and treatment of hepatitis B virus infection and associated diseases.

10 Claims, 67 Drawing Sheets
Specification includes a Sequence Listing.

(56) References Cited

FOREIGN PATENT DOCUMENTS

| WO | 97/32572 A2 | 9/1997 |
|---|---|---|
| WO | 97/44013 A1 | 11/1997 |
| WO | 97/47653 A1 | 12/1997 |
| WO | 98/31346 A1 | 7/1998 |
| WO | 99/15154 A1 | 4/1999 |
| WO | 99/20253 A1 | 4/1999 |
| WO | 99/54342 A1 | 10/1999 |
| WO | 99/66903 A2 | 12/1999 |
| WO | 00/42072 A2 | 7/2000 |
| WO | 03/035835 A2 | 5/2003 |
| WO | 2003/105894 A1 | 12/2003 |
| WO | 2006/121168 A1 | 11/2006 |
| WO | 2007/005874 A2 | 1/2007 |
| WO | 2009/101611 A1 | 8/2009 |
| WO | 2009/114335 A2 | 9/2009 |
| WO | 2010/027423 A2 | 3/2010 |
| WO | 2010/027827 A2 | 3/2010 |
| WO | 2010/077634 A1 | 7/2010 |
| WO | 2011/066342 A2 | 6/2011 |
| WO | 2011066389 A1 | 6/2011 |
| WO | 2012065950 A1 | 5/2012 |
| WO | 2014/048910 A1 | 4/2014 |
| WO | 2015/026684 A1 | 2/2015 |
| WO | 2016/057846 A1 | 4/2016 |
| WO | 2016/061142 A1 | 4/2016 |
| WO | 2017/059813 | 4/2017 |
| WO | 2017/060504 | 4/2017 |

OTHER PUBLICATIONS

Lipsky et al., "Infliximab and Methotrexate in the Treatment of Rheumatoid Arthritis," New Engl. J. Med. 343:1594-1602, 2000.
MacCallum et al., "Antibody-antigen Interactions: Contact Analysis and Binding Site Topography," J. Mol. Biol., 262:732-745 (1996).
Martin et al., "Modeling antibody hypervariable loops: A combined algorithm," Proc. Natl. Acad. Sci. USA, 86:9268-9272 (1989).
Martin et al., "Molecular modeling of antibody combining sites,," Methods Enzymol., 203:121-153 (1991).
Mattila et al., "Fidelity of DNA synthesis by the Thermococcus litoralis DNA polymerase—an extremely heat stable enzyme with proofreading activity," Nucleic Acids Res. 19:4967, 1991.
Meier et al., "Hepatitis B virus covalently closed circular DNA homeostasis is independent of the lymphotoxin pathway during chronic HBV infection," J. Virol Hepat. 2017; 24: 662-671.
Milgrom et al., "Treatment of Allergic Asthma with Monoclonal Anti-IgE Antibody," New Engl. J. Med. 341:1966-1973, 1999.
Narang et al., "Improved phosphotriester method for the synthesis of gene fragments," Meth. Enzymol. 68:90, 1979.
Needleman and Wunsch, "A general method applicable to the search for similarities in the amino acid sequence of two proteins," J. Mol. Biol. 48:443 (1970).
Ning et al., "Intratumoral radioimmunotherapy of a human colon cancer xenograft using a sustained-release gel," Radiotherapy & Oncology 39:179-189, 1996.
O'Shannessy et al., "Determination of rate and equilibrium binding constants for macromolecular interactions using surface plasmon resonance: use of nonlinear least squares analysis methods," Anal. Biochem 1993 212: 457-468.
Ohtsuka et al., "An alternative approach to deoxyoligonucleotides as hybridization probes by insertion of deoxyinosine at ambiguous codon positions," (1985) J. Biol. Chem. 260:2605-2608.
Owais et al., "Chloroquine encapsulated in malaria-infected erythrocyte-specific antibody-bearing liposomes effectively controls chloroquine-resistant Plasmodium berghei infections in mice," (1995) Antimicrob. Agents Chemother. 39:180.
Pearson, et al., "Improved tools for biological sequence comparison.," Proc. Natl. Acad. Sci. USA 85:2444 (1988).
Queen et al., "Cell-type specific regulation of a kappa immuno-globulin gene by promoter and enhancer elements," Immunol. Rev. 89:49-68, 1986.

Ranade, "Drug Delivery Systems. 1. Site-Specific Drug Delivery Using Liposomes as Carriers," (1989) J. Clin. Pharmacol. 29:685.
Rees et al., "Antibody combining sites: structure and prediction," Oxford University Press, Oxford, 141-172 (1996).
Rosenfeld et al., "In vivo transfer of the human cystic fibrosis transmembrane conductance regulator gene to the airway epithelium," Cell 68:143, 1992.
Rossolini et al., "Use of deoxyinosine-containing primers vs degenerate primers for polymerase chain reaction based on ambiguous sequence information," (1994) Mol. Cell. Probes 8:91-98).
Ruiz et al., "IMGT, the international ImMunoGeneTics database," Nucleic Acids Res., 28:219-221 (2000).
Saudek et al.,"A preliminary trial of the programmable implantable medication system for insulin delivery," N. Engl. J. Med. 321:574, 1989.
Scharf et al., "Heat Stress Promoters and Transcription Factors," Results Probl. Cell Differ. 20:125, 1994.
Schreier et al., "Targeting of Liposomes to Cells Expressing CD4 Using Glycosylphosphatidylinositol-anchored gp120," (1994) J. Biol. Chem. 269:9090-9098.
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem. 276:6591-6604, 2001.
Shields et al., "Lack of fucose on human IgG1 N-linked oligosaccharide improves binding to human Fcgamma RIII and antibody-dependent cellular toxicity,"(2002) J. Biol. Chem. 277:26733-26740.
Sidman et al., "Controlled release of macromolecules and pharmaceuticals from synthetic polypeptides based on glutamic acid," Biopolymers 22:547-556, 1983.
Slamon et al., "Use of Chemotherapy plus a Monoclonal Antibody against HER2 for Metastatic Breast Cancer That Overexpresses HER2," New Engl. J. Med. 344:783-792, 2001.
Smith and Waterman, "Comparison of biosequences," Adv. Appl. Math. 2:482c (1981).
Smith, A.E., "Viral vectors in gene therapy," Annu. Rev. Microbiol. 49:807, 1995.
Song et al.. "Antibody Mediated Lung Targeting of Long Circulating Emulsions," PDA Journal of Pharmaceutical Science & Technology 50:372, 1996.
Strohl, W., "Optimization of Fc-mediated effector functions of monoclonal antibodies," 2009, Curr. Opin. Biotechnol. vol. 20(6):685-691.
Thimme et al., "CD8(+) T cells mediate viral clearance and disease pathogenesis during acute hepatitis B virus infection," J Virol. 2003; 77(1):68-76.
Tropberger et al., "Mapping of histone modifications in episomal HBV cccDNA uncovers an unusual chromatin organization amenable to epigenetic manipulation," Proc. Natl. Acad. Sci. U. S. A. 2015; 112: E5715-E5724.
Umana et al., "Engineered glycoforms of an antineuroblastoma IgG1 with optimized antibody-dependent cellular cytotoxic activity," Nat. Biotech. 17:176-180, 1999.
Umezawa et al., "Liposome targeting to mouse brain: Mannose as a recognition marker," (1988) Biochem. Biophys. Res. Commun. 153:1038.
Ward et al., "Binding activities of a repertoire of single immuno-globulin variable domains secreted from Escherichia coli," Nature 341:544-546, 1989.
Wieland et al., "Genomic analysis of the host response to hepatitis B virus infection," Proc Natl Acad Sci U S A. 2004; 101(17):6669-74.
Zapata et al., "Engineering linear F(ab')2 fragments for efficient production in Escherichia coli and enhanced antiproliferative activity," Protein Eng. 8:1057-1062, 1995.
Al-Lazikani et al., "Standard Conformations for the Canonical Structures of Immunoglobulins," J.Mol.Biol., 273:927-748 (1997).
Zhang et al., "Prolonged suppression of HBV in mice by a novel antibody that targets a unique epitope on hepatitis B surface antigen," Gut, 2016; (4) 65: 658-671.
Altschul et al., "Basic local alignment search tool," J. Mol. Biol. 215:403-410, 1990.

(56) References Cited

OTHER PUBLICATIONS

Altschul et al., "Gapped BLAST and PSI-BLAST: a new generation of protein database search programs," Nuc. Acids Res. 25:3389-3402, 1977.
Asabe, et al., "The size of the viral inoculum contributes to the outcome of hepatitis B virus infection," J Virol. 2009; 83 (19):9652-62.
Baert et al., "Influence of immunogenicity on the long-term efficacy of infliximab in Crohn's disease," New Engl. J. Med. 348:601-608, 2003.
Batzer et al., "Enhanced evolutionary PCR using oligonucleotides with inosine at the 3'-terminus," Nucleic Acid Res. 19:5081 (1991).
Baudino et al., "Crucial role of aspartic acid at position 265 in the CH2 domain for murine IgG2a and IgG2b Fc-associated effector functions," J. Immunol. 181 : 6664-69 (2008).
Beaucage et al., "Deoxynucleoside phosphoramidites—A new class of key intermediates for deoxypolynucleotide synthesis," Tetra. Lett., 22:1859, 1981.
Beniaminovitz et al., "Prevention of rejection in cardiac transplantation by blockade of the interleukin-2 receptor with a monoclonal antibody," New Engl. J. Med. 342:613-619, 2000.
Bird et al., "Single-chain antigen-binding proteins," Science 242:423-426, 1988.
Biswas et al., "Shift in the hepatitis B virus genotype distribution in the last decade among the HBV carriers from eastern India: possible effects on the disease status and HBV epidemiology," Med. Virol. 2013; 85:1340-1347.
Bitter et al., "Expression and secretion vectors for yeast," Meth. Enzymol., 153:516, 1987.
Bloeman et al., "Adhesion molecules: a new target for immunoliposome-mediated drug delivery," (1995) FEBS Lett. 357:140.
Boni et al., "Lamivudine treatment can overcome cytotoxic T-cell hyporesponsiveness in chronic hepatitis B: new perspectives for immune therapy," Hepatology. 2001; 33(4):963-71.
Briscoe et al., "Delivery of superoxide dismutase to pulmonary epithelium via pH-sensitive liposomes," (1995) Am. J. Physiol., vol. 12(3), p. L374-L380).
Brown et al., "Chemical synthesis and cloning of a tyrosine tRNA gene," Meth. Enzymol. 68:109, 1979.
Buchwald et al., "Long-term, continuous intravenous heparin administration by an implantable infusion pump in ambulatory patients with recurrent venous thrombosis," Surgery 88:507, 1980.
Chisari, et al., "Hepatitis B virus immunopathogenesis," Annu Rev Immunol. 1995; 13:29-60.
Chothia et al., "Conformations of immunoglobulin hypervariable regions," Nature, 342:877-883 (1989).
Chothia et al., "Structural repertoire of the human VH segments," J. Mol. Biol., 227:799-817 (1992).
Chothia, et al., "Canonical structures for the hypervariable regions of immunoglobulins," J. Mol. Biol., 196:901-917 (1987).
Cleek et al., "Biodegradable Polymeric Carriers for a bFGF Antibody for Cardiovascular Application," Pro. Int'l. Symp. Control. Rel. Bioact. Mater. 24:853-854, 1997.
Dagan, et al., "Therapeutic antibodies against viral hepatitis," Current Opinion in Molecular Therapeutics, 2003, 5 (2):148-155.
DeRienzo et al., "Evaluation of the half-life of intravenous human cytomegalovirus immune globulin in patients receiving partially mismatched related donor bone marrow transplantation," Pharmacotherapy 2000; 20:1175-8.
During et al., "Controlled release of dopamine from a polymeric brain implant: In vivo characterization," Ann. Neurol. 25:351, 1989.

Meyers, et al., "Optimal alignments in linear space," Bioinformatics, vol. 4, Issue 1, Mar. 1988, pp. 11-17.
Eckert et al., "DNA polymerase fidelity and the polymerase chain reaction.," PCR Methods and Applications 1:17, 1991.
Ehrlich, et al., "Characterization of human monoclonal antibodies directed against hepatitis B surface antigen," Hum. Antibod. Hybridomas, 1992, vol. 3, 6 pages.
Elliot and O'Hare, "Intercellular Trafficking and Protein Delivery by a Herpesvirus Structural Protein," Cell 88:223, 1997.
Eppstein et al., "Biological activity of liposome-encapsulated murine interferon y is mediated by a cell membrane receptor," Proc. Natl. Acad. Sci. USA 82:3688-3692, 1985.
Ghosh et al., "Natalizumab for Active Crohn's Disease," New Engl. J. Med. 348:24-32, 2003.
Goodson, in Medical Applications of Controlled Release, vol. 2, pp. 115-138, 1984.
Guidotti et al., "Immunobiology and Pathogenesis of Viral Hepatitis," Annu Rev Pathol. 2006; 1:23-61.
Hamid, O. et al., "Safety and Tumor Responses with Lambrolizumab (Anti-PD-1) in Melanoma," (2013) New England Journal of Medicine 369 (2): 134-44.
Harrington et al., "Formation of de novo centromeres and construction of first-generation human artificial microchromosomes," Nature Genetics, 15:345-355, 1997.
Henikoff and Henikoff, "Amino acid substitution matrices from protein blocks," Proc. Natl. Acad. Sci. USA 89:10915-10919, 1992.
Hollinger and Hudson, "Engineered antibody fragments and the rise of single domains," Nature Biotechnology 23:1126-1136, 2005.
Howard et al., "Acute subdural hematomas: an age-dependent clinical entity," J. Neurosurg. 7 1:105, 1989.
Huston et al., "Protein engineering of antibody binding sites: Recovery of specific activity in an anti-digoxin single-chain Fv analogue produced in *Escherichia coli*," Proc. Natl. Acad. Sci. 85:5879-5883, 1988.
Hwang et al., "Hepatic uptake and degradation of unilamellar sphingomyelin/cholesterol liposomes: A kinetic study," Proc. Natl. Acad. Sci. USA 77:4030-4034, 1980.
Jefferis et al., "Human immunoglobulin allotypes," MAbs. 1:332-338 (2009).
Johnson et al., "Kabat Database and its applications: future directions," Nucleic Acids Res., 29:205-206 (2001).
Karlin et al., "Applications and statistics for multiple high-scoring segments in molecular sequences," Proc. Natl. Acad. Sci. USA 90:5873-5787, 1993.
Karlsson, et al., "Experimental design for kinetic analysis of protein-protein interactions with surface plasmon resonance biosensors," J. Immunol. Methods. 1997; 200: 121-133.
Keinanen et al., "Biosynthetic lipid-tagging of antibodies," (1994) FEBS Lett. 346:123.
Killion et al., "Systemic Targeting of Liposome-Encapsulated Immunomodulators to Macrophages for Treatment of Cancer Metastasis," (1994) Immunomethods 4:273.
Knappik et al., "Fully synthetic human combinatorial antibody libraries (HuCAL) based on modular consensus frameworks and CDRs randomized with trinucleotides," J. Mol. Biol. 296:57-86, 2000.
Lam et al., "Microencapsulation of recombinant humanized monoclonal antibody for local delivery," Proc. Int'l. Symp. Control Rel. Bioact. Mater. 24:759-760, 1997.
Langer et al., "Biocompatibility of polymeric delivery systems for macromolecules," J. Biomed. Mater. Res. 15:267-277, 1981.

* cited by examiner

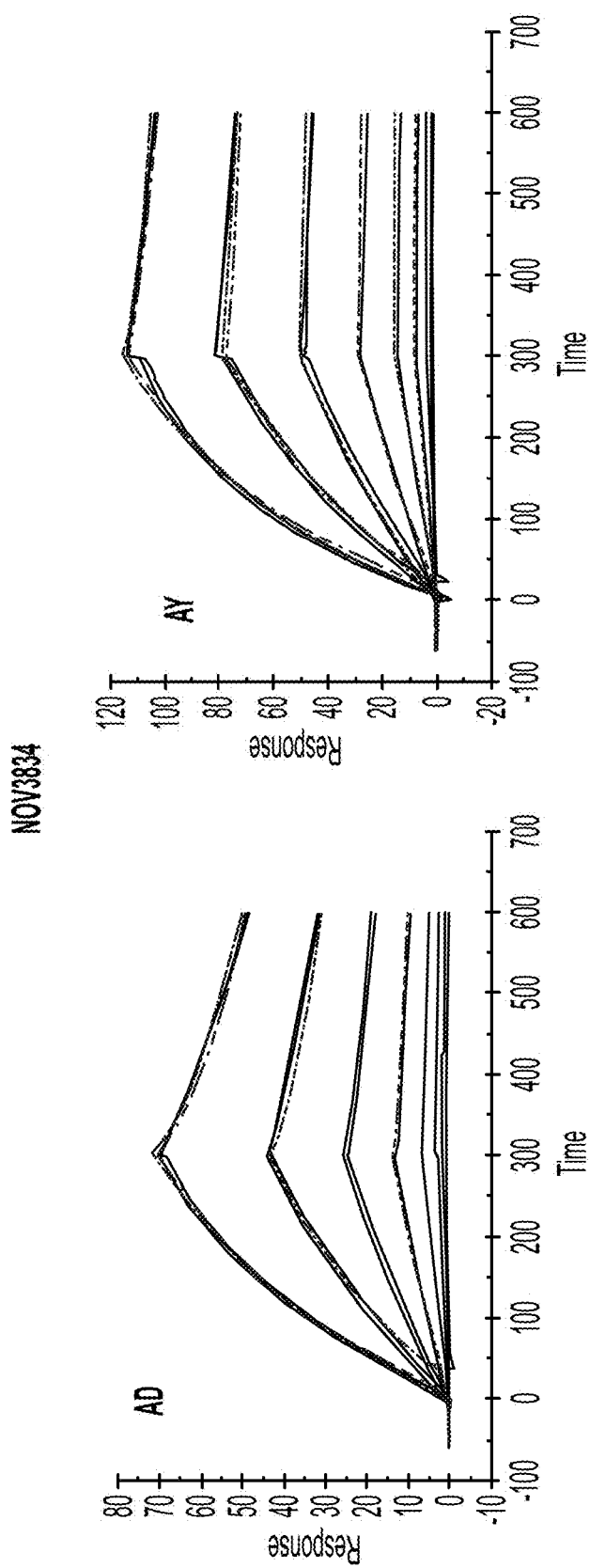

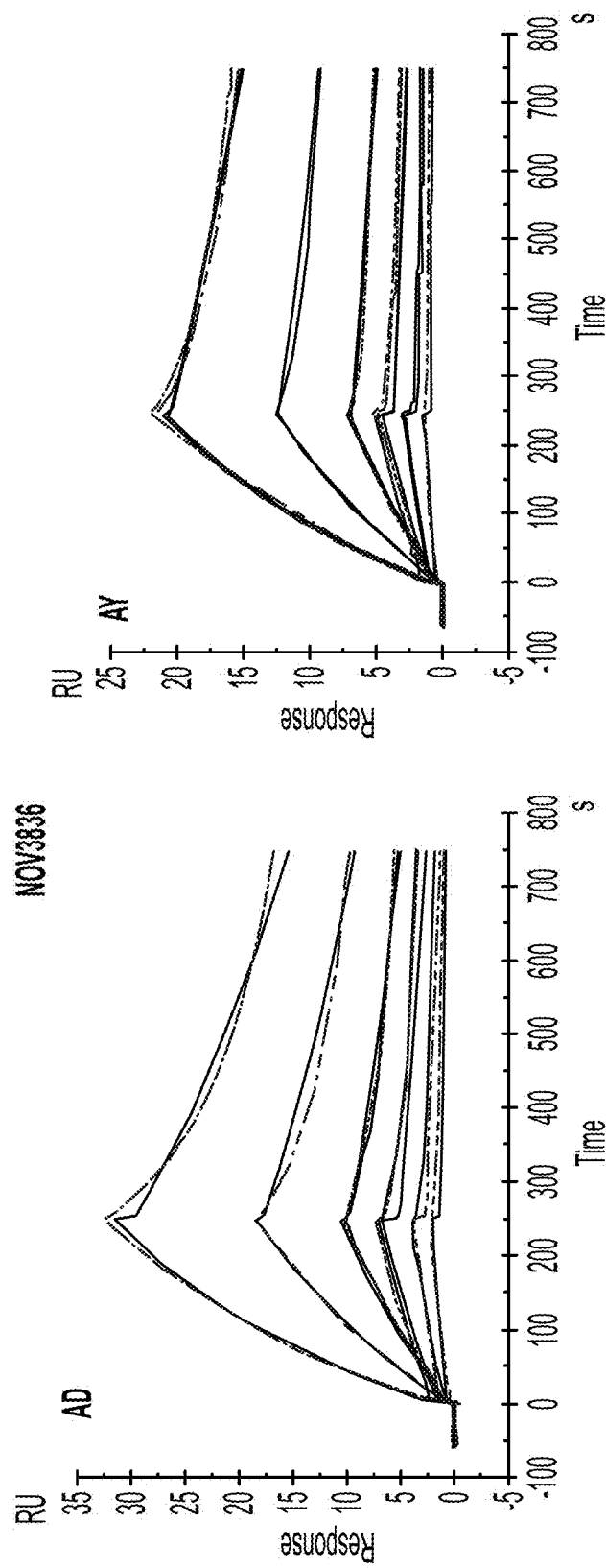

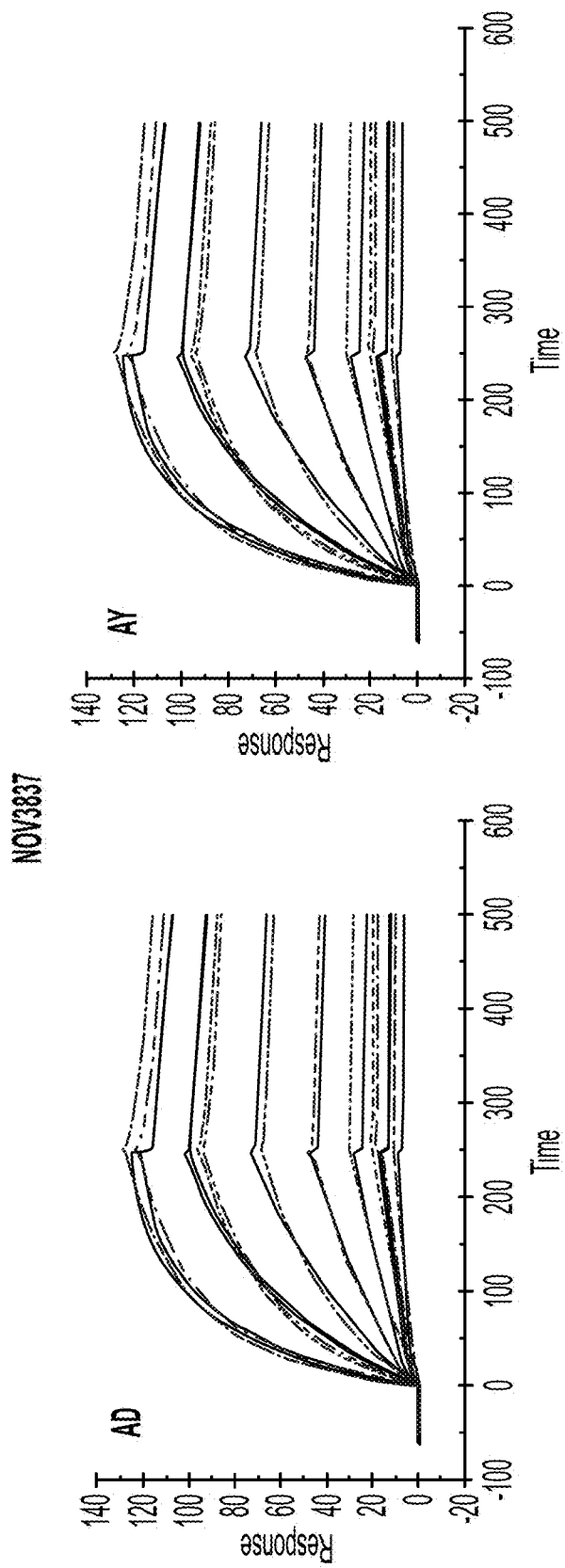

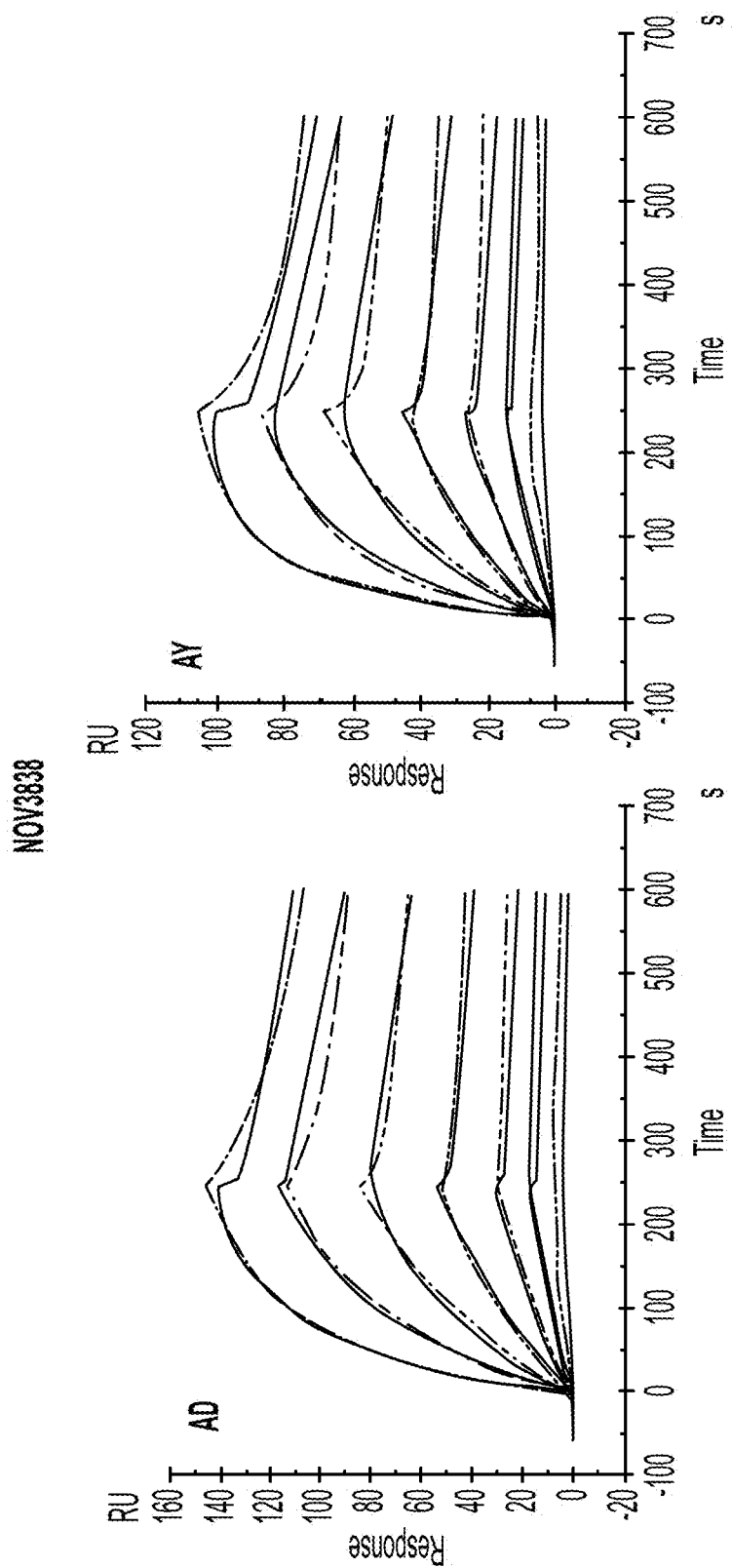

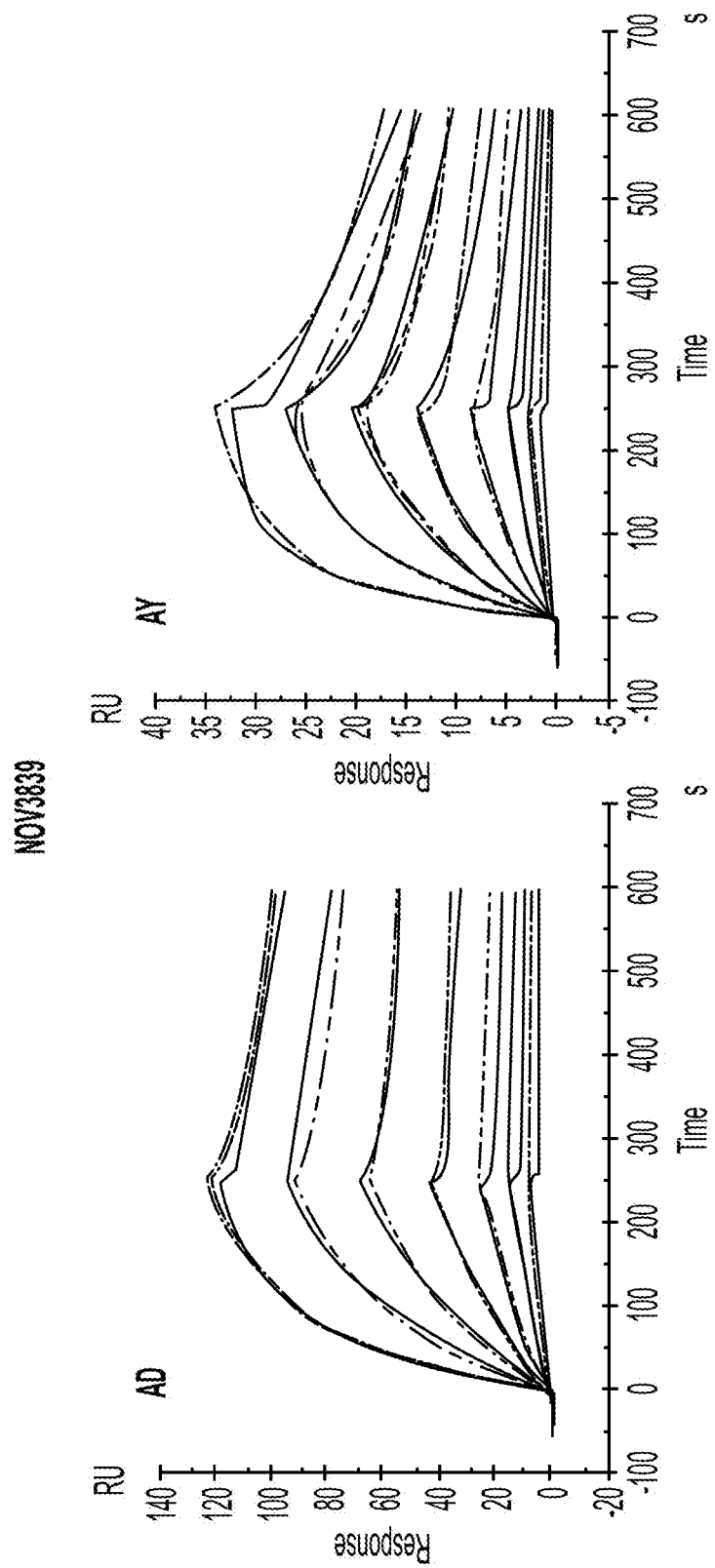

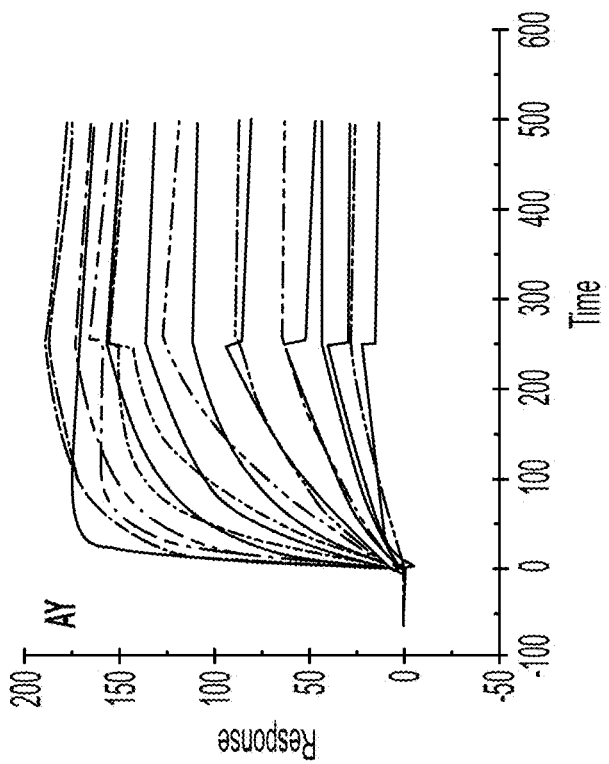
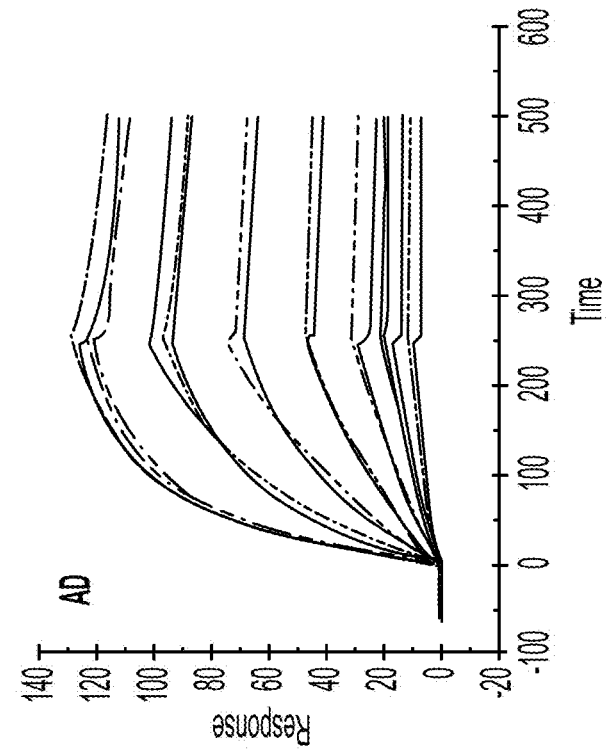
FIG. 14A
FIG. 14B

SEQUENCE LISTING

```
Sequence total quantity: 517
SEQ ID NO: 1              moltype = AA  length = 226
FEATURE                   Location/Qualifiers
source                    1..226
                          mol_type = protein
                          organism = Hepatitis B virus
SEQUENCE: 1
MENITSGFLG PLLVLQAGFF LLTRILTIPQ SLDSWWTSLN FLGGAPTCPG QNSQSPTSNH    60
SPTSCPPTCP GYRWMCLRRF IIFLFILLLC LIFLLVLLDY QGMLPVCPLL PGSSTTSTGP   120
CKTCTIPAQG TSMFPSCCCT KPSDGNCTCI PIPSSWAFAK FLWEWASARF SWLSLLVPFV   180
QWFVGLSPTV WLSVIWMMWY WGPSLYNILS PFLPLLPIFF CLWVYI                  226

SEQ ID NO: 2              moltype = AA  length = 226
FEATURE                   Location/Qualifiers
source                    1..226
                          mol_type = protein
                          organism = Hepatitis B virus
SEQUENCE: 2
MESTTSGFLG PLLVLQAGFF LLTRILTIPQ SLDSWWTSLN FLGGAPTCPG QNSQSPTSNH    60
SPTSCPPTCP GYRWMCLRRF IIFLFILLLC LIFLLVLLDY QGMLPVCPLL PGTSTTSTGP   120
CRTCTIPAQG TSMFPSCCCT KPSDGNCTCI PIPSSWAFAR FLWEWASVRF SWLSLLVPFV   180
QWFVGLSPTV WLSAIWMMWY WGPSLYNILS PFLPLLPIFF CLWVYI                  226

SEQ ID NO: 3              moltype = AA  length = 226
FEATURE                   Location/Qualifiers
source                    1..226
                          mol_type = protein
                          organism = Hepatitis B virus
SEQUENCE: 3
MESTTSGFLG PLLVLQAGFF LLTRILTIPQ SLDSWWTSLN FLGGAPTCPG QNLQSPTSNH    60
SPTSCPPICP GYRWMCLRRF IIFLFILLLC LIFLLVLLDY QGMLPVCPLL PGTSTTSTGP   120
CKTCTIPAQG TSMFPSCCCT KPSDGNCTCI PIPSSWAFAR FLWEWASVRF SWLSLLVPFV   180
QWFVGLSPTV WLSVIWMMWY WGPSLYNILS PFLPLLPIFF CLWVYI                  226

SEQ ID NO: 4              moltype = AA  length = 226
FEATURE                   Location/Qualifiers
source                    1..226
                          mol_type = protein
                          organism = Hepatitis B virus
SEQUENCE: 4
MENITSGFLG PLLVLQAGFF LLTRILTIPQ SLDSWWTSLN FLGGTTVCLG QNSQSPTSNH    60
SPTSCPPTCP GYRWMCLRRF IIFLFILLLC LIFLLVLLDY QGMLPVCPLI PGSSTTSTGP   120
CRTCTTPAQG TSMYPSCCCT KPSDGNCTCI PIPSSWAFGK FLWEWASARF SWLSLLVPFV   180
QWFVGLSPTV WLSVIWMMWY WGPSLYSILS PFLPLLPIFF CLWVYI                  226

SEQ ID NO: 5              moltype = AA  length = 226
FEATURE                   Location/Qualifiers
source                    1..226
                          mol_type = protein
                          organism = Hepatitis B virus
SEQUENCE: 5
MENITSGLLG PLLVLQAVCF LLTKILTIPK SLDSWWTSLN FLGVPPGCPG QNSQSPISNH    60
LPTSCPPTCP GYRWMCLRRF IIFLFILLLC LIFLLVLLDY QGMLPVCPLL PGSTTTSTGP   120
CKTCTTLAQG TSMFPSCCCT KPSDGNCTCI PIPSSWAFGK YLWEWASARF SWLSLLVQFV   180
QWCVGLSPTV WLLVIWMIWY WGPNLCSILS PFIPLLPIFC YLWASI                  226

SEQ ID NO: 6              moltype = AA  length = 10
FEATURE                   Location/Qualifiers
REGION                    1..10
                          note = source = /note="Description of Artificial Sequence:
                          Synthetic peptide"
source                    1..10
                          mol_type = protein
                          organism = synthetic construct
SEQUENCE: 6
GFTFDNYAMS                                                           10

SEQ ID NO: 7              moltype = AA  length = 17
FEATURE                   Location/Qualifiers
REGION                    1..17
                          note = source = /note="Description of Artificial Sequence:
                          Synthetic peptide"
source                    1..17
                          mol_type = protein
                          organism = synthetic construct
SEQUENCE: 7
SISGSGGSTY YADSVKG                                                   17
```

```
SEQ ID NO: 8              moltype = AA  length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 8
SSILSGGHAR VYGIDV                                                            16

SEQ ID NO: 9              moltype = AA  length = 5
FEATURE                   Location/Qualifiers
REGION                    1..5
                          note = source = /note="Description of Artificial Sequence:
                          Synthetic peptide"
source                    1..5
                          mol_type = protein
                          organism = synthetic construct
SEQUENCE: 9
NYAMS                                                                         5

SEQ ID NO: 10             moltype = AA  length = 17
FEATURE                   Location/Qualifiers
REGION                    1..17
                          note = source = /note="Description of Artificial Sequence:
                          Synthetic peptide"
source                    1..17
                          mol_type = protein
                          organism = synthetic construct
SEQUENCE: 10
SISGSGGSTY YADSVKG                                                           17

SEQ ID NO: 11             moltype = AA  length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 11
SSILSGGHAR VYGIDV                                                            16

SEQ ID NO: 12             moltype = AA  length = 7
FEATURE                   Location/Qualifiers
REGION                    1..7
                          note = source = /note="Description of Artificial Sequence:
                          Synthetic peptide"
source                    1..7
                          mol_type = protein
                          organism = synthetic construct
SEQUENCE: 12
GFTFDNY                                                                       7

SEQ ID NO: 13             moltype = AA  length = 6
FEATURE                   Location/Qualifiers
REGION                    1..6
                          note = source = /note="Description of Artificial Sequence:
                          Synthetic peptide"
source                    1..6
                          mol_type = protein
                          organism = synthetic construct
SEQUENCE: 13
SGSGGS                                                                        6

SEQ ID NO: 14             moltype = AA  length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 14
SSILSGGHAR VYGIDV                                                            16

SEQ ID NO: 15             moltype = AA  length = 8
FEATURE                   Location/Qualifiers
```

```
REGION                      1..8
                            note = source = /note="Description of Artificial Sequence:
                             Synthetic peptide"
source                      1..8
                            mol_type = protein
                            organism = synthetic construct
SEQUENCE: 15
GFTFDNYA                                                                    8

SEQ ID NO: 16               moltype = AA  length = 8
FEATURE                     Location/Qualifiers
REGION                      1..8
                            note = source = /note="Description of Artificial Sequence:
                             Synthetic peptide"
source                      1..8
                            mol_type = protein
                            organism = synthetic construct
SEQUENCE: 16
ISGSGGST                                                                    8

SEQ ID NO: 17               moltype = AA  length = 18
FEATURE                     Location/Qualifiers
REGION                      1..18
                            note = source = /note="Description of Artificial Sequence:
                             Synthetic peptide"
source                      1..18
                            mol_type = protein
                            organism = synthetic construct
SEQUENCE: 17
AKSSILSGGH ARVYGIDV                                                         18

SEQ ID NO: 18               moltype = AA  length = 125
FEATURE                     Location/Qualifiers
REGION                      1..125
                            note = source = /note="Description of Artificial Sequence:
                             Synthetic polypeptide"
source                      1..125
                            mol_type = protein
                            organism = synthetic construct
SEQUENCE: 18
EMQVLESGGG LVQPGGSLRL SCAASGFTFD NYAMSWVRQV PGKGLEWVSS ISGSGGSTYY           60
ADSVKGQFTI SRDNSKNTLY LQMNSLRAED TAVYYCAKSS ILSGGHARVY GIDVWGQGTT          120
VTVSS                                                                     125

SEQ ID NO: 19               moltype = DNA  length = 375
FEATURE                     Location/Qualifiers
misc_feature                1..375
                            note = source = /note="Description of Artificial Sequence:
                             Synthetic polynucleotide"
source                      1..375
                            mol_type = other DNA
                            organism = synthetic construct
SEQUENCE: 19
gagatgcagg tcttggaatc tggcggagga ctggttcaac tggcggctc tctgagactg           60
tcttgtgccg ccagcggctt caccttcgat aactacgcca tgtcctgggt ccgacaggtg         120
ccaggcaaag gactggaatg ggtgtcctct atcagcggct ctggcggcag cacatattac         180
gccgatagcg tgaagggcca gttcaccatc agccgggaca acagcaagaa caccctgtac         240
ctccagatga acagcctgag agccgaggat accgccgtgt actactgtgc caagagcagc         300
attctgtctg gcggccacgc cagagtgtat ggcattgatg tttggggcca gggaaccacc         360
gtgaccgtta gttct                                                          375

SEQ ID NO: 20               moltype = AA  length = 455
FEATURE                     Location/Qualifiers
REGION                      1..455
                            note = source = /note="Description of Artificial Sequence:
                             Synthetic polypeptide"
source                      1..455
                            mol_type = protein
                            organism = synthetic construct
SEQUENCE: 20
EMQVLESGGG LVQPGGSLRL SCAASGFTFD NYAMSWVRQV PGKGLEWVSS ISGSGGSTYY           60
ADSVKGQFTI SRDNSKNTLY LQMNSLRAED TAVYYCAKSS ILSGGHARVY GIDVWGQGTT          120
VTVSSASTKG PSVFPLAPSS KSTSGGTAAL GCLVKDYFPE PVTVSWNSGA LTSGVHTFPA          180
VLQSSGLYSL SSVVTVPSSS LGTQTYICNV NHKPSNTKVD KRVEPKSCDK THTCPPCPAP          240
ELLGGPSVFL FPPKPKDTLM ISRTPEVTCV VVDVSHEDPE VKFNWYVDGV EVHNAKTKPR          300
EEQYNSTYRV VSVLTVLHQD WLNGKEYKCK VSNKALPAPI EKTISKAKGQ PREPQVYTLP          360
PSREEMTKNQ VSLTCLVKGF YPSDIAVEWE SNGQPENNYK TTPPVLDSDG SFFLYSKLTV          420
DKSRWQQGNV FSCSVMHEAL HNHYTQKSLS LSPGK                                    455
```

-continued

| | | |
|---|---|---|
| SEQ ID NO: 21 | moltype = DNA length = 1365 | |
| FEATURE | Location/Qualifiers | |
| misc_feature | 1..1365 | |
| | note = source = /note="Description of Artificial Sequence: Synthetic polynucleotide" | |
| source | 1..1365 | |
| | mol_type = other DNA | |
| | organism = synthetic construct | |

SEQUENCE: 21
```
gagatgcagg tcttggaatc tggcggagga ctggttcaac ctggcggctc tctgagactg   60
tcttgtgccg ccagcggctt caccttcgat aactacgcca tgtcctgggt ccgacaggtg  120
ccaggcaaag gactggaatg ggtgtcctct atcagcggct ctggcggcag cacatattac  180
gccgatagcg tgaagggcca gttcaccatc agcgggaca cagcaagaa caccctgtac  240
ctccagatga acagcctgag agccgaggat accgccgtgt actactgtgc caagagcagc  300
attctgtctg gcggccacgc cagagtgtat ggcattgatg tttggggcca gggaaccacc  360
gtgaccgtta gttctgctag caccaagggc cccagcgtgt tccccctggc ccccagcagc  420
aagagcacca gcggcggcac agccgccctg ggctgcctgg tgaaggacta cttccccgag  480
cccgtgaccg tgtcctggaa cagcggagcc ctgacctccg gcgtgcacac cttccccgcc  540
gtgctgcaga gcagcggcct gtacagcctg tccagcgtgg tgacagtgcc cagcagcagc  600
ctgggcaccc agacctacat ctgcaacgtg aaccacaagc ccagcaacac caaggtggac  660
aagagagtgg agcccaagag ctgcgacaag acccacacat gccccctg cccggcgcca  720
gagctgctgg gcggacccc cgtgttcctg ttcccccca aggcccaagga cacctgatg  780
atcagcagga ccccccaggt gacctgcgtg tggtggacg tgagccacga ggacccagag  840
gtgaagttca actggtacgt ggacggcgtg gaggtgcaca acgccaagac caagcccaga  900
gaggagcagt acaacagcac ctacagggtg gtgtccgtgc tgaccgtgct gcaccaggac  960
tggctgaacg gcaaggaata caagtgcaag gtctccaaca aggccctgcc agcccccatc 1020
gaaaagacca tcagcaaggc caagggccag ccacgggagc cccaggtgta caccctgccc 1080
ccctcccggg aggagatgac caagaaccag gtgtccctga cctgtctggt gaagggcttc 1140
taccccagcg acatcgccgt ggagtgggag agcaacggcc agcccgagaa caactacaag 1200
accacccccc cagtgctgga cagcgacggc agcttcttcc tgtacagcaa gctgaccgtg 1260
gacaagtcca ggtggcagca gggcaacgtg ttcagctgca gcgtgatgca cgaggccctg 1320
cacaaccact acacccagaa gagcctgagc ttaagcccg gcaag           1365
```

| | | |
|---|---|---|
| SEQ ID NO: 22 | moltype = AA length = 11 | |
| FEATURE | Location/Qualifiers | |
| REGION | 1..11 | |
| | note = source = /note="Description of Artificial Sequence: Synthetic peptide" | |
| source | 1..11 | |
| | mol_type = protein | |
| | organism = synthetic construct | |

SEQUENCE: 22
GGNNIGSQSV H                                                       11

| | | |
|---|---|---|
| SEQ ID NO: 23 | moltype = AA length = 7 | |
| FEATURE | Location/Qualifiers | |
| REGION | 1..7 | |
| | note = source = /note="Description of Artificial Sequence: Synthetic peptide" | |
| source | 1..7 | |
| | mol_type = protein | |
| | organism = synthetic construct | |

SEQUENCE: 23
DDTDRPS                                                             7

| | | |
|---|---|---|
| SEQ ID NO: 24 | moltype = AA length = 11 | |
| FEATURE | Location/Qualifiers | |
| REGION | 1..11 | |
| | note = source = /note="Description of Artificial Sequence: Synthetic peptide" | |
| source | 1..11 | |
| | mol_type = protein | |
| | organism = synthetic construct | |

SEQUENCE: 24
QVWDSSSDHV V                                                       11

| | | |
|---|---|---|
| SEQ ID NO: 25 | moltype = AA length = 11 | |
| FEATURE | Location/Qualifiers | |
| REGION | 1..11 | |
| | note = source = /note="Description of Artificial Sequence: Synthetic peptide" | |
| source | 1..11 | |
| | mol_type = protein | |
| | organism = synthetic construct | |

SEQUENCE: 25
GGNNIGSQSV H                                                       11

| | | |
|---|---|---|
| SEQ ID NO: 26 | moltype = AA length = 7 | |
| FEATURE | Location/Qualifiers | |

```
REGION                  1..7
                        note = source = /note="Description of Artificial Sequence:
                         Synthetic peptide"
source                  1..7
                        mol_type = protein
                        organism = synthetic construct
SEQUENCE: 26
DDTDRPS                                                                          7

SEQ ID NO: 27           moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 27
QVWDSSSDHV V                                                                    11

SEQ ID NO: 28           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 28
NNIGSQS                                                                          7

SEQ ID NO: 29           moltype =    length =
SEQUENCE: 29
000

SEQ ID NO: 30           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 30
WDSSSDHV                                                                         8

SEQ ID NO: 31           moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 31
NIGSQS                                                                           6

SEQ ID NO: 32           moltype =    length =
SEQUENCE: 32
000

SEQ ID NO: 33           moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 33
QVWDSSSDHV V                                                                    11

SEQ ID NO: 34           moltype = AA  length = 108
FEATURE                 Location/Qualifiers
REGION                  1..108
                        note = source = /note="Description of Artificial Sequence:
                         Synthetic polypeptide"
source                  1..108
                        mol_type = protein
```

```
                         organism = synthetic construct
SEQUENCE: 34
QSALTQPPSV SVAPGQTARI TCGGNNIGSQ SVHWYQQKPG QAPILVVYDD TDRPSGIPAR    60
FSGSSSGSTA TLTIGRVEAG DEADYYCQVW DSSSDHVVFG GGTKLTVL                108

SEQ ID NO: 35            moltype = DNA  length = 324
FEATURE                  Location/Qualifiers
misc_feature             1..324
                         note = source = /note="Description of Artificial Sequence:
                          Synthetic polynucleotide"
source                   1..324
                         mol_type = other DNA
                         organism = synthetic construct
SEQUENCE: 35
cagtctgccc tgactcagcc accctcggtg tcagtggccc caggacagac ggccaggatt    60
acctgtgggg gaaacaacat tggaagtcaa agtgtgcact ggtaccagca gaagccaggc   120
caggccccta tactggtcgt ctatgatgat accgaccggc cctcaggat ccctgcgcga    180
ttctctggct ccagctctgg gagcacggcc accctgacca tcggcagggt cgaagccggg   240
gatgaggccg actattactg tcaggtgtgg gatagtagta gtgatcatgt ggtattcggc   300
ggagggacca agctgaccgt ctta                                          324

SEQ ID NO: 36            moltype = AA  length = 214
FEATURE                  Location/Qualifiers
REGION                   1..214
                         note = source = /note="Description of Artificial Sequence:
                          Synthetic polypeptide"
source                   1..214
                         mol_type = protein
                         organism = synthetic construct
SEQUENCE: 36
QSALTQPPSV SVAPGQTARI TCGGNNIGSQ SVHWYQQKPG QAPILVVYDD TDRPSGIPAR    60
FSGSSSGSTA TLTIGRVEAG DEADYYCQVW DSSSDHVVFG GGTKLTVLSQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 37            moltype = DNA  length = 642
FEATURE                  Location/Qualifiers
misc_feature             1..642
                         note = source = /note="Description of Artificial Sequence:
                          Synthetic polynucleotide"
source                   1..642
                         mol_type = other DNA
                         organism = synthetic construct
SEQUENCE: 37
cagtctgccc tgactcagcc accctcggtg tcagtggccc caggacagac ggccaggatt    60
acctgtgggg gaaacaacat tggaagtcaa agtgtgcact ggtaccagca gaagccaggc   120
caggccccta tactggtcgt ctatgatgat accgaccggc cctcaggat ccctgcgcga    180
ttctctggct ccagctctgg gagcacggcc accctgacca tcggcagggt cgaagccggg   240
gatgaggccg actattactg tcaggtgtgg gatagtagta gtgatcatgt ggtattcggc   300
ggagggacca agctgaccgt cttaagtcag cccaaggctg ccccctcggt cactctgttc   360
ccgccctcct ctgaggagct tcaagccaac aaggccacac tggtgtgtct cataagtgac   420
ttctacccgg gagccgtgac agtggcctgg aaggcagata gcagccccgt caaggcggga   480
gtggagacca ccacccctcc caaacaaagc aacaacaagt acgccgccag cagctacctg   540
agcctgaccc ccgagcagtg gaagagccac agaagctaca gctgccaggt cacccacgag   600
ggcagcaccg tggagaaaac cgtggccccc accgagtgca gc                      642

SEQ ID NO: 38            moltype = AA  length = 10
FEATURE                  Location/Qualifiers
REGION                   1..10
                         note = source = /note="Description of Artificial Sequence:
                          Synthetic peptide"
source                   1..10
                         mol_type = protein
                         organism = synthetic construct
SEQUENCE: 38
GFTFHNYAMS                                                           10

SEQ ID NO: 39            moltype = AA  length = 17
FEATURE                  Location/Qualifiers
REGION                   1..17
                         note = source = /note="Description of Artificial Sequence:
                          Synthetic peptide"
source                   1..17
                         mol_type = protein
                         organism = synthetic construct
SEQUENCE: 39
SISGSGGSTY YADSVKG                                                   17

SEQ ID NO: 40            moltype = AA  length = 16
```

```
FEATURE               Location/Qualifiers
REGION                1..16
                      note = source = /note="Description of Artificial Sequence:
                       Synthetic peptide"
source                1..16
                      mol_type = protein
                      organism = synthetic construct
SEQUENCE: 40
SSILSGGHAR VYGIDV                                                              16

SEQ ID NO: 41         moltype = AA  length = 5
FEATURE               Location/Qualifiers
REGION                1..5
                      note = source = /note="Description of Artificial Sequence:
                       Synthetic peptide"
source                1..5
                      mol_type = protein
                      organism = synthetic construct
SEQUENCE: 41
NYAMS                                                                           5

SEQ ID NO: 42         moltype = AA  length = 17
FEATURE               Location/Qualifiers
REGION                1..17
                      note = source = /note="Description of Artificial Sequence:
                       Synthetic peptide"
source                1..17
                      mol_type = protein
                      organism = synthetic construct
SEQUENCE: 42
SISGSGGSTY YADSVKG                                                             17

SEQ ID NO: 43         moltype = AA  length = 16
FEATURE               Location/Qualifiers
REGION                1..16
                      note = source = /note="Description of Artificial Sequence:
                       Synthetic peptide"
source                1..16
                      mol_type = protein
                      organism = synthetic construct
SEQUENCE: 43
SSILSGGHAR VYGIDV                                                              16

SEQ ID NO: 44         moltype = AA  length = 7
FEATURE               Location/Qualifiers
REGION                1..7
                      note = source = /note="Description of Artificial Sequence:
                       Synthetic peptide"
source                1..7
                      mol_type = protein
                      organism = synthetic construct
SEQUENCE: 44
GFTFHNY                                                                         7

SEQ ID NO: 45         moltype = AA  length = 6
FEATURE               Location/Qualifiers
REGION                1..6
                      note = source = /note="Description of Artificial Sequence:
                       Synthetic peptide"
source                1..6
                      mol_type = protein
                      organism = synthetic construct
SEQUENCE: 45
SGSGGS                                                                          6

SEQ ID NO: 46         moltype = AA  length = 16
FEATURE               Location/Qualifiers
REGION                1..16
                      note = source = /note="Description of Artificial Sequence:
                       Synthetic peptide"
source                1..16
                      mol_type = protein
                      organism = synthetic construct
SEQUENCE: 46
SSILSGGHAR VYGIDV                                                              16

SEQ ID NO: 47         moltype = AA  length = 8
FEATURE               Location/Qualifiers
REGION                1..8
```

```
                        note = source = /note="Description of Artificial Sequence:
                         Synthetic peptide"
source                  1..8
                        mol_type = protein
                        organism = synthetic construct
SEQUENCE: 47
GFTFHNYA                                                                        8

SEQ ID NO: 48           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 48
ISGSGGST                                                                        8

SEQ ID NO: 49           moltype = AA  length = 18
FEATURE                 Location/Qualifiers
REGION                  1..18
                        note = source = /note="Description of Artificial Sequence:
                         Synthetic peptide"
source                  1..18
                        mol_type = protein
                        organism = synthetic construct
SEQUENCE: 49
AKSSILSGGH ARVYGIDV                                                            18

SEQ ID NO: 50           moltype = AA  length = 125
FEATURE                 Location/Qualifiers
REGION                  1..125
                        note = source = /note="Description of Artificial Sequence:
                         Synthetic polypeptide"
source                  1..125
                        mol_type = protein
                        organism = synthetic construct
SEQUENCE: 50
EMQVLESGGG LVQPGGSLRL SCAASGFTFH NYAMSWVRQV PGKGLEWVSS ISGSGGSTYY              60
ADSVKGQFTI SRDNSKNTLY LQMNSLRAED TAVYYCAKSS ILSGGHARVY GIDVWGQGTT             120
VTVSS                                                                         125

SEQ ID NO: 51           moltype = DNA  length = 375
FEATURE                 Location/Qualifiers
misc_feature            1..375
                        note = source = /note="Description of Artificial Sequence:
                         Synthetic polynucleotide"
source                  1..375
                        mol_type = other DNA
                        organism = synthetic construct
SEQUENCE: 51
gagatgcagg tcttggaatc tggcggagga ctggttcaac ctggcggctc tctgagactg              60
tcttgtgccg ccagcggctt caccttccat aactacgcca tgtcctgggt ccgacaggtg             120
ccaggcaaag gactggaatg ggtgtcctct atcagcggct ctggcggcag cacatattac             180
gccgatagcg tgaagggcca gttcaccatc agccgggaca acagcaagaa caccctgtac             240
ctccagatga acagcctgag agccgaggat accgccgtgt actactgtgc aagagcagc              300
attctgtctg gcggccacgc cagagtgtat ggcattgatg tttggggcca gggaaccacc             360
gtgaccgtta gttct                                                              375

SEQ ID NO: 52           moltype = AA  length = 455
FEATURE                 Location/Qualifiers
REGION                  1..455
                        note = source = /note="Description of Artificial Sequence:
                         Synthetic polypeptide"
source                  1..455
                        mol_type = protein
                        organism = synthetic construct
SEQUENCE: 52
EMQVLESGGG LVQPGGSLRL SCAASGFTFH NYAMSWVRQV PGKGLEWVSS ISGSGGSTYY              60
ADSVKGQFTI SRDNSKNTLY LQMNSLRAED TAVYYCAKSS ILSGGHARVY GIDVWGQGTT             120
VTVSSASTKG PSVFPLAPSS KSTSGGTAAL GCLVKDYFPE PVTVSWNSGA LTSGVHTFPA             180
VLQSSGLYSL SSVVTVPSSS LGTQTYICNV NHKPSNTKVD KRVEPKSCDK THTCPPCPAP             240
ELLGGPSVFL FPPKPKDTLM ISRTPEVTCV VVDVSHEDPE VKFNWYVDGV EVHNAKTKPR             300
EEQYNSTYRV VSVLTVLHQD WLNGKEYKCK VSNKALPAPI EKTISKAKGQ PREPQVYTLP             360
PSREEMTKNQ VSLTCLVKGF YPSDIAVEWE SNGQPENNYK TTPPVLDSDG SFFLYSKLTV             420
DKSRWQQGNV FSCSVMHEAL HNHYTQKSLS LSPGK                                       455

SEQ ID NO: 53           moltype = DNA  length = 1365
```

| | | |
|---|---|---|
| FEATURE | Location/Qualifiers | |
| misc_feature | 1..1365 | |
| | note = source = /note="Description of Artificial Sequence: Synthetic polynucleotide" | |
| source | 1..1365 | |
| | mol_type = other DNA | |
| | organism = synthetic construct | |

SEQUENCE: 53

```
gagatgcagg tcttggaatc tggcggagga ctggttcaac ctggcggctc tctgagactg    60
tcttgtgccg ccagcggctt caccttccat aactacgcca tgtcctgggt ccgacaggtg   120
ccaggcaaag gactgaatg gtgtcctct atcagcggct ctggcggcag cacatattac    180
gccgatagcg tgaagggcca gttcaccatc agcgggaca acagcaagaa caccctgtac   240
ctccagatga acagcctgag agccgaggat accgccgtgt actactgtgc caagagcagc   300
attctgtctg gcggccacgc cagagtgtat ggcattgatg tttggggcca gggaaccacc   360
gtgaccgtta gttctgctag caccaagggc cccagcgtgt tcccctggc cccagcagc   420
aagagcacca gcggcggcac agccgccctg ggctgcctgg tgaaggacta cttccccgag   480
cccgtgaccg tgtcctggaa cagcggagcc ctgacctccg gcgtgcacac cttccccgcc   540
gtgctgcaga gcagcggcct gtacagcctg tccagcgtgg tgacagtgcc cagcagcagc   600
ctgggcaccc agacctacat ctgcaacgtg aaccacaagc ccagcaacac caaggtggac   660
aagagagtgg agcccaagag ctgcgacaag acccacacat gccccccctg cccggcgcca   720
gagctgctgg gcggaccctc cgtgttcctg ttccccccca gcccaagga caccctgatg   780
atcagcagga cccccgaggt gacctgcgtg gtggtggacg tgagccacga ggacccagaa   840
gtgaagttca actggtacgt ggacggcgtg gaggtgcaca acgccaagac caagcccaga   900
gaggagcagt acaacagcac ctacagggtg gtgtccgtgc tgaccgtgct gcaccaggac   960
tggctgaacg gcaaggaata caagtgcaag gtctccaaca aggccctgcc agcccccatc  1020
gaaaagacca tcagcaaggc caagggccag ccacgggtgta cccctgccc  1080
cctcccggg aggagatgac caagaaccag gtgtccctga cctgtctggt gaagggcttc  1140
taccccagcg acatcgccgt ggagtgggag agcaacggcc agcccgagaa caactacaag  1200
accacccccc cagtgctgga cagcgacggc agcttcttcc tgtacagcaa gctgaccgtg  1260
gacaagtcca ggtggcagca gggcaacgtg ttcagctgca gcgtgatgca cgaggccctg  1320
cacaaccact acacccagaa gagcctgagc ttaagccccg gcaag              1365
```

| | | |
|---|---|---|
| SEQ ID NO: 54 | moltype = AA  length = 11 | |
| FEATURE | Location/Qualifiers | |
| REGION | 1..11 | |
| | note = source = /note="Description of Artificial Sequence: Synthetic peptide" | |
| source | 1..11 | |
| | mol_type = protein | |
| | organism = synthetic construct | |

SEQUENCE: 54
GGNNIGSQSV H                                                       11

| | | |
|---|---|---|
| SEQ ID NO: 55 | moltype = AA  length = 7 | |
| FEATURE | Location/Qualifiers | |
| REGION | 1..7 | |
| | note = source = /note="Description of Artificial Sequence: Synthetic peptide" | |
| source | 1..7 | |
| | mol_type = protein | |
| | organism = synthetic construct | |

SEQUENCE: 55
DDTDRPS                                                             7

| | | |
|---|---|---|
| SEQ ID NO: 56 | moltype = AA  length = 11 | |
| FEATURE | Location/Qualifiers | |
| REGION | 1..11 | |
| | note = source = /note="Description of Artificial Sequence: Synthetic peptide" | |
| source | 1..11 | |
| | mol_type = protein | |
| | organism = synthetic construct | |

SEQUENCE: 56
QVWDSSSDHV V                                                       11

| | | |
|---|---|---|
| SEQ ID NO: 57 | moltype = AA  length = 11 | |
| FEATURE | Location/Qualifiers | |
| REGION | 1..11 | |
| | note = source = /note="Description of Artificial Sequence: Synthetic peptide" | |
| source | 1..11 | |
| | mol_type = protein | |
| | organism = synthetic construct | |

SEQUENCE: 57
GGNNIGSQSV H                                                       11

| | | |
|---|---|---|
| SEQ ID NO: 58 | moltype = AA  length = 7 | |
| FEATURE | Location/Qualifiers | |
| REGION | 1..7 | |

```
                        note = source = /note="Description of Artificial Sequence:
                         Synthetic peptide"
source                  1..7
                        mol_type = protein
                        organism = synthetic construct
SEQUENCE: 58
DDTDRPS                                                                         7

SEQ ID NO: 59           moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 59
QVWDSSSDHV V                                                                   11

SEQ ID NO: 60           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 60
NNIGSQS                                                                         7

SEQ ID NO: 61           moltype =   length =
SEQUENCE: 61
000

SEQ ID NO: 62           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 62
WDSSSDHV                                                                        8

SEQ ID NO: 63           moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 63
NIGSQS                                                                          6

SEQ ID NO: 64           moltype =   length =
SEQUENCE: 64
000

SEQ ID NO: 65           moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 65
QVWDSSSDHV V                                                                   11

SEQ ID NO: 66           moltype = AA  length = 108
FEATURE                 Location/Qualifiers
REGION                  1..108
                        note = source = /note="Description of Artificial Sequence:
                         Synthetic polypeptide"
source                  1..108
                        mol_type = protein
                        organism = synthetic construct
```

```
SEQUENCE: 66
QSALTQPPSV SVAPGQTARI TCGGNNIGSQ SVHWYQQKPG QAPILVVYDD TDRPSGIPAR      60
FSGSSSGSTA TLTIGRVEAG DEADYYCQVW DSSSDHVVFG GGTKLTVL                 108

SEQ ID NO: 67           moltype = DNA  length = 324
FEATURE                 Location/Qualifiers
misc_feature            1..324
                        note = source = /note="Description of Artificial Sequence:
                         Synthetic polynucleotide"
source                  1..324
                        mol_type = other DNA
                        organism = synthetic construct
SEQUENCE: 67
cagtctgccc tgactcagcc accctcggtg tcagtggccc caggacagac ggccaggatt     60
acctgtgggg gaaacaacat tggaagtcaa agtgtgcact ggtaccagca gaagccaggc   120
caggccccta tactggtcgt ctatgatgat accgaccggc cctcagggat ccctgcgcga   180
ttctctggct ccagctctgg gagcacggcc accctgacca tcggcagggt cgaagccggg   240
gatgaggccg actattactg tcaggtgtgg gatagtagta gtgatcatgt ggtattcggc   300
ggagggacca agctgaccgt ctta                                          324

SEQ ID NO: 68           moltype = AA  length = 214
FEATURE                 Location/Qualifiers
REGION                  1..214
                        note = source = /note="Description of Artificial Sequence:
                         Synthetic polypeptide"
source                  1..214
                        mol_type = protein
                        organism = synthetic construct
SEQUENCE: 68
QSALTQPPSV SVAPGQTARI TCGGNNIGSQ SVHWYQQKPG QAPILVVYDD TDRPSGIPAR      60
FSGSSSGSTA TLTIGRVEAG DEADYYCQVW DSSSDHVVFG GGTKLTVLSQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 69           moltype = DNA  length = 642
FEATURE                 Location/Qualifiers
misc_feature            1..642
                        note = source = /note="Description of Artificial Sequence:
                         Synthetic polynucleotide"
source                  1..642
                        mol_type = other DNA
                        organism = synthetic construct
SEQUENCE: 69
cagtctgccc tgactcagcc accctcggtg tcagtggccc caggacagac ggccaggatt     60
acctgtgggg gaaacaacat tggaagtcaa agtgtgcact ggtaccagca gaagccaggc   120
caggccccta tactggtcgt ctatgatgat accgaccggc cctcagggat ccctgcgcga   180
ttctctggct ccagctctgg gagcacggcc accctgacca tcggcagggt cgaagccggg   240
gatgaggccg actattactg tcaggtgtgg gatagtagta gtgatcatgt ggtattcggc   300
ggagggacca agctgaccgt cttaagtcag cccaaggctg ccccctcggt cactctgttc   360
ccgccctcct ctgaggagct tcaagccaac aaggccacac tggtgtgtct cataagtgac   420
ttctacccgg gagccgtgac agtggcctgg aaggcagata gcagcccgt caaggcggga   480
gtggagacca ccacccctc caaacaaagc aacaacaagt acgccgccag cagctacctg   540
agcctgaccc ccgagcagtg gaagagccac agaagctaca gctgccaggt cacccacgag   600
ggcagcaccg tggagaaaac cgtggccccc accgagtgca gc                      642

SEQ ID NO: 70           moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 70
GFTFNNYAMS                                                            10

SEQ ID NO: 71           moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 71
SISGSGGSTY YADSVKG                                                    17

SEQ ID NO: 72           moltype = AA  length = 16
FEATURE                 Location/Qualifiers
```

```
REGION                  1..16
                        note = source = /note="Description of Artificial Sequence:
                         Synthetic peptide"
source                  1..16
                        mol_type = protein
                        organism = synthetic construct
SEQUENCE: 72
SSILSGGHAR VYGIDV                                                         16

SEQ ID NO: 73           moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 73
NYAMS                                                                      5

SEQ ID NO: 74           moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 74
SISGSGGSTY YADSVKG                                                        17

SEQ ID NO: 75           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 75
SSILSGGHAR VYGIDV                                                         16

SEQ ID NO: 76           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 76
GFTFNNY                                                                    7

SEQ ID NO: 77           moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 77
SGSGGS                                                                     6

SEQ ID NO: 78           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 78
SSILSGGHAR VYGIDV                                                         16

SEQ ID NO: 79           moltype = AA  length = 8
FEATURE                 Location/Qualifiers
REGION                  1..8
                        note = source = /note="Description of Artificial Sequence:
```

```
                        Synthetic peptide"
source                  1..8
                        mol_type = protein
                        organism = synthetic construct
SEQUENCE: 79
GFTFNNYA                                                                    8

SEQ ID NO: 80           moltype = AA  length = 8
FEATURE                 Location/Qualifiers
REGION                  1..8
                        note = source = /note="Description of Artificial Sequence:
                        Synthetic peptide"
source                  1..8
                        mol_type = protein
                        organism = synthetic construct
SEQUENCE: 80
ISGSGGST                                                                    8

SEQ ID NO: 81           moltype = AA  length = 18
FEATURE                 Location/Qualifiers
REGION                  1..18
                        note = source = /note="Description of Artificial Sequence:
                        Synthetic peptide"
source                  1..18
                        mol_type = protein
                        organism = synthetic construct
SEQUENCE: 81
AKSSILSGGH ARVYGIDV                                                        18

SEQ ID NO: 82           moltype = AA  length = 125
FEATURE                 Location/Qualifiers
REGION                  1..125
                        note = source = /note="Description of Artificial Sequence:
                        Synthetic polypeptide"
source                  1..125
                        mol_type = protein
                        organism = synthetic construct
SEQUENCE: 82
EMQVLESGGG LVQPGGSLRL SCAASGFTFN NYAMSWVRQV PGKGLEWVSS ISGSGGSTYY           60
ADSVKGQFTI SRDNSKNTLY LQMNSLRAED TAVYYCAKSS ILSGGHARVY GIDVWGQGTT          120
VTVSS                                                                     125

SEQ ID NO: 83           moltype = DNA  length = 375
FEATURE                 Location/Qualifiers
misc_feature            1..375
                        note = source = /note="Description of Artificial Sequence:
                        Synthetic polynucleotide"
source                  1..375
                        mol_type = other DNA
                        organism = synthetic construct
SEQUENCE: 83
gaaatgcagg tgttggagtc tgggggaggc ctggtacagc ctggggggtc cctgagactc           60
tcctgtgcag cctctggatt cacctttaac aactatgcca tgagctgggt ccgccaggtt         120
ccagggaagg ggctggagtg ggtctcaagt attagtggta gtggaggtag cacgtactac         180
gcagactccg tgaagggcca gttcaccatc tccagagaca attccaagaa tacgctgtat         240
ctgcaaatga acagcctgag agccgaggac acggccgtat attactgtgc gaaatcctct         300
atcttgagtg gtggtcacgc gcgggtctac ggcatagacg tctggggcca agggaccacg         360
gtcaccgtct cctca                                                          375

SEQ ID NO: 84           moltype = AA  length = 455
FEATURE                 Location/Qualifiers
REGION                  1..455
                        note = source = /note="Description of Artificial Sequence:
                        Synthetic polypeptide"
source                  1..455
                        mol_type = protein
                        organism = synthetic construct
SEQUENCE: 84
EMQVLESGGG LVQPGGSLRL SCAASGFTFN NYAMSWVRQV PGKGLEWVSS ISGSGGSTYY           60
ADSVKGQFTI SRDNSKNTLY LQMNSLRAED TAVYYCAKSS ILSGGHARVY GIDVWGQGTT          120
VTVSSASTKG PSVFPLAPSS KSTSGGTAAL GCLVKDYFPE PVTVSWNSGA LTSGVHTFPA          180
VLQSSGLYSL SSVVTVPSSS LGTQTYICNV NHKPSNTKVD KRVEPKSCDK THTCPPCPAP          240
ELLGGPSVFL FPPKPKDTLM ISRTPEVTCV VVDVSHEDPE VKFNWYVDGV EVHNAKTKPR          300
EEQYNSTYRV VSVLTVLHQD WLNGKEYKCK VSNKALPAPI EKTISKAKGQ PREPQVYTLP          360
PSREEMTKNQ VSLTCLVKGF YPSDIAVEWE SNGQPENNYK TTPPVLDSDG SFFLYSKLTV          420
DKSRWQQGNV FSCSVMHEAL HNHYTQKSLS LSPGK                                    455

SEQ ID NO: 85           moltype = DNA  length = 1365
FEATURE                 Location/Qualifiers
```

```
misc_feature            1..1365
                        note = source = /note="Description of Artificial Sequence:
                         Synthetic polynucleotide"
source                  1..1365
                        mol_type = other DNA
                        organism = synthetic construct
SEQUENCE: 85
gaaatgcagg tgttggagtc tgggggaggc ctggtacagc ctgggggtc cctgagactc      60
tcctgtgcag cctctggatt cacctttaac aactatgcca tgagctgggt ccgccaggtt   120
ccagggaagg ggctggagtg ggtctcaagt attagtggta gtggaggtag cacgtactac   180
gcagactccg tgaagggcca gttcaccatc tccagagaca attccaagaa tacgctgtat   240
ctgcaaatga acagcctgag agccgaggac acggccgtat attactgtgc gaaatcctct   300
atcttgagtg gtggtcacgc gcgggtctac ggcatagacg tctggggcca agggaccacg   360
gtcaccgtct cctcagcctc caccaagggc ccatcggtct tccccctggc accctcctcc   420
aagagcacct ctgggggcac agcggccctg ggctgcctgg tcaaggacta cttccccgaa   480
ccggtgacgg tgtcatggaa ctcaggcgcc ctgaccagcg gcgtgcacac cttcccggct   540
gtcctacagt cctcaggact ctactccctc agcagcgtgg tgaccgtgcc ctccagcagc   600
ttgggcaccc agacctacat ctgcaacgtg aaccacaagc ccagcaacac caaggtggac   660
aagagagtgg agcccaagag ctgcgacaag acccacacct gccccccctg cccagcccca   720
gagctgctgg gcggaccctc cgtgttcctg ttccccccca gcccaagga caccctgatg    780
atcagcagga ccccgaggt gacctgcgtg gtggtggacg tgagccacga ggacccagag    840
gtgaagttca actggtacgt ggacggcgtg gaggtgcata atgccaagac caagcccgag   900
gaggagcagt acaacagcac ctacagggtg gtgtccgtgc tgaccgtgct gcaccaggac   960
tggctgaacg gcaaggaata caagtgcaag gtctccaaca aggccctgcc agccccatc   1020
gaaaagacca tcagcaaggc caagggccag ccacgggagc cccaggtgta caccctgccc   1080
cctcccgggg aggagatgac caagaaccag gtgtccctga cctgtctggt gaagggcttc   1140
taccccagcg acatcgccgt ggagtgggag agcaacggcc agcccgagaa caactacaag   1200
accacccccc cagtgctgga cagcgacggc agcttcttcc tgtacagcaa gctgaccgtg   1260
gacaagtcca ggtggcagca gggcaacgtg ttcagctgca gcgtgatgca cgaggccctg   1320
cacaaccact acacccagaa gagcctgagc ctgtcccccg gcaag                   1365

SEQ ID NO: 86           moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 86
GGNNIGSQSV H                                                          11

SEQ ID NO: 87           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 87
DDTDRPS                                                                7

SEQ ID NO: 88           moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 88
QVWDSSSDHV V                                                          11

SEQ ID NO: 89           moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 89
GGNNIGSQSV H                                                          11

SEQ ID NO: 90           moltype = AA  length = 7
FEATURE                 Location/Qualifiers
REGION                  1..7
                        note = source = /note="Description of Artificial Sequence:
```

|  |  |  |
|---|---|---|
| source | 1..7<br>mol_type = protein<br>organism = synthetic construct | |
| SEQUENCE: 90<br>DDTDRPS | | 7 |
| SEQ ID NO: 91<br>FEATURE<br>REGION | moltype = AA  length = 11<br>Location/Qualifiers<br>1..11<br>note = source = /note="Description of Artificial Sequence:<br>Synthetic peptide" | |
| source | 1..11<br>mol_type = protein<br>organism = synthetic construct | |
| SEQUENCE: 91<br>QVWDSSSDHV V | | 11 |
| SEQ ID NO: 92<br>FEATURE<br>REGION | moltype = AA  length = 7<br>Location/Qualifiers<br>1..7<br>note = source = /note="Description of Artificial Sequence:<br>Synthetic peptide" | |
| source | 1..7<br>mol_type = protein<br>organism = synthetic construct | |
| SEQUENCE: 92<br>NNIGSQS | | 7 |
| SEQ ID NO: 93<br>SEQUENCE: 93<br>000 | moltype =   length = | |
| SEQ ID NO: 94<br>FEATURE<br>REGION | moltype = AA  length = 8<br>Location/Qualifiers<br>1..8<br>note = source = /note="Description of Artificial Sequence:<br>Synthetic peptide" | |
| source | 1..8<br>mol_type = protein<br>organism = synthetic construct | |
| SEQUENCE: 94<br>WDSSSDHV | | 8 |
| SEQ ID NO: 95<br>FEATURE<br>REGION | moltype = AA  length = 6<br>Location/Qualifiers<br>1..6<br>note = source = /note="Description of Artificial Sequence:<br>Synthetic peptide" | |
| source | 1..6<br>mol_type = protein<br>organism = synthetic construct | |
| SEQUENCE: 95<br>NIGSQS | | 6 |
| SEQ ID NO: 96<br>SEQUENCE: 96<br>000 | moltype =   length = | |
| SEQ ID NO: 97<br>FEATURE<br>REGION | moltype = AA  length = 11<br>Location/Qualifiers<br>1..11<br>note = source = /note="Description of Artificial Sequence:<br>Synthetic peptide" | |
| source | 1..11<br>mol_type = protein<br>organism = synthetic construct | |
| SEQUENCE: 97<br>QVWDSSSDHV V | | 11 |
| SEQ ID NO: 98<br>FEATURE<br>REGION | moltype = AA  length = 108<br>Location/Qualifiers<br>1..108<br>note = source = /note="Description of Artificial Sequence:<br>Synthetic polypeptide" | |
| source | 1..108<br>mol_type = protein<br>organism = synthetic construct | |
| SEQUENCE: 98 | | |

```
QSALTQPPSV SVAPGQTARI TCGGNNIGSQ SVHWYQQKPG QAPILVVYDD TDRPSGIPAR    60
FSGSSSGSTA TLTIGRVEAG DEADYYCQVW DSSSDHVVFG GGTKLTVL               108

SEQ ID NO: 99           moltype = DNA   length = 324
FEATURE                 Location/Qualifiers
misc_feature            1..324
                        note = source = /note="Description of Artificial Sequence:
                        Synthetic polynucleotide"
source                  1..324
                        mol_type = other DNA
                        organism = synthetic construct
SEQUENCE: 99
cagtctgccc tgactcagcc accctcggtg tcagtggccc caggacagac ggccaggatt    60
acctgtgggg gaaacaacat tggaagtcaa agtgtgcact ggtaccagca gaagccaggc   120
caggccccta tactggtcgt ctatgatgat accgaccggc cctcagggat ccctgcgcga   180
ttctctggct ccagctctgg gagcacggcc accctgacca tcgcagggt cgaagccggg    240
gatgaggccg actattactg tcaggtgtgg gatagtagta gtgatcatgt ggtattcggc   300
ggagggacca agctgaccgt ctta                                         324

SEQ ID NO: 100          moltype = AA   length = 214
FEATURE                 Location/Qualifiers
REGION                  1..214
                        note = source = /note="Description of Artificial Sequence:
                        Synthetic polypeptide"
source                  1..214
                        mol_type = protein
                        organism = synthetic construct
SEQUENCE: 100
QSALTQPPSV SVAPGQTARI TCGGNNIGSQ SVHWYQQKPG QAPILVVYDD TDRPSGIPAR    60
FSGSSSGSTA TLTIGRVEAG DEADYYCQVW DSSSDHVVFG GGTKLTVLSQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                              214

SEQ ID NO: 101          moltype = DNA   length = 642
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 101
cagtctgccc tgactcagcc accctcggtg tcagtggccc caggacagac ggccaggatt    60
acctgtgggg gaaacaacat tggaagtcaa agtgtgcact ggtaccagca gaagccaggc   120
caggccccta tactggtcgt ctatgatgat accgaccggc cctcagggat ccctgcgcga   180
ttctctggct ccagctctgg gagcacggcc accctgacca tcgcagggt cgaagccggg    240
gatgaggccg actattactg tcaggtgtgg gatagtagta gtgatcatgt ggtattcggc   300
ggagggacca agctgaccgt cttaagtcag cccaaggctg ccccctcggt cactctgttc   360
ccgccctcct ctgaggagct tcaagccaac aaggccacac tggtgtgtct cataagtgac   420
ttctacccgg gagccgtgac agtggcctgg aaggcagata gcagccccgt caaggcggga   480
gtggagacca ccacacctcc aaacaaagc aacaacaagt acgccgccag cagctacctg   540
agcctgaccc cgagcagtg gaagagccac agaagctaca gctgccaggt cacccacgag   600
ggcagcaccg tggagaaaac cgtggccccc accgagtgca gc                    642

SEQ ID NO: 102          moltype = AA   length = 10
FEATURE                 Location/Qualifiers
REGION                  1..10
                        note = source = /note="Description of Artificial Sequence:
                        Synthetic peptide"
source                  1..10
                        mol_type = protein
                        organism = synthetic construct
SEQUENCE: 102
GFTFSPHAMS                                                          10

SEQ ID NO: 103          moltype = AA   length = 17
FEATURE                 Location/Qualifiers
REGION                  1..17
                        note = source = /note="Description of Artificial Sequence:
                        Synthetic peptide"
source                  1..17
                        mol_type = protein
                        organism = synthetic construct
SEQUENCE: 103
AISDSGGSTH YADSVKG                                                  17

SEQ ID NO: 104          moltype = AA   length = 14
FEATURE                 Location/Qualifiers
REGION                  1..14
```

```
                        note = source = /note="Description of Artificial Sequence:
                         Synthetic peptide"
source                  1..14
                        mol_type = protein
                        organism = synthetic construct
SEQUENCE: 104
DDDAWSGYDY WFDY                                                         14

SEQ ID NO: 105          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 105
PHAMS                                                                    5

SEQ ID NO: 106          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 106
AISDSGGSTH YADSVKG                                                      17

SEQ ID NO: 107          moltype = AA  length = 14
FEATURE                 Location/Qualifiers
REGION                  1..14
                        note = source = /note="Description of Artificial Sequence:
                         Synthetic peptide"
source                  1..14
                        mol_type = protein
                        organism = synthetic construct
SEQUENCE: 107
DDDAWSGYDY WFDY                                                         14

SEQ ID NO: 108          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 108
GFTFSPH                                                                  7

SEQ ID NO: 109          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 109
SDSGGS                                                                   6

SEQ ID NO: 110          moltype = AA  length = 14
FEATURE                 Location/Qualifiers
REGION                  1..14
                        note = source = /note="Description of Artificial Sequence:
                         Synthetic peptide"
source                  1..14
                        mol_type = protein
                        organism = synthetic construct
SEQUENCE: 110
DDDAWSGYDY WFDY                                                         14

SEQ ID NO: 111          moltype = AA  length = 8
FEATURE                 Location/Qualifiers
REGION                  1..8
                        note = source = /note="Description of Artificial Sequence:
                         Synthetic peptide"
```

```
source                           1..8
                                 mol_type = protein
                                 organism = synthetic construct
SEQUENCE: 111
GFTFSPHA                                                                 8

SEQ ID NO: 112                   moltype = AA   length = 8
FEATURE                          Location/Qualifiers
REGION                           1..8
                                 note = source = /note="Description of Artificial Sequence:
                                 Synthetic peptide"
source                           1..8
                                 mol_type = protein
                                 organism = synthetic construct
SEQUENCE: 112
ISDSGGST                                                                 8

SEQ ID NO: 113                   moltype = AA   length = 16
FEATURE                          Location/Qualifiers
REGION                           1..16
                                 note = source = /note="Description of Artificial Sequence:
                                 Synthetic peptide"
source                           1..16
                                 mol_type = protein
                                 organism = synthetic construct
SEQUENCE: 113
ARDDDAWSGY DYWFDY                                                       16

SEQ ID NO: 114                   moltype = AA   length = 123
FEATURE                          Location/Qualifiers
REGION                           1..123
                                 note = source = /note="Description of Artificial Sequence:
                                 Synthetic polypeptide"
source                           1..123
                                 mol_type = protein
                                 organism = synthetic construct
SEQUENCE: 114
EVQLLESGGG LVQPGGSLRL SCAASGFTFS PHAMSWVRQA PGKGLEWVSA ISDSGGSTHY        60
ADSVKGRFTI SRDNSKNTLY LQMNSLRAED TAVYYCARDD DAWSGYDYWF DYWGQGTLVT       120
VSS                                                                    123

SEQ ID NO: 115                   moltype = DNA   length = 369
FEATURE                          Location/Qualifiers
misc_feature                     1..369
                                 note = source = /note="Description of Artificial Sequence:
                                 Synthetic polynucleotide"
source                           1..369
                                 mol_type = other DNA
                                 organism = synthetic construct
SEQUENCE: 115
gaggtccaat tgctggaatc tggcggagga ctggttcagc ctggtggctc tctgagactg        60
tcttgtgccg ccagcggctt caccttagc cctcatgcca tgtcctgggt ccgacaggct       120
cctggaaaag gactcgagtg ggtgtccgcc atttctgatt ctggcggcag cacacactac       180
gccgatagcg tgaagggcag attcaccatc agccgggaca acagcaagaa caccctgtac       240
ctgcagatga acagcctgag agccgaggac acagccgtgt actattgcgc gcgtgacgat       300
gatgcttggt ccggctacga ctattggttc gattactggg gccagggcac cctggtcaca       360
gttagctca                                                              369

SEQ ID NO: 116                   moltype = AA   length = 453
FEATURE                          Location/Qualifiers
REGION                           1..453
                                 note = source = /note="Description of Artificial Sequence:
                                 Synthetic polypeptide"
source                           1..453
                                 mol_type = protein
                                 organism = synthetic construct
SEQUENCE: 116
EVQLLESGGG LVQPGGSLRL SCAASGFTFS PHAMSWVRQA PGKGLEWVSA ISDSGGSTHY        60
ADSVKGRFTI SRDNSKNTLY LQMNSLRAED TAVYYCARDD DAWSGYDYWF DYWGQGTLVT       120
VSSASTKGPS VFPLAPSSKS TSGGTAALGC LVKDYFPEPV TVSWNSGALT SGVHTFPAVL       180
QSSGLYSLSS VVTVPSSSLG TQTYICNVNH KPSNTKVDKR VEPKSCDKTH TCPPCPAPEL       240
LGGPSVFLFP PKPKDTLMIS RTPEVTCVVV DVSHEDPEVK FNWYVDGVEV HNAKTKPREE       300
QYNSTYRVVS VLTVLHQDWL NGKEYKCKVS NKALPAPIEK TISKAKGQPR EPQVYTLPPS       360
REEMTKNQVS LTCLVKGFYP SDIAVEWESN GQPENNYKTT PPVLDSDGSF FLYSKLTVDK       420
SRWQQGNVFS CSVMHEALHN HYTQKSLSLS PGK                                   453

SEQ ID NO: 117                   moltype = DNA   length = 1359
FEATURE                          Location/Qualifiers
misc_feature                     1..1359
```

```
                        note = source = /note="Description of Artificial Sequence:
                           Synthetic polynucleotide"
source                  1..1359
                        mol_type = other DNA
                        organism = synthetic construct
SEQUENCE: 117
gaggtccaat tgctggaatc tggcggagga ctggttcagc ctggtggctc tctgagactg    60
tcttgtgccg ccagcggctt cacctttagc cctcatgcca tgtcctgggt ccgacaggct   120
cctggaaaag gactcgagtg ggtgtccgcc atttctgatt ctggcggcag cacacactac   180
gccgatagcg tgaagggcag attcaccatc agccgggaca acagcaagaa caccctgtac   240
ctgcagatga acagcctgag agccgaggac acagccgtgt actattgcgc gcgtgacgat   300
gatgcttggt ccggctacga ctattggttc gattactggg gccagggcac cctggtcaca   360
gttagctcag ctagcaccaa gggccccagc gtgttccccc tggcccccag cagcaagagc   420
accagcggcg gcacagccgc cctggctgc ctggtgaagg actacttccc cgagcccgtg    480
accgtgtcct ggaacagcgg agccctgacc tccggcgtgc acaccttccc cgccgtgctg   540
cagagcagcg gcctgtacag cctgtccagc gtggtgacag tgcccagcag cagcctgggc   600
acccagacct acatctgcaa cgtgaaccac aagcccagca caccaaggt ggacaagaga    660
gtggagccca agagctgcga caagacccac catgccccc cctgcccggc gccagagctg    720
ctgggcggac cctccgtgtt cctgttcccc cccaagccca aggacaccct gatgatcagc   780
aggacccccg aggtgacctg cgtggtggtg gacgtgagcc acgaggaccc agaggtgaag   840
ttcaactggt acgtggacgg cgtggaggtg cacaacgcca agaccaagcc cagagaggag   900
cagtacaaca gcacctacag ggtggtgtcc gtgctgaccg tgctgcacca ggactggctg   960
aacggcaagg aatacaagtg caaggtctcc aacaagccc tgccagcccc catcgaaaag    1020
accatcagca aggccaaggg ccagccacgg gagcccagg tgtacaccct gcccccctcc    1080
cgggaggaga tgaccaagaa ccaggtgtcc ctgacctgtc tggtgaaggg cttctacccc   1140
agcgacatcg ccgtggagtg ggagagcaac ggccagcccg agaacaacta caagaccacc   1200
cccccagtgc tggacagcga cggcagcttc ttcctgtaca gcaagctgac cgtggacaag   1260
tccaggtggc agcagggcaa cgtgttcagc tgcagcgtga tgcacgaggc cctgcacaac   1320
cactacaccc agaagagcct gagcttaagc cccggcaag                          1359

SEQ ID NO: 118          moltype = AA  length = 11
FEATURE                 Location/Qualifiers
REGION                  1..11
                        note = source = /note="Description of Artificial Sequence:
                           Synthetic peptide"
source                  1..11
                        mol_type = protein
                        organism = synthetic construct
SEQUENCE: 118
RASQSISPYL N                                                         11

SEQ ID NO: 119          moltype = AA  length = 7
FEATURE                 Location/Qualifiers
REGION                  1..7
                        note = source = /note="Description of Artificial Sequence:
                           Synthetic peptide"
source                  1..7
                        mol_type = protein
                        organism = synthetic construct
SEQUENCE: 119
AADSLQS                                                              7

SEQ ID NO: 120          moltype = AA  length = 9
FEATURE                 Location/Qualifiers
REGION                  1..9
                        note = source = /note="Description of Artificial Sequence:
                           Synthetic peptide"
source                  1..9
                        mol_type = protein
                        organism = synthetic construct
SEQUENCE: 120
QQSYKIPLT                                                            9

SEQ ID NO: 121          moltype = AA  length = 11
FEATURE                 Location/Qualifiers
REGION                  1..11
                        note = source = /note="Description of Artificial Sequence:
                           Synthetic peptide"
source                  1..11
                        mol_type = protein
                        organism = synthetic construct
SEQUENCE: 121
RASQSISPYL N                                                         11

SEQ ID NO: 122          moltype = AA  length = 7
FEATURE                 Location/Qualifiers
REGION                  1..7
                        note = source = /note="Description of Artificial Sequence:
                           Synthetic peptide"
```

```
source                  1..7
                        mol_type = protein
                        organism = synthetic construct
SEQUENCE: 122
AADSLQS                                                                        7

SEQ ID NO: 123          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 123
QQSYKIPLT                                                                      9

SEQ ID NO: 124          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 124
SQSISPY                                                                        7

SEQ ID NO: 125          moltype =     length =
SEQUENCE: 125
000

SEQ ID NO: 126          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 126
SYKIPL                                                                         6

SEQ ID NO: 127          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 127
QSISPY                                                                         6

SEQ ID NO: 128          moltype =     length =
SEQUENCE: 128
000

SEQ ID NO: 129          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 129
QQSYKIPLT                                                                      9

SEQ ID NO: 130          moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 130
DIQMTQSPSS LSASVGDRVT ITCRASQSIS PYLNWYQQKP GKAPKLLIYA ADSLQSGVPS   60
```

```
RFSGSGSGTD FTLTISSLQP EDFATYYCQQ SYKIPLTFGQ GTKVEIK                    107

SEQ ID NO: 131           moltype = DNA   length = 321
FEATURE                  Location/Qualifiers
misc_feature             1..321
                         note = source = /note="Description of Artificial Sequence:
                         Synthetic polynucleotide"
source                   1..321
                         mol_type = other DNA
                         organism = synthetic construct
SEQUENCE: 131
gatatccaga tgacacagag ccctagcagc ctgtctgcct ctgtgggcga tagagtgacc    60
atcacctgta gagccagcca gagcatcagc ccctacctga attggtacca gcagaagcct   120
ggcaaggccc ctaagctgct gatctatgct gccgactctc tgcagtctgg cgtgccaagc   180
agattttctg gcagcggctc tggcaccgac ttcaccctga caattagctc cctgcagcct   240
gaagacttcg ccacctacta ctgccagcag agctacaaga tccctctgac ctttggccag   300
ggcaccaagg tggaaatcaa g                                             321

SEQ ID NO: 132           moltype = AA   length = 214
FEATURE                  Location/Qualifiers
REGION                   1..214
                         note = source = /note="Description of Artificial Sequence:
                         Synthetic polypeptide"
source                   1..214
                         mol_type = protein
                         organism = synthetic construct
SEQUENCE: 132
DIQMTQSPSS LSASVGDRVT ITCRASQSIS PYLNWYQQKP GKAPKLLIYA ADSLQSGVPS     60
RFSGSGSGTD FTLTISSLQP EDFATYYCQQ SYKIPLTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 133           moltype = DNA   length = 642
FEATURE                  Location/Qualifiers
misc_feature             1..642
                         note = source = /note="Description of Artificial Sequence:
                         Synthetic polynucleotide"
source                   1..642
                         mol_type = other DNA
                         organism = synthetic construct
SEQUENCE: 133
gatatccaga tgacacagag ccctagcagc ctgtctgcct ctgtgggcga tagagtgacc    60
atcacctgta gagccagcca gagcatcagc ccctacctga attggtacca gcagaagcct   120
ggcaaggccc ctaagctgct gatctatgct gccgactctc tgcagtctgg cgtgccaagc   180
agattttctg gcagcggctc tggcaccgac ttcaccctga caattagctc cctgcagcct   240
gaagacttcg ccacctacta ctgccagcag agctacaaga tccctctgac ctttggccag   300
ggcaccaagg tggaaatcaa gcgtacggtg gccgctccca gcgtgttcat cttcccccc    360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga gaagcataag gtgtacgcct gcgaggtgac ccaccagggc   600
ctgtccagcc ccgtgaccaa gagcttcaac agggggcgagt gc                     642

SEQ ID NO: 134           moltype = AA   length = 10
FEATURE                  Location/Qualifiers
REGION                   1..10
                         note = source = /note="Description of Artificial Sequence:
                         Synthetic peptide"
source                   1..10
                         mol_type = protein
                         organism = synthetic construct
SEQUENCE: 134
GFTFSPHAMS                                                           10

SEQ ID NO: 135           moltype = AA   length = 17
FEATURE                  Location/Qualifiers
REGION                   1..17
                         note = source = /note="Description of Artificial Sequence:
                         Synthetic peptide"
source                   1..17
                         mol_type = protein
                         organism = synthetic construct
SEQUENCE: 135
AISDSGGSTH YADSVKG                                                   17

SEQ ID NO: 136           moltype = AA   length = 14
FEATURE                  Location/Qualifiers
REGION                   1..14
                         note = source = /note="Description of Artificial Sequence:
```

```
                           Synthetic peptide"
source                     1..14
                           mol_type = protein
                           organism = synthetic construct
SEQUENCE: 136
DDDGWSGYDY WFDY                                                                  14

SEQ ID NO: 137             moltype = AA   length = 5
FEATURE                    Location/Qualifiers
REGION                     1..5
                           note = source = /note="Description of Artificial Sequence:
                           Synthetic peptide"
source                     1..5
                           mol_type = protein
                           organism = synthetic construct
SEQUENCE: 137
PHAMS                                                                             5

SEQ ID NO: 138             moltype = AA   length = 17
FEATURE                    Location/Qualifiers
REGION                     1..17
                           note = source = /note="Description of Artificial Sequence:
                           Synthetic peptide"
source                     1..17
                           mol_type = protein
                           organism = synthetic construct
SEQUENCE: 138
AISDSGGSTH YADSVKG                                                               17

SEQ ID NO: 139             moltype = AA   length = 14
FEATURE                    Location/Qualifiers
REGION                     1..14
                           note = source = /note="Description of Artificial Sequence:
                           Synthetic peptide"
source                     1..14
                           mol_type = protein
                           organism = synthetic construct
SEQUENCE: 139
DDDGWSGYDY WFDY                                                                  14

SEQ ID NO: 140             moltype = AA   length = 7
FEATURE                    Location/Qualifiers
REGION                     1..7
                           note = source = /note="Description of Artificial Sequence:
                           Synthetic peptide"
source                     1..7
                           mol_type = protein
                           organism = synthetic construct
SEQUENCE: 140
GFTFSPH                                                                           7

SEQ ID NO: 141             moltype = AA   length = 6
FEATURE                    Location/Qualifiers
REGION                     1..6
                           note = source = /note="Description of Artificial Sequence:
                           Synthetic peptide"
source                     1..6
                           mol_type = protein
                           organism = synthetic construct
SEQUENCE: 141
SDSGGS                                                                            6

SEQ ID NO: 142             moltype = AA   length = 14
FEATURE                    Location/Qualifiers
REGION                     1..14
                           note = source = /note="Description of Artificial Sequence:
                           Synthetic peptide"
source                     1..14
                           mol_type = protein
                           organism = synthetic construct
SEQUENCE: 142
DDDGWSGYDY WFDY                                                                  14

SEQ ID NO: 143             moltype = AA   length = 8
FEATURE                    Location/Qualifiers
REGION                     1..8
                           note = source = /note="Description of Artificial Sequence:
                           Synthetic peptide"
source                     1..8
```

```
                        mol_type = protein
                        organism = synthetic construct
SEQUENCE: 143
GFTFSPHA                                                                    8

SEQ ID NO: 144          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 144
ISDSGGST                                                                    8

SEQ ID NO: 145          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 145
ARDDDGWSGY DYWFDY                                                          16

SEQ ID NO: 146          moltype = AA  length = 123
FEATURE                 Location/Qualifiers
REGION                  1..123
                        note = source = /note="Description of Artificial Sequence:
                         Synthetic polypeptide"
source                  1..123
                        mol_type = protein
                        organism = synthetic construct
SEQUENCE: 146
EVQLLESGGG LVQPGGSLRL SCAASGFTFS PHAMSWVRQA PGKGLEWVSA ISDSGGSTHY           60
ADSVKGRFTI SRDNSKNTLY LQMNSLRAED TAVYYCARDD DGWSGYDYWF DYWGQGTLVT          120
VSS                                                                       123

SEQ ID NO: 147          moltype = DNA  length = 369
FEATURE                 Location/Qualifiers
misc_feature            1..369
                        note = source = /note="Description of Artificial Sequence:
                         Synthetic polynucleotide"
source                  1..369
                        mol_type = other DNA
                        organism = synthetic construct
SEQUENCE: 147
gaggtccaat tgctggaatc tggcggagga ctggttcagc ctggtggctc tctgagactg          60
tcttgtgccg ccagcggctt cacattcagc cctcatgcca tgtcctgggt ccgacaggct         120
cctggaaaag gactcgagtg ggtgtccgcc atttctgatt ctggcggcag cacacactac         180
gccgatagcg tgaagggcag attcaccatc agccgggaca acagcaagaa caccctgtac         240
ctgcagatga cagcctgag agccgaggac acagccgtgt actattgcgc gcgtgacgat          300
gatggatggt ccggctacga ctattggttc gattactggg gccagggcac cctggtcaca         360
gttagctca                                                                 369

SEQ ID NO: 148          moltype = AA  length = 453
FEATURE                 Location/Qualifiers
REGION                  1..453
                        note = source = /note="Description of Artificial Sequence:
                         Synthetic polypeptide"
source                  1..453
                        mol_type = protein
                        organism = synthetic construct
SEQUENCE: 148
EVQLLESGGG LVQPGGSLRL SCAASGFTFS PHAMSWVRQA PGKGLEWVSA ISDSGGSTHY           60
ADSVKGRFTI SRDNSKNTLY LQMNSLRAED TAVYYCARDD DGWSGYDYWF DYWGQGTLVT          120
VSSASTKGPS VFPLAPSSKS TSGGTAALGC LVKDYFPEPV TVSWNSGALT SGVHTFPAVL          180
QSSGLYSLSS VVTVPSSSLG TQTYICNVNH KPSNTKVDKR VEPKSCDKTH TCPPCPAPEL          240
LGGPSVFLFP PKPKDTLMIS RTPEVTCVVV DVSHEDPEVK FNWYVDGVEV HNAKTKPREE          300
QYNSTYRVVS VLTVLHQDWL NGKEYKCKVS NKALPAPIEK TISKAKGQPR EPQVYTLPPS          360
REEMTKNQVS LTCLVKGFYP SDIAVEWESN GQPENNYKTT PPVLDSDGSF FLYSKLTVDK          420
SRWQQGNVFS CSVMHEALHN HYTQKSLSLS PGK                                      453

SEQ ID NO: 149          moltype = DNA  length = 1359
FEATURE                 Location/Qualifiers
misc_feature            1..1359
                        note = source = /note="Description of Artificial Sequence:
```

```
                        Synthetic polynucleotide"
source                  1..1359
                        mol_type = other DNA
                        organism = synthetic construct
SEQUENCE: 149
gaggtccaat tgctggaatc tggcggagga ctggttcagc ctggtggctc tctgagactg    60
tcttgtgccg ccagcggctt cacattcagc cctcatgcca tgtcctgggt ccgacaggct   120
cctggaaaag gactcgagtg ggtgtccgcc atttctgatt ctgcggcag cacacactac    180
gccgatagcg tgaagggcag attcaccatc agccgggaca acagcaagaa cacccctgtac  240
ctgcagatga cagcctgag agccgaggac acagccgtgt actattgcgc gcgtgacgat    300
gatggatggt ccggctacga ctattggttc gattactggg gccagggcac cctggtcaca   360
gttagctcag ctagcaccaa gggccccagc gtgttccccc tggccccag cagcaagagc    420
accagcggcg gcacagccgc cctgggctgc ctggtgaagg actacttccc cgagcccgtg   480
accgtgtcct ggaacagcgg agccctgacc tccggcgtgc acaccttccc cgccgtgctg   540
cagagcagcg gcctgtacag cctgtccagc gtggtgacag tgcccagcag cagcctgggc   600
acccagacct acatctgcaa cgtgaaccac aagcccagca acaccaaggt ggacaagaga   660
gtggagccca gagctgcga caagacccac acatgccccc cctgcccggc gccagagctg    720
ctgggcggac cctccgtgtt cctgttcccc ccaagccca gaccacct gatgatcagt     780
aggaccccg aggtgacctg cgtggtggtg gacgtgagcc acgaggaccc agaggtgaag    840
ttcaactggt acgtggacgg cgtggaggtg cacaacgcca agaccaagcc cagagaggag    900
cagtacaaca gcacctacag ggtggtgtcc gtgctgaccg tgctgcacca ggactggctg    960
aacggcaagg aatacaagtg caaggtctcc aacaagccca tcgaaaag                1020
accatcagca aggccaaggg ccagccacgg gagcccagg tgtacaccct gccccctcc     1080
cgggaggaga tgaccaagaa ccaggtgtcc ctgacctgtc tggtgaaggg cttctacccc  1140
agcgacatcg ccgtggagtg ggagagcaac ggccagcccg agaacaacta caagaccacc   1200
cccccagtgc tggacagcga cggcagcttc ttcctgtaca gcaagctgac cgtggacaag   1260
tccaggtggc agcagggcaa cgtgttcagc tgcagcgtga tgcacgaggc cctgcacaac  1320
cactacaccc agaagagcct gagcttaagc cccggcaag                          1359

SEQ ID NO: 150            moltype = AA  length = 11
FEATURE                   Location/Qualifiers
REGION                    1..11
                          note = source = /note="Description of Artificial Sequence:
                          Synthetic peptide"
source                    1..11
                          mol_type = protein
                          organism = synthetic construct
SEQUENCE: 150
RASQSISPYL N                                                          11

SEQ ID NO: 151            moltype = AA  length = 7
FEATURE                   Location/Qualifiers
REGION                    1..7
                          note = source = /note="Description of Artificial Sequence:
                          Synthetic peptide"
source                    1..7
                          mol_type = protein
                          organism = synthetic construct
SEQUENCE: 151
AADSLQS                                                               7

SEQ ID NO: 152            moltype = AA  length = 9
FEATURE                   Location/Qualifiers
REGION                    1..9
                          note = source = /note="Description of Artificial Sequence:
                          Synthetic peptide"
source                    1..9
                          mol_type = protein
                          organism = synthetic construct
SEQUENCE: 152
QQSYKIPLT                                                             9

SEQ ID NO: 153            moltype = AA  length = 11
FEATURE                   Location/Qualifiers
REGION                    1..11
                          note = source = /note="Description of Artificial Sequence:
                          Synthetic peptide"
source                    1..11
                          mol_type = protein
                          organism = synthetic construct
SEQUENCE: 153
RASQSISPYL N                                                          11

SEQ ID NO: 154            moltype = AA  length = 7
FEATURE                   Location/Qualifiers
REGION                    1..7
                          note = source = /note="Description of Artificial Sequence:
                          Synthetic peptide"
source                    1..7
```

```
                        mol_type = protein
                        organism = synthetic construct
SEQUENCE: 154
AADSLQS                                                                 7

SEQ ID NO: 155          moltype = AA   length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 155
QQSYKIPLT                                                               9

SEQ ID NO: 156          moltype = AA   length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 156
SQSISPY                                                                 7

SEQ ID NO: 157          moltype =    length =
SEQUENCE: 157
000

SEQ ID NO: 158          moltype = AA   length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 158
SYKIPL                                                                  6

SEQ ID NO: 159          moltype = AA   length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 159
QSISPY                                                                  6

SEQ ID NO: 160          moltype =    length =
SEQUENCE: 160
000

SEQ ID NO: 161          moltype = AA   length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 161
QQSYKIPLT                                                               9

SEQ ID NO: 162          moltype = AA   length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 162
DIQMTQSPSS LSASVGDRVT ITCRASQSIS PYLNWYQQKP GKAPKLLIYA ADSLQSGVPS     60
RFSGSGSGTD FTLTISSLQP EDFATYYCQQ SYKIPLTFGQ GTKVEIK                  107
```

```
SEQ ID NO: 163          moltype = DNA  length = 321
FEATURE                 Location/Qualifiers
misc_feature            1..321
                        note = source = /note="Description of Artificial Sequence:
                        Synthetic polynucleotide"
source                  1..321
                        mol_type = other DNA
                        organism = synthetic construct
SEQUENCE: 163
gatatccaga tgacacagag ccctagcagc ctgtctgcct ctgtgggcga tagagtgacc    60
atcacctgta gagccagcca gagcatcagc cctacctga attggtacca gcagaagcct   120
ggcaaggccc ctaagctgct gatctatgct gccgactctc tgcagtctgg cgtgccaagc   180
agattttctg gcagcggctc tggcaccgac ttcaccctga caattagctc cctgcagcct   240
gaagacttcg ccacctacta ctgccagcag agctacaaga tccctctgac ctttggccag   300
ggcaccaagg tggaaatcaa g                                             321

SEQ ID NO: 164          moltype = AA  length = 214
FEATURE                 Location/Qualifiers
REGION                  1..214
                        note = source = /note="Description of Artificial Sequence:
                        Synthetic polypeptide"
source                  1..214
                        mol_type = protein
                        organism = synthetic construct
SEQUENCE: 164
DIQMTQSPSS LSASVGDRVT ITCRASQSIS PYLNWYQQKP GKAPKLLIYA ADSLQSGVPS    60
RFSGSGSGTD FTLTISSLQP EDFATYYCQQ SYKIPLTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 165          moltype = DNA  length = 642
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 165
gatatccaga tgacacagag ccctagcagc ctgtctgcct ctgtgggcga tagagtgacc    60
atcacctgta gagccagcca gagcatcagc cctacctga attggtacca gcagaagcct   120
ggcaaggccc ctaagctgct gatctatgct gccgactctc tgcagtctgg cgtgccaagc   180
agattttctg gcagcggctc tggcaccgac ttcaccctga caattagctc cctgcagcct   240
gaagacttcg ccacctacta ctgccagcag agctacaaga tccctctgac ctttggccag   300
ggcaccaagg tggaaatcaa gcgtacggtg gccgctccca gcgtgttcat cttcccccc   360
agcgacgagc agctgaagag cggcaccgcc agctgtggt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag cacccctgacc   540
ctgagcaagg ccgactacga aagcataag gtgtacgcct gcgaggtgac ccaccagggc   600
ctgtccagcc ccgtgaccaa gagcttcaac agggcgagt gc                      642

SEQ ID NO: 166          moltype = AA  length = 10
FEATURE                 Location/Qualifiers
REGION                  1..10
                        note = source = /note="Description of Artificial Sequence:
                        Synthetic peptide"
source                  1..10
                        mol_type = protein
                        organism = synthetic construct
SEQUENCE: 166
GFTFNRYGMH                                                          10

SEQ ID NO: 167          moltype = AA  length = 17
FEATURE                 Location/Qualifiers
REGION                  1..17
                        note = source = /note="Description of Artificial Sequence:
                        Synthetic peptide"
source                  1..17
                        mol_type = protein
                        organism = synthetic construct
SEQUENCE: 167
GIWHDGSHKY YADSLRG                                                  17

SEQ ID NO: 168          moltype = AA  length = 13
FEATURE                 Location/Qualifiers
REGION                  1..13
                        note = source = /note="Description of Artificial Sequence:
                        Synthetic peptide"
```

```
source                  1..13
                        mol_type = protein
                        organism = synthetic construct
SEQUENCE: 168
QTNRGRLDDA FDI                                                               13

SEQ ID NO: 169          moltype = AA  length = 5
FEATURE                 Location/Qualifiers
REGION                  1..5
                        note = source = /note="Description of Artificial Sequence:
                        Synthetic peptide"
source                  1..5
                        mol_type = protein
                        organism = synthetic construct
SEQUENCE: 169
RYGMH                                                                         5

SEQ ID NO: 170          moltype = AA  length = 17
FEATURE                 Location/Qualifiers
REGION                  1..17
                        note = source = /note="Description of Artificial Sequence:
                        Synthetic peptide"
source                  1..17
                        mol_type = protein
                        organism = synthetic construct
SEQUENCE: 170
GIWHDGSHKY YADSLRG                                                           17

SEQ ID NO: 171          moltype = AA  length = 13
FEATURE                 Location/Qualifiers
REGION                  1..13
                        note = source = /note="Description of Artificial Sequence:
                        Synthetic peptide"
source                  1..13
                        mol_type = protein
                        organism = synthetic construct
SEQUENCE: 171
QTNRGRLDDA FDI                                                               13

SEQ ID NO: 172          moltype = AA  length = 7
FEATURE                 Location/Qualifiers
REGION                  1..7
                        note = source = /note="Description of Artificial Sequence:
                        Synthetic peptide"
source                  1..7
                        mol_type = protein
                        organism = synthetic construct
SEQUENCE: 172
GFTFNRY                                                                       7

SEQ ID NO: 173          moltype = AA  length = 6
FEATURE                 Location/Qualifiers
REGION                  1..6
                        note = source = /note="Description of Artificial Sequence:
                        Synthetic peptide"
source                  1..6
                        mol_type = protein
                        organism = synthetic construct
SEQUENCE: 173
WHDGSH                                                                        6

SEQ ID NO: 174          moltype = AA  length = 13
FEATURE                 Location/Qualifiers
REGION                  1..13
                        note = source = /note="Description of Artificial Sequence:
                        Synthetic peptide"
source                  1..13
                        mol_type = protein
                        organism = synthetic construct
SEQUENCE: 174
QTNRGRLDDA FDI                                                               13

SEQ ID NO: 175          moltype = AA  length = 8
FEATURE                 Location/Qualifiers
REGION                  1..8
                        note = source = /note="Description of Artificial Sequence:
                        Synthetic peptide"
source                  1..8
                        mol_type = protein
```

```
                          organism = synthetic construct
SEQUENCE: 175
GFTFNRYG                                                              8

SEQ ID NO: 176            moltype = AA  length = 8
FEATURE                   Location/Qualifiers
REGION                    1..8
                          note = source = /note="Description of Artificial Sequence:
                           Synthetic peptide"
source                    1..8
                          mol_type = protein
                          organism = synthetic construct
SEQUENCE: 176
IWHDGSHK                                                              8

SEQ ID NO: 177            moltype = AA  length = 15
FEATURE                   Location/Qualifiers
REGION                    1..15
                          note = source = /note="Description of Artificial Sequence:
                           Synthetic peptide"
source                    1..15
                          mol_type = protein
                          organism = synthetic construct
SEQUENCE: 177
VRQTNRGRLD DAFDI                                                     15

SEQ ID NO: 178            moltype = AA  length = 122
FEATURE                   Location/Qualifiers
REGION                    1..122
                          note = source = /note="Description of Artificial Sequence:
                           Synthetic polypeptide"
source                    1..122
                          mol_type = protein
                          organism = synthetic construct
SEQUENCE: 178
QVQLVESGGG VVQPGRSLRL SCAASGFTFN RYGMHWVRQA PGKGLEWVAG IWHDGSHKYY     60
ADSLRGRFTI SRDNAKNTLD LQLNRLRAED TSVYYCVRQT NRGRLDDAFD IWGQGTMVTV    120
SS                                                                  122

SEQ ID NO: 179            moltype = DNA  length = 366
FEATURE                   Location/Qualifiers
misc_feature              1..366
                          note = source = /note="Description of Artificial Sequence:
                           Synthetic polynucleotide"
source                    1..366
                          mol_type = other DNA
                          organism = synthetic construct
SEQUENCE: 179
caggtgcagc tggtggagtc tgggggaggc gtggtccagc ctggggggtc cctgagactc     60
tcctgtgcag cgtcaggatt cacattcaat agatatggca tgcactgggt ccgccaggct    120
ccaggcaagg ggttggagtg ggtggctggt atatggcatg atggaagtca taaatactat    180
gcagactctc tgaggggccg attcaccatc tccagagaca atgccaagaa cacgctggat    240
ctgcaattga acaggctgag agccgaagac acgtctgtgt attattgtgt gaggcaaacc    300
aacaggggac gtctcgatga tgcttttgac atctggggcc aagggacaat ggtcaccgtt    360
agctca                                                              366

SEQ ID NO: 180            moltype = AA  length = 452
FEATURE                   Location/Qualifiers
REGION                    1..452
                          note = source = /note="Description of Artificial Sequence:
                           Synthetic polypeptide"
source                    1..452
                          mol_type = protein
                          organism = synthetic construct
SEQUENCE: 180
QVQLVESGGG VVQPGRSLRL SCAASGFTFN RYGMHWVRQA PGKGLEWVAG IWHDGSHKYY     60
ADSLRGRFTI SRDNAKNTLD LQLNRLRAED TSVYYCVRQT NRGRLDDAFD IWGQGTMVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKRV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                 452

SEQ ID NO: 181            moltype = DNA  length = 1356
FEATURE                   Location/Qualifiers
misc_feature              1..1356
                          note = source = /note="Description of Artificial Sequence:
                           Synthetic polynucleotide"
```

```
source                      1..1356
                            mol_type = other DNA
                            organism = synthetic construct
SEQUENCE: 181
caggtgcagc tggtggagtc tgggggaggc gtggtccagc ctggggaggtc cctgagactc    60
tcctgtgcag cgtcaggatt cacattcaat agatatggca tgcactgggt ccgccaggct    120
ccaggcaagg ggttggagtg ggtggctggt atatggcatg atggaagtca taaatactat    180
gcagactctc tgaggggccg attcaccatc tccagagaca atgccaagaa cacgctggat    240
ctgcaattga acaggctgag agccgaagac acgtctgtgt attattgtgt gaggcaaacc    300
aacaggggac gtctcgatga tgcttttgac atctgggggcc aagggacaat ggtcaccgtt    360
agctcagcta gcaccaaggg ccccagcgtg ttccccctgg ccccagcag caagagcacc    420
agcggcggca cagccgccct gggctgcctg gtgaaggact acttccccga gcccgtgacc    480
gtgtcctgga acagcggagc cctgacctcc ggcgtgcaca ccttccccgc cgtgctgcag    540
agcagcggcc tgtacagcct gtccagcgtg gtgacagtgc ccagcagcag cctgggcacc    600
cagacctaca tctgcaacgt gaaccacaag cccagcaaca ccaaggtgga cagagagtgc    660
gagcccaaga gctgcgacaa gacccacacc tgccccccct gcccagcccc agagctgctg    720
ggcggaccct ccgtgttcct gttccccccc aagcccaagg acaccctgat gatcagcagg    780
acccccgagg tgacctgcgt ggtggtggac gtgagccacg aggaccccga ggtgaagttc    840
aactggtacg tggacggcgt ggaggtgcac aacgccaaga ccaagccag agaggagcag    900
tacaacagca cctacagggt ggtgtccgtg ctgaccgtgc tgcaccagga ctggctgaac    960
ggcaaggaat acaagtgcaa ggtctccaac aaggccctgc cagcccccat cgaaaagacc    1020
atcagcaagg ccaaggggca gccacggag ccccaggtgt acaccctgcc ccctcccgg     1080
gaggagatga ccaagaacca ggtgtccctg acctgtctgg tgaagggctt ctaccccagc    1140
gacatcgccg tggagtggga gagcaacggc cagcccgaga caactacaa gaccaccccc    1200
ccagtgctgg acagcgacgg cagcttcttc ctgtacagca gctgaccgt ggacaagtcc    1260
aggtggcagc agggcaacgt gttcagctgc agcgtgatgc acgaggccct gcacaaccac    1320
tacacccaga gagcctgag cctgtccccc ggcaag                              1356

SEQ ID NO: 182              moltype = AA  length = 11
FEATURE                     Location/Qualifiers
REGION                      1..11
                            note = source = /note="Description of Artificial Sequence:
                             Synthetic peptide"
source                      1..11
                            mol_type = protein
                            organism = synthetic construct
SEQUENCE: 182
RASQTISSYL N                                                          11

SEQ ID NO: 183              moltype = AA  length = 7
FEATURE                     Location/Qualifiers
REGION                      1..7
                            note = source = /note="Description of Artificial Sequence:
                             Synthetic peptide"
source                      1..7
                            mol_type = protein
                            organism = synthetic construct
SEQUENCE: 183
AASTLQS                                                                7

SEQ ID NO: 184              moltype = AA  length = 9
FEATURE                     Location/Qualifiers
REGION                      1..9
                            note = source = /note="Description of Artificial Sequence:
                             Synthetic peptide"
source                      1..9
                            mol_type = protein
                            organism = synthetic construct
SEQUENCE: 184
QQNYDTLWT                                                              9

SEQ ID NO: 185              moltype = AA  length = 11
FEATURE                     Location/Qualifiers
REGION                      1..11
                            note = source = /note="Description of Artificial Sequence:
                             Synthetic peptide"
source                      1..11
                            mol_type = protein
                            organism = synthetic construct
SEQUENCE: 185
RASQTISSYL N                                                          11

SEQ ID NO: 186              moltype = AA  length = 7
FEATURE                     Location/Qualifiers
REGION                      1..7
                            note = source = /note="Description of Artificial Sequence:
                             Synthetic peptide"
source                      1..7
                            mol_type = protein
```

```
                            organism = synthetic construct
SEQUENCE: 186
AASTLQS                                                                              7

SEQ ID NO: 187              moltype = AA   length = 9
FEATURE                     Location/Qualifiers
REGION                      1..9
                            note = source = /note="Description of Artificial Sequence:
                             Synthetic peptide"
source                      1..9
                            mol_type = protein
                            organism = synthetic construct
SEQUENCE: 187
QQNYDTLWT                                                                            9

SEQ ID NO: 188              moltype = AA   length = 7
FEATURE                     Location/Qualifiers
REGION                      1..7
                            note = source = /note="Description of Artificial Sequence:
                             Synthetic peptide"
source                      1..7
                            mol_type = protein
                            organism = synthetic construct
SEQUENCE: 188
SQTISSY                                                                              7

SEQ ID NO: 189              moltype =    length =
SEQUENCE: 189
000

SEQ ID NO: 190              moltype = AA   length = 6
FEATURE                     Location/Qualifiers
REGION                      1..6
                            note = source = /note="Description of Artificial Sequence:
                             Synthetic peptide"
source                      1..6
                            mol_type = protein
                            organism = synthetic construct
SEQUENCE: 190
NYDTLW                                                                               6

SEQ ID NO: 191              moltype = AA   length = 6
FEATURE                     Location/Qualifiers
REGION                      1..6
                            note = source = /note="Description of Artificial Sequence:
                             Synthetic peptide"
source                      1..6
                            mol_type = protein
                            organism = synthetic construct
SEQUENCE: 191
QTISSY                                                                               6

SEQ ID NO: 192              moltype =    length =
SEQUENCE: 192
000

SEQ ID NO: 193              moltype = AA   length = 9
FEATURE                     Location/Qualifiers
REGION                      1..9
                            note = source = /note="Description of Artificial Sequence:
                             Synthetic peptide"
source                      1..9
                            mol_type = protein
                            organism = synthetic construct
SEQUENCE: 193
QQNYDTLWT                                                                            9

SEQ ID NO: 194              moltype = AA   length = 107
FEATURE                     Location/Qualifiers
REGION                      1..107
                            note = source = /note="Description of Artificial Sequence:
                             Synthetic polypeptide"
source                      1..107
                            mol_type = protein
                            organism = synthetic construct
SEQUENCE: 194
DIQMTQSPSS LSAAVGDRVT ISCRASQTIS SYLNWYQQKP GEAPKLLIYA ASTLQSGVPS            60
RFGGSGSGTD FTLTISSLQP EDSATYYCQQ NYDTLWTFGQ GTKVEIK                         107
```

| SEQ ID NO: 195 | moltype = DNA length = 321 |
|---|---|
| FEATURE | Location/Qualifiers |
| misc_feature | 1..321 |
| | note = source = /note="Description of Artificial Sequence: Synthetic polynucleotide" |
| source | 1..321 |
| | mol_type = other DNA |
| | organism = synthetic construct |

SEQUENCE: 195

```
gatatccaga tgacccagtc tccatcctcc ctgtctgcag ctgtaggaga cagagtcacc    60
atctcttgcc gggcaagtca gaccattagt agttatttaa attggtatca gcagaaacca   120
ggggaagccc ctaagctcct gatctatgct gcctccacct tgcaaagtgg ggtcccttca   180
aggttcggtg gcagtggatc tgggacagat ttcactctca ccatcagcag tctgcaacct   240
gaagattctg caacttacta ctgtcaacag aattacgata ctttgtggac gttcggccaa   300
gggaccaagg tggaaatcaa a                                              321
```

| SEQ ID NO: 196 | moltype = AA length = 214 |
|---|---|
| FEATURE | Location/Qualifiers |
| REGION | 1..214 |
| | note = source = /note="Description of Artificial Sequence: Synthetic polypeptide" |
| source | 1..214 |
| | mol_type = protein |
| | organism = synthetic construct |

SEQUENCE: 196

```
DIQMTQSPSS LSAAVGDRVT ISCRASQTIS SYLNWYQQKP GEAPKLLIYA ASTLQSGVPS    60
RFGGSGSGTD FTLTISSLQP EDSATYYCQQ NYDTLWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214
```

| SEQ ID NO: 197 | moltype = DNA length = 642 |
|---|---|
| FEATURE | Location/Qualifiers |
| misc_feature | 1..642 |
| | note = source = /note="Description of Artificial Sequence: Synthetic polynucleotide" |
| source | 1..642 |
| | mol_type = other DNA |
| | organism = synthetic construct |

SEQUENCE: 197

```
gatatccaga tgacccagtc tccatcctcc ctgtctgcag ctgtaggaga cagagtcacc    60
atctcttgcc gggcaagtca gaccattagt agttatttaa attggtatca gcagaaacca   120
ggggaagccc ctaagctcct gatctatgct gcctccacct tgcaaagtgg ggtcccttca   180
aggttcggtg gcagtggatc tgggacagat ttcactctca ccatcagcag tctgcaacct   240
gaagattctg caacttacta ctgtcaacag aattacgata ctttgtggac gttcggccaa   300
gggaccaagg tggaaatcaa acgtacggtg gccgctccca gcgtgttcat cttccccccc   360
agcgacgagc agctgaagag cggcaccgcc agcgtggtgt gcctgctgaa caacttctac   420
ccccgggagg ccaaggtgca gtggaaggtg gacaacgcgg caacagccag                              480
gagagcgtca ccgagcagga cagcaaggac tccacctaca gcctgagcag cacctgacc   540
ctgagcaagg ccgactacga aagcataag gtgtacgcct gcgaggtgac ccaccagggc   600
ctgtccagcc ccgtgaccaa gagcttcaac aggggcgagt gc                       642
```

| SEQ ID NO: 198 | moltype = AA length = 10 |
|---|---|
| FEATURE | Location/Qualifiers |
| REGION | 1..10 |
| | note = source = /note="Description of Artificial Sequence: Synthetic peptide" |
| source | 1..10 |
| | mol_type = protein |
| | organism = synthetic construct |

SEQUENCE: 198

```
GFTFDRYGMH                                                            10
```

| SEQ ID NO: 199 | moltype = AA length = 17 |
|---|---|
| FEATURE | Location/Qualifiers |
| REGION | 1..17 |
| | note = source = /note="Description of Artificial Sequence: Synthetic peptide" |
| source | 1..17 |
| | mol_type = protein |
| | organism = synthetic construct |

SEQUENCE: 199

```
GIWHEGSHKY YADSLRG                                                    17
```

| SEQ ID NO: 200 | moltype = AA length = 13 |
|---|---|
| FEATURE | Location/Qualifiers |
| REGION | 1..13 |
| | note = source = /note="Description of Artificial Sequence: Synthetic peptide" |
| source | 1..13 |

```
                        mol_type = protein
                        organism = synthetic construct
SEQUENCE: 200
QTNRGRLDDA FDI                                                      13

SEQ ID NO: 201          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 201
RYGMH                                                               5

SEQ ID NO: 202          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 202
GIWHEGSHKY YADSLRG                                                  17

SEQ ID NO: 203          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 203
QTNRGRLDDA FDI                                                      13

SEQ ID NO: 204          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 204
GFTFDRY                                                             7

SEQ ID NO: 205          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 205
WHEGSH                                                              6

SEQ ID NO: 206          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 206
QTNRGRLDDA FDI                                                      13

SEQ ID NO: 207          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
```

```
SEQUENCE: 207
GFTFDRYG                                                                          8

SEQ ID NO: 208         moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 208
IWHEGSHK                                                                          8

SEQ ID NO: 209         moltype = AA  length = 15
FEATURE                Location/Qualifiers
REGION                 1..15
                       note = source = /note="Description of Artificial Sequence:
                        Synthetic peptide"
source                 1..15
                       mol_type = protein
                       organism = synthetic construct
SEQUENCE: 209
VRQTNRGRLD DAFDI                                                                 15

SEQ ID NO: 210         moltype = AA  length = 122
FEATURE                Location/Qualifiers
REGION                 1..122
                       note = source = /note="Description of Artificial Sequence:
                        Synthetic polypeptide"
source                 1..122
                       mol_type = protein
                       organism = synthetic construct
SEQUENCE: 210
QVQLVESGGG VVQPGRSLRL SCAASGFTFD RYGMHWVRQA PGKGLEWVAG IWHEGSHKYY                 60
ADSLRGRFTI SRDNAKNTLD LQLNRLRAED TSVYYCVRQT NRGRLDDAFD IWGQGTMVTV                120
SS                                                                              122

SEQ ID NO: 211         moltype = DNA  length = 366
FEATURE                Location/Qualifiers
misc_feature           1..366
                       note = source = /note="Description of Artificial Sequence:
                        Synthetic polynucleotide"
source                 1..366
                       mol_type = other DNA
                       organism = synthetic construct
SEQUENCE: 211
caggtgcagc tggttgaatc tggtggcgga gtggtgcagc ctggcagatc tctgagactg                 60
tcttgtgccg ccagcggctt caccttcgac agatatggca tgcactgggt ccgacaggcc                120
cctggaaaag gacttgaatg ggtggccgga atctggcacg aaggcagcca caagtactac                180
gccgatagcc tgagaggccg gttcaccatc agcagagaca cgccaagaa cacccctgga                 240
ctccagctga acagactgag agccgaggat accagcgtgt actactgcgt gcggcagacc                300
aacagaggca gactggacga tgccttcgat atctgggcc aagggacaat ggtcaccgtt                 360
agctca                                                                          366

SEQ ID NO: 212         moltype = AA  length = 452
FEATURE                Location/Qualifiers
REGION                 1..452
                       note = source = /note="Description of Artificial Sequence:
                        Synthetic polypeptide"
source                 1..452
                       mol_type = protein
                       organism = synthetic construct
SEQUENCE: 212
QVQLVESGGG VVQPGRSLRL SCAASGFTFD RYGMHWVRQA PGKGLEWVAG IWHEGSHKYY                 60
ADSLRGRFTI SRDNAKNTLD LQLNRLRAED TSVYYCVRQT NRGRLDDAFD IWGQGTMVTV                120
SSASTKGPSV FPLAPSSKST SGGTAALGCL VKDYFPEPVT VSWNSGALTS GVHTFPAVLQ                180
SSGLYSLSSV VTVPSSSLGT QTYICNVNHK PSNTKVDKRV EPKSCDKTHT CPPCPAPELL                240
GGPSVFLFPP KPKDTLMISR TPEVTCVVVD VSHEDPEVKF NWYVDGVEVH NAKTKPREEQ                300
YNSTYRVVSV LTVLHQDWLN GKEYKCKVSN KALPAPIEKT ISKAKGQPRE PQVYTLPPSR                360
EEMTKNQVSL TCLVKGFYPS DIAVEWESNG QPENNYKTTP PVLDSDGSFF LYSKLTVDKS                420
RWQQGNVFSC SVMHEALHNH YTQKSLSLSP GK                                              452

SEQ ID NO: 213         moltype = DNA  length = 1356
FEATURE                Location/Qualifiers
misc_feature           1..1356
                       note = source = /note="Description of Artificial Sequence:
                        Synthetic polynucleotide"
source                 1..1356
```

```
                        mol_type = other DNA
                        organism = synthetic construct
SEQUENCE: 213
caggtgcagc tggttgaatc tgtggcgga gtggtgcagc ctggcagatc tctgagactg    60
tcttgtgccg ccagcggctt caccttcgac agatatggca tgcactgggt ccgacaggcc   120
cctggaaaag gacttgaatg ggtggccgga atctggcacg aaggcagcca caagtactac   180
gccgatagcc tgagaggccg gttcaccatc agcagagaca cgccaagaa caccctggac    240
ctccagctga acagactgag agccgaggat accagcgtgt actactgcgt gcggcagacc   300
aacagaggca gactggacga tgccttcgat atctggggcc aagggacaat ggtcaccgtt   360
agctcagcta gcaccaaggg ccccagcgtg ttccccctgg ccccagcag caagagcacc    420
agcggcggca cagccgccct gggctgcctg gtgaaggact acttccccga gcccgtgacc   480
gtgtcctgga cagcggagc cctgacctcc ggcgtgcaca ccttccccgc cgtgctgcag    540
agcagcggcc tgtacagcct gtccagcgtg gtgacagtgc ccagcagcag cctgggcacc   600
cagacctaca tctgcaacgt gaaccacaag cccagcaaca ccaaggtgga caagagagtg   660
gagcccaaga gctgcgacaa gacccacacc tgcccccct gcccagcccc agagctgctg    720
ggcggaccct ccgtgttcct gttccccccc aagcccaagg acaccctgat gatcagcagg   780
accccccgagg tgacctgcgt ggtggtggac gtgagccacg aggacccaga ggtgaagttc   840
aactgtacg tggacggcgt ggaggtgcac aacgccaaga ccaagcccag agaggagcag   900
tacaacagca cctacagggt ggtgtccgtg ctgaccgtgc tgcaccagga ctggctgaac    960
ggcaaggaat acaagtgcaa ggtctccaac aaggccctgc cagcccccat cgaaaagacc   1020
atcagcaagg ccaagggcca gccacgggag ccccaggtgt acaccctgcc ccctcccgg    1080
gaggagatga ccaagaacca ggtgtccctg acctgtctgg tgaagggctt ctacccagc    1140
gacatcgccg tggagtggga gagcaacggc cagcccgaga caactacaa gaccaccccc   1200
ccagtgctgg acagcgacgg cagcttcttc ctgtacagca agctgaccgt ggacaagtcc   1260
aggtggcagc agggcaacgt gttcagctgc agcgtgatgc acgaggccct gcacaaccac   1320
tacacccaga gagcctgag cctgtcccc ggcaag                              1356

SEQ ID NO: 214           moltype = AA  length = 11
FEATURE                  Location/Qualifiers
REGION                   1..11
                         note = source = /note="Description of Artificial Sequence:
                          Synthetic peptide"
source                   1..11
                         mol_type = protein
                         organism = synthetic construct
SEQUENCE: 214
RASQTISSYL N                                                           11

SEQ ID NO: 215           moltype = AA  length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 215
AASTLQS                                                                7

SEQ ID NO: 216           moltype = AA  length = 9
FEATURE                  Location/Qualifiers
REGION                   1..9
                         note = source = /note="Description of Artificial Sequence:
                          Synthetic peptide"
source                   1..9
                         mol_type = protein
                         organism = synthetic construct
SEQUENCE: 216
QQNYDTLWT                                                              9

SEQ ID NO: 217           moltype = AA  length = 11
FEATURE                  Location/Qualifiers
REGION                   1..11
                         note = source = /note="Description of Artificial Sequence:
                          Synthetic peptide"
source                   1..11
                         mol_type = protein
                         organism = synthetic construct
SEQUENCE: 217
RASQTISSYL N                                                           11

SEQ ID NO: 218           moltype = AA  length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
```

```
SEQUENCE: 218
AASTLQS                                                             7

SEQ ID NO: 219        moltype = AA  length = 9
FEATURE               Location/Qualifiers
REGION                1..9
                      note = source = /note="Description of Artificial Sequence:
                       Synthetic peptide"
source                1..9
                      mol_type = protein
                      organism = synthetic construct
SEQUENCE: 219
QQNYDTLWT                                                           9

SEQ ID NO: 220        moltype = AA  length = 7
FEATURE               Location/Qualifiers
REGION                1..7
                      note = source = /note="Description of Artificial Sequence:
                       Synthetic peptide"
source                1..7
                      mol_type = protein
                      organism = synthetic construct
SEQUENCE: 220
SQTISSY                                                             7

SEQ ID NO: 221        moltype =    length =
SEQUENCE: 221
000

SEQ ID NO: 222        moltype = AA  length = 6
FEATURE               Location/Qualifiers
REGION                1..6
                      note = source = /note="Description of Artificial Sequence:
                       Synthetic peptide"
source                1..6
                      mol_type = protein
                      organism = synthetic construct
SEQUENCE: 222
NYDTLW                                                              6

SEQ ID NO: 223        moltype = AA  length = 6
FEATURE               Location/Qualifiers
REGION                1..6
                      note = source = /note="Description of Artificial Sequence:
                       Synthetic peptide"
source                1..6
                      mol_type = protein
                      organism = synthetic construct
SEQUENCE: 223
QTISSY                                                              6

SEQ ID NO: 224        moltype =    length =
SEQUENCE: 224
000

SEQ ID NO: 225        moltype = AA  length = 9
FEATURE               Location/Qualifiers
REGION                1..9
                      note = source = /note="Description of Artificial Sequence:
                       Synthetic peptide"
source                1..9
                      mol_type = protein
                      organism = synthetic construct
SEQUENCE: 225
QQNYDTLWT                                                           9

SEQ ID NO: 226        moltype = AA  length = 107
FEATURE               Location/Qualifiers
REGION                1..107
                      note = source = /note="Description of Artificial Sequence:
                       Synthetic polypeptide"
source                1..107
                      mol_type = protein
                      organism = synthetic construct
SEQUENCE: 226
DIQMTQSPSS LSAAVGDRVT ISCRASQTIS SYLNWYQQKP GEAPKLLIYA ASTLQSGVPS   60
RFGGSGSGTD FTLTISSLQP EDSATYYCQQ NYDTLWTFGQ GTKVEIK                107

SEQ ID NO: 227        moltype = DNA  length = 321
```

```
FEATURE                 Location/Qualifiers
misc_feature            1..321
                        note = source = /note="Description of Artificial Sequence:
                        Synthetic polynucleotide"
source                  1..321
                        mol_type = other DNA
                        organism = synthetic construct
SEQUENCE: 227
gatatccaga tgacccagtc tccatcctcc ctgtctgcag ctgtaggaga cagagtcacc    60
atctcttgcc gggcaagtca gaccattagt agttatttaa attggtatca gcagaaacca   120
ggggaagccc ctaagctcct gatctatgct gcctccacct tgcaaagtgg ggtcccttca   180
aggttcggtg gcagtggatc tgggacagat ttcactctca ccatcagcag tctgcaacct   240
gaagattctg caacttacta ctgtcaacag aattacgata ctttgtggac gttcggccaa   300
gggaccaagg tggaaatcaa a                                             321

SEQ ID NO: 228          moltype = AA  length = 214
FEATURE                 Location/Qualifiers
REGION                  1..214
                        note = source = /note="Description of Artificial Sequence:
                        Synthetic polypeptide"
source                  1..214
                        mol_type = protein
                        organism = synthetic construct
SEQUENCE: 228
DIQMTQSPSS LSAAVGDRVT ISCRASQTIS SYLNWYQQKP GEAPKLLIYA ASTLQSGVPS     60
RPGGSGSGTD FTLTISSLQP EDSATYYCQQ NYDTLWTFGQ GTKVEIKRTV AAPSVFIFPP    120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 229          moltype = DNA  length = 642
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 229
gatatccaga tgacccagtc tccatcctcc ctgtctgcag ctgtaggaga cagagtcacc    60
atctcttgcc gggcaagtca gaccattagt agttatttaa attggtatca gcagaaacca   120
ggggaagccc ctaagctcct gatctatgct gcctccacct tgcaaagtgg ggtcccttca   180
aggttcggtg gcagtggatc tgggacagat ttcactctca ccatcagcag tctgcaacct   240
gaagattctg caacttacta ctgtcaacag aattacgata ctttgtggac gttcggccaa   300
gggaccaagg tggaaatcaa acgtacggtg gccgctccca gcgtgttcat cttccccccc   360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga gaagcataag gtgtacgcct gcgaggtgac ccaccagggc   600
ctgtccagcc ccgtgaccaa gagcttcaac aggggcgagt gc                     642

SEQ ID NO: 230          moltype = AA  length = 10
FEATURE                 Location/Qualifiers
REGION                  1..10
                        note = source = /note="Description of Artificial Sequence:
                        Synthetic peptide"
source                  1..10
                        mol_type = protein
                        organism = synthetic construct
SEQUENCE: 230
GFTFERYGMH                                                          10

SEQ ID NO: 231          moltype = AA  length = 17
FEATURE                 Location/Qualifiers
REGION                  1..17
                        note = source = /note="Description of Artificial Sequence:
                        Synthetic peptide"
source                  1..17
                        mol_type = protein
                        organism = synthetic construct
SEQUENCE: 231
GIWHEGSHKY YADSLRG                                                  17

SEQ ID NO: 232          moltype = AA  length = 13
FEATURE                 Location/Qualifiers
REGION                  1..13
                        note = source = /note="Description of Artificial Sequence:
                        Synthetic peptide"
source                  1..13
                        mol_type = protein
```

```
                        organism = synthetic construct
SEQUENCE: 232
QTNRGRLDDA FDI                                                              13

SEQ ID NO: 233          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 233
RYGMH                                                                       5

SEQ ID NO: 234          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 234
GIWHEGSHKY YADSLRG                                                          17

SEQ ID NO: 235          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 235
QTNRGRLDDA FDI                                                              13

SEQ ID NO: 236          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 236
GFTFERY                                                                     7

SEQ ID NO: 237          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 237
WHEGSH                                                                      6

SEQ ID NO: 238          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 238
QTNRGRLDDA FDI                                                              13

SEQ ID NO: 239          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 239
```

```
GFTFERYG                                                                   8

SEQ ID NO: 240          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 240
IWHEGSHK                                                                   8

SEQ ID NO: 241          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 241
VRQTNRGRLD DAFDI                                                          15

SEQ ID NO: 242          moltype = AA  length = 122
FEATURE                 Location/Qualifiers
REGION                  1..122
                        note = source = /note="Description of Artificial Sequence:
                         Synthetic polypeptide"
source                  1..122
                        mol_type = protein
                        organism = synthetic construct
SEQUENCE: 242
QVQLVESGGG VVQPGRSLRL SCAASGFTFE RYGMHWVRQA PGKGLEWVAG IWHEGSHKYY           60
ADSLRGRFTI SRDNAKNTLD LQLNRLRAED TSVYYCVRQT NRGRLDDAFD IWGQGTMVTV          120
SS                                                                       122

SEQ ID NO: 243          moltype = DNA  length = 366
FEATURE                 Location/Qualifiers
misc_feature            1..366
                        note = source = /note="Description of Artificial Sequence:
                         Synthetic polynucleotide"
source                  1..366
                        mol_type = other DNA
                        organism = synthetic construct
SEQUENCE: 243
caggtgcagc tggttgaatc tggtggcgga gtggtgcagc ctggcagatc tctgagactg           60
tcttgtgccg ccagcggctt caccttcgag agatatggca tgcactgggt ccgacaggcc         120
cctggaaaag gacttgaatg ggtggccgga atctggcacg aaggcagcca caagtactac         180
gccgatagcc tgagaggccg gttcaccatc agcagagaca cgccaagaa caccctggac          240
ctccagctga acagactgag agccgaggat accagcgtgt actactgcgt gcggcagacc         300
aacagaggca gactggacga tgccttcgat atctggggcc aagggacaat ggtcaccgtt         360
agctca                                                                   366

SEQ ID NO: 244          moltype = AA  length = 452
FEATURE                 Location/Qualifiers
REGION                  1..452
                        note = source = /note="Description of Artificial Sequence:
                         Synthetic polypeptide"
source                  1..452
                        mol_type = protein
                        organism = synthetic construct
SEQUENCE: 244
QVQLVESGGG VVQPGRSLRL SCAASGFTFE RYGMHWVRQA PGKGLEWVAG IWHEGSHKYY           60
ADSLRGRFTI SRDNAKNTLD LQLNRLRAED TSVYYCVRQT NRGRLDDAFD IWGQGTMVTV          120
SSASTKGPSV FPLAPSSKST SGGTAALGCL VKDYFPEPVT VSWNSGALTS GVHTFPAVLQ          180
SSGLYSLSSV VTVPSSSLGT QTYICNVNHK PSNTKVDKRV EPKSCDKTHT CPPCPAPELL          240
GGPSVFLFPP KPKDTLMISR TPEVTCVVVD VSHEDPEVKF NWYVDGVEVH NAKTKPREEQ          300
YNSTYRVVSV LTVLHQDWLN GKEYKCKVSN KALPAPIEKT ISKAKGQPRE PQVYTLPPSR          360
EEMTKNQVSL TCLVKGFYPS DIAVEWESNG QPENNYKTTP PVLDSDGSFF LYSKLTVDKS          420
RWQQGNVFSC SVMHEALHNH YTQKSLSLSP GK                                       452

SEQ ID NO: 245          moltype = DNA  length = 1356
FEATURE                 Location/Qualifiers
misc_feature            1..1356
                        note = source = /note="Description of Artificial Sequence:
                         Synthetic polynucleotide"
source                  1..1356
                        mol_type = other DNA
```

```
                        organism = synthetic construct
SEQUENCE: 245
caggtgcagc tggttgaatc tggtggcgga gtggtgcagc ctggcagatc tctgagactg    60
tcttgtgccg ccagcggctt caccttcgag agatatggca tgcactgggt ccgacaggcc   120
cctggaaaag gacttgaatg ggtggccgga atctggccac aaggcagcca caagtactac   180
gccgatagcc tgagaggccg gttcaccatc agcagagaca cgccaagaa caccctggac    240
ctccagctga acagactgag agccgaggat accagcgtgt actactgcgt gcggcagacc   300
aacagaggca gactggacga tgccttcgat atctggggcc aagggacaat ggtcaccgtt   360
agctcagcta gcaccaaggg ccccagcgtg ttccccctgg ccccagcag caagagcacc    420
agcggcggca cagccgccct gggctgcctc gtgaaggact acttcccga gcccgtgacc    480
gtgtcctgga acagcggagc cctgacctcc ggcgtgcaca ccttcccgc cgtgctgcag    540
agcagcggc tgtacagcct gtccagcgtg gtgacagtgc ccagcagcag cctgggcacc    600
cagacctaca tctgcaacgt gaaccacaag cccagcaaca ccaaggtgga caagagagtg   660
gagcccaaga gctgcgacaa gacccacacc tgcccccct gcccagcccc agagctgctg    720
ggcggaccct ccgtgttcct gttccccccc aagcccaagg acaccctgat gatcagcagg   780
acccccgagg tgacctgcgt ggtggtggac gtgagccacg aggacccaga ggtgaagttc    840
aactggtacg tggacggcgt ggaggtgcac aacgccaaga ccaagcccag agaggagcag   900
tacaacagca cctacagggt ggtgtccgtg ctgaccgtgc tgcaccagga ctggctgaac   960
ggcaaggaat acaagtgcaa ggtctccaac aaggccctgc cagcccccat cgaaaagacc   1020
atcagcaagg ccaagggcca gccacgggag cccaggtgt acaccctgcc cccctccgg     1080
gaggagatga ccaagaacca ggtgtccctg acctgtctgg tgaagggctt ctaccccagc   1140
gacatcgccg tggagtggga gagcaacggc cagcccgaca acaactacaa gaccacccc    1200
ccagtgctgg acagcgacgg cagcttcttc ctgtacagca agctgaccgt ggacaagtcc   1260
aggtggcagc agggcaacgt gttcagctgc agcgtgatgc acgaggccct gcacaaccac   1320
tacacccaga gagcctgag cctgtccccc ggcaag                              1356

SEQ ID NO: 246         moltype = AA  length = 11
FEATURE                Location/Qualifiers
REGION                 1..11
                       note = source = /note="Description of Artificial Sequence:
                         Synthetic peptide"
source                 1..11
                       mol_type = protein
                       organism = synthetic construct
SEQUENCE: 246
RASQTISSYL N                                                          11

SEQ ID NO: 247         moltype = AA  length = 7
FEATURE                Location/Qualifiers
REGION                 1..7
                       note = source = /note="Description of Artificial Sequence:
                         Synthetic peptide"
source                 1..7
                       mol_type = protein
                       organism = synthetic construct
SEQUENCE: 247
AASTLQS                                                               7

SEQ ID NO: 248         moltype = AA  length = 9
FEATURE                Location/Qualifiers
REGION                 1..9
                       note = source = /note="Description of Artificial Sequence:
                         Synthetic peptide"
source                 1..9
                       mol_type = protein
                       organism = synthetic construct
SEQUENCE: 248
QQNYDTLWT                                                             9

SEQ ID NO: 249         moltype = AA  length = 11
FEATURE                Location/Qualifiers
REGION                 1..11
                       note = source = /note="Description of Artificial Sequence:
                         Synthetic peptide"
source                 1..11
                       mol_type = protein
                       organism = synthetic construct
SEQUENCE: 249
RASQTISSYL N                                                          11

SEQ ID NO: 250         moltype = AA  length = 7
FEATURE                Location/Qualifiers
REGION                 1..7
                       note = source = /note="Description of Artificial Sequence:
                         Synthetic peptide"
source                 1..7
                       mol_type = protein
                       organism = synthetic construct
SEQUENCE: 250
```

```
AASTLQS                                                                        7

SEQ ID NO: 251          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 251
QQNYDTLWT                                                                      9

SEQ ID NO: 252          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 252
SQTISSY                                                                        7

SEQ ID NO: 253          moltype =   length =
SEQUENCE: 253
000

SEQ ID NO: 254          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 254
NYDTLW                                                                         6

SEQ ID NO: 255          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 255
QTISSY                                                                         6

SEQ ID NO: 256          moltype =   length =
SEQUENCE: 256
000

SEQ ID NO: 257          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 257
QQNYDTLWT                                                                      9

SEQ ID NO: 258          moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 258
DIQMTQSPSS LSAAVGDRVT ISCRASQTIS SYLNWYQQKP GEAPKLLIYA ASTLQSGVPS               60
RFGGSGSGTD FTLTISSLQP EDSATYYCQQ NYDTLWTFGQ GTKVEIK                             107

SEQ ID NO: 259          moltype = DNA  length = 321
FEATURE                 Location/Qualifiers
```

```
misc_feature            1..321
                        note = source = /note="Description of Artificial Sequence:
                        Synthetic polynucleotide"
source                  1..321
                        mol_type = other DNA
                        organism = synthetic construct
SEQUENCE: 259
gatatccaga tgacccagtc tccatcctcc ctgtctgcag ctgtaggaga cagagtcacc     60
atctcttgcc gggcaagtca gaccattagt agttatttaa attggtatca gcagaaacca    120
ggggaagccc ctaagctcct gatctatgct gcctccacct tgcaaagtgg ggtcccttca    180
aggttcggtg gcagtggatc tgggacagat ttcactctca ccatcagcag tctgcaacct    240
gaagattctg caacttacta ctgtcaacag aattacgata ctttgtggac gttcggccaa    300
gggaccaagg tggaaatcaa a                                              321

SEQ ID NO: 260          moltype = AA  length = 214
FEATURE                 Location/Qualifiers
REGION                  1..214
                        note = source = /note="Description of Artificial Sequence:
                        Synthetic polypeptide"
source                  1..214
                        mol_type = protein
                        organism = synthetic construct
SEQUENCE: 260
DIQMTQSPSS LSAAVGDRVT ISCRASQTIS SYLNWYQQKP GEAPKLLIYA ASTLQSGVPS     60
RFGGSGSGTD FTLTISSLQP EDSATYYCQQ NYDTLWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 261          moltype = DNA  length = 642
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 261
gatatccaga tgacccagtc tccatcctcc ctgtctgcag ctgtaggaga cagagtcacc     60
atctcttgcc gggcaagtca gaccattagt agttatttaa attggtatca gcagaaacca    120
ggggaagccc ctaagctcct gatctatgct gcctccacct tgcaaagtgg ggtcccttca    180
aggttcggtg gcagtggatc tgggacagat ttcactctca ccatcagcag tctgcaacct    240
gaagattctg caacttacta ctgtcaacag aattacgata ctttgtggac gttcggccaa    300
gggaccaagg tggaaatcaa acgtacggtg gccgctccca gcgtcttcat cttccccccc    360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga aagcataag gtgtacgcct gcgaggtgac ccaccagggc    600
ctgtccagcc ccgtgaccaa gagcttcaac aggggcgagt gc                       642

SEQ ID NO: 262          moltype = AA  length = 10
FEATURE                 Location/Qualifiers
REGION                  1..10
                        note = source = /note="Description of Artificial Sequence:
                        Synthetic peptide"
source                  1..10
                        mol_type = protein
                        organism = synthetic construct
SEQUENCE: 262
GFIFTDYYMT                                                            10

SEQ ID NO: 263          moltype = AA  length = 17
FEATURE                 Location/Qualifiers
REGION                  1..17
                        note = source = /note="Description of Artificial Sequence:
                        Synthetic peptide"
source                  1..17
                        mol_type = protein
                        organism = synthetic construct
SEQUENCE: 263
FITSGGETTY YADSVKG                                                    17

SEQ ID NO: 264          moltype = AA  length = 20
FEATURE                 Location/Qualifiers
REGION                  1..20
                        note = source = /note="Description of Artificial Sequence:
                        Synthetic peptide"
source                  1..20
                        mol_type = protein
                        organism = synthetic construct
```

```
SEQUENCE: 264
AHFDGYQYDT RGDFTYYFDN                                                    20

SEQ ID NO: 265          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 265
DYYMT                                                                     5

SEQ ID NO: 266          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 266
FITSGGETTY YADSVKG                                                       17

SEQ ID NO: 267          moltype = AA  length = 20
FEATURE                 Location/Qualifiers
REGION                  1..20
                        note = source = /note="Description of Artificial Sequence:
                         Synthetic peptide"
source                  1..20
                        mol_type = protein
                        organism = synthetic construct
SEQUENCE: 267
AHFDGYQYDT RGDFTYYFDN                                                    20

SEQ ID NO: 268          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 268
GFIFTDY                                                                   7

SEQ ID NO: 269          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 269
TSGGET                                                                    6

SEQ ID NO: 270          moltype = AA  length = 20
FEATURE                 Location/Qualifiers
REGION                  1..20
                        note = source = /note="Description of Artificial Sequence:
                         Synthetic peptide"
source                  1..20
                        mol_type = protein
                        organism = synthetic construct
SEQUENCE: 270
AHFDGYQYDT RGDFTYYFDN                                                    20

SEQ ID NO: 271          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 271
GFIFTDYY                                                                  8
```

```
SEQ ID NO: 272           moltype = AA  length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 272
ITSGGETT                                                                 8

SEQ ID NO: 273           moltype = AA  length = 22
FEATURE                  Location/Qualifiers
REGION                   1..22
                         note = source = /note="Description of Artificial Sequence:
                          Synthetic peptide"
source                   1..22
                         mol_type = protein
                         organism = synthetic construct
SEQUENCE: 273
VRAHFDGYQY DTRGDFTYYF DN                                                22

SEQ ID NO: 274           moltype = AA  length = 129
FEATURE                  Location/Qualifiers
REGION                   1..129
                         note = source = /note="Description of Artificial Sequence:
                          Synthetic polypeptide"
source                   1..129
                         mol_type = protein
                         organism = synthetic construct
SEQUENCE: 274
QVQLQESGGR LVRPGGSLRL SCAASGFIFT DYYMTWIRQA PGKGPEWIAF ITSGGETTYY        60
ADSVKGRFTI SRDNAKKSLF LQMYSLRADD TAVYYCVRAH FDGYQYDTRG DFTYYFDNWG       120
LGTLVSVSS                                                              129

SEQ ID NO: 275           moltype = DNA  length = 387
FEATURE                  Location/Qualifiers
misc_feature             1..387
                         note = source = /note="Description of Artificial Sequence:
                          Synthetic polynucleotide"
source                   1..387
                         mol_type = other DNA
                         organism = synthetic construct
SEQUENCE: 275
caggtgcagc tgcaggagtc gggggggacgc ttggtcaggc ctggagggtc cctgagactc       60
tcctgtgcag cctccggatt catcttcact gactactaca tgacctggat ccgccaggct      120
ccagggaagg ggccggagtg gattgcattt atcacaagtg ggggcgagac cacatactac      180
gcagactctg tgaagggccg cttcaccatt tccaggaca acgccaagaa gtcactcttt       240
ctgcaaatgt acagcctgag agccgacgac acggccgtgt attattgtgt gagagcccac      300
tttgatggtt atcagtatga tactcgtggt gacttcactt attactttga caactgggc       360
ctgggaaccc tggtcagcgt ctcctca                                          387

SEQ ID NO: 276           moltype = AA  length = 459
FEATURE                  Location/Qualifiers
REGION                   1..459
                         note = source = /note="Description of Artificial Sequence:
                          Synthetic polypeptide"
source                   1..459
                         mol_type = protein
                         organism = synthetic construct
SEQUENCE: 276
QVQLQESGGR LVRPGGSLRL SCAASGFIFT DYYMTWIRQA PGKGPEWIAF ITSGGETTYY        60
ADSVKGRFTI SRDNAKKSLF LQMYSLRADD TAVYYCVRAH FDGYQYDTRG DFTYYFDNWG       120
LGTLVSVSSA STKGPSVFPL APSSKSTSGG TAALGCLVKD YFPEPVTVSW NSGALTSGVH       180
TFPAVLQSSG LYSLSSVVTV PSSSLGTQTY ICNVNHKPSN TKVDKRVEPK SCDKTHTCPP       240
CPAPELLGGP SVFLFPPKPK DTLMISRTPE VTCVVVDVSH EDPEVKFNWY VDGVEVHNAK       300
TKPREEQYNS TYRVVSVLTV LHQDWLNGKE YKCKVSNKAL PAPIEKTISK AKGQPREPQV       360
YTLPPSREEM TKNQVSLTCL VKGFYPSDIA VEWESNGQPE NNYKTTPPVL DSDGSFFLYS       420
KLTVDKSRWQ QGNVFSCSVM HEALHNHYTQ KSLSLSPGK                             459

SEQ ID NO: 277           moltype = DNA  length = 1377
FEATURE                  Location/Qualifiers
misc_feature             1..1377
                         note = source = /note="Description of Artificial Sequence:
                          Synthetic polynucleotide"
source                   1..1377
                         mol_type = other DNA
                         organism = synthetic construct
```

```
SEQUENCE: 277
caggtgcagc tgcaggagtc ggggggacgc ttggtcaggc ctggagggtc cctgagactc    60
tcctgtgcag cctccggatt catcttcact gactactaca tgacctggat ccgccaggct   120
ccagggaagg ggccggagtg gattgcattt atcacaagtg ggggcgagac cacatactac   180
gcagactctg tgaagggccg cttcaccatt tccaggaca acgccaagaa gtcactcttt    240
ctgcaaatgt acagcctgag agccgacgac acggccgtgt attattgtgt gagagcccac   300
tttgatggtt atcagtatga tactcgtggt gacttcactt attactttga caactggggc   360
ctgggaaccc tggtcagcgt ctcctcagct agcaccaagg gcccagcgt gttccccctg    420
gcccccagca gcaagagcac cagcggcggc acagccgccc tgggctgcct ggtgaaggac   480
tacttccccg agcccgtgac cgtgtcctgg aacagcggag ccctgacctc cggcgtgcac   540
accttccccg ccgtgctgca gagcagcggc ctgtacagcc tgtccagcgt ggtgacagtg   600
cccagcagca gcctgggcac ccagacctac atctgcaacg tgaaccacaa gcccagcaac   660
accaaggtgg acaagagagt ggagcccaag agctgcgaca gacccacac ctgccccccc    720
tgcccagccc cagagctgct gggcggaccc tccgtgttcc tgttccccc caagcccaag   780
gacacccctg atgatcagcag gacccccgag gtgacctgc tggtggtgga cgtgagccac    840
gaggacccag aggtgaagtt caactggtac gtggacggcg tggaggtgca aacgccaag    900
accaagccca gagaggagca gtacaacagc acctacaggg tggtgtccgt gctgaccgtg   960
ctgcaccagg actggctgaa cggcaaggaa tacaagtgca aggtctccaa caagccccag  1020
ccagccccca tcgaaaagac catcagcaag gccaagggcc agccacggga gccccaggtg  1080
tacaccctgc ccccctcccg ggaggagatg accaagaacc aggtgtccct gacctgtctg  1140
gtgaagggct tctaccccag cgacatcgcc gtggagtggg agagcaacgg ccagcccgag  1200
aacaactaca agaccacccc cccagtgctg gacagcgacg gcagcttctt cctgtacagc  1260
aagctgaccg tggacaagtc caggtggcag cagggcaacg tgttcagctg cagcgtgatg  1320
cacgaggccc tgcacaacca ctacacccag aagagcctga gcctgtcccc cggcaag    1377

SEQ ID NO: 278          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 278
RASQSVSSSL A                                                          11

SEQ ID NO: 279          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 279
GASTRAT                                                                7

SEQ ID NO: 280          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 280
HQYINWPPGD T                                                          11

SEQ ID NO: 281          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 281
RASQSVSSSL A                                                          11

SEQ ID NO: 282          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 282
GASTRAT                                                                7
```

```
SEQ ID NO: 283              moltype = AA   length = 11
FEATURE                     Location/Qualifiers
REGION                      1..11
                            note = source = /note="Description of Artificial Sequence:
                             Synthetic peptide"
source                      1..11
                            mol_type = protein
                            organism = synthetic construct
SEQUENCE: 283
HQYINWPPGD T                                                                11

SEQ ID NO: 284              moltype = AA   length = 7
FEATURE                     Location/Qualifiers
REGION                      1..7
                            note = source = /note="Description of Artificial Sequence:
                             Synthetic peptide"
source                      1..7
                            mol_type = protein
                            organism = synthetic construct
SEQUENCE: 284
SQSVSSS                                                                     7

SEQ ID NO: 285              moltype =     length =
SEQUENCE: 285
000

SEQ ID NO: 286              moltype = AA   length = 8
FEATURE                     Location/Qualifiers
REGION                      1..8
                            note = source = /note="Description of Artificial Sequence:
                             Synthetic peptide"
source                      1..8
                            mol_type = protein
                            organism = synthetic construct
SEQUENCE: 286
YINWPPGD                                                                    8

SEQ ID NO: 287              moltype = AA   length = 6
FEATURE                     Location/Qualifiers
REGION                      1..6
                            note = source = /note="Description of Artificial Sequence:
                             Synthetic peptide"
source                      1..6
                            mol_type = protein
                            organism = synthetic construct
SEQUENCE: 287
QSVSSS                                                                      6

SEQ ID NO: 288              moltype =     length =
SEQUENCE: 288
000

SEQ ID NO: 289              moltype = AA   length = 11
FEATURE                     Location/Qualifiers
REGION                      1..11
                            note = source = /note="Description of Artificial Sequence:
                             Synthetic peptide"
source                      1..11
                            mol_type = protein
                            organism = synthetic construct
SEQUENCE: 289
HQYINWPPGD T                                                                11

SEQ ID NO: 290              moltype = AA   length = 109
FEATURE                     Location/Qualifiers
REGION                      1..109
                            note = source = /note="Description of Artificial Sequence:
                             Synthetic polypeptide"
source                      1..109
                            mol_type = protein
                            organism = synthetic construct
SEQUENCE: 290
EIVMTQSPAT LSVSPGERVT LSCRASQSVS SSLAWYQQKP GRAPRLLIYG ASTRATGVPA            60
RFSGGGSGTD FTLTISSLQS EDFAVYYCHQ YINWPPGDTF GQGTRLDIK                       109

SEQ ID NO: 291              moltype = DNA   length = 327
FEATURE                     Location/Qualifiers
misc_feature                1..327
```

```
                        note = source = /note="Description of Artificial Sequence:
                            Synthetic polynucleotide"
source                  1..327
                        mol_type = other DNA
                        organism = synthetic construct
SEQUENCE: 291
gaaatagtga tgactcagtc tccagccacc ctgtctgtgt ctccagggga aagagtcacc    60
ctctcctgca gggccagtca gagtgttagt agcagcttag cctggtacca gcagaaacct   120
ggccgggctc ccaggctcct catttatgga gcatccacca gggccactgg tgtcccagcc   180
aggttcagtg gcggtgggtc tgggacagac ttcactctca ccatcagcag cctgcagtct   240
gaagattttg cagtttatta ctgtcaccag tatattaatt ggcctccggg ggacactttt   300
ggccagggga cgaggctgga tatcaaa                                       327

SEQ ID NO: 292          moltype = AA  length = 216
FEATURE                 Location/Qualifiers
REGION                  1..216
                        note = source = /note="Description of Artificial Sequence:
                            Synthetic polypeptide"
source                  1..216
                        mol_type = protein
                        organism = synthetic construct
SEQUENCE: 292
EIVMTQSPAT LSVSPGERVT LSCRASQSVS SSLAWYQQKP GRAPRLLIYG ASTRATGVPA    60
RFSGGGSGTD FTLTISSLQS EDFAVYYCHQ YINWPPGDTF GQGTRLDIKR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                             216

SEQ ID NO: 293          moltype = DNA  length = 648
FEATURE                 Location/Qualifiers
misc_feature            1..648
                        note = source = /note="Description of Artificial Sequence:
                            Synthetic polynucleotide"
source                  1..648
                        mol_type = other DNA
                        organism = synthetic construct
SEQUENCE: 293
gaaatagtga tgactcagtc tccagccacc ctgtctgtgt ctccagggga aagagtcacc    60
ctctcctgca gggccagtca gagtgttagt agcagcttag cctggtacca gcagaaacct   120
ggccgggctc ccaggctcct catttatgga gcatccacca gggccactgg tgtcccagcc   180
aggttcagtg gcggtgggtc tgggacagac ttcactctca ccatcagcag cctgcagtct   240
gaagattttg cagtttatta ctgtcaccag tatattaatt ggcctccggg ggacactttt   300
ggccagggga cgaggctgga tatcaaacgt acggtggccg ctcccagcgt gttcatcttc   360
cccccatcgg acgagcagct gaagagcggc accgccagcg tggtgtgcct gctgaacaac   420
ttctaccccc gggaggccaa ggtgcagtgg aaggtggaca acgccctgca gagcggcaac   480
agccaggaga gcgtcaccga gcaggacagc aaggactcca cctacagcct gagcagcacc   540
ctgaccctga gcaaggccga ctacgagaag cataaggtgt acgcctgcga ggtgacccac   600
cagggcctgt ccagccccgt gaccaagagc ttcaacaggg gcgagtgc                648

SEQ ID NO: 294          moltype = AA  length = 10
FEATURE                 Location/Qualifiers
REGION                  1..10
                        note = source = /note="Description of Artificial Sequence:
                            Synthetic peptide"
source                  1..10
                        mol_type = protein
                        organism = synthetic construct
SEQUENCE: 294
GFIFTDYYMT                                                           10

SEQ ID NO: 295          moltype = AA  length = 17
FEATURE                 Location/Qualifiers
REGION                  1..17
                        note = source = /note="Description of Artificial Sequence:
                            Synthetic peptide"
source                  1..17
                        mol_type = protein
                        organism = synthetic construct
SEQUENCE: 295
FITSGGETTY YADSVKG                                                   17

SEQ ID NO: 296          moltype = AA  length = 20
FEATURE                 Location/Qualifiers
REGION                  1..20
                        note = source = /note="Description of Artificial Sequence:
                            Synthetic peptide"
source                  1..20
                        mol_type = protein
                        organism = synthetic construct
SEQUENCE: 296
```

AHFDLYQYDT RGDFTYYFDN                                                            20

```
SEQ ID NO: 297          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 297
DYYMT                                                                            5

SEQ ID NO: 298          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 298
FITSGGETTY YADSVKG                                                               17

SEQ ID NO: 299          moltype = AA  length = 20
FEATURE                 Location/Qualifiers
REGION                  1..20
                        note = source = /note="Description of Artificial Sequence:
                         Synthetic peptide"
source                  1..20
                        mol_type = protein
                        organism = synthetic construct
SEQUENCE: 299
AHFDLYQYDT RGDFTYYFDN                                                            20

SEQ ID NO: 300          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 300
GFIFTDY                                                                          7

SEQ ID NO: 301          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 301
TSGGET                                                                           6

SEQ ID NO: 302          moltype = AA  length = 20
FEATURE                 Location/Qualifiers
REGION                  1..20
                        note = source = /note="Description of Artificial Sequence:
                         Synthetic peptide"
source                  1..20
                        mol_type = protein
                        organism = synthetic construct
SEQUENCE: 302
AHFDLYQYDT RGDFTYYFDN                                                            20

SEQ ID NO: 303          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 303
GFIFTDYY                                                                         8
```

| | | |
|---|---|---|
| SEQ ID NO: 304 | moltype = AA  length = 8 | |
| FEATURE | Location/Qualifiers | |
| REGION | 1..8 | |
| | note = source = /note="Description of Artificial Sequence: Synthetic peptide" | |
| source | 1..8 | |
| | mol_type = protein | |
| | organism = synthetic construct | |
| SEQUENCE: 304 | | |
| ITSGGETT | | 8 |
| | | |
| SEQ ID NO: 305 | moltype = AA  length = 22 | |
| FEATURE | Location/Qualifiers | |
| REGION | 1..22 | |
| | note = source = /note="Description of Artificial Sequence: Synthetic peptide" | |
| source | 1..22 | |
| | mol_type = protein | |
| | organism = synthetic construct | |
| SEQUENCE: 305 | | |
| VRAHFDLYQY DTRGDFTYYF DN | | 22 |
| | | |
| SEQ ID NO: 306 | moltype = AA  length = 129 | |
| FEATURE | Location/Qualifiers | |
| REGION | 1..129 | |
| | note = source = /note="Description of Artificial Sequence: Synthetic polypeptide" | |
| source | 1..129 | |
| | mol_type = protein | |
| | organism = synthetic construct | |
| SEQUENCE: 306 | | |

```
QVQLQESGGR LVRPGGSLRL SCAASGFIFT DYYMTWIRQA PGKGPEWIAF ITSGGETTYY    60
ADSVKGRFTI SRDNAKKSLF LQMYSLRADD TAVYYCVRAH FDLYQYDTRG DFTYYFDNWG   120
LGTLVSVSS                                                          129
```

| | | |
|---|---|---|
| SEQ ID NO: 307 | moltype = DNA  length = 387 | |
| FEATURE | Location/Qualifiers | |
| misc_feature | 1..387 | |
| | note = source = /note="Description of Artificial Sequence: Synthetic polynucleotide" | |
| source | 1..387 | |
| | mol_type = other DNA | |
| | organism = synthetic construct | |
| SEQUENCE: 307 | | |

```
caggttcagc tgcaagaatc tggcggcaga ctcgttagac ctggcggctc tctgagactg    60
tcttgtgccg ccagcggctt catcttcacc gactactaca tgacctggat cagacaggcc   120
cctggcaagg gacctgagtg gatcgccttt atcacaagcg gcggagagac aacctactac   180
gccgatagcg tgaagggcag attcaccatc agccgggaca cgccaagaa gtccctgttc    240
ctccagatgt acagcctgag agccgacgat accgccgtgt attattgcgt gcgggcccac   300
tttgacctgt accagtacga taccagaggc gatttcacct actacttcga caactgggc    360
ctgggaaccc tggtgtctgt ctcttct                                      387
```

| | | |
|---|---|---|
| SEQ ID NO: 308 | moltype = AA  length = 459 | |
| FEATURE | Location/Qualifiers | |
| REGION | 1..459 | |
| | note = source = /note="Description of Artificial Sequence: Synthetic polypeptide" | |
| source | 1..459 | |
| | mol_type = protein | |
| | organism = synthetic construct | |
| SEQUENCE: 308 | | |

```
QVQLQESGGR LVRPGGSLRL SCAASGFIFT DYYMTWIRQA PGKGPEWIAF ITSGGETTYY    60
ADSVKGRFTI SRDNAKKSLF LQMYSLRADD TAVYYCVRAH FDLYQYDTRG DFTYYFDNWG   120
LGTLVSVSSA STKGPSVFPL APSSKSTSGG TAALGCLVKD YFPEPVTVSW NSGALTSGVH   180
TFPAVLQSSG LYSLSSVVTV PSSSLGTQTY ICNVNHKPSN TKVDKRVEPK SCDKTHTCPP   240
CPAPELLGGP SVFLFPPKPK DTLMISRTPE VTCVVVDVSH EDPEVKFNWY VDGVEVHNAK   300
TKPREEQYNS TYRVVSVLTV LHQDWLNGKE YKCKVSNKAL PAPIEKTISK AKGQPREPQV   360
YTLPPSREEM TKNQVSLTCL VKGFYPSDIA VEWESNGQPE NNYKTTPPVL DSDGSFFLYS   420
KLTVDKSRWQ QGNVFSCSVM HEALHNHYTQ KSLSLSPGK                         459
```

| | | |
|---|---|---|
| SEQ ID NO: 309 | moltype = DNA  length = 1377 | |
| FEATURE | Location/Qualifiers | |
| misc_feature | 1..1377 | |
| | note = source = /note="Description of Artificial Sequence: Synthetic polynucleotide" | |
| source | 1..1377 | |
| | mol_type = other DNA | |
| | organism = synthetic construct | |
| SEQUENCE: 309 | | |

```
caggttcagc tgcaagaatc tggcggcaga ctcgttagac ctggcggctc tctgagactg   60
tcttgtgccg ccagcggctt catcttcacc gactactaca tgacctggat cagacaggcc  120
cctggcaagg gacctgagtg gatcgccttt atcacaagcg gcggagagac aacctactac  180
gccgatagcg tgaagggcag attcaccatc agccgggaca cgccaagaa gtccctgttc  240
ctccagatgt acagcctgag agccgacgat accgccgtgt attattgcgt gcgggcccac  300
tttgacctgt accagtacga taccagaggc gatttcacct actacttcga caactggggc  360
ctgggaaccc tggtgtctgt ctcttctgct agcaccaagg gcccagcgt gttccccctg  420
gcccccagca gcaagagcac cagcggcggc acagccgccc tgggctgcct ggtgaaggac  480
tacttcccccg agcccgtgac cgtgtcctgg aacagcggag ccctgacctc cggcgtgcac  540
accttccccg ccgtgctgca gagcagcggg ctgtacagcc tgtccagcgt ggtgacagtg  600
cccagcagca gcctgggcac ccagacctac atctgcaacg tgaaccacaa gcccagcaac  660
accaaggtgg acaagagagt ggagcccaag agctgcgaca gaccacac atgcccccccc  720
tgcccggcgc cagagctgct gggcggaccc tccgtgttcc tgttcccccc caagcccaag  780
gacacccctga tgatcagcag gacccccgag gtgacctgcg tggtggtgga cgtgagccac  840
gaggacccag aggtgaagtt caactggtac gtggacggcg tggaggtgca caacgccaag  900
accaagccca gagaggagca gtacaacagc acctacaggg tggtgtccgt gctgaccgtg  960
ctgcaccagg actggctgaa cggcaaggaa tacaagtgca aggtctccaa caaggccctg 1020
ccagccccca tcgaaaagac catcagcaag gccaagggca gccacggga gccccaggtg 1080
tacaccctgc cccctcccg ggaggagatg accaagaacc aggtgtccct gacctgtctg 1140
gtgaagggct tctaccccag cgacatcgcc gtggagtggg agagcaacgg ccagcccgag 1200
aacaactaca gaccaccccc cccagtgctg gacagcgacg gcagcttctt cctgtacagc 1260
aagctgaccg tggacaagtc caggtggcag caggggaaca gttcagctg cagcgtgatg 1320
cacgaggccc tgcacaacca ctacacccag aagagcctga gcttaagccc cggcaag    1377

SEQ ID NO: 310         moltype = AA  length = 11
FEATURE                Location/Qualifiers
REGION                 1..11
                       note = source = /note="Description of Artificial Sequence:
                       Synthetic peptide"
source                 1..11
                       mol_type = protein
                       organism = synthetic construct
SEQUENCE: 310
RASQSVSSSL A                                                        11

SEQ ID NO: 311         moltype = AA  length = 7
FEATURE                Location/Qualifiers
REGION                 1..7
                       note = source = /note="Description of Artificial Sequence:
                       Synthetic peptide"
source                 1..7
                       mol_type = protein
                       organism = synthetic construct
SEQUENCE: 311
GASTRAT                                                             7

SEQ ID NO: 312         moltype = AA  length = 11
FEATURE                Location/Qualifiers
REGION                 1..11
                       note = source = /note="Description of Artificial Sequence:
                       Synthetic peptide"
source                 1..11
                       mol_type = protein
                       organism = synthetic construct
SEQUENCE: 312
HQYINWPPGD T                                                        11

SEQ ID NO: 313         moltype = AA  length = 11
FEATURE                Location/Qualifiers
REGION                 1..11
                       note = source = /note="Description of Artificial Sequence:
                       Synthetic peptide"
source                 1..11
                       mol_type = protein
                       organism = synthetic construct
SEQUENCE: 313
RASQSVSSSL A                                                        11

SEQ ID NO: 314         moltype = AA  length = 7
FEATURE                Location/Qualifiers
REGION                 1..7
                       note = source = /note="Description of Artificial Sequence:
                       Synthetic peptide"
source                 1..7
                       mol_type = protein
                       organism = synthetic construct
SEQUENCE: 314
GASTRAT                                                             7
```

| | | |
|---|---|---|
| SEQ ID NO: 315<br>FEATURE<br>REGION<br><br>source<br><br>SEQUENCE: 315<br>HQYINWPPGD T | moltype = AA length = 11<br>Location/Qualifiers<br>1..11<br>note = source = /note="Description of Artificial Sequence:<br>Synthetic peptide"<br>1..11<br>mol_type = protein<br>organism = synthetic construct<br><br> | <br><br><br><br><br><br><br><br><br>11 |
| SEQ ID NO: 316<br>FEATURE<br>REGION<br><br>source<br><br>SEQUENCE: 316<br>SQSVSSS | moltype = AA length = 7<br>Location/Qualifiers<br>1..7<br>note = source = /note="Description of Artificial Sequence:<br>Synthetic peptide"<br>1..7<br>mol_type = protein<br>organism = synthetic construct<br><br> | <br><br><br><br><br><br><br><br><br>7 |
| SEQ ID NO: 317<br>SEQUENCE: 317<br>000 | moltype = length =<br> | |
| SEQ ID NO: 318<br>FEATURE<br>REGION<br><br>source<br><br>SEQUENCE: 318<br>YINWPPGD | moltype = AA length = 8<br>Location/Qualifiers<br>1..8<br>note = source = /note="Description of Artificial Sequence:<br>Synthetic peptide"<br>1..8<br>mol_type = protein<br>organism = synthetic construct<br><br> | <br><br><br><br><br><br><br><br><br>8 |
| SEQ ID NO: 319<br>FEATURE<br>REGION<br><br>source<br><br>SEQUENCE: 319<br>QSVSSS | moltype = AA length = 6<br>Location/Qualifiers<br>1..6<br>note = source = /note="Description of Artificial Sequence:<br>Synthetic peptide"<br>1..6<br>mol_type = protein<br>organism = synthetic construct<br><br> | <br><br><br><br><br><br><br><br><br>6 |
| SEQ ID NO: 320<br>SEQUENCE: 320<br>000 | moltype = length =<br> | |
| SEQ ID NO: 321<br>FEATURE<br>REGION<br><br>source<br><br>SEQUENCE: 321<br>HQYINWPPGD T | moltype = AA length = 11<br>Location/Qualifiers<br>1..11<br>note = source = /note="Description of Artificial Sequence:<br>Synthetic peptide"<br>1..11<br>mol_type = protein<br>organism = synthetic construct<br><br> | <br><br><br><br><br><br><br><br><br>11 |
| SEQ ID NO: 322<br>FEATURE<br>REGION<br><br>source<br><br>SEQUENCE: 322<br>EIVMTQSPAT LSVSPGERVT LSCRASQSVS SSLAWYQQKP GRAPRLLIYG ASTRATGVPA<br>RFSGGGSGTD FTLTISSLQS EDFAVYYCHQ YINWPPGDTF GQGTRLDIK | moltype = AA length = 109<br>Location/Qualifiers<br>1..109<br>note = source = /note="Description of Artificial Sequence:<br>Synthetic polypeptide"<br>1..109<br>mol_type = protein<br>organism = synthetic construct<br><br><br> | <br><br><br><br><br><br><br><br><br>60<br>109 |
| SEQ ID NO: 323<br>FEATURE<br>misc_feature<br> | moltype = DNA length = 327<br>Location/Qualifiers<br>1..327<br>note = source = /note="Description of Artificial Sequence: | |

```
                          Synthetic polynucleotide"
source                    1..327
                          mol_type = other DNA
                          organism = synthetic construct
SEQUENCE: 323
gaaatagtga tgactcagtc tccagccacc ctgtctgtgt ctccagggga aagagtcacc    60
ctctcctgca gggccagtca gagtgttagt agcagcttag cctggtacca gcagaaacct   120
ggccgggctc ccaggctcct catttatgga gcatccacca gggccactgg tgtcccagcc   180
aggttcagtg gcggtgggtc tgggacagac ttcactctca ccatcagcag cctgcagtct   240
gaagattttg cagtttatta ctgtcaccag tatattaatt ggcctccggg ggacactttt   300
ggccagggga cgaggctgga tatcaaa                                       327

SEQ ID NO: 324            moltype = AA  length = 216
FEATURE                   Location/Qualifiers
REGION                    1..216
                          note = source = /note="Description of Artificial Sequence:
                          Synthetic polypeptide"
source                    1..216
                          mol_type = protein
                          organism = synthetic construct
SEQUENCE: 324
EIVMTQSPAT LSVSPGERVT LSCRASQSVS SSLAWYQQKP GRAPRLLIYG ASTRATGVPA    60
RFSGGGSGTD FTLTISSLQS EDFAVYYCHQ YINWPPGDTF GQGTRLDIKR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                             216

SEQ ID NO: 325            moltype = DNA  length = 648
FEATURE                   Location/Qualifiers
misc_feature              1..648
                          note = source = /note="Description of Artificial Sequence:
                          Synthetic polynucleotide"
source                    1..648
                          mol_type = other DNA
                          organism = synthetic construct
SEQUENCE: 325
gaaatagtga tgactcagtc tccagccacc ctgtctgtgt ctccagggga aagagtcacc    60
ctctcctgca gggccagtca gagtgttagt agcagcttag cctggtacca gcagaaacct   120
ggccgggctc ccaggctcct catttatgga gcatccacca gggccactgg tgtcccagcc   180
aggttcagtg gcggtgggtc tgggacagac ttcactctca ccatcagcag cctgcagtct   240
gaagattttg cagtttatta ctgtcaccag tatattaatt ggcctccggg ggacactttt   300
ggccagggga cgaggctgga tatcaaacgt acggtggccg ctcccagcgt gttcatcttc   360
ccccccagcg acgagcagct gaagagcggc accgccagct ggtgtgtcct gctgaacaac   420
ttctacccccc gggaggccaa ggtgcagtgg aaggtggaca acgccctgca gagcggcaac   480
agccaggaga gcgtcaccga gcaggacagc aaggactcca cctacagcct gagcagcacc   540
ctgaccctga gcaaggccga ctacgagaag cataaggtgt acgcctgcga ggtgacccac   600
cagggcctgt ccagccccgt gaccaagagc ttcaacaggg gcgagtgc                648

SEQ ID NO: 326            moltype = AA  length = 10
FEATURE                   Location/Qualifiers
REGION                    1..10
                          note = source = /note="Description of Artificial Sequence:
                          Synthetic peptide"
source                    1..10
                          mol_type = protein
                          organism = synthetic construct
SEQUENCE: 326
GFIFTDYYMT                                                           10

SEQ ID NO: 327            moltype = AA  length = 17
FEATURE                   Location/Qualifiers
REGION                    1..17
                          note = source = /note="Description of Artificial Sequence:
                          Synthetic peptide"
source                    1..17
                          mol_type = protein
                          organism = synthetic construct
SEQUENCE: 327
FITSGGETTY YADSVKG                                                   17

SEQ ID NO: 328            moltype = AA  length = 20
FEATURE                   Location/Qualifiers
REGION                    1..20
                          note = source = /note="Description of Artificial Sequence:
                          Synthetic peptide"
source                    1..20
                          mol_type = protein
                          organism = synthetic construct
SEQUENCE: 328
AHFDIYQYDT RGDFTYYFDN                                                20
```

```
SEQ ID NO: 329          moltype = AA   length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 329
DYYMT                                                                    5

SEQ ID NO: 330          moltype = AA   length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 330
FITSGGETTY YADSVKG                                                      17

SEQ ID NO: 331          moltype = AA   length = 20
FEATURE                 Location/Qualifiers
REGION                  1..20
                        note = source = /note="Description of Artificial Sequence:
                         Synthetic peptide"
source                  1..20
                        mol_type = protein
                        organism = synthetic construct
SEQUENCE: 331
AHFDIYQYDT RGDFTYYFDN                                                   20

SEQ ID NO: 332          moltype = AA   length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 332
GFIFTDY                                                                  7

SEQ ID NO: 333          moltype = AA   length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 333
TSGGET                                                                   6

SEQ ID NO: 334          moltype = AA   length = 20
FEATURE                 Location/Qualifiers
REGION                  1..20
                        note = source = /note="Description of Artificial Sequence:
                         Synthetic peptide"
source                  1..20
                        mol_type = protein
                        organism = synthetic construct
SEQUENCE: 334
AHFDIYQYDT RGDFTYYFDN                                                   20

SEQ ID NO: 335          moltype = AA   length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 335
GFIFTDYY                                                                 8

SEQ ID NO: 336          moltype = AA   length = 8
```

```
FEATURE              Location/Qualifiers
REGION               1..8
                     note = source = /note="Description of Artificial Sequence:
                        Synthetic peptide"
source               1..8
                     mol_type = protein
                     organism = synthetic construct
SEQUENCE: 336
ITSGGETT                                                                    8

SEQ ID NO: 337       moltype = AA  length = 22
FEATURE              Location/Qualifiers
REGION               1..22
                     note = source = /note="Description of Artificial Sequence:
                        Synthetic peptide"
source               1..22
                     mol_type = protein
                     organism = synthetic construct
SEQUENCE: 337
VRAHFDIYQY DTRGDFTYYF DN                                                   22

SEQ ID NO: 338       moltype = AA  length = 129
FEATURE              Location/Qualifiers
REGION               1..129
                     note = source = /note="Description of Artificial Sequence:
                        Synthetic polypeptide"
source               1..129
                     mol_type = protein
                     organism = synthetic construct
SEQUENCE: 338
QVQLQESGGR LVRPGGSLRL SCAASGFIFT DYYMTWIRQA PGKGPEWIAF ITSGGETTYY           60
ADSVKGRFTI SRDNAKKSLF LQMYSLRADD TAVYYCVRAH FDIYQYDTRG DFTYYFDNWG          120
LGTLVSVSS                                                                 129

SEQ ID NO: 339       moltype = DNA  length = 387
FEATURE              Location/Qualifiers
misc_feature         1..387
                     note = source = /note="Description of Artificial Sequence:
                        Synthetic polynucleotide"
source               1..387
                     mol_type = other DNA
                     organism = synthetic construct
SEQUENCE: 339
caggttcagc tgcaagaatc tggcggcaga ctcgttagac ctggcggctc tctgagactg          60
tcttgtgccg ccagcggctt catcttcacc gactactaca tgacctggat cagacaggcc        120
cctggcaagg gacctgagtg gatcgccttt atcacaagcg gcggagagac aacctactac        180
gccgatagcg tgaagggcag attcaccatc agccggacac accaagaa gtccctgttc          240
ctccagatgt acagcctgag agccgacgat accgccgtgt attattgcgt gcgggccac         300
tttgacatct accagtacga taccagaggc gatttcacct actacttcga caactgggc         360
ctgggaaccc tggtgtctgt ctcttct                                             387

SEQ ID NO: 340       moltype = AA  length = 459
FEATURE              Location/Qualifiers
REGION               1..459
                     note = source = /note="Description of Artificial Sequence:
                        Synthetic polypeptide"
source               1..459
                     mol_type = protein
                     organism = synthetic construct
SEQUENCE: 340
QVQLQESGGR LVRPGGSLRL SCAASGFIFT DYYMTWIRQA PGKGPEWIAF ITSGGETTYY           60
ADSVKGRFTI SRDNAKKSLF LQMYSLRADD TAVYYCVRAH FDIYQYDTRG DFTYYFDNWG          120
LGTLVSVSSA STKGPSVFPL APSSKSTSGG TAALGCLVKD YFPEPVTVSW NSGALTSGVH          180
TFPAVLQSSG LYSLSSVVTV PSSSLGTQTY ICNVNHKPSN TKVDKRVEPK SCDKTHTCPP          240
CPAPELLGGP SVFLFPPKPK DTLMISRTPE VTCVVVDVSH EDPEVKFNWY VDGVEVHNAK          300
TKPREEQYNS TYRVVSVLTV LHQDWLNGKE YKCKVSNKAL PAPIEKTISK AKGQPREPQV          360
YTLPPSREEM TKNQVSLTCL VKGFYPSDIA VEWESNGQPE NNYKTTPPVL DSDGSFFLYS          420
KLTVDKSRWQ QGNVFSCSVM HEALHNHYTQ KSLSLSPGK                                 459

SEQ ID NO: 341       moltype = DNA  length = 1377
FEATURE              Location/Qualifiers
misc_feature         1..1377
                     note = source = /note="Description of Artificial Sequence:
                        Synthetic polynucleotide"
source               1..1377
                     mol_type = other DNA
                     organism = synthetic construct
SEQUENCE: 341
caggttcagc tgcaagaatc tggcggcaga ctcgttagac ctggcggctc tctgagactg          60
```

```
tcttgtgccg ccagcggctt catcttcacc gactactaca tgacctggat cagacaggcc    120
cctggcaagg gacctgagtg gatcgccttt atcacaagcg gcggagagac aacctactac    180
gccgatagcg tgaagggcag attcaccatc agccgggaca acgccaagaa gtccctgttc    240
ctccagatgt acagcctgag agccgacgat accgccgtgt attattgcgt gcgggccac     300
tttgacatct accagtacga taccagaggc gatttcacct actacttcga caactggggc    360
ctgggaaccc tggtgtctgt ctcttctgct agcaccaagg gcccagcgt gttccccctg     420
gcccccagca gcaagagcac cagcggcggc acagccgccc tgggctgcct ggtgaaggac    480
tacttccccg agcccgtgac cgtgtcctgg aacagcggag ccctgacctc cggcgtgcac    540
accttccccg ccgtgctgca gagcagcggc ctgtacagcc tgtccagcgt ggtgacagtg    600
cccagcagca gcctgggcac ccagacctac atctgcaacg tgaaccacaa gcccagcaac    660
accaaggtgg acaagagagt ggagcccaag agctgcgaca gaccccacac atgcccccc    720
tgcccggcgc cagagctgct gggcggaccc tccgtgttcc tgttccccc caagcccaag    780
gacaccctga tgatcagcag gacccccgag gtgacctgcg tggtggtgga cgtgagccac    840
gaggacccag aggtgaagtt caactggtac gtggacggcg tggaggtgca caacgccaag    900
accaagccca gagaggagca gtacaacagc acctacaggg tggtgtccgt gctgaccgtg    960
ctgcaccagg actggctgaa cggcaaggaa tacaagtgca aggtctccaa caaggccctg   1020
ccagccccca tcgaaaagac catcagcaag gccaagggcc agccacggga gccccaggtg   1080
tacaccctgc cccccctcccg ggaggagatg accaagaacc aggtgtccct gacctgtctg   1140
gtgaagggct tctaccccag cgacatcgcc gtggagtggg agagcaacgg ccagcccgag   1200
aacaactaca agaccacccc ccccagtgctg gacagcgacg gcagcttctt cctgtacagc   1260
aagctgaccg tggacaagtc caggtggcag cagggcaacg tgttcagctg cagcgtgatg   1320
cacgaggccc tgcacaacca ctacacccag aagagcctga gcttaagccc cggcaag     1377

SEQ ID NO: 342           moltype = AA   length = 11
FEATURE                  Location/Qualifiers
REGION                   1..11
                         note = source = /note="Description of Artificial Sequence:
                          Synthetic peptide"
source                   1..11
                         mol_type = protein
                         organism = synthetic construct
SEQUENCE: 342
RASQSVSSSL A                                                           11

SEQ ID NO: 343           moltype = AA   length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 343
GASTRAT                                                                7

SEQ ID NO: 344           moltype = AA   length = 11
FEATURE                  Location/Qualifiers
REGION                   1..11
                         note = source = /note="Description of Artificial Sequence:
                          Synthetic peptide"
source                   1..11
                         mol_type = protein
                         organism = synthetic construct
SEQUENCE: 344
HQYINWPPGD T                                                           11

SEQ ID NO: 345           moltype = AA   length = 11
FEATURE                  Location/Qualifiers
REGION                   1..11
                         note = source = /note="Description of Artificial Sequence:
                          Synthetic peptide"
source                   1..11
                         mol_type = protein
                         organism = synthetic construct
SEQUENCE: 345
RASQSVSSSL A                                                           11

SEQ ID NO: 346           moltype = AA   length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 346
GASTRAT                                                                7

SEQ ID NO: 347           moltype = AA   length = 11
```

```
FEATURE              Location/Qualifiers
REGION               1..11
                     note = source = /note="Description of Artificial Sequence:
                      Synthetic peptide"
source               1..11
                     mol_type = protein
                     organism = synthetic construct
SEQUENCE: 347
HQYINWPPGD T                                                          11

SEQ ID NO: 348       moltype = AA  length = 7
FEATURE              Location/Qualifiers
REGION               1..7
                     note = source = /note="Description of Artificial Sequence:
                      Synthetic peptide"
source               1..7
                     mol_type = protein
                     organism = synthetic construct
SEQUENCE: 348
SQSVSSS                                                               7

SEQ ID NO: 349       moltype =   length =
SEQUENCE: 349
000

SEQ ID NO: 350       moltype = AA  length = 8
FEATURE              Location/Qualifiers
REGION               1..8
                     note = source = /note="Description of Artificial Sequence:
                      Synthetic peptide"
source               1..8
                     mol_type = protein
                     organism = synthetic construct
SEQUENCE: 350
YINWPPGD                                                              8

SEQ ID NO: 351       moltype = AA  length = 6
FEATURE              Location/Qualifiers
REGION               1..6
                     note = source = /note="Description of Artificial Sequence:
                      Synthetic peptide"
source               1..6
                     mol_type = protein
                     organism = synthetic construct
SEQUENCE: 351
QSVSSS                                                                6

SEQ ID NO: 352       moltype =   length =
SEQUENCE: 352
000

SEQ ID NO: 353       moltype = AA  length = 11
FEATURE              Location/Qualifiers
REGION               1..11
                     note = source = /note="Description of Artificial Sequence:
                      Synthetic peptide"
source               1..11
                     mol_type = protein
                     organism = synthetic construct
SEQUENCE: 353
HQYINWPPGD T                                                          11

SEQ ID NO: 354       moltype = AA  length = 109
FEATURE              Location/Qualifiers
REGION               1..109
                     note = source = /note="Description of Artificial Sequence:
                      Synthetic polypeptide"
source               1..109
                     mol_type = protein
                     organism = synthetic construct
SEQUENCE: 354
EIVMTQSPAT LSVSPGERVT LSCRASQSVS SSLAWYQQKP GRAPRLLIYG ASTRATGVPA      60
RFSGGGSGTD FTLTISSLQS EDFAVYYCHQ YINWPPGDTF GQGTRLDIK                109

SEQ ID NO: 355       moltype = DNA  length = 327
FEATURE              Location/Qualifiers
misc_feature         1..327
                     note = source = /note="Description of Artificial Sequence:
                      Synthetic polynucleotide"
```

```
source                  1..327
                        mol_type = other DNA
                        organism = synthetic construct
SEQUENCE: 355
gaaatagtga tgactcagtc tccagccacc ctgtctgtgt ctccagggga aagagtcacc    60
ctctcctgca gggccagtca gagtgttagt agcagcttag cctggtacca gcagaaacct   120
ggccgggctc ccaggctcct catttatgga gcatccacca gggccactgg tgtcccagcc   180
aggttcagtg gcggtgggtc tgggacagac ttcactctca ccatcagcag cctgcagtct   240
gaagattttg cagtttatta ctgtcaccag tatattaatt ggcctccggg ggacactttt   300
ggccagggga cgaggctgga tatcaaa                                       327

SEQ ID NO: 356          moltype = AA  length = 216
FEATURE                 Location/Qualifiers
REGION                  1..216
                        note = source = /note="Description of Artificial Sequence:
                        Synthetic polypeptide"
source                  1..216
                        mol_type = protein
                        organism = synthetic construct
SEQUENCE: 356
EIVMTQSPAT LSVSPGERVT LSCRASQSVS SSLAWYQQKP GRAPRLLIYG ASTRATGVPA    60
RFSGGGSGTD FTLTISSLQS EDFAVYYCHQ YINWPPGDTF GQGTRLDIKR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                             216

SEQ ID NO: 357          moltype = DNA  length = 648
FEATURE                 Location/Qualifiers
misc_feature            1..648
                        note = source = /note="Description of Artificial Sequence:
                        Synthetic polynucleotide"
source                  1..648
                        mol_type = other DNA
                        organism = synthetic construct
SEQUENCE: 357
gaaatagtga tgactcagtc tccagccacc ctgtctgtgt ctccagggga aagagtcacc    60
ctctcctgca gggccagtca gagtgttagt agcagcttag cctggtacca gcagaaacct   120
ggccgggctc ccaggctcct catttatgga gcatccacca gggccactgg tgtcccagcc   180
aggttcagtg gcggtgggtc tgggacagac ttcactctca ccatcagcag cctgcagtct   240
gaagattttg cagtttatta ctgtcaccag tatattaatt ggcctccggg ggacactttt   300
ggccagggga cgaggctgga tatcaaacgt acggtggccg ctcccagcgt gttcatcttc   360
ccccccagcg acgagcagct gaagagcggc accgccagcg tggtgtgcct gctgaacaac   420
ttctaccccc gggaggccaa ggtgcagtgg aaggtggaca acgccctgca gagcggcaac   480
agccaggaga gcgtcaccga gcaggacagc aaggactcca cctacagcct gagcagcacc   540
ctgaccctga gcaaggccga ctacgagaag cataaggtgt acgcctgcga ggtgacccac   600
cagggcctgt ccagccccgt gaccaagagc ttcaacaggg gcgagtgc                648

SEQ ID NO: 358          moltype = AA  length = 10
FEATURE                 Location/Qualifiers
REGION                  1..10
                        note = source = /note="Description of Artificial Sequence:
                        Synthetic peptide"
source                  1..10
                        mol_type = protein
                        organism = synthetic construct
SEQUENCE: 358
GFTFSYYGMN                                                           10

SEQ ID NO: 359          moltype = AA  length = 17
FEATURE                 Location/Qualifiers
REGION                  1..17
                        note = source = /note="Description of Artificial Sequence:
                        Synthetic peptide"
source                  1..17
                        mol_type = protein
                        organism = synthetic construct
SEQUENCE: 359
GITNSGSITY YADSVKG                                                   17

SEQ ID NO: 360          moltype = AA  length = 14
FEATURE                 Location/Qualifiers
REGION                  1..14
                        note = source = /note="Description of Artificial Sequence:
                        Synthetic peptide"
source                  1..14
                        mol_type = protein
                        organism = synthetic construct
SEQUENCE: 360
VGVRSSSGMW DLDY                                                      14
```

| | |
|---|---|
| SEQ ID NO: 361<br>FEATURE<br>REGION<br><br>source | moltype = AA length = 5<br>Location/Qualifiers<br>1..5<br>note = source = /note="Description of Artificial Sequence:<br>Synthetic peptide"<br>1..5<br>mol_type = protein<br>organism = synthetic construct |
| SEQUENCE: 361<br>YYGMN | 5 |
| SEQ ID NO: 362<br>FEATURE<br>REGION<br><br>source | moltype = AA length = 17<br>Location/Qualifiers<br>1..17<br>note = source = /note="Description of Artificial Sequence:<br>Synthetic peptide"<br>1..17<br>mol_type = protein<br>organism = synthetic construct |
| SEQUENCE: 362<br>GITNSGSITY YADSVKG | 17 |
| SEQ ID NO: 363<br>FEATURE<br>REGION<br><br>source | moltype = AA length = 14<br>Location/Qualifiers<br>1..14<br>note = source = /note="Description of Artificial Sequence:<br>Synthetic peptide"<br>1..14<br>mol_type = protein<br>organism = synthetic construct |
| SEQUENCE: 363<br>VGVRSSSGMW DLDY | 14 |
| SEQ ID NO: 364<br>FEATURE<br>REGION<br><br>source | moltype = AA length = 7<br>Location/Qualifiers<br>1..7<br>note = source = /note="Description of Artificial Sequence:<br>Synthetic peptide"<br>1..7<br>mol_type = protein<br>organism = synthetic construct |
| SEQUENCE: 364<br>GFTFSYY | 7 |
| SEQ ID NO: 365<br>FEATURE<br>REGION<br><br>source | moltype = AA length = 6<br>Location/Qualifiers<br>1..6<br>note = source = /note="Description of Artificial Sequence:<br>Synthetic peptide"<br>1..6<br>mol_type = protein<br>organism = synthetic construct |
| SEQUENCE: 365<br>TNSGSI | 6 |
| SEQ ID NO: 366<br>FEATURE<br>REGION<br><br>source | moltype = AA length = 14<br>Location/Qualifiers<br>1..14<br>note = source = /note="Description of Artificial Sequence:<br>Synthetic peptide"<br>1..14<br>mol_type = protein<br>organism = synthetic construct |
| SEQUENCE: 366<br>VGVRSSSGMW DLDY | 14 |
| SEQ ID NO: 367<br>FEATURE<br>REGION<br><br>source | moltype = AA length = 8<br>Location/Qualifiers<br>1..8<br>note = source = /note="Description of Artificial Sequence:<br>Synthetic peptide"<br>1..8<br>mol_type = protein<br>organism = synthetic construct |
| SEQUENCE: 367<br>GFTFSYYG | 8 |
| SEQ ID NO: 368<br>FEATURE | moltype = AA length = 8<br>Location/Qualifiers |

```
REGION                      1..8
                            note = source = /note="Description of Artificial Sequence:
                             Synthetic peptide"
source                      1..8
                            mol_type = protein
                            organism = synthetic construct
SEQUENCE: 368
ITNSGSIT                                                                    8

SEQ ID NO: 369              moltype = AA  length = 16
FEATURE                     Location/Qualifiers
REGION                      1..16
                            note = source = /note="Description of Artificial Sequence:
                             Synthetic peptide"
source                      1..16
                            mol_type = protein
                            organism = synthetic construct
SEQUENCE: 369
AKVGVRSSSG MWDLDY                                                           16

SEQ ID NO: 370              moltype = AA  length = 123
FEATURE                     Location/Qualifiers
REGION                      1..123
                            note = source = /note="Description of Artificial Sequence:
                             Synthetic polypeptide"
source                      1..123
                            mol_type = protein
                            organism = synthetic construct
SEQUENCE: 370
EVQLLESGGG LVQPGGSRRL SCAASGFTFS YYGMNWVRQA PGKGLEWVSG ITNSGSITYY            60
ADSVKGRFSI SRDNSKNTLF LQMNSLRAED TAVYYCAKVG VRSSSGMWDL DYWGQGTLVT           120
VSS                                                                        123

SEQ ID NO: 371              moltype = DNA  length = 369
FEATURE                     Location/Qualifiers
misc_feature                1..369
                            note = source = /note="Description of Artificial Sequence:
                             Synthetic polynucleotide"
source                      1..369
                            mol_type = other DNA
                            organism = synthetic construct
SEQUENCE: 371
gaggttcaat tgttggagtc tgggggaggc ctggtacagc cggggggggtc ccggagactg           60
tcctgtgcag cctctggatt cacctttagc tactatggca tgaactgggt ccgccaggct          120
ccagggaagg gactgaatg ggtctcaggt attactaata gtggtagtat cacatactac           180
gcagactccg tgaagggccg gttcagcatc tccagagaca attccaagaa cacgttgttt          240
ctgcaaatga acagcctgag agccgaggac acggccgtat attactgtgc gaaggtggga          300
gtgcgcagtt cgtccgggat gtgggacctt gactactggg gccaggaac cctggtcacc           360
gtcagctca                                                                  369

SEQ ID NO: 372              moltype = AA  length = 453
FEATURE                     Location/Qualifiers
REGION                      1..453
                            note = source = /note="Description of Artificial Sequence:
                             Synthetic polypeptide"
source                      1..453
                            mol_type = protein
                            organism = synthetic construct
SEQUENCE: 372
EVQLLESGGG LVQPGGSRRL SCAASGFTFS YYGMNWVRQA PGKGLEWVSG ITNSGSITYY            60
ADSVKGRFSI SRDNSKNTLF LQMNSLRAED TAVYYCAKVG VRSSSGMWDL DYWGQGTLVT           120
VSSASTKGPS VFPLAPSSKS TSGGTAALGC LVKDYFPEPV TVSWNSGALT SGVHTFPAVL           180
QSSGLYSLSS VVTVPSSSLG TQTYICNVNH KPSNTKVDKR VEPKSCDKTH TCPPCPAPEL           240
LGGPSVFLFP PKPKDTLMIS RTPEVTCVVV DVSHEDPEVK FNWYVDGVEV HNAKTKPREE           300
QYNSTYRVVS VLTVLHQDWL NGKEYKCKVS NKALPAPIEK TISKAKGQPR EPQVYTLPPS           360
REEMTKNQVS LTCLVKGFYP SDIAVEWESN GQPENNYKTT PPVLDSDGSF FLYSKLTVDK           420
SRWQQGNVFS CSVMHEALHN HYTQKSLSLS PGK                                        453

SEQ ID NO: 373              moltype = DNA  length = 1359
FEATURE                     Location/Qualifiers
misc_feature                1..1359
                            note = source = /note="Description of Artificial Sequence:
                             Synthetic polynucleotide"
source                      1..1359
                            mol_type = other DNA
                            organism = synthetic construct
SEQUENCE: 373
gaggttcaat tgttggagtc tgggggaggc ctggtacagc cggggggggtc ccggagactg           60
tcctgtgcag cctctggatt cacctttagc tactatggca tgaactgggt ccgccaggct          120
```

```
ccagggaagg gactggaatg ggtctcaggt attactaata gtggtagtat cacatactac    180
gcagactccg tgaagggccg gttcagcatc tccagagaca attccaagaa cacgttgttt    240
ctgcaaatga acagcctgag agccgaggac acggccgtat attactgtgc gaaggtggga    300
gtgcgcagtt cgtccgggat gtgggacctt gactactggg gccagggaac cctggtcacc    360
gtcagctcag ctagcaccaa gggcccagc gtgttccccc tggccccag cagcaagagc     420
accagcggcg gcacagccgc cctgggctgc ctggtgaagg actacttccc cgagcccgtg    480
accgtgtcct ggaacagcgg agccctgacc tccggcgtgc acaccttccc cgccgtgctg    540
cagagcagcg gcctgtacag cctgtccagc gtggtgacag tgcccagcag cagcctgggc    600
acccagacct acatctgcaa cgtgaaccac aagcccagca acaccaaggt ggacaagaga    660
gtggagccca agagctgcga caagacccac acctgcccc cctgcccagc cccagagctg     720
ctgggcggac cctccgtgtt cctgttcccc ccaagcccca aggacaccct gatgatcagc    780
aggaccccg aggtgacctg cgtggtggtg gacgtgagcc acgaggaccc agaggtgaag     840
ttcaactggt acgtggacgg cgtggaggtg cacaacgcca agaccaagcc cagagaggag    900
cagtacaaca gcacctacag ggtggtgtcc gtgctgaccg tgctgcacca ggactggctg    960
aacggcaagg aatacaagtg caaggtctcc aacaaggccc tgccagcccc catcgaaaag   1020
accatcagca aggccaaggg ccagccacgg gagcccagg tgtacaccct gccccctcc    1080
cgggaggaga tgaccaagaa ccaggtgtcc ctgacctgtc tggtgaaggg cttctacccc   1140
agcgacatcg ccgtggagtg ggagagcaac ggccagcccg agaacaacta caagaccacc   1200
ccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac   1320
cactacaccc agaagagcct gagcctgtcc cccggcaag                          1359

SEQ ID NO: 374          moltype = AA   length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 374
GGNNIGSKSL Q                                                         11

SEQ ID NO: 375          moltype = AA   length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 375
DDSDRPS                                                              7

SEQ ID NO: 376          moltype = AA   length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 376
QVWDTSSDHV V                                                         11

SEQ ID NO: 377          moltype = AA   length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 377
GGNNIGSKSL Q                                                         11

SEQ ID NO: 378          moltype = AA   length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 378
DDSDRPS                                                              7

SEQ ID NO: 379          moltype = AA   length = 11
FEATURE                 Location/Qualifiers
```

| | |
|---|---|
| REGION | 1..11<br>note = source = /note="Description of Artificial Sequence: Synthetic peptide" |
| source | 1..11<br>mol_type = protein<br>organism = synthetic construct |

SEQUENCE: 379
QVWDTSSDHV V                                                          11

| | |
|---|---|
| SEQ ID NO: 380<br>FEATURE<br>REGION | moltype = AA   length = 7<br>Location/Qualifiers<br>1..7<br>note = source = /note="Description of Artificial Sequence: Synthetic peptide" |
| source | 1..7<br>mol_type = protein<br>organism = synthetic construct |

SEQUENCE: 380
NNIGSKS                                                                7

| | |
|---|---|
| SEQ ID NO: 381<br>SEQUENCE: 381<br>000 | moltype =    length = |

| | |
|---|---|
| SEQ ID NO: 382<br>FEATURE<br>REGION | moltype = AA   length = 8<br>Location/Qualifiers<br>1..8<br>note = source = /note="Description of Artificial Sequence: Synthetic peptide" |
| source | 1..8<br>mol_type = protein<br>organism = synthetic construct |

SEQUENCE: 382
WDTSSDHV                                                               8

| | |
|---|---|
| SEQ ID NO: 383<br>FEATURE<br>REGION | moltype = AA   length = 6<br>Location/Qualifiers<br>1..6<br>note = source = /note="Description of Artificial Sequence: Synthetic peptide" |
| source | 1..6<br>mol_type = protein<br>organism = synthetic construct |

SEQUENCE: 383
NIGSKS                                                                 6

| | |
|---|---|
| SEQ ID NO: 384<br>SEQUENCE: 384<br>000 | moltype =    length = |

| | |
|---|---|
| SEQ ID NO: 385<br>FEATURE<br>REGION | moltype = AA   length = 11<br>Location/Qualifiers<br>1..11<br>note = source = /note="Description of Artificial Sequence: Synthetic peptide" |
| source | 1..11<br>mol_type = protein<br>organism = synthetic construct |

SEQUENCE: 385
QVWDTSSDHV V                                                          11

| | |
|---|---|
| SEQ ID NO: 386<br>FEATURE<br>REGION | moltype = AA   length = 108<br>Location/Qualifiers<br>1..108<br>note = source = /note="Description of Artificial Sequence: Synthetic polypeptide" |
| source | 1..108<br>mol_type = protein<br>organism = synthetic construct |

SEQUENCE: 386
SYVLTQPPSV SVAPGQTARL SCGGNNIGSK SLQWYQQKPG QAPVLVVNDD SDRPSGIPER   60
FSGSNSGNTA TLTISRVEAG DEADYYCQVW DTSSDHVVFG GGTKLTVL                108

| | |
|---|---|
| SEQ ID NO: 387<br>FEATURE<br>misc_feature | moltype = DNA   length = 324<br>Location/Qualifiers<br>1..324<br>note = source = /note="Description of Artificial Sequence: Synthetic polynucleotide" |
| source | 1..324 |

```
                            mol_type = other DNA
                            organism = synthetic construct
SEQUENCE: 387
tcctatgtgc tgactcagcc accctcggtg tcagtggccc caggacagac ggccagactt    60
tcctgtgggg gaaacaacat tggaagtaaa agtctgcagt ggtaccagca gaagccaggc   120
caggcccctg tgctggtcgt caatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatactagta gtgatcatgt ggtcttcggc   300
ggagggacca agctgaccgt ccta                                          324

SEQ ID NO: 388        moltype = AA  length = 214
FEATURE               Location/Qualifiers
REGION                1..214
                      note = source = /note="Description of Artificial Sequence:
                       Synthetic polypeptide"
source                1..214
                      mol_type = protein
                      organism = synthetic construct
SEQUENCE: 388
SYVLTQPPSV SVAPGQTARL SCGGNNIGSK SLQWYQQKPG QAPVLVVNDD SDRPSGIPER    60
FSGSNSGNTA TLTISRVEAG DEADYYCQVW DTSSDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 389        moltype = DNA  length = 642
FEATURE               Location/Qualifiers
misc_feature          1..642
                      note = source = /note="Description of Artificial Sequence:
                       Synthetic polynucleotide"
source                1..642
                      mol_type = other DNA
                      organism = synthetic construct
SEQUENCE: 389
tcctatgtgc tgactcagcc accctcggtg tcagtggccc caggacagac ggccagactt    60
tcctgtgggg gaaacaacat tggaagtaaa agtctgcagt ggtaccagca gaagccaggc   120
caggcccctg tgctggtcgt caatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatactagta gtgatcatgt ggtcttcggc   300
ggagggacca agctgaccgt cctaggccag cctaaggccg ctccctccgt gaccctgttc   360
ccccccagct ccgaggaact gcaggccaac aaggccaccc tggtgtgcct gatcagcgac   420
ttctaccctg gcgccgtgac cgtggcctgg aaggccgaca gcagcccgt gaaggccggc   480
gtggagacaa ccaccccag caagcagagc aacaacaagt acgccgccag cagctacctg   540
agcctgaccc ccgagcagtg gaagagccac agaagctaca gctgccaggt cacccacgag   600
ggcagcaccg tggagaaaac cgtggccccc accgagtgca gc                      642

SEQ ID NO: 390        moltype = AA  length = 10
FEATURE               Location/Qualifiers
REGION                1..10
                      note = source = /note="Description of Artificial Sequence:
                       Synthetic peptide"
source                1..10
                      mol_type = protein
                      organism = synthetic construct
SEQUENCE: 390
GFTFSYYGMN                                                           10

SEQ ID NO: 391        moltype = AA  length = 17
FEATURE               Location/Qualifiers
REGION                1..17
                      note = source = /note="Description of Artificial Sequence:
                       Synthetic peptide"
source                1..17
                      mol_type = protein
                      organism = synthetic construct
SEQUENCE: 391
GITQSGSITY YADTVKG                                                   17

SEQ ID NO: 392        moltype = AA  length = 14
FEATURE               Location/Qualifiers
REGION                1..14
                      note = source = /note="Description of Artificial Sequence:
                       Synthetic peptide"
source                1..14
                      mol_type = protein
                      organism = synthetic construct
SEQUENCE: 392
VGVRSSSGMW DLDY                                                      14

SEQ ID NO: 393        moltype = AA  length = 5
```

```
FEATURE            Location/Qualifiers
REGION             1..5
                   note = source = /note="Description of Artificial Sequence:
                    Synthetic peptide"
source             1..5
                   mol_type = protein
                   organism = synthetic construct
SEQUENCE: 393
YYGMN                                                                       5

SEQ ID NO: 394     moltype = AA  length = 17
FEATURE            Location/Qualifiers
REGION             1..17
                   note = source = /note="Description of Artificial Sequence:
                    Synthetic peptide"
source             1..17
                   mol_type = protein
                   organism = synthetic construct
SEQUENCE: 394
GITQSGSITY YADTVKG                                                         17

SEQ ID NO: 395     moltype = AA  length = 14
FEATURE            Location/Qualifiers
REGION             1..14
                   note = source = /note="Description of Artificial Sequence:
                    Synthetic peptide"
source             1..14
                   mol_type = protein
                   organism = synthetic construct
SEQUENCE: 395
VGVRSSSGMW DLDY                                                            14

SEQ ID NO: 396     moltype = AA  length = 7
FEATURE            Location/Qualifiers
REGION             1..7
                   note = source = /note="Description of Artificial Sequence:
                    Synthetic peptide"
source             1..7
                   mol_type = protein
                   organism = synthetic construct
SEQUENCE: 396
GFTFSYY                                                                     7

SEQ ID NO: 397     moltype = AA  length = 6
FEATURE            Location/Qualifiers
REGION             1..6
                   note = source = /note="Description of Artificial Sequence:
                    Synthetic peptide"
source             1..6
                   mol_type = protein
                   organism = synthetic construct
SEQUENCE: 397
TQSGSI                                                                      6

SEQ ID NO: 398     moltype = AA  length = 14
FEATURE            Location/Qualifiers
REGION             1..14
                   note = source = /note="Description of Artificial Sequence:
                    Synthetic peptide"
source             1..14
                   mol_type = protein
                   organism = synthetic construct
SEQUENCE: 398
VGVRSSSGMW DLDY                                                            14

SEQ ID NO: 399     moltype = AA  length = 8
FEATURE            Location/Qualifiers
REGION             1..8
                   note = source = /note="Description of Artificial Sequence:
                    Synthetic peptide"
source             1..8
                   mol_type = protein
                   organism = synthetic construct
SEQUENCE: 399
GFTFSYYG                                                                    8

SEQ ID NO: 400     moltype = AA  length = 8
FEATURE            Location/Qualifiers
REGION             1..8
```

```
                        note = source = /note="Description of Artificial Sequence:
                         Synthetic peptide"
source                  1..8
                        mol_type = protein
                        organism = synthetic construct
SEQUENCE: 400
ITQSGSIT                                                                8

SEQ ID NO: 401          moltype = AA   length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 401
AKVGVRSSSG MWDLDY                                                       16

SEQ ID NO: 402          moltype = AA   length = 123
FEATURE                 Location/Qualifiers
REGION                  1..123
                        note = source = /note="Description of Artificial Sequence:
                         Synthetic polypeptide"
source                  1..123
                        mol_type = protein
                        organism = synthetic construct
SEQUENCE: 402
EVQLLESGGG LVQPGGSRRL SCAASGFTFS YYGMNWVRQA PGKGLEWVSG ITQSGSITYY        60
ADTVKGRFSI SRDNSKNTLF LQMNSLRAED TAVYYCAKVG VRSSSGMWDL DYWGQGTLVT        120
VSS                                                                     123

SEQ ID NO: 403          moltype = DNA   length = 369
FEATURE                 Location/Qualifiers
misc_feature            1..369
                        note = source = /note="Description of Artificial Sequence:
                         Synthetic polynucleotide"
source                  1..369
                        mol_type = other DNA
                        organism = synthetic construct
SEQUENCE: 403
gaggttcaat tgttggagtc tgggggaggc ctggtacagc cggggggtc ccggagactg         60
tcctgtgcag cctctggatt cacctttagc tactatggca tgaactgggt ccgccaggct       120
ccagggaagg gactgaatg gtctcaggt attactcaga gtggtagtat cacatactac        180
gcagacaccg tgaaggggcg gttcagcatc tccagagaca attccaagaa cacgttgttt       240
ctgcaaatga acagcctgag agccgaggac acggccgtat attactgtgc gaaggtggga       300
gtgcgcagtt cgtccgggat gtgggacctt gactactggg gccagggaac cctggtcacc       360
gtcagctca                                                               369

SEQ ID NO: 404          moltype = AA   length = 453
FEATURE                 Location/Qualifiers
REGION                  1..453
                        note = source = /note="Description of Artificial Sequence:
                         Synthetic polypeptide"
source                  1..453
                        mol_type = protein
                        organism = synthetic construct
SEQUENCE: 404
EVQLLESGGG LVQPGGSRRL SCAASGFTFS YYGMNWVRQA PGKGLEWVSG ITQSGSITYY        60
ADTVKGRFSI SRDNSKNTLF LQMNSLRAED TAVYYCAKVG VRSSSGMWDL DYWGQGTLVT        120
VSSASTKGPS VFPLAPSSKS TSGGTAALGC LVKDYFPEPV TVSWNSGALT SGVHTFPAVL        180
QSSGLYSLSS VVTVPSSSLG TQTYICNVNH KPSNTKVDKR VEPKSCDKTH TCPPCPAPEL        240
LGGPSVFLFP PKPKDTLMIS RTPEVTCVVV DVSHEDPEVK FNWYVDGVEV HNAKTKPREE        300
QYNSTYRVVS VLTVLHQDWL NGKEYKCKVS NKALPAPIEK TISKAKGQPR EPQVYTLPPS        360
REEMTKNQVS LTCLVKGFYP SDIAVEWESN GQPENNYKTT PPVLDSDGSF FLYSKLTVDK        420
SRWQQGNVFS CSVMHEALHN HYTQKSLSLS PGK                                    453

SEQ ID NO: 405          moltype = DNA   length = 1359
FEATURE                 Location/Qualifiers
misc_feature            1..1359
                        note = source = /note="Description of Artificial Sequence:
                         Synthetic polynucleotide"
source                  1..1359
                        mol_type = other DNA
                        organism = synthetic construct
SEQUENCE: 405
gaggttcaat tgttggagtc tgggggaggc ctggtacagc cggggggtc ccggagactg         60
tcctgtgcag cctctggatt cacctttagc tactatggca tgaactgggt ccgccaggct       120
ccagggaagg gactgaatg gtctcaggt attactcaga gtggtagtat cacatactac        180
```

```
gcagacaccg tgaagggccg gttcagcatc tccagagaca attccaagaa cacgttgttt   240
ctgcaaatga acagcctgag agccgaggac acgccgtat attactgtgc gaaggtggga    300
gtgcgcagtt cgtccgggat gtgggacctt gactactggg gccagggaac cctggtcacc   360
gtcagctcag ctagcaccaa gggccccagc gtgttccccc tggccccag cagcaagagc    420
accagcggcg gcacagccgc cctgggctgc ctggtgaagg actacttccc cgagcccgtg   480
accgtgtcct ggaacagcgg agccctgacc tccggcgtgc acaccttccc cgccgtgctg   540
cagagcagcg gcctgtacag cctgtccagc gtggtgacag tgcccagcag cagcctgggc   600
acccagacct acatctgcaa cgtgaaccac aagcccagca acaccaaggt ggacaagaga   660
gtggagccca agagctgcga caagacccac acctgccccc cctgcccagc cccagagctg   720
ctgggcggac cctccgtgtt cctgttcccc cccaagccca aggacaccct gatgatcagc   780
aggacccccg aggtgacctg cgtggtggtg gacgtgagcc acgaggaccc agaggtgaag   840
ttcaactggt acgtggacgg cgtggaggtg cacaacgcca agaccaagcc cagagaggag   900
cagtacaaca gcacctacag ggtggtgtcc gtgctgaccg tgctgcacca ggactggctg   960
aacggcaagg aatacaagtg caaggtctcc aacaaagcc tgccagcccc catcgaaaag   1020
accatcagca aggccaaggg ccagccacgg gagcccagg tgtacaccct gcccccctcc   1080
cgggaggaga tgaccaagaa ccaggtgtcc ctgacctgtc tggtgaaggg cttctacccc   1140
agcgacatcg ccgtggagtg ggagagcaac ggccagcccg agaacaacta caagaccacc   1200
cccccagtgc tggacagcga cggcagcttc ttcctgtaca gcaagctgac cgtggacaag   1260
tccaggtggc agcagggcaa cgtgttcagc tgcagcgtga tgcacgaggc cctgcacaac   1320
cactacaccc agaagagcct gagcctgtcc cccggcaag                          1359

SEQ ID NO: 406         moltype = AA  length = 11
FEATURE                Location/Qualifiers
REGION                 1..11
                       note = source = /note="Description of Artificial Sequence:
                       Synthetic peptide"
source                 1..11
                       mol_type = protein
                       organism = synthetic construct
SEQUENCE: 406
GGNNIGSKSL Q                                                        11

SEQ ID NO: 407         moltype = AA  length = 7
FEATURE                Location/Qualifiers
REGION                 1..7
                       note = source = /note="Description of Artificial Sequence:
                       Synthetic peptide"
source                 1..7
                       mol_type = protein
                       organism = synthetic construct
SEQUENCE: 407
DESDRPS                                                             7

SEQ ID NO: 408         moltype = AA  length = 11
FEATURE                Location/Qualifiers
REGION                 1..11
                       note = source = /note="Description of Artificial Sequence:
                       Synthetic peptide"
source                 1..11
                       mol_type = protein
                       organism = synthetic construct
SEQUENCE: 408
QVWDTSSDHV V                                                        11

SEQ ID NO: 409         moltype = AA  length = 11
FEATURE                Location/Qualifiers
REGION                 1..11
                       note = source = /note="Description of Artificial Sequence:
                       Synthetic peptide"
source                 1..11
                       mol_type = protein
                       organism = synthetic construct
SEQUENCE: 409
GGNNIGSKSL Q                                                        11

SEQ ID NO: 410         moltype = AA  length = 7
FEATURE                Location/Qualifiers
REGION                 1..7
                       note = source = /note="Description of Artificial Sequence:
                       Synthetic peptide"
source                 1..7
                       mol_type = protein
                       organism = synthetic construct
SEQUENCE: 410
DESDRPS                                                             7

SEQ ID NO: 411         moltype = AA  length = 11
FEATURE                Location/Qualifiers
REGION                 1..11
```

```
                        note = source = /note="Description of Artificial Sequence:
                         Synthetic peptide"
source                  1..11
                        mol_type = protein
                        organism = synthetic construct
SEQUENCE: 411
QVWDTSSDHV V                                                                    11

SEQ ID NO: 412          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 412
NNIGSKS                                                                         7

SEQ ID NO: 413          moltype =    length =
SEQUENCE: 413
000

SEQ ID NO: 414          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 414
WDTSSDHV                                                                        8

SEQ ID NO: 415          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 415
NIGSKS                                                                          6

SEQ ID NO: 416          moltype =    length =
SEQUENCE: 416
000

SEQ ID NO: 417          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 417
QVWDTSSDHV V                                                                    11

SEQ ID NO: 418          moltype = AA  length = 108
FEATURE                 Location/Qualifiers
REGION                  1..108
                        note = source = /note="Description of Artificial Sequence:
                         Synthetic polypeptide"
source                  1..108
                        mol_type = protein
                        organism = synthetic construct
SEQUENCE: 418
SYVLTQPPSV SVAPGQTARL SCGGNNIGSK SLQWYQQKPG QAPVLVVNDE SDRPSGIPER   60
FSGSNSGNTA TLTISRVEAG DEADYYCQVW DTSSDHVVFG GGTKLTVL                108

SEQ ID NO: 419          moltype = DNA  length = 324
FEATURE                 Location/Qualifiers
misc_feature            1..324
                        note = source = /note="Description of Artificial Sequence:
                         Synthetic polynucleotide"
source                  1..324
                        mol_type = other DNA
```

```
                        organism = synthetic construct
SEQUENCE: 419
tcctatgtgc tgactcagcc accctcggtg tcagtggccc caggacagac ggccagactt    60
tcctgtgggg gaaacaacat tggaagtaaa agtctgcagt ggtaccagca gaagccaggc   120
caggcccctg tgctggtcgt caatgatgag agcgaccggc cctcagggat ccctgagcga   180
ttctctggct ccaactctgg gaacacggcc accctgacca tcagcagggt cgaagccggg   240
gatgaggccg actattactg tcaggtgtgg gatactagta gtgatcatgt ggtcttcggc   300
ggagggacca agctgaccgt ccta                                          324

SEQ ID NO: 420          moltype = AA  length = 214
FEATURE                 Location/Qualifiers
REGION                  1..214
                        note = source = /note="Description of Artificial Sequence:
                         Synthetic polypeptide"
source                  1..214
                        mol_type = protein
                        organism = synthetic construct
SEQUENCE: 420
SYVLTQPPSV SVAPGQTARL SCGGNNIGSK SLQWYQQKPG QAPVLVVNDE SDRPSGIPER    60
FSGSNSGNTA TLTISRVEAG DEADYYCQVW DTSSDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 421          moltype = DNA  length = 642
FEATURE                 Location/Qualifiers
misc_feature            1..642
                        note = source = /note="Description of Artificial Sequence:
                         Synthetic polynucleotide"
source                  1..642
                        mol_type = other DNA
                        organism = synthetic construct
SEQUENCE: 421
tcctatgtgc tgactcagcc accctcggtg tcagtggccc caggacagac ggccagactt    60
tcctgtgggg gaaacaacat tggaagtaaa agtctgcagt ggtaccagca gaagccaggc   120
caggcccctg tgctggtcgt caatgatgag agcgaccggc cctcagggat ccctgagcga   180
ttctctggct ccaactctgg gaacacggcc accctgacca tcagcagggt cgaagccggg   240
gatgaggccg actattactg tcaggtgtgg gatactagta gtgatcatgt ggtcttcggc   300
ggagggacca agctgaccgt cctaggcagc ctaaggccg ctccctccgt gaccctgttc    360
ccccccagct ccgaggaact gcaggccaac aaggcgacc tggtgtgcct gatcagcgac    420
ttctaccctg gcgccgtgac cgtggcctgg aaggccgaca gcagcccgt gaaggccggc    480
gtggagacaa ccacccccag caagcagagc aacaacaagt acgccgccag cagctacctg   540
agcctgaccc cgagcagtg gaaagagcac agaagctaca gctgccaggt cacccacgag    600
ggcagcaccg tggagaaaac cgtggccccc accgagtgca gc                      642

SEQ ID NO: 422          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 422
GFTFSYYGMN                                                           10

SEQ ID NO: 423          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 423
GITNVGSITY YADTVKG                                                   17

SEQ ID NO: 424          moltype = AA  length = 14
FEATURE                 Location/Qualifiers
REGION                  1..14
                        note = source = /note="Description of Artificial Sequence:
                         Synthetic peptide"
source                  1..14
                        mol_type = protein
                        organism = synthetic construct
SEQUENCE: 424
VGVRSSSGMW DLDY                                                      14

SEQ ID NO: 425          moltype = AA  length = 5
FEATURE                 Location/Qualifiers
```

```
REGION                    1..5
                          note = source = /note="Description of Artificial Sequence:
                           Synthetic peptide"
source                    1..5
                          mol_type = protein
                          organism = synthetic construct
SEQUENCE: 425
YYGMN                                                                        5

SEQ ID NO: 426            moltype = AA   length = 17
FEATURE                   Location/Qualifiers
REGION                    1..17
                          note = source = /note="Description of Artificial Sequence:
                           Synthetic peptide"
source                    1..17
                          mol_type = protein
                          organism = synthetic construct
SEQUENCE: 426
GITNVGSITY YADTVKG                                                          17

SEQ ID NO: 427            moltype = AA   length = 14
FEATURE                   Location/Qualifiers
REGION                    1..14
                          note = source = /note="Description of Artificial Sequence:
                           Synthetic peptide"
source                    1..14
                          mol_type = protein
                          organism = synthetic construct
SEQUENCE: 427
VGVRSSSGMW DLDY                                                             14

SEQ ID NO: 428            moltype = AA   length = 7
FEATURE                   Location/Qualifiers
REGION                    1..7
                          note = source = /note="Description of Artificial Sequence:
                           Synthetic peptide"
source                    1..7
                          mol_type = protein
                          organism = synthetic construct
SEQUENCE: 428
GFTFSYY                                                                      7

SEQ ID NO: 429            moltype = AA   length = 6
FEATURE                   Location/Qualifiers
REGION                    1..6
                          note = source = /note="Description of Artificial Sequence:
                           Synthetic peptide"
source                    1..6
                          mol_type = protein
                          organism = synthetic construct
SEQUENCE: 429
TNVGSI                                                                       6

SEQ ID NO: 430            moltype = AA   length = 14
FEATURE                   Location/Qualifiers
REGION                    1..14
                          note = source = /note="Description of Artificial Sequence:
                           Synthetic peptide"
source                    1..14
                          mol_type = protein
                          organism = synthetic construct
SEQUENCE: 430
VGVRSSSGMW DLDY                                                             14

SEQ ID NO: 431            moltype = AA   length = 8
FEATURE                   Location/Qualifiers
REGION                    1..8
                          note = source = /note="Description of Artificial Sequence:
                           Synthetic peptide"
source                    1..8
                          mol_type = protein
                          organism = synthetic construct
SEQUENCE: 431
GFTFSYYG                                                                     8

SEQ ID NO: 432            moltype = AA   length = 8
FEATURE                   Location/Qualifiers
REGION                    1..8
                          note = source = /note="Description of Artificial Sequence:
```

```
                          Synthetic peptide"
source                  1..8
                        mol_type = protein
                        organism = synthetic construct
SEQUENCE: 432
ITNVGSIT                                                                8

SEQ ID NO: 433          moltype = AA  length = 16
FEATURE                 Location/Qualifiers
REGION                  1..16
                        note = source = /note="Description of Artificial Sequence:
                          Synthetic peptide"
source                  1..16
                        mol_type = protein
                        organism = synthetic construct
SEQUENCE: 433
AKVGVRSSSG MWDLDY                                                      16

SEQ ID NO: 434          moltype = AA  length = 123
FEATURE                 Location/Qualifiers
REGION                  1..123
                        note = source = /note="Description of Artificial Sequence:
                          Synthetic polypeptide"
source                  1..123
                        mol_type = protein
                        organism = synthetic construct
SEQUENCE: 434
EVQLLESGGG LVQPGGSRRL SCAASGFTFS YYGMNWVRQA PGKGLEWVSG ITNVGSITYY       60
ADTVKGRFSI SRDNSKNTLF LQMNSLRAED TAVYYCAKVG VRSSSGMWDL DYWGQGTLVT      120
VSS                                                                   123

SEQ ID NO: 435          moltype = DNA  length = 369
FEATURE                 Location/Qualifiers
misc_feature            1..369
                        note = source = /note="Description of Artificial Sequence:
                          Synthetic polynucleotide"
source                  1..369
                        mol_type = other DNA
                        organism = synthetic construct
SEQUENCE: 435
gaggttcaat tgttggagtc tgggggaggc ctggtacagc cggggggatc cggagactg        60
tcctgtgcag cctctggatt caccttttagc tactatggca tgaactgggt ccgccaggct    120
ccagggaagg gactggaatg ggtctcaggt attactaatg tgggtagtat cacatactac     180
gcagacaccg tgaagggccg gttcagcatc tccagagaca attccaagaa cacgttgttt     240
ctgcaaatga acagcctgag agccgaggac acggccgtat attactgtgc gaaggtggga     300
gtgcgcagtt cgtccgggat gtgggacctt gactactggg gccagggaac cctggtcacc     360
gtcagctca                                                             369

SEQ ID NO: 436          moltype = AA  length = 453
FEATURE                 Location/Qualifiers
REGION                  1..453
                        note = source = /note="Description of Artificial Sequence:
                          Synthetic polypeptide"
source                  1..453
                        mol_type = protein
                        organism = synthetic construct
SEQUENCE: 436
EVQLLESGGG LVQPGGSRRL SCAASGFTFS YYGMNWVRQA PGKGLEWVSG ITNVGSITYY       60
ADTVKGRFSI SRDNSKNTLF LQMNSLRAED TAVYYCAKVG VRSSSGMWDL DYWGQGTLVT      120
VSSASTKGPS VFPLAPSSKS TSGGTAALGC LVKDYFPEPV TVSWNSGALT SGVHTFPAVL      180
QSSGLYSLSS VVTVPSSSLG TQTYICNVNH KPSNTKVDKR VEPKSCDKTH TCPPCPAPEL      240
LGGPSVFLFP PKPKDTLMIS RTPEVTCVVV DVSHEDPEVK FNWYVDGVEV HNAKTKPREE      300
QYNSTYRVVS VLTVLHQDWL NGKEYKCKVS NKALPAPIEK TISKAKGQPR EPQVYTLPPS      360
REEMTKNQVS LTCLVKGFYP SDIAVEWESN GQPENNYKTT PPVLDSDGSF FLYSKLTVDK      420
SRWQQGNVFS CSVMHEALHN HYTQKSLSLS PGK                                  453

SEQ ID NO: 437          moltype = DNA  length = 1359
FEATURE                 Location/Qualifiers
misc_feature            1..1359
                        note = source = /note="Description of Artificial Sequence:
                          Synthetic polynucleotide"
source                  1..1359
                        mol_type = other DNA
                        organism = synthetic construct
SEQUENCE: 437
gaggttcaat tgttggagtc tgggggaggc ctggtacagc cggggggatc cggagactg        60
tcctgtgcag cctctggatt caccttttagc tactatggca tgaactgggt ccgccaggct    120
ccagggaagg gactggaatg ggtctcaggt attactaatg tgggtagtat cacatactac     180
gcagacaccg tgaagggccg gttcagcatc tccagagaca attccaagaa cacgttgttt     240
```

```
ctgcaaatga acagcctgag agccgaggac acggccgtat attactgtgc gaaggtggga    300
gtgcgcagtt cgtccgggat gtgggacctt gactactggg gccagggaac cctggtcacc    360
gtcagctcag ctagcaccaa gggcccagc gtgttccccc tggcccccag cagcaagagc     420
accagcggcg gcacagccgc cctgggctgc ctggtgaagg actacttccc cgagcccgtg    480
accgtgtcct ggaacagcgg agccctgacc tccggcgtgc acaccttccc cgccgtgctg    540
cagagcagcg gcctgtacag cctgtccagc gtggtgacag tgcccagcag cagcctgggc    600
acccagacct acatctgcaa cgtgaaccac aagcccagca acaccaaggt ggacaagaga    660
gtggagccca gagctgcga caagacccac acctgccccc cctgcccagc ccagagctg     720
ctgggcggac cctccgtgtt cctgttcccc ccaagcccaa aggacaccct gatgatcagc    780
aggaccccg aggtgacctg cgtggtggtg gacgtgagcc acgaggaccc agaggtgaag    840
ttcaactggt acgtggacgg cgtggaggtg cacaacgcca agaccaagcc cagagaggag    900
cagtacaaca gcacctacag ggtggtgtcc gtgctgaccg tgctgcacca ggactggctg    960
aacggcaagg aatacaagtg caaggtctcc aacaaggccc tgcagccccc catcgaaaag    1020
accatcagca aggcccaggg ccagccacgg gagcccaagg tgtacaccct gccccctcc    1080
cgggaggaga tgaccaagaa ccaggtgtcc ctgacctgtc tggtgaaggg cttctacccc    1140
agcgacatcg ccgtggagtg ggagagcaac ggccagcccg agaacaacta caagaccacc    1200
cccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac    1320
cactacaccc agaagagcct gagcctgtcc cccggcaag                         1359

SEQ ID NO: 438          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 438
GGNNIGSKSL Q                                                         11

SEQ ID NO: 439          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 439
DESDRPS                                                              7

SEQ ID NO: 440          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 440
QVWDTSSDHV V                                                         11

SEQ ID NO: 441          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 441
GGNNIGSKSL Q                                                         11

SEQ ID NO: 442          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 442
DESDRPS                                                              7

SEQ ID NO: 443          moltype = AA  length = 11
FEATURE                 Location/Qualifiers
REGION                  1..11
                        note = source = /note="Description of Artificial Sequence:
```

```
                        Synthetic peptide"
source                  1..11
                        mol_type = protein
                        organism = synthetic construct
SEQUENCE: 443
QVWDTSSDHV V                                                                            11

SEQ ID NO: 444          moltype = AA   length = 7
FEATURE                 Location/Qualifiers
REGION                  1..7
                        note = source = /note="Description of Artificial Sequence:
                        Synthetic peptide"
source                  1..7
                        mol_type = protein
                        organism = synthetic construct
SEQUENCE: 444
NNIGSKS                                                                                 7

SEQ ID NO: 445          moltype =    length =
SEQUENCE: 445
000

SEQ ID NO: 446          moltype = AA   length = 8
FEATURE                 Location/Qualifiers
REGION                  1..8
                        note = source = /note="Description of Artificial Sequence:
                        Synthetic peptide"
source                  1..8
                        mol_type = protein
                        organism = synthetic construct
SEQUENCE: 446
WDTSSDHV                                                                                8

SEQ ID NO: 447          moltype = AA   length = 6
FEATURE                 Location/Qualifiers
REGION                  1..6
                        note = source = /note="Description of Artificial Sequence:
                        Synthetic peptide"
source                  1..6
                        mol_type = protein
                        organism = synthetic construct
SEQUENCE: 447
NIGSKS                                                                                  6

SEQ ID NO: 448          moltype =    length =
SEQUENCE: 448
000

SEQ ID NO: 449          moltype = AA   length = 11
FEATURE                 Location/Qualifiers
REGION                  1..11
                        note = source = /note="Description of Artificial Sequence:
                        Synthetic peptide"
source                  1..11
                        mol_type = protein
                        organism = synthetic construct
SEQUENCE: 449
QVWDTSSDHV V                                                                            11

SEQ ID NO: 450          moltype = AA   length = 108
FEATURE                 Location/Qualifiers
REGION                  1..108
                        note = source = /note="Description of Artificial Sequence:
                        Synthetic polypeptide"
source                  1..108
                        mol_type = protein
                        organism = synthetic construct
SEQUENCE: 450
SYVLTQPPSV SVAPGQTARL SCGGNNIGSK SLQWYQQKPG QAPVLVVNDE SDRPSGIPER   60
FSGSNSGNTA TLTISRVEAG DEADYYCQVW DTSSDHVVFG GGTKLTVL                108

SEQ ID NO: 451          moltype = DNA   length = 324
FEATURE                 Location/Qualifiers
misc_feature            1..324
                        note = source = /note="Description of Artificial Sequence:
                        Synthetic polynucleotide"
source                  1..324
                        mol_type = other DNA
                        organism = synthetic construct
```

```
SEQUENCE: 451
tcctatgtgc tgactcagcc accctcggtg tcagtggccc caggacagac ggccagactt    60
tcctgtgggg gaaacaacat tggaagtaaa agtctgcagt ggtaccagca gaagccaggc   120
caggcccctg tgctggtcgt caatgatgag agcgaccggc cctcagggat ccctgagcga   180
ttctctggct ccaactctgg gaacacggcc accctgacca tcagcagggt cgaagccggg   240
gatgaggccg actattactg tcaggtgtgg gatactagta gtgatcatgt ggtcttcggc   300
ggagggacca agctgaccgt ccta                                          324

SEQ ID NO: 452          moltype = AA  length = 214
FEATURE                 Location/Qualifiers
REGION                  1..214
                        note = source = /note="Description of Artificial Sequence:
                        Synthetic polypeptide"
source                  1..214
                        mol_type = protein
                        organism = synthetic construct
SEQUENCE: 452
SYVLTQPPSV SVAPGQTARL SCGGNNIGSK SLQWYQQKPG QAPVLVVNDE SDRPSGIPER    60
FSGSNSGNTA TLTISRVEAG DEADYYCQVW DTSSDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 453          moltype = DNA  length = 642
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 453
tcctatgtgc tgactcagcc accctcggtg tcagtggccc caggacagac ggccagactt    60
tcctgtgggg gaaacaacat tggaagtaaa agtctgcagt ggtaccagca gaagccaggc   120
caggcccctg tgctggtcgt caatgatgag agcgaccggc cctcagggat ccctgagcga   180
ttctctggct ccaactctgg gaacacggcc accctgacca tcagcagggt cgaagccggg   240
gatgaggccg actattactg tcaggtgtgg gatactagta gtgatcatgt ggtcttcggc   300
ggagggacca agctgaccgt cctaggccag cctaaggccg ctccctccgt gaccctgttc   360
ccccccagct ccgaggaact gcaggccaac aaggccaccc tggtgtgcct gatcagcgac   420
ttctaccctg gcgccgtgac cgtggcctgg aaggccgaca gcagccccgt gaaggccggg   480
gtggagacaa ccaccccag caagcagagc aacaacaagt acgccgccag cagctacctg   540
agcctgaccc ccgagcagtg gaagagccac agaagctaca gctgccaggt cacccacgag   600
ggcagcaccg tggagaaaac cgtggccccc accgagtgca gc                      642

SEQ ID NO: 454          moltype = AA  length = 10
FEATURE                 Location/Qualifiers
REGION                  1..10
                        note = source = /note="Description of Artificial Sequence:
                        Synthetic peptide"
source                  1..10
                        mol_type = protein
                        organism = synthetic construct
SEQUENCE: 454
GYTFTSYYMH                                                           10

SEQ ID NO: 455          moltype = AA  length = 17
FEATURE                 Location/Qualifiers
REGION                  1..17
                        note = source = /note="Description of Artificial Sequence:
                        Synthetic peptide"
source                  1..17
                        mol_type = protein
                        organism = synthetic construct
SEQUENCE: 455
IISPSGGSTS YAQKFQG                                                   17

SEQ ID NO: 456          moltype = AA  length = 16
FEATURE                 Location/Qualifiers
REGION                  1..16
                        note = source = /note="Description of Artificial Sequence:
                        Synthetic peptide"
source                  1..16
                        mol_type = protein
                        organism = synthetic construct
SEQUENCE: 456
DWEGGDPYGY YYAFDY                                                    16

SEQ ID NO: 457          moltype = AA  length = 5
FEATURE                 Location/Qualifiers
REGION                  1..5
```

```
                         note = source = /note="Description of Artificial Sequence:
                          Synthetic peptide"
source                   1..5
                         mol_type = protein
                         organism = synthetic construct
SEQUENCE: 457
SYYMH                                                                         5

SEQ ID NO: 458           moltype = AA  length = 17
FEATURE                  Location/Qualifiers
REGION                   1..17
                         note = source = /note="Description of Artificial Sequence:
                          Synthetic peptide"
source                   1..17
                         mol_type = protein
                         organism = synthetic construct
SEQUENCE: 458
IISPSGGSTS YAQKFQG                                                           17

SEQ ID NO: 459           moltype = AA  length = 16
FEATURE                  Location/Qualifiers
REGION                   1..16
                         note = source = /note="Description of Artificial Sequence:
                          Synthetic peptide"
source                   1..16
                         mol_type = protein
                         organism = synthetic construct
SEQUENCE: 459
DWEGGDPYGY YYAFDY                                                            16

SEQ ID NO: 460           moltype = AA  length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 460
GYTFTSY                                                                       7

SEQ ID NO: 461           moltype = AA  length = 6
FEATURE                  Location/Qualifiers
REGION                   1..6
                         note = source = /note="Description of Artificial Sequence:
                          Synthetic peptide"
source                   1..6
                         mol_type = protein
                         organism = synthetic construct
SEQUENCE: 461
SPSGGS                                                                        6

SEQ ID NO: 462           moltype = AA  length = 16
FEATURE                  Location/Qualifiers
REGION                   1..16
                         note = source = /note="Description of Artificial Sequence:
                          Synthetic peptide"
source                   1..16
                         mol_type = protein
                         organism = synthetic construct
SEQUENCE: 462
DWEGGDPYGY YYAFDY                                                            16

SEQ ID NO: 463           moltype = AA  length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 463
GYTFTSYY                                                                      8

SEQ ID NO: 464           moltype = AA  length = 8
FEATURE                  Location/Qualifiers
REGION                   1..8
                         note = source = /note="Description of Artificial Sequence:
                          Synthetic peptide"
```

```
source                          1..8
                                mol_type = protein
                                organism = synthetic construct
SEQUENCE: 464
ISPSGGST                                                                    8

SEQ ID NO: 465                  moltype = AA   length = 18
FEATURE                         Location/Qualifiers
REGION                          1..18
                                note = source = /note="Description of Artificial Sequence:
                                Synthetic peptide"
source                          1..18
                                mol_type = protein
                                organism = synthetic construct
SEQUENCE: 465
ARDWEGGDPY GYYYAFDY                                                        18

SEQ ID NO: 466                  moltype = AA   length = 125
FEATURE                         Location/Qualifiers
REGION                          1..125
                                note = source = /note="Description of Artificial Sequence:
                                Synthetic polypeptide"
source                          1..125
                                mol_type = protein
                                organism = synthetic construct
SEQUENCE: 466
QVQLVQSGAE VKKPGASVKV SCKASGYTFT SYYMHWVRQA PGQGLEWMGI ISPSGGSTSY           60
AQKFQGRVTM TRDTSTSTVY MELSSLRSED TAVYYCARDW EGGDPYGYYY AFDYWGQGTL          120
VTVSS                                                                     125

SEQ ID NO: 467                  moltype = DNA   length = 375
FEATURE                         Location/Qualifiers
misc_feature                    1..375
                                note = source = /note="Description of Artificial Sequence:
                                Synthetic polynucleotide"
source                          1..375
                                mol_type = other DNA
                                organism = synthetic construct
SEQUENCE: 467
caggtgcaat tggtgcagag cggagccgaa gtgaaaaaac ctggggccag cgtgaaagtg          60
tcctgcaaag cctccggata caccttcacc agctactaca tgcactgggt ccgccaggcc        120
ccaggccagg gactcgagtg gatgggcatc atcagcccta gcggcggcag caccagctac        180
gcccagaaat tccagggccg ggtgaccatg acccgcgaca ccagcaccag caccgtgtac        240
atggaactga gcagcctgcg cagcgaggac accgccgtgt attattgcgc gcgtgactgg        300
gaaggtggtg acccgtacgg ttactactac gctttcgact actgggtca aggcaccctg        360
gttacagtca gctca                                                         375

SEQ ID NO: 468                  moltype = AA   length = 455
FEATURE                         Location/Qualifiers
REGION                          1..455
                                note = source = /note="Description of Artificial Sequence:
                                Synthetic polypeptide"
source                          1..455
                                mol_type = protein
                                organism = synthetic construct
SEQUENCE: 468
QVQLVQSGAE VKKPGASVKV SCKASGYTFT SYYMHWVRQA PGQGLEWMGI ISPSGGSTSY           60
AQKFQGRVTM TRDTSTSTVY MELSSLRSED TAVYYCARDW EGGDPYGYYY AFDYWGQGTL          120
VTVSSASTKG PSVFPLAPSS KSTSGGTAAL GCLVKDYFPE PVTVSWNSGA LTSGVHTFPA          180
VLQSSGLYSL SSVVTVPSSS LGTQTYICNV NHKPSNTKVD KRVEPKSCDK THTCPPCPAP          240
ELLGGPSVFL FPPKPKDTLM ISRTPEVTCV VVDVSHEDPE VKFNWYVDGV EVHNAKTKPR          300
EEQYNSTYRV VSVLTVLHQD WLNGKEYKCK VSNKALPAPI EKTISKAKGQ PREPQVYTLP          360
PSREEMTKNQ VSLTCLVKGF YPSDIAVEWE SNGQPENNYK TTPPVLDSDG SFFLYSKLTV          420
DKSRWQQGNV FSCSVMHEAL HNHYTQKSLS LSPGK                                    455

SEQ ID NO: 469                  moltype = DNA   length = 1365
FEATURE                         Location/Qualifiers
misc_feature                    1..1365
                                note = source = /note="Description of Artificial Sequence:
                                Synthetic polynucleotide"
source                          1..1365
                                mol_type = other DNA
                                organism = synthetic construct
SEQUENCE: 469
caggtgcaat tggtgcagag cggagccgaa gtgaaaaaac ctggggccag cgtgaaagtg          60
tcctgcaaag cctccggata caccttcacc agctactaca tgcactgggt ccgccaggcc        120
ccaggccagg gactcgagtg gatgggcatc atcagcccta gcggcggcag caccagctac        180
gcccagaaat tccagggccg ggtgaccatg acccgcgaca ccagcaccag caccgtgtac        240
atggaactga gcagcctgcg cagcgaggac accgccgtgt attattgcgc gcgtgactgg        300
```

```
gaaggtggtg acccgtacgg ttactactac gctttcgact actggggtca aggcaccctg  360
gttacagtca gctcagctag caccaagggc cccagcgtgt tccccctggc cccagcagc   420
aagagcacca gcggcggcac agccgccctg ggctgcctgg tgaaggacta cttccccgag  480
cccgtgaccg tgtcctggaa cagcggagcc ctgacctccg gcgtgcacac cttccccgcc  540
gtgctgcaga gcagcggcct gtacagcctg tccagcgtgg tgacagtgcc cagcagcagc  600
ctgggcaccc agacctacat ctgcaacgtg aaccacaagc ccagcaacac caaggtggac  660
aagagagtgg agcccaagag ctgcgacaag acccacacct gccccccctg cccagcccca  720
gagctgctgg gcggaccctc cgtgttcctg ttccccccca gcccaaggac accctgatg   780
atcagcagga ccccgaggt gacctgcgtg gtggtggacg tgagccacga ggacccagag   840
gtgaagttca actggtacgt ggacggcgtg gaggtgcaca acgccaagac caagcccaga   900
gaggagcagt acaacagcac ctacagggtg gtgtccgtgc tgaccgtgct gcaccaggac   960
tggctgaacg gcaaggaata caagtgcaag gtctccaaca aggccctgcc agcccccatc  1020
gaaaagacca tcagcaaggc caagggccag ccacgggagc ccaggtgta caccctgccc  1080
ccctcccggg aggagatgac caagaaccag gtgtccctga cctgtctggt gaagggcttc  1140
taccccagcg acatcgccgt ggagtgggag agcaacggcc agcccgagaa caactacaag  1200
accacccccc cagtgctgga cagcgacggc agcttcttcc tgtacagcaa gctgaccgtg  1260
gacaagtcca ggtggcagca gggcaacgtg ttcagctgca cgtgatgca cgaggccctg   1320
cacaaccact acacccagaa gagcctgagc ctgtcccccg gcaag                  1365

SEQ ID NO: 470         moltype = AA  length = 11
FEATURE                Location/Qualifiers
REGION                 1..11
                       note = source = /note="Description of Artificial Sequence:
                        Synthetic peptide"
source                 1..11
                       mol_type = protein
                       organism = synthetic construct
SEQUENCE: 470
RASQSISSYL N                                                                   11

SEQ ID NO: 471         moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 471
AASSLQS                                                                         7

SEQ ID NO: 472         moltype = AA  length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 472
QQSYSTPLT                                                                       9

SEQ ID NO: 473         moltype = AA  length = 11
FEATURE                Location/Qualifiers
REGION                 1..11
                       note = source = /note="Description of Artificial Sequence:
                        Synthetic peptide"
source                 1..11
                       mol_type = protein
                       organism = synthetic construct
SEQUENCE: 473
RASQSISSYL N                                                                   11

SEQ ID NO: 474         moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 474
AASSLQS                                                                         7

SEQ ID NO: 475         moltype = AA  length = 9
FEATURE                Location/Qualifiers
REGION                 1..9
                       note = source = /note="Description of Artificial Sequence:
                        Synthetic peptide"
```

```
source                  1..9
                        mol_type = protein
                        organism = synthetic construct
SEQUENCE: 475
QQSYSTPLT                                                                    9

SEQ ID NO: 476          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 476
SQSISSY                                                                      7

SEQ ID NO: 477          moltype =   length =
SEQUENCE: 477
000

SEQ ID NO: 478          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 478
SYSTPL                                                                       6

SEQ ID NO: 479          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 479
QSISSY                                                                       6

SEQ ID NO: 480          moltype =   length =
SEQUENCE: 480
000

SEQ ID NO: 481          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 481
QQSYSTPLT                                                                    9

SEQ ID NO: 482          moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 482
DIQMTQSPSS LSASVGDRVT ITCRASQSIS SYLNWYQQKP GKAPKLLIYA ASSLQSGVPS            60
RFSGSGSGTD FTLTISSLQP EDFATYYCQQ SYSTPLTFGQ GTKVEIK                         107

SEQ ID NO: 483          moltype = DNA  length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 483
```

```
gatatccaga tgacccagag ccctagcagc ctgagcgcca gcgtgggcga ccgcgtgacc    60
attacctgca gagccagcca gagcatcagc agctacctga actggtacca gcagaaacct   120
ggcaaggcgc ccaaactatt aatctacgcc gccagcagcc ttcagagcgg cgtgccaagc   180
cgctttagcg gatccggcag cggcaccgac ttcaccctga ccatcagctc ccttcagcct   240
gaagacttcg ccacctacta ctgccagcag agctacagca cccctctgac ctttggccag   300
ggcaccaaag tggaaatcaa a                                             321
```

| | |
|---|---|
| SEQ ID NO: 484 | moltype = AA   length = 214 |
| FEATURE | Location/Qualifiers |
| REGION | 1..214 |
| | note = source = /note="Description of Artificial Sequence: Synthetic polypeptide" |
| source | 1..214 |
| | mol_type = protein |
| | organism = synthetic construct |

```
SEQUENCE: 484
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPLTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

| | |
|---|---|
| SEQ ID NO: 485 | moltype = DNA   length = 642 |
| FEATURE | Location/Qualifiers |
| misc_feature | 1..642 |
| | note = source = /note="Description of Artificial Sequence: Synthetic polynucleotide" |
| source | 1..642 |
| | mol_type = other DNA |
| | organism = synthetic construct |

```
SEQUENCE: 485
gatatccaga tgacccagag ccctagcagc ctgagcgcca gcgtgggcga ccgcgtgacc    60
attacctgca gagccagcca gagcatcagc agctacctga actggtacca gcagaaacct   120
ggcaaggcgc ccaaactatt aatctacgcc gccagcagcc ttcagagcgg cgtgccaagc   180
cgctttagcg gatccggcag cggcaccgac ttcaccctga ccatcagctc ccttcagcct   240
gaagacttcg ccacctacta ctgccagcag agctacagca cccctctgac ctttggccag   300
ggcaccaaag tggaaatcaa acgtacggtg gccgctccca gcgtgttcat cttcccccccc  360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga gaagcataag gtgtacgcct gcgaggtgac ccaccagggc   600
ctgtccagcc ccgtgaccaa gagcttcaac aggggcgagt gc                      642
```

| | |
|---|---|
| SEQ ID NO: 486 | moltype = AA   length = 10 |
| FEATURE | Location/Qualifiers |
| REGION | 1..10 |
| | note = source = /note="Description of Artificial Sequence: Synthetic peptide" |
| source | 1..10 |
| | mol_type = protein |
| | organism = synthetic construct |

```
SEQUENCE: 486
GYTFTSLEMH                                                           10
```

| | |
|---|---|
| SEQ ID NO: 487 | moltype = AA   length = 17 |
| FEATURE | Location/Qualifiers |
| REGION | 1..17 |
| | note = source = /note="Description of Artificial Sequence: Synthetic peptide" |
| source | 1..17 |
| | mol_type = protein |
| | organism = synthetic construct |

```
SEQUENCE: 487
IIEPSGGSTS YAQKFQG                                                   17
```

| | |
|---|---|
| SEQ ID NO: 488 | moltype = AA   length = 16 |
| FEATURE | Location/Qualifiers |
| REGION | 1..16 |
| | note = source = /note="Description of Artificial Sequence: Synthetic peptide" |
| source | 1..16 |
| | mol_type = protein |
| | organism = synthetic construct |

```
SEQUENCE: 488
DWEGGDPYGY YYAFDY                                                    16
```

| | |
|---|---|
| SEQ ID NO: 489 | moltype = AA   length = 5 |
| FEATURE | Location/Qualifiers |
| REGION | 1..5 |
| | note = source = /note="Description of Artificial Sequence: |

```
source                   1..5
                         mol_type = protein
                         organism = synthetic construct
SEQUENCE: 489
SLEMH                                                                     5

SEQ ID NO: 490           moltype = AA  length = 17
FEATURE                  Location/Qualifiers
REGION                   1..17
                         note = source = /note="Description of Artificial Sequence:
                         Synthetic peptide"
source                   1..17
                         mol_type = protein
                         organism = synthetic construct
SEQUENCE: 490
IIEPSGGSTS YAQKFQG                                                       17

SEQ ID NO: 491           moltype = AA  length = 16
FEATURE                  Location/Qualifiers
REGION                   1..16
                         note = source = /note="Description of Artificial Sequence:
                         Synthetic peptide"
source                   1..16
                         mol_type = protein
                         organism = synthetic construct
SEQUENCE: 491
DWEGGDPYGY YYAFDY                                                        16

SEQ ID NO: 492           moltype = AA  length = 7
FEATURE                  Location/Qualifiers
REGION                   1..7
                         note = source = /note="Description of Artificial Sequence:
                         Synthetic peptide"
source                   1..7
                         mol_type = protein
                         organism = synthetic construct
SEQUENCE: 492
GYTFTSL                                                                   7

SEQ ID NO: 493           moltype = AA  length = 6
FEATURE                  Location/Qualifiers
REGION                   1..6
                         note = source = /note="Description of Artificial Sequence:
                         Synthetic peptide"
source                   1..6
                         mol_type = protein
                         organism = synthetic construct
SEQUENCE: 493
EPSGGS                                                                    6

SEQ ID NO: 494           moltype = AA  length = 16
FEATURE                  Location/Qualifiers
REGION                   1..16
                         note = source = /note="Description of Artificial Sequence:
                         Synthetic peptide"
source                   1..16
                         mol_type = protein
                         organism = synthetic construct
SEQUENCE: 494
DWEGGDPYGY YYAFDY                                                        16

SEQ ID NO: 495           moltype = AA  length = 8
FEATURE                  Location/Qualifiers
REGION                   1..8
                         note = source = /note="Description of Artificial Sequence:
                         Synthetic peptide"
source                   1..8
                         mol_type = protein
                         organism = synthetic construct
SEQUENCE: 495
GYTFTSLE                                                                  8

SEQ ID NO: 496           moltype = AA  length = 8
FEATURE                  Location/Qualifiers
REGION                   1..8
                         note = source = /note="Description of Artificial Sequence:
                         Synthetic peptide"
source                   1..8
```

```
                        mol_type = protein
                        organism = synthetic construct
SEQUENCE: 496
IEPSGGST                                                                     8

SEQ ID NO: 497          moltype = AA   length = 18
FEATURE                 Location/Qualifiers
REGION                  1..18
                        note = source = /note="Description of Artificial Sequence:
                         Synthetic peptide"
source                  1..18
                        mol_type = protein
                        organism = synthetic construct
SEQUENCE: 497
ARDWEGGDPY GYYYAFDY                                                         18

SEQ ID NO: 498          moltype = AA   length = 125
FEATURE                 Location/Qualifiers
REGION                  1..125
                        note = source = /note="Description of Artificial Sequence:
                         Synthetic polypeptide"
source                  1..125
                        mol_type = protein
                        organism = synthetic construct
SEQUENCE: 498
QVQLVQSGAE VKKPGASVKV SCKASGYTFT SLEMHWVRQA PGQGLEWMGI IEPSGGSTSY           60
AQKFQGRVTM TRDTSTSTVY MELSSLRSED TAVYYCARDW EGGDPYGYYY AFDYWGQGTL          120
VTVSS                                                                      125

SEQ ID NO: 499          moltype = DNA   length = 375
FEATURE                 Location/Qualifiers
misc_feature            1..375
                        note = source = /note="Description of Artificial Sequence:
                         Synthetic polynucleotide"
source                  1..375
                        mol_type = other DNA
                        organism = synthetic construct
SEQUENCE: 499
caggtccaat tggtgcagtc tggcgccgaa gtgaagaaac caggcgccag cgtgaaggtg           60
tcctgtaaag ccagcggcta cacctttacc agcctggaaa tgcattgggt ccgacaggct          120
ccaggacagg gactcgagtg gatgggaatt atcgagccta gcggcggcag cacaagctac          180
gcccagaaat tccagggcag agtgaccatg accagagaca ccagcacctc caccgtgtac          240
atggaactga gcagcctgag aagcgaggac accgccgtgt attattgcgc gcgtgattgg          300
gaaggcggcg acccttatgg ctactactac gcctttgatt actggggcca gggcaccctg          360
gtcacagtta gctca                                                           375

SEQ ID NO: 500          moltype = AA   length = 455
FEATURE                 Location/Qualifiers
REGION                  1..455
                        note = source = /note="Description of Artificial Sequence:
                         Synthetic polypeptide"
source                  1..455
                        mol_type = protein
                        organism = synthetic construct
SEQUENCE: 500
QVQLVQSGAE VKKPGASVKV SCKASGYTFT SLEMHWVRQA PGQGLEWMGI IEPSGGSTSY           60
AQKFQGRVTM TRDTSTSTVY MELSSLRSED TAVYYCARDW EGGDPYGYYY AFDYWGQGTL          120
VTVSSASTKG PSVFPLAPSS KSTSGGTAAL GCLVKDYFPE PVTVSWNSGA LTSGVHTFPA          180
VLQSSGLYSL SSVVTVPSSS LGTQTYICNV NHKPSNTKVD KRVEPKSCDK THTCPPCPAP          240
ELLGGPSVFL FPPKPKDTLM ISRTPEVTCV VVDVSHEDPE VKFNWYVDGV EVHNAKTKPR          300
EEQYNSTYRV VSVLTVLHQD WLNGKEYKCK VSNKALPAPI EKTISKAKGQ PREPQVYTLP          360
PSREEMTKNQ VSLTCLVKGF YPSDIAVEWE SNGQPENNYK TTPPVLDSDG SFFLYSKLTV          420
DKSRWQQGNV FSCSVMHEAL HNHYTQKSLS LSPGK                                    455

SEQ ID NO: 501          moltype = DNA   length = 1365
FEATURE                 Location/Qualifiers
misc_feature            1..1365
                        note = source = /note="Description of Artificial Sequence:
                         Synthetic polynucleotide"
source                  1..1365
                        mol_type = other DNA
                        organism = synthetic construct
SEQUENCE: 501
caggtccaat tggtgcagtc tggcgccgaa gtgaagaaac caggcgccag cgtgaaggtg           60
tcctgtaaag ccagcggcta cacctttacc agcctggaaa tgcattgggt ccgacaggct          120
ccaggacagg gactcgagtg gatgggaatt atcgagccta gcggcggcag cacaagctac          180
gcccagaaat tccagggcag agtgaccatg accagagaca ccagcacctc caccgtgtac          240
atggaactga gcagcctgag aagcgaggac accgccgtgt attattgcgc gcgtgattgg          300
gaaggcggcg acccttatgg ctactactac gcctttgatt actggggcca gggcaccctg          360
```

```
gtcacagtta gctcagctag caccaagggc cccagcgtgt tcccctggc ccccagcagc    420
aagagcacca gcggcggcac agccgccctg ggctgcctgg tgaaggacta cttccccgag    480
cccgtgaccg tgtcctggaa cagcggagcc ctgacctccg gcgtgcacac cttccccgcc    540
gtgctgcaga gcagcggcct gtacagcctg tccagcgtgg tgacagtgcc cagcagcagc    600
ctgggcaccc agacctacat ctgcaacgtg aaccacaagc ccagcaacac caaggtggac    660
aagagagtgg agcccaagag ctgcgacaag acccacacat gccccccctg cccggcgcca    720
gagctgctgg gcggaccctc cgtgttcctg ttccccccca gcccaaggga caccctgatg    780
atcagcagga cccccgaggt gacctgcgtg gtggtggacg tgagccacga ggacccagag    840
gtgaagttca actggtacgt ggacggcgtg gaggtgcaca acgccaagac caagccccga    900
gaggagcagt acaacagcac ctacagggtg gtgtccgtgc tgaccgtgct gcaccaggac    960
tggctgaacg gcaaggaata caagtgcaag gtctccaaca aggccctgcc agccccccatc   1020
gaaaagacca tcagcaaggc caagggccag ccacggagc cccaggtgta caccctgccc    1080
ccctcccggg aggagatgac caagaaccag gtgtccctga cctgtctggt gaagggcttc    1140
taccccagcg acatcgccgt ggagtgggag agcaacggcc agcccgagaa caactacaag    1200
accaccccc cagtgctgga cagcgacggc agcttcttcc tgtacagcaa gctgaccgtg    1260
gacaagtcca ggtggcagca gggcaacgtg ttcagctgca gcgtgatgca cgaggccctg    1320
cacaaccact acacccagaa gagcctgagc ttaagccccg gcaag                    1365

SEQ ID NO: 502           moltype = AA   length = 11
FEATURE                  Location/Qualifiers
REGION                   1..11
                         note = source = /note="Description of Artificial Sequence:
                          Synthetic peptide"
source                   1..11
                         mol_type = protein
                         organism = synthetic construct
SEQUENCE: 502
RASQSISSYL N                                                                11

SEQ ID NO: 503           moltype = AA   length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 503
AASSLQS                                                                     7

SEQ ID NO: 504           moltype = AA   length = 9
FEATURE                  Location/Qualifiers
REGION                   1..9
                         note = source = /note="Description of Artificial Sequence:
                          Synthetic peptide"
source                   1..9
                         mol_type = protein
                         organism = synthetic construct
SEQUENCE: 504
QQSYSTPLT                                                                   9

SEQ ID NO: 505           moltype = AA   length = 11
FEATURE                  Location/Qualifiers
REGION                   1..11
                         note = source = /note="Description of Artificial Sequence:
                          Synthetic peptide"
source                   1..11
                         mol_type = protein
                         organism = synthetic construct
SEQUENCE: 505
RASQSISSYL N                                                                11

SEQ ID NO: 506           moltype = AA   length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 506
AASSLQS                                                                     7

SEQ ID NO: 507           moltype = AA   length = 9
FEATURE                  Location/Qualifiers
REGION                   1..9
                         note = source = /note="Description of Artificial Sequence:
                          Synthetic peptide"
source                   1..9
```

```
                        mol_type = protein
                        organism = synthetic construct
SEQUENCE: 507
QQSYSTPLT                                                              9

SEQ ID NO: 508          moltype = AA   length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 508
SQSISSY                                                                7

SEQ ID NO: 509          moltype =    length =
SEQUENCE: 509
000

SEQ ID NO: 510          moltype = AA   length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 510
SYSTPL                                                                 6

SEQ ID NO: 511          moltype = AA   length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 511
QSISSY                                                                 6

SEQ ID NO: 512          moltype =    length =
SEQUENCE: 512
000

SEQ ID NO: 513          moltype = AA   length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 513
QQSYSTPLT                                                              9

SEQ ID NO: 514          moltype = AA   length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 514
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPLTFGQ GTKVEIK                 107

SEQ ID NO: 515          moltype = DNA   length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 515
gatatccaga tgacccagag ccctagcagc ctgagcgcca gcgtgggcga ccgcgtgacc    60
```

```
attacctgca gagccagcca gagcatcagc agctacctga actggtacca gcagaaacct    120
ggcaaggcgc ccaaactatt aatctacgcc gccagcagcc ttcagagcgg cgtgccaagc    180
cgctttagcg gatccggcag cggcaccgac ttcaccctga ccatcagctc ccttcagcct    240
gaagacttcg ccacctacta ctgccagcag agctacagca cccctctgac ctttggccag    300
ggcaccaaag tggaaatcaa a                                              321

SEQ ID NO: 516          moltype = AA  length = 214
FEATURE                 Location/Qualifiers
REGION                  1..214
                        note = source = /note="Description of Artificial Sequence:
                        Synthetic polypeptide"
source                  1..214
                        mol_type = protein
                        organism = synthetic construct
SEQUENCE: 516
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPLTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 517          moltype = DNA  length = 642
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 517
gatatccaga tgacccagag ccctagcagc ctgagcgcca gcgtgggcga ccgcgtgacc    60
attacctgca gagccagcca gagcatcagc agctacctga actggtacca gcagaaacct   120
ggcaaggcgc ccaaactatt aatctacgcc gccagcagcc ttcagagcgg cgtgccaagc   180
cgctttagcg gatccggcag cggcaccgac ttcaccctga ccatcagctc ccttcagcct   240
gaagacttcg ccacctacta ctgccagcag agctacagca cccctctgac ctttggccag   300
ggcaccaaag tggaaatcaa acgtacggtg gccgctccca gcgtgttcat cttcccccc    360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga gaagcataag gtgtacgcct gcgaggtgac ccaccagggc   600
ctgtccagcc ccgtgaccaa gagcttcaac aggggcgagt gc                      642
```

HEPATITIS B ANTIBODIES

CROSS REFERENCE TO RELATED APPLICATIONS

This application is a continuation of U.S. patent application Ser. No. 17/059,934 filed Nov. 30, 2020, now U.S. Pat. No. 11,932,681, which is national phase application of International Patent Application PCT/IB2019/054498 filed May 30, 2019, which claims the benefit of priority to U.S. Provisional Patent Application 62/678,756, filed May 31, 2018. The entire contents of each of these applications is incorporated herein by reference.

SEQUENCE LISTING

This application contains a sequence listing having the filename 1403586.00110_Sequence_Listing.xml, which is 682 KB in size, and was created on Jun. 13, 2024. The entire content of this sequence listing is incorporated herein by reference.

FIELD OF THE INVENTION

The present disclosure is directed to anti-hepatitis B surface antigen antibodies, antibody fragments, and their uses for the reducing the likelihood or treatment of hepatitis B viral infection.

BACKGROUND OF THE INVENTION

Hepatitis B virus (HBV) is an enveloped, hepatotropic virus that infects the liver and may result Chronic hepatitis B(CHB), liver cirrhosis and hepatocellular carcinoma (HCC). While there is a safe vaccine against HBV, at least 600,000 people worldwide die annually of HBV related disorders. Disease progression is affected by viral load, genotype and specific viral mutations (Biswas et al., Med. Virol. 2013; 85:1340-1347). HBV is classified into ten genotypes or classified into four serotypes (asw, adr, ayw and ayr) based on the antigenic determinants found in HBV surface antigen (HBsAg).

HBV is a member of the Hepadnaviridae family and can only infect humans and primates. The virion is constituted by a small 3.2 kb partially double-stranded circular DNA, surrounded by the envelope that interact with hepatocytes. HBV first binds with low-affinity to heparin sulfate proteoglycans on hepatocytes. Subsequently, the pre-S1 lipopeptide of the large envelope protein binds to its higher affinity receptor on the hepatocyte, the bile acid transporter NCTP (sodium taurocholate cotransporting polypeptide). Then, the virus enters the cytoplasm by endocytosis.

HBV clearance and pathogenesis are largely mediated by the adaptive immune response in HBV infection (Guidotti et al., Annu Rev Pathol. 2006; 1:23-61). For HBV to persist it must either not induce a response or it must evade or overwhelm it. Interestingly, HBV "evades" the innate immune response by simply not inducing it (Wieland et al., Proc Natl Acad Sci USA. 2004; 101 (17): 6669-74). On the other hand, viral persistence is characterized by a state of relative hyporesponsiveness of HBV-specific T cells (Chisari Annu Rev Immunol. 1995; 13:29-60). Several viral proteins have been shown to regulate the adaptive immune response to HBV, suggesting that HBV may employ active evasion strategies that target the adaptive immune response (Thimme et al., J Virol. 2003; 77 (1): 68-76). It has previously reported that antiviral treatment can overcome CD8+ T cell hyporesponsiveness in chronic HBV infection, suggesting that the T cells are present in these subjects but exhausted (Boni et al., Hepatology. 2001; 33 (4): 963-71). Induction of an effective HBV specific CD8+ T cell response may be dependent on early CD4+ T cell priming which is regulated by the size of the viral inoculum (Asabe J Virol. 2009; 83 (19): 9652-62).

The currently approved antiviral therapeutics are two formulations of alpha-interferon (IFN-α) and five nucleoside analogues. While the nucleosides inhibit HBV DNA polymerase activity with varying potencies and barriers to resistance, the therapy does not eliminate the virus and the patient is on this therapy for life. Therefore, better therapeutics to inhibit Hepatitis B infection are needed.

SUMMARY OF THE INVENTION

The present disclosure is directed to neutralizing antibodies to hepatitis B and/or fragments thereof, and antibodies that reduce the amounts of hepatitis B surface antigen (HBsAg).

An antibody, wherein said antibody or antigen binding fragment thereof specifically binds HBsAg.

The antibody wherein said antibody or antigen binding fragment thereof specifically binds HBsAg. In one embodiment, the antibody or antigen binding fragment thereof binds to HBsAg and mutations thereof.

The antibody wherein said antibody or antigen binding fragment specifically binds to and neutralizes hepatitis B. In one embodiment, the antibody or antigen binding fragment thereof neutralizes hepatitis B and hepatitis B containing mutations in HBsAg. In another embodiment, the antibody or antigen binding fragment thereof reduces the amount of HBsAg. In another embodiment, the antibody or antigen binding fragment thereof reduces the amount of circulating HBsAg in the blood.

An isolated antibody, wherein said antibody or antigen binding fragment thereof comprises: (i) a heavy chain variable region that comprises (a) a HCDR1 (CDR-Complementarity Determining Region) of SEQ ID NO: 9, (b) a HCDR2 of SEQ ID NO:10, (c) a HCDR3 of SEQ ID NO:11 and a light chain variable region that comprises: (d) a LCDR1 of SEQ ID NO:25, (e) a LCDR2 of SEQ ID NO:26, and (f) a LCDR3 of SEQ ID NO:27;
 (ii) a heavy chain variable region that comprises (a) a HCDR1 of SEQ ID NO:41, (b) a HCDR2 of SEQ ID NO:42, (c) a HCDR3 of SEQ ID NO:43; and a light chain variable region that comprises: (d) a LCDR1 of SEQ ID NO:57, (e) a LCDR2 of SEQ ID NO: 58, and (f) a LCDR3 of SEQ ID NO:59;
 (iii) a heavy chain variable region that comprises (a) a HCDR1 of SEQ ID NO:73, (b) a HCDR2 of SEQ ID NO:74, (c) a HCDR3 of SEQ ID NO:75; and a light chain variable region that comprises: (d) a LCDR1 of SEQ ID NO:89, (e) a LCDR2 of SEQ ID NO: 90, and (f) a LCDR3 of SEQ ID NO:91;
 (iv) a heavy chain variable region that comprises: (a) a HCDR1 of SEQ ID NO:105, (b) a HCDR2 of SEQ ID NO:106, (c) a HCDR3 of SEQ ID NO:107; and a light chain variable region that comprises: (d) a LCDR1 of SEQ ID NO: 121, (e) a LCDR2 of SEQ ID NO: 122, and (f) a LCDR3 of SEQ ID NO:123;
 (v) a heavy chain variable region that comprises: (a) a HCDR1 of SEQ ID NO:137, (b) a HCDR2 of SEQ ID NO:138, (c) a HCDR3 of SEQ ID NO:139; and a light chain variable region that comprises: (d) a LCDR1 of SEQ ID NO:153, (e) a LCDR2 of SEQ ID NO: 154, and (f) a LCDR3 of SEQ ID NO: 155;
(vi) a heavy chain variable region that comprises: (a) a HCDR1 of SEQ ID NO:169, (b) a HCDR2 of SEQ ID NO:170, (c) a HCDR3 of SEQ ID NO:171; and a light chain variable region that comprises: (d) a LCDR1 of SEQ ID NO: 185, (e) a LCDR2 of SEQ ID NO: 186, and (f) a LCDR3 of SEQ ID NO:187;
(vii) a heavy chain variable region that comprises: (a) a HCDR1 of SEQ ID NO:201, (b) a HCDR2 of SEQ ID NO: 202, (c) a HCDR3 of SEQ ID NO:203; and a light chain variable region that comprises: (d) a LCDR1 of SEQ ID NO:217, (e) a LCDR2 of SEQ ID NO: 218, and (f) a LCDR3 of SEQ ID NO:219;
(viii) a heavy chain variable region that comprises: (a) a HCDR1 of SEQ ID NO:233, (b) a HCDR2 of SEQ ID NO:234, (c) a HCDR3 of SEQ ID NO:235; and a light chain variable region that comprises: (d) a LCDR1 of SEQ ID NO:249, (e) a LCDR2 of SEQ ID NO: 250, and (f) a LCDR3 of SEQ ID NO:251;
(ix) a heavy chain variable region that comprises: (a) a HCDR1 of SEQ ID NO:265, (b) a HCDR2 of SEQ ID NO: 266, (c) a HCDR3 of SEQ ID NO:267; and a light chain variable region that comprises: (d) a LCDR1 of SEQ ID NO:281, (e) a LCDR2 of SEQ ID NO: 282, and (f) a LCDR3 of SEQ ID NO: 283;
(x) a heavy chain variable region that comprises: (a) a HCDR1 of SEQ ID NO:297, (b) a HCDR2 of SEQ ID NO: 298, (c) a HCDR3 of SEQ ID NO:299; and a light chain variable region that comprises: (d) a LCDR1 of SEQ ID NO:313, (e) a LCDR2 of SEQ ID NO: 314, and (f) a LCDR3 of SEQ ID NO: 315;
(xi) a heavy chain variable region that comprises: (a) a HCDR1 of SEQ ID NO:329, (b) a HCDR2 of SEQ ID NO:330, (c) a HCDR3 of SEQ ID NO:331; and a light chain variable region that comprises: (d) a LCDR1 of SEQ ID NO:345, (e) a LCDR2 of SEQ ID NO: 346, and (f) a LCDR3 of SEQ ID NO: 347;
(xii) a heavy chain variable region that comprises: (a) a HCDR1 of SEQ ID NO:361, (b) a HCDR2 of SEQ ID NO:362, (c) a HCDR3 of SEQ ID NO:363; and a light chain variable region that comprises: (d) a LCDR1 of SEQ ID NO:377, (e) a LCDR2 of SEQ ID NO: 378, and (f) a LCDR3 of SEQ ID NO: 379;
(xiii) a heavy chain variable region that comprises: (a) a HCDR1 of SEQ ID NO:393, (b) a HCDR2 of SEQ ID NO:394, (c) a HCDR3 of SEQ ID NO:395; and a light chain variable region that comprises: (d) a LCDR1 of SEQ ID NO:409, (e) a LCDR2 of SEQ ID NO: 410, and (f) a LCDR3 of SEQ ID NO:411;
(xiv) a heavy chain variable region that comprises: (a) a HCDR1 of SEQ ID NO:425, (b) a HCDR2 of SEQ ID NO:426, (c) a HCDR3 of SEQ ID NO:427; and a light chain variable region that comprises: (d) a LCDR1 of SEQ ID NO:441, (e) a LCDR2 of SEQ ID NO: 442, and (f) a LCDR3 of SEQ ID NO: 443;
(xv) a heavy chain variable region that comprises: (a) a HCDR1 of SEQ ID NO:457, (b) a HCDR2 of SEQ ID NO:458, (c) a HCDR3 of SEQ ID NO:459; and a light chain variable region that comprises: (d) a LCDR1 of SEQ ID NO:473, (e) a LCDR2 of SEQ ID NO: 474, and (f) a LCDR3 of SEQ ID NO:475; or
(xvi) a heavy chain variable region that comprises: (a) a HCDR1 of SEQ ID NO:489, (b) a HCDR2 of SEQ ID NO:490, (c) a HCDR3 of SEQ ID NO:491; and a light chain variable region that comprises: (d) a LCDR1 of SEQ ID NO:505, (e) a LCDR2 of SEQ ID NO: 506, and (f) a LCDR3 of SEQ ID NO: 507.

The antibody wherein one or two amino acids within a CDR have been modified, deleted or substituted.

The antibody that retains at least 90, 91, 92, 93, 94, 95, 96, 97, 98 or 99% identity over either the variable heavy chain region or the variable light chain region.

The antibody wherein the antibody is a monoclonal antibody, a chimeric antibody, a humanized antibody, a human engineered antibody, a human antibody, a single chain antibody (scFv) or an antibody fragment.

An isolated antibody or antigen binding fragment thereof, wherein said antibody or antigen binding fragment thereof comprises:
(i) a heavy chain variable region (vH) that comprises SEQ ID NO:18, and a light chain variable region (vL) that comprises SEQ ID NO: 34;
(ii) a heavy chain variable region (vH) that comprises SEQ ID NO: 50, and a light chain variable region (vL) that comprises SEQ ID NO: 66;
(iii) a heavy chain variable region (vH) that comprises SEQ ID NO: 82, and a light chain variable region (vL) that comprises SEQ ID NO:98;
(iv) a heavy chain variable region (vH) that comprises SEQ ID NO:114, and a light chain variable region (vL) that comprises SEQ ID NO:130;
(v) a heavy chain variable region (vH) that comprises SEQ ID NO:146, and a light chain variable region (vL) that comprises SEQ ID NO: 162;
(vi) a heavy chain variable region (vH) that comprises SEQ ID NO:178, and a light chain variable region (vL) that comprises SEQ ID NO:194;
(vii) a heavy chain variable region (vH) that comprises SEQ ID NO:210, and a light chain variable region (vL) that comprises SEQ ID NO:226;
(viii) a heavy chain variable region (vH) that comprises SEQ ID NO:242, and a light chain variable region (vL) that comprises SEQ ID NO:258;
(ix) a heavy chain variable region (vH) that comprises SEQ ID NO:274, and a light chain variable region (vL) that comprises SEQ ID NO:290;
(x) a heavy chain variable region (vH) that comprises SEQ ID NO:306, and a light chain variable region (vL) that comprises SEQ ID NO:322;
(xi) a heavy chain variable region (vH) that comprises SEQ ID NO:338, and a light chain variable region (vL) that comprises SEQ ID NO:354;
(xii) a heavy chain variable region (vH) that comprises SEQ ID NO:370, and a light chain variable region (vL) that comprises SEQ ID NO:386;
(xiii) a heavy chain variable region (vH) that comprises SEQ ID NO:402, and a light chain variable region (vL) that comprises SEQ ID NO:418;
(xiv) a heavy chain variable region (vH) that comprises SEQ ID NO:434, and a light chain variable region (vL) that comprises SEQ ID NO:450;
(xv) a heavy chain variable region (vH) that comprises SEQ ID NO:466, and a light chain variable region (vL) that comprises SEQ ID NO:482; or
(xvi) a heavy chain variable region (vH) that comprises SEQ ID NO:498, and a light chain variable region (vL) that comprises SEQ ID NO:514.

The antibody or fragment thereof, that retains at least 90, 91, 92, 93, 94, 95, 96, 97, 98 or 99% identity over either the variable light or variable heavy region.

The antibody wherein one, two, three, four or five, but less than 10 amino acids within the variable light or variable heavy region have been modified, deleted or substituted.

The antibody wherein the antibody is a monoclonal antibody, a chimeric antibody, a humanized antibody, a human engineered antibody, a human antibody, a single chain antibody (scFv) or an antibody fragment.

The antibody wherein the antibody or fragment thereof has reduced glycosylation or no glycosylation or is hypofucosylated.

A pharmaceutical composition comprising the antibody or fragment thereof, further comprising a pharmaceutically acceptable carrier.

The pharmaceutical composition wherein the pharmaceutically acceptable carrier contains histadine or a sugar.

The pharmaceutical composition wherein the sugar is sucrose.

A pharmaceutical composition comprising a plurality of an antibody or antigen binding fragment wherein at least 0.05%, 0.1%, 0.5%, 1%, 2%, 3%, 5% or more or more of the antibodies in the composition have an α2,3-linked sialic acid residue.

A pharmaceutical composition comprising a plurality of an antibody or antigen binding fragment, wherein none of the antibodies comprise a bisecting GlcNAc.

The pharmaceutical composition comprising the antibody or fragment thereof, wherein the composition is prepared as a lyophilisate.

A method of neutralizing a hepatitis B virus infection comprising administering via injection or infusion to a patient in need an effective amount of the antibody.

The method wherein the patient in need is diagnosed with hepatitis B viruria or hepatitis B viremia.

The method wherein the patient in need is diagnosed with hepatitis B surface antigen (HBsAg) in the blood or serum.

A method of treating or reducing the likelihood of hepatitis B virus associated disorder, comprising administering via injection or infusion to a patient in need an effective amount of the antibody and wherein the disorder is: liver failure, cirrhosis, or hepatocellular carcinoma.

The method wherein the antibody or composition is reconstituted prior to injection or infusion.

The method wherein the antibody or the pharmaceutical composition is administered in combination with another therapeutic agent.

The method wherein the therapeutic agent is an anti-viral agent.

The method wherein the anti-viral agent is: lamivudine, entecavir and tenofovir or alpha-interferon.

The method wherein the therapeutic agent is an antagonist of immune checkpoint inhibitor.

The method wherein the antagonist of the immune checkpoint inhibitor is selected from the group consisting of: PD-1, PD-L1, PD-L2, TIM3, CTLA-4, LAG-3, CEACAM-1, CEACAM-5, VISTA, BTLA, TIGIT, LAIR1, CD160, 2B4 and TGFR.

The method wherein the antagonist of the immune checkpoint inhibitor is an anti-PD-L1 antibody.

The method wherein the therapeutic agent is an additional anti-HBsAg antibody.

The antibody or fragment thereof for use as a medicament.

The antibody or fragment thereof, for use in the neutralization hepatitis B virus infection.

The antibody or fragment thereof, for use in the treatment or reducing the likelihood of: liver failure, cirrhosis, and/or hepatocellular carcinoma.

The use according to any of the above, administered in combination with another therapeutic agent.

The use according to any of the above, wherein the therapeutic agent is an anti-viral agent.

The use according to any of the above, wherein the anti-viral agent is: lamivudine, entecavir and tenofovir or alpha-interferon.

The use according to any of the above, wherein the therapeutic agent is an antagonist of immune checkpoint inhibitor.

The use according to any of the above, wherein the antagonist of the immune checkpoint inhibitor is selected from the group consisting of: PD-1, PD-L1, PD-L2, TIM3, CTLA-4, LAG-3, CEACAM-1, CEACAM-5, VISTA, BTLA, TIGIT, LAIR1, CD160, 2B4 and TGFR.

The use according to the above, wherein the antagonist of the immune checkpoint inhibitor is an anti-PD-L1 antibody.

The use according to any of the above, wherein the therapeutic agent is an additional anti-HBsAg antibody.

A nucleic acid that encodes the antibody or antigen binding fragment.

A vector comprising the nucleic acid.

A host cell comprising the vector.

A diagnostic reagent comprising the antibody or antigen binding fragment thereof, which is labeled.

The diagnostic reagent, wherein the label is selected from the group consisting of a radiolabel, a fluorophore, a chromophore, an imaging agent, and a metal ion.

Definitions

Unless stated otherwise, the following terms and phrases as used herein are intended to have the following meanings:

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementarity-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting in total about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, IMGT, and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Lefranc, M. P., Nucleic Acids Res., 29:207-209 (2001); Al-Lazikani et al., J. Mol. Biol., 273: 927-748 (1997)). Definitions of antigen combining sites are also described in the following: Ruiz et al., Nucleic Acids Res., 28:219-221 (2000); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HC CDR1), 50-65 (HC CDR2), and 95-102 (HC CDR3) in a VH, e.g., a mammalian VH, e.g., a human VH; and amino acid residues 24-34 (LC CDR1), 50-56 (LC CDR2), and 89-97 (LC CDR3) in a VL, e.g., a mammalian VL, e.g., a human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2, or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment," as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR, and bis-scFv (see, e.g., Hollinger and Hudson, Nature Biotechnology 23:1126-1136, 2005). Antigen binding fragments can be grafted into scaffolds based on polypeptides such as fibronectin type III(Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody," as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the disclosure specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)), or electron microscopy. A "paratope" is the part of the antibody which recognizes the epitope of the antigen.

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one aspect, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some aspects, antibodies or antibody fragments are selected that cross-react with certain desired molecules.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known or inferred variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91% 92%, 93%, 94%, 95%, 96%, 97%, 98%, 99%, or 100% sequence identity with the reference variable region nucleic acid or amino acid sequence.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically, a specific or selective binding reaction will produce a signal at least twice over the background signal and, more typically, at least 10 to 100 times over the background.

The term "equilibrium dissociation constant (KD, M)" refers to the dissociation rate constant (kd, time−1) divided by the association rate constant (ka, time−1, M−1). Equilibrium dissociation constants can be measured using any known method in the art. The antibodies of the present disclosure generally will have an equilibrium dissociation constant of less than about $10^{-7}$ or $10^{-8}$ M, for example, less than about $10^{-9}$ M or $10^{-10}$ M, in some aspects, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an anti-HBsAg antibody of the present disclosure. In some aspects, the phrase "consisting essentially of" expressly excludes the inclusion of one or more additional active agents other than an anti-HBsAg antibody of the present disclosure and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For example, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine(S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2: 482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as a basis for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, (Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, (J. Mol. Biol. 48:444-453, 1970), algorithm which has been incorporated into the GAP program in the GCG software package (available from University of South Florida), using either a BLOSUM 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "hepatitis B," "hepatitis B virus" or "HBV" refer to a member of the family Hepadnaviridae, genus *Orthohepadnavirus*. HBV is a double stranded DNA virus. The virus is divided into four major serotypes (adr, adw, ayr, ayw) based on HBsAg.

The term "Hepatitis B surface antigen," "HBsAg" or "HBVsAg" refers to a protein produced by Hepatitis B virus.

TABLE 1

| SEQ ID NO: | Name/ accession number | SEQUENCE |
|---|---|---|
| SEQ ID NO: 1 | HBsAg consensus | MENITSGFLGPLLVLQAGFFLLTRILTIPQ SLDSWWTSLNFLGGAPTCPGQNSQSPTSNH SPTSCPPTCPGYRWMCLRRFIIFLFILLLC LIFLLVLLDYQGMLPVCPLLPGSSTTSTGP CKTCTIPAQGTSMFPSCCCTKPSDGNCTCI PIPSSWAFAKFLWEWASARFSWLSLLVPFV QWFVGLSPTVWLSVIWMMWYWGPSLYNILS PFLPLLPIFFCLWVYI |
| SEQ ID NO: 2 | HBsAg Serotype ayr X04615.1 | MESTTSGFLGPLLVLQAGFFLLTRILTIPQ SLDSWWTSLNFLGGAPTCPGQNSQSPTSNH SPTSCPPTCPGYRWMCLRRFIIFLFILLLC LIFLLVLLDYQGMLPVCPLLPGTSTTSTGP CRTCTIPAQGTSMFPSCCCTKPSDGNCTCI PIPSSWAFARFLWEWASVRFSWLSLLVPFV QWFVGLSPTVWLSAIWMMWYWGPSLYNILS PFLPLLPIFFCLWVYI |
| SEQ ID NO: 3 | HBsAg Serotype adr AF068756.1 | MESTTSGFLGPLLVLQAGFFLLTRILTIPQ SLDSWWTSLNFLGGAPTCPGQNLQSPTSNH SPTSCPPICPGYRWMCLRRFIIFLFILLLC LIFLLVLLDYQGMLPVCPLLPGTSTTSTGP CKTCTIPAQGTSMFPSCCCTKPSDGNCTCI PIPSSWAFARFLWEWASVRFSWLSLLVPFV QWFVGLSPTVWLSVIWMMWYWGPSLYNILS PFLPLLPIFFCLWVYI |
| SEQ ID NO: 4 | HBsAg Serotype ayw AY661792.1 | MENITSGFLGPLLVLQAGFFLLTRILTIPQ SLDSWWTSLNFLGGTTVCLGQNSQSPTSNH SPTSCPPTCPGYRWMCLRRFIIFLFILLLC LIFLLVLLDYQGMLPVCPLIPGSSTTSTGP CRTCTTPAQGTSMYPSCCCTKPSDGNCTCI PIPSSWAFGKFLWEWASARFSWLSLLVPFV QWFVGLSPTVWLSVIWMMWYWGPSLYSILS PFLPLLPIFFCLWVYI |
| SEQ ID NO: 5 | HBsAg Serotype adw HM066946.2 | MENITSGLLGPLLVLQAVCFLLTKILTIPK SLDSWWTSLNFLGVPPGCPGQNSQSPISNH LPTSCPPTCPGYRWMCLRRFIIFLFILLLC LIFLLVLLDYQGMLPVCPLLPGSTTSTGP CKTCTTLAQGTSMFPSCCCTKPSDGNCTCI PIPSSWAFGKYLWEWASARFSWLSLLVQFV QWCVGLSPTVWLLVIWMIWYWGPNLCSILS PFIPLLPIFCYLWASI |

"IC50" (half-maximal inhibitory concentration) refers to the concentration of a particular antibody which induces a signal halfway (50%) between the baseline control and the maximum possible signal.

"EC50" (half-maximal effective concentration) refers to the concentration of a particular antibody which induces a response halfway (50%) between the baseline control and the maximum possible effect after a specific exposure or treatment time. For example, the EC50 is the concentration of antibody at which virus infection is neutralized by 50%.

"EC90" refers to the concentration of a particular antibody which induces a response corresponding to 90% of the maximum possible effect after a specific exposure or treatment time. For example, the EC90 is the concentration of antibody at which virus infection is neutralized by 90%.

"Neutralization" refers to the inhibition of viral infection of a host cell, as demonstrated by the absence of viral gene expression. Without being held to any one theory, mechanisms of neutralization by a particular antibody could include blocking the interaction of viral capsid proteins with cell surface receptors or disruption of any stage of the entry and trafficking process prior to delivery of the viral genome to the nucleus of the host cell.

As used herein, the terms "treat," "treating," or "treatment" of any disease or disorder refer in one aspect, to ameliorating the disease or disorder (i.e., slowing or arresting or reducing the development of the disease or at least one of the clinical symptoms thereof). In another aspect, "treat," "treating," or "treatment" refers to alleviating or ameliorating at least one physical parameter including those which may not be discernible by the patient. In yet another aspect, "treat," "treating," or "treatment" refers to modulating the disease or disorder, either physically, (e.g., stabilization of a discernible symptom), physiologically, (e.g., stabilization of a physical parameter), or both.

The phrase "reducing the likelihood" refers to delaying the onset or development or progression of the disease, infection or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of the molecules of the present disclosure can prevent the onset of, or result in a decrease in severity of, respectively, disease symptoms, including symptoms associated polyoma viral infection.

The term "co-administer" refers to the simultaneous presence of two active agents in the blood of an individual. Active agents that are co-administered can be concurrently or sequentially delivered.

BRIEF DESCRIPTION OF THE DRAWINGS

FIGS. 8A and 8B depict SPR/Biacore measurements of the NOV3834 antibody, showing the Kd for the AD and AY HBV serotypes.

FIGS. 10A and 10B depict SPR/Biacore measurements of the NOV3836 antibody, showing the Kd for the AD and AY HBV serotypes.

FIGS. 11A and 11B depict SPR/Biacore measurements of the NOV3837 antibody, showing the Kd for the AD and AY HBV serotypes.

FIGS. 12A and 12B depict SPR/Biacore measurements of the NOV3838 antibody, showing the Kd for the AD and AY HBV serotypes.

FIGS. 13A and 13B depict SPR/Biacore measurements of the NOV3839 antibody, showing the Kd for the AD and AY HBV serotypes.

FIGS. 14A and 14B depict SPR/Biacore measurements of the NOV3840 antibody, showing the Kd for the AD and AY HBV serotypes.

DETAILED DESCRIPTION

Figures 1A, 1B:
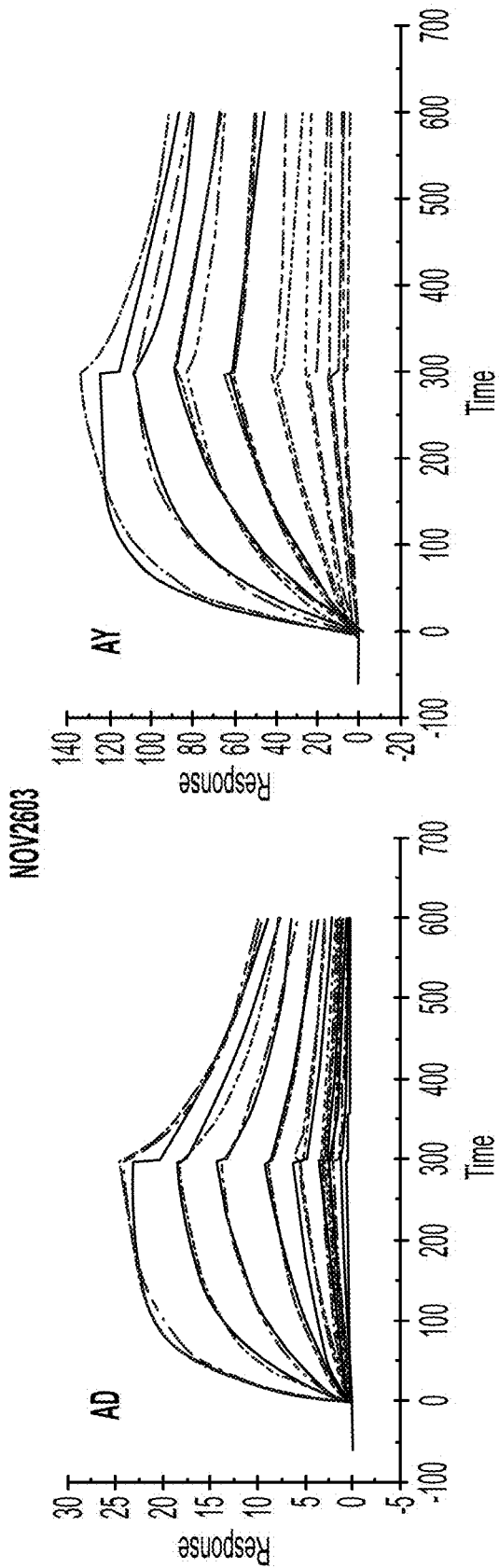
FIGS. 1A and 1B depict surface plasmon resonance (SPR/Biacore) measurements of the NOV2603 antibody, showing the Kd for the AD and AY HBV serotypes.
Figures 2A, 2B:
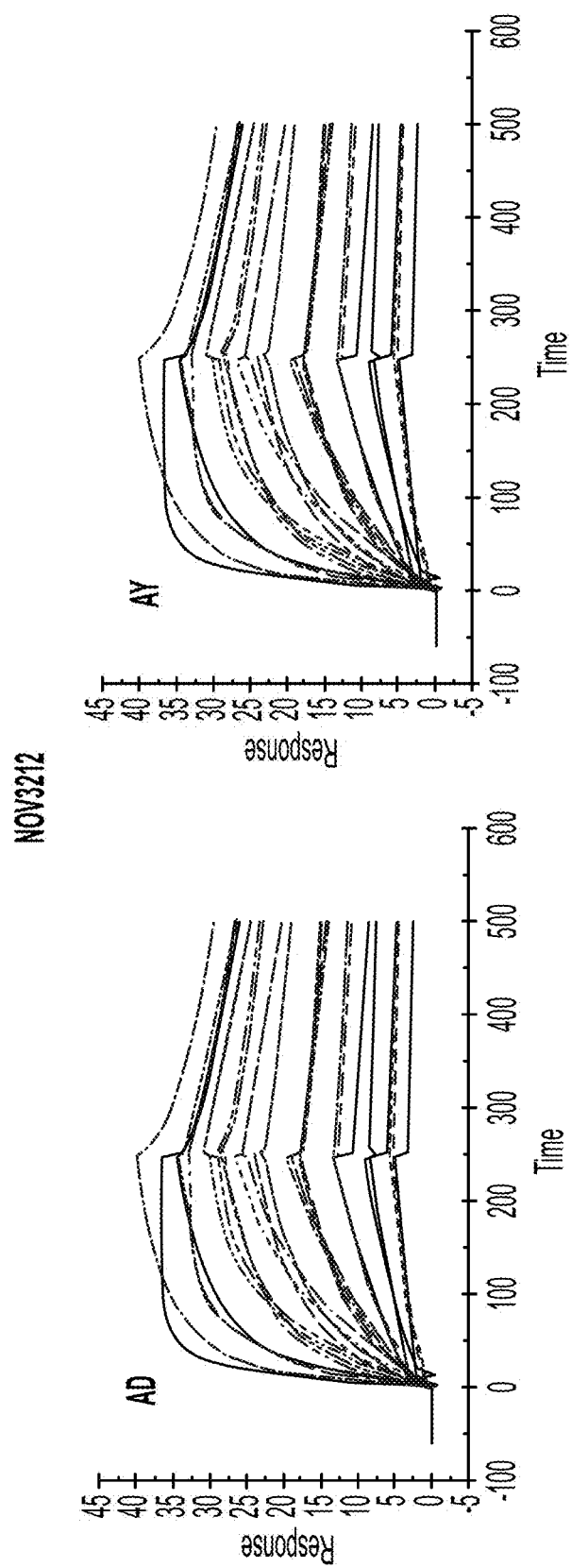
FIGS. 2A and 2B depict SPR/Biacore measurements of the NOV3212 antibody, showing the Kd for the AD and AY HBV serotypes.
Figures 3A, 3B:
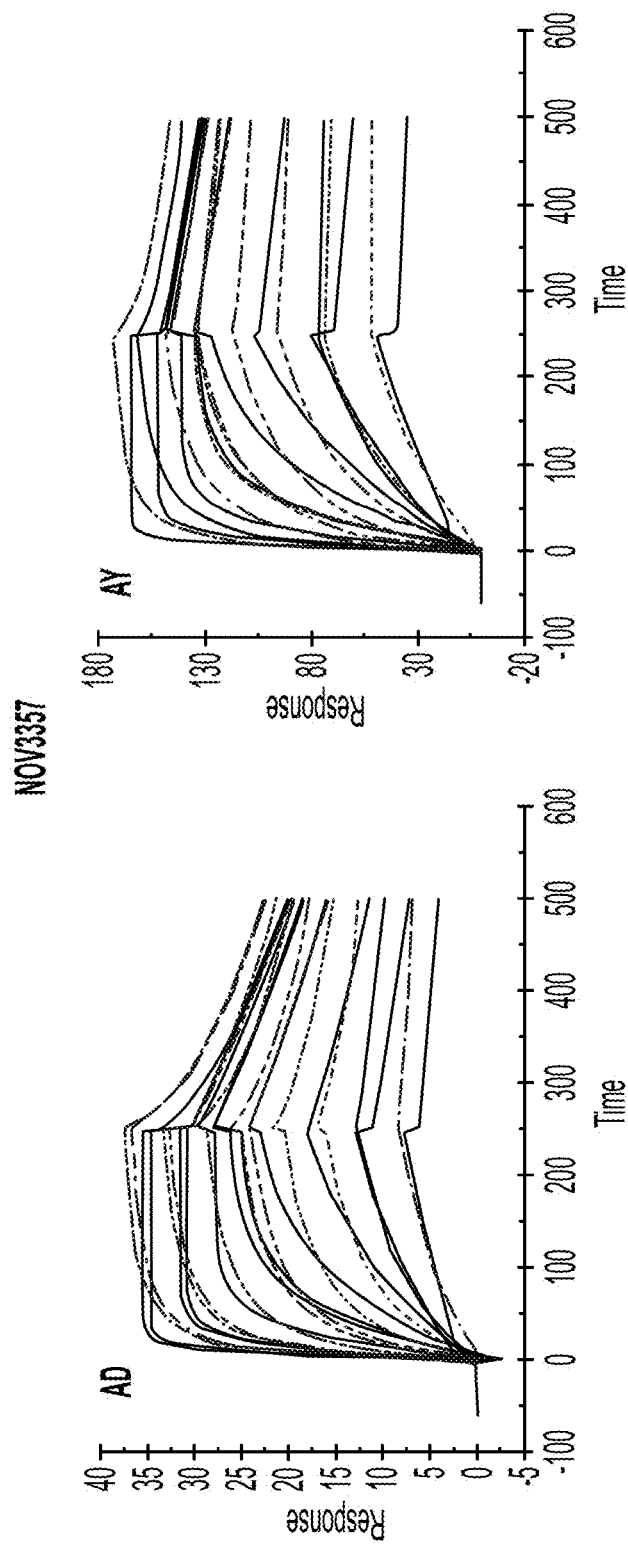
FIGS. 3A and 3B depict SPR/Biacore measurements of the NOV3357 antibody, showing the Kd for the AD and AY HBV serotypes.
Figures 4A, 4B:
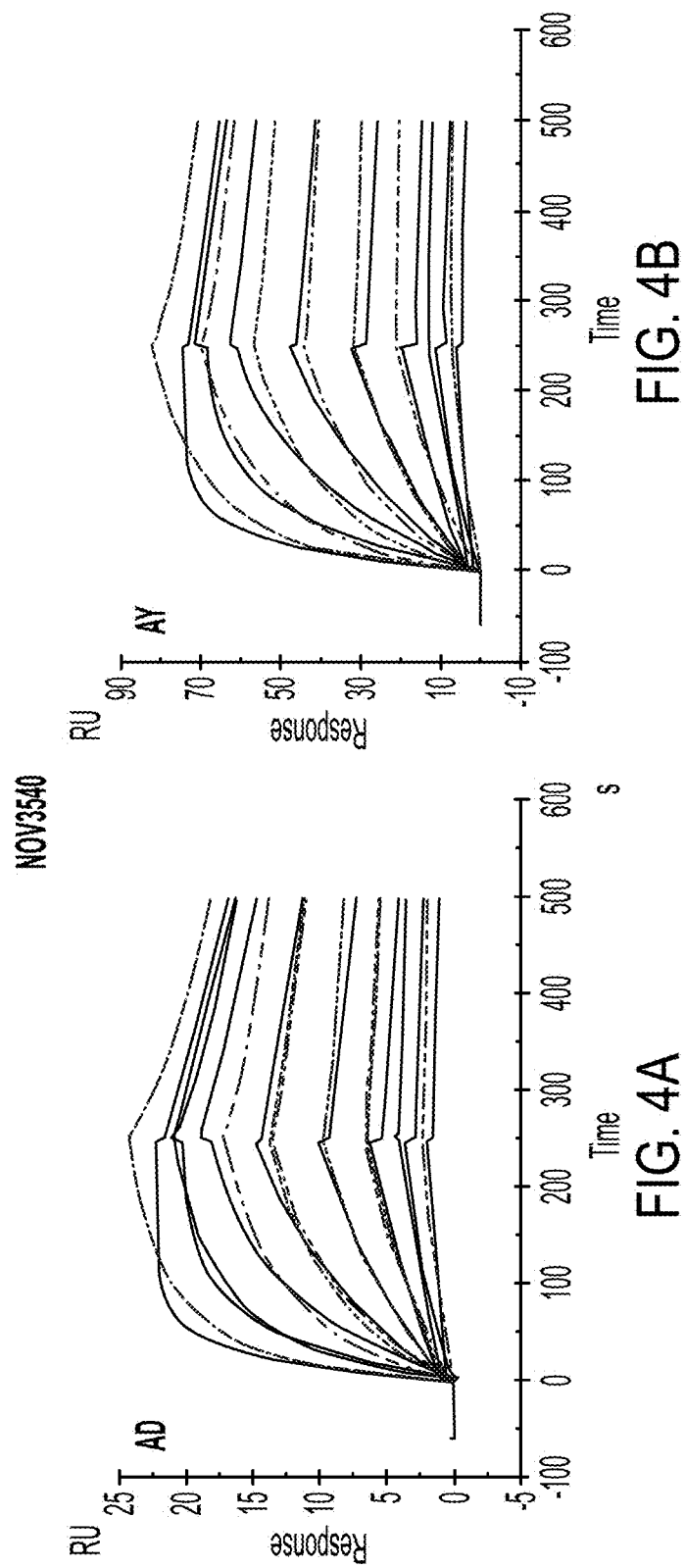
FIGS. 4A and 4B depict SPR/Biacore measurements of the NOV3540 antibody, showing the Kd for the AD and AY HBV serotypes.
Figures 5A, 5B:
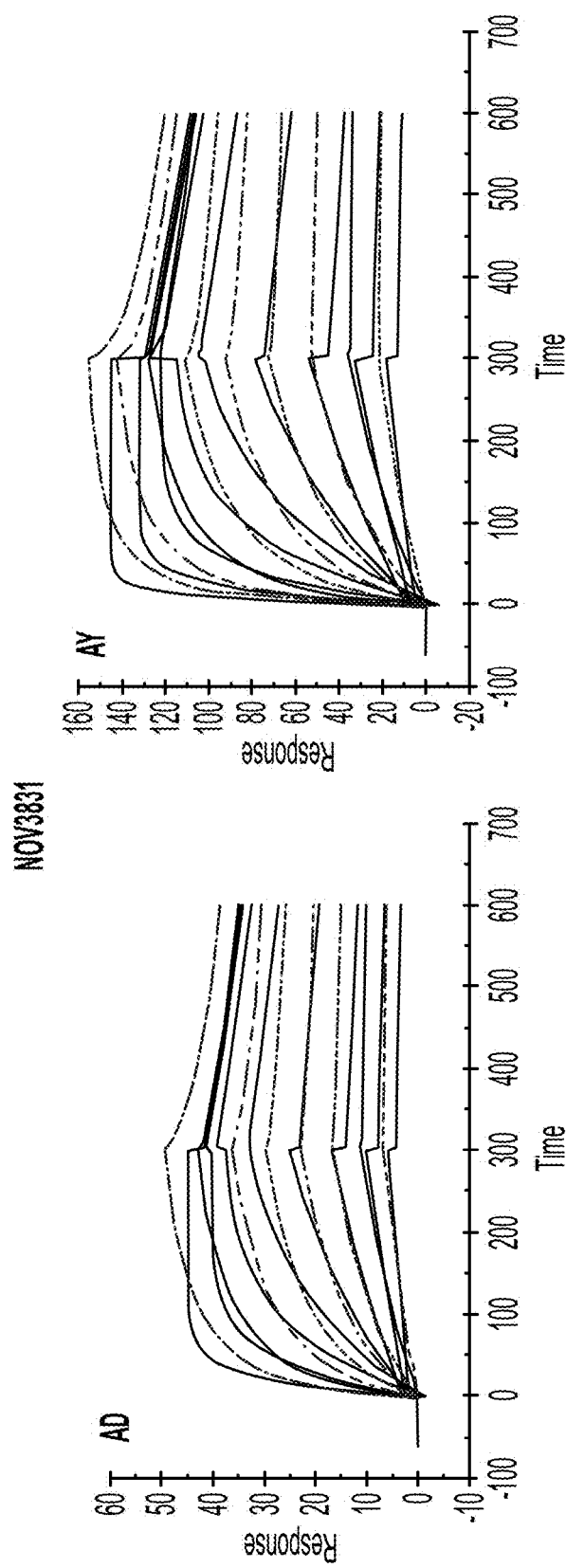
FIGS. 5A and 5B depict SPR/Biacore measurements of the NOV3831 antibody, showing the Kd for the AD and AY HBV serotypes.
Figures 6A, 6B:
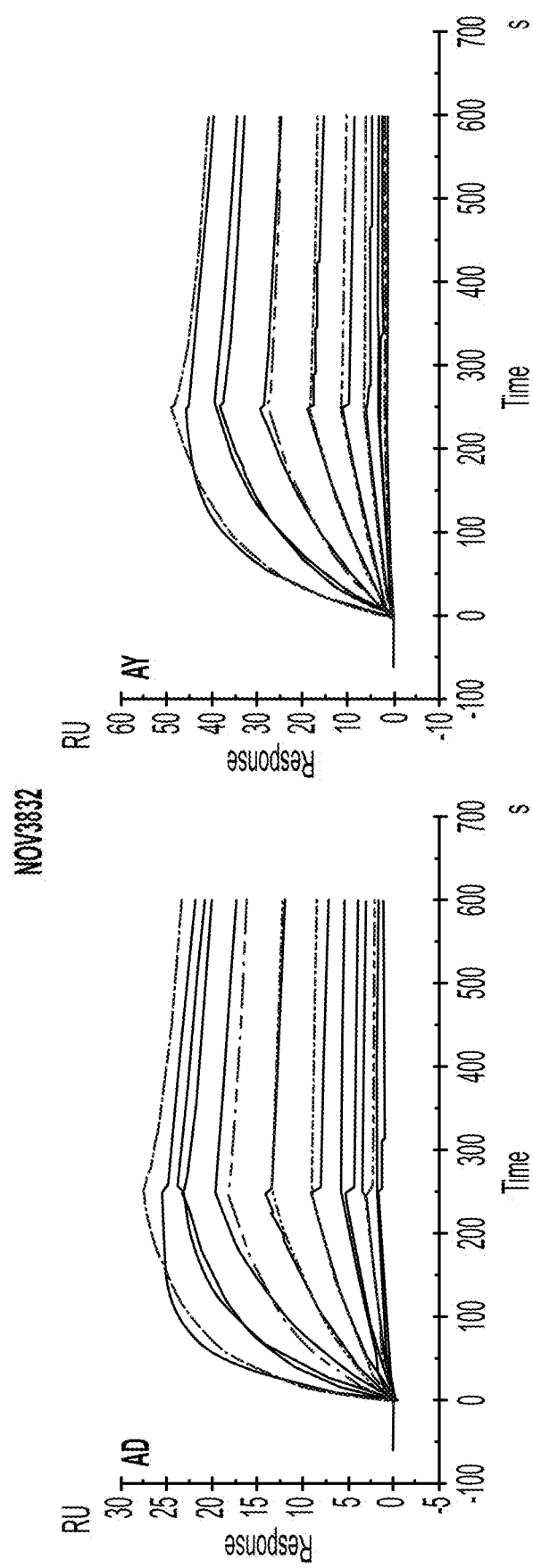
FIGS. 6A and 6B depict SPR/Biacore measurements of the NOV3832 antibody, showing the Kd for the AD and AY HBV serotypes.
Figures 7A, 7B:
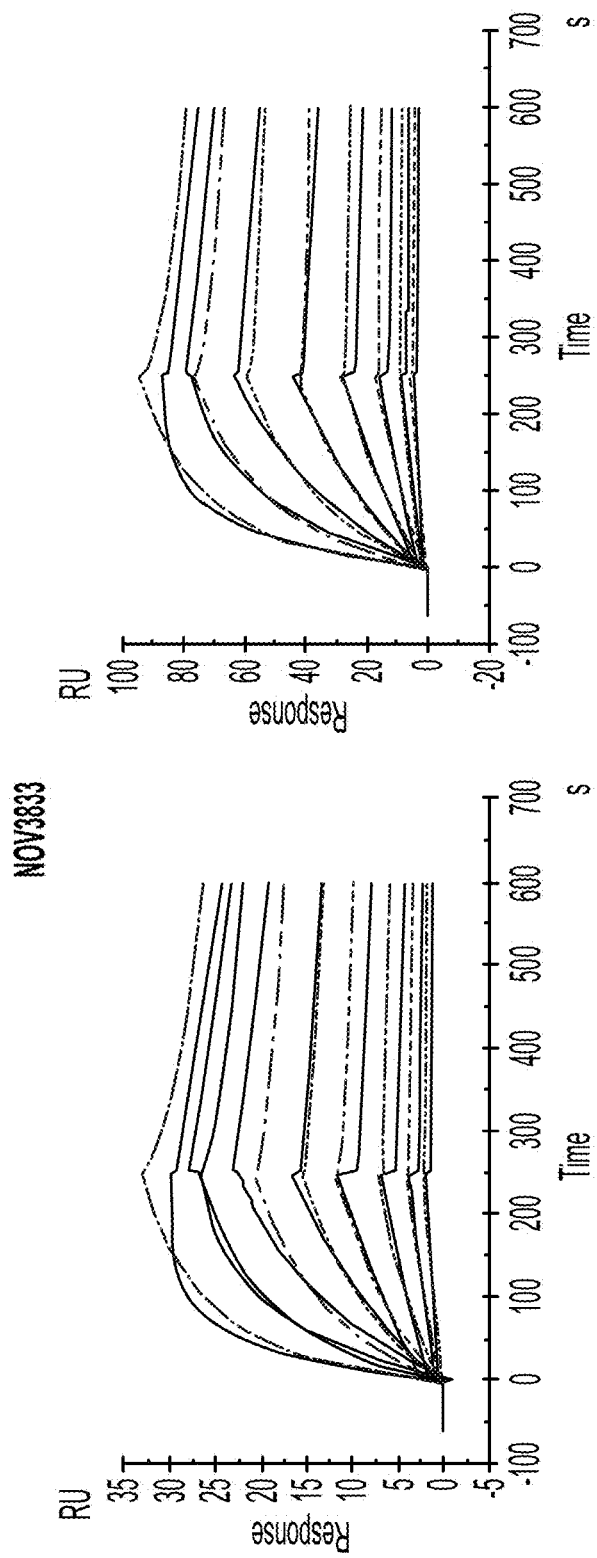
FIGS. 7A and 7B depict SPR/Biacore measurements of the NOV3833 antibody, showing the Kd for the AD and AY HBV serotypes.
Figures 9A, 9B:
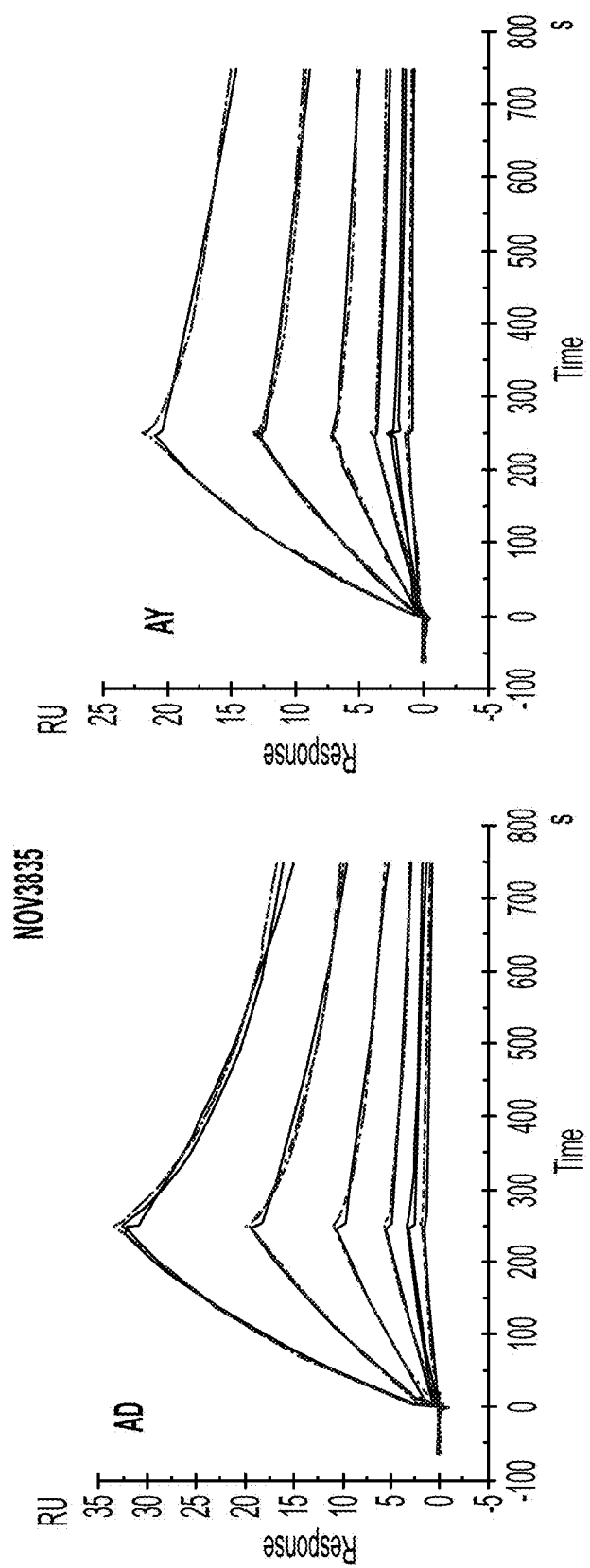
FIGS. 9A and 9B depict SPR/Biacore measurements of the NOV3835 antibody, showing the Kd for the AD and AY HBV serotypes.
Figure 15A:
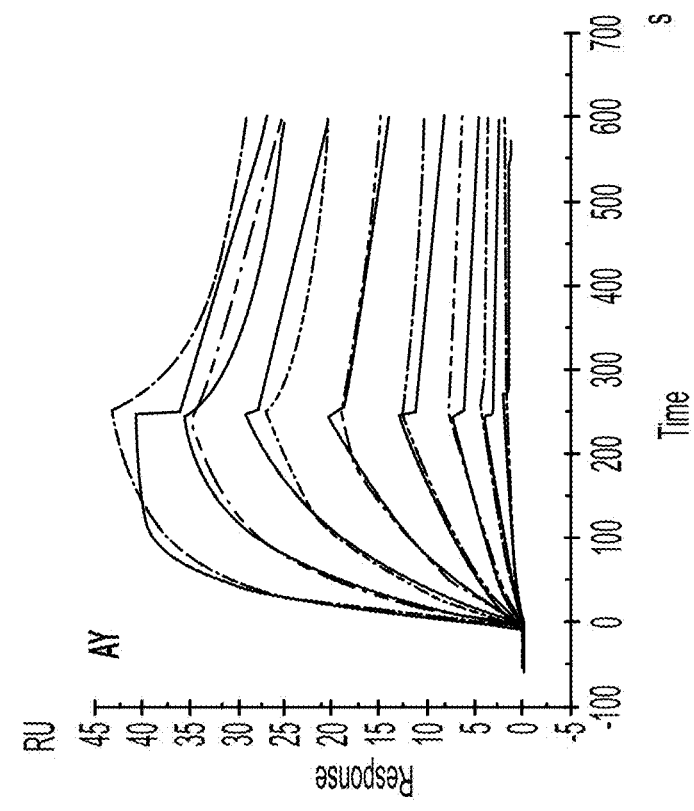
FIGS. 15A and 15B depict SPR/Biacore measurements of the NOV3841 antibody, showing the Kd for the AD and AY HBV serotypes.
Figure 15B:
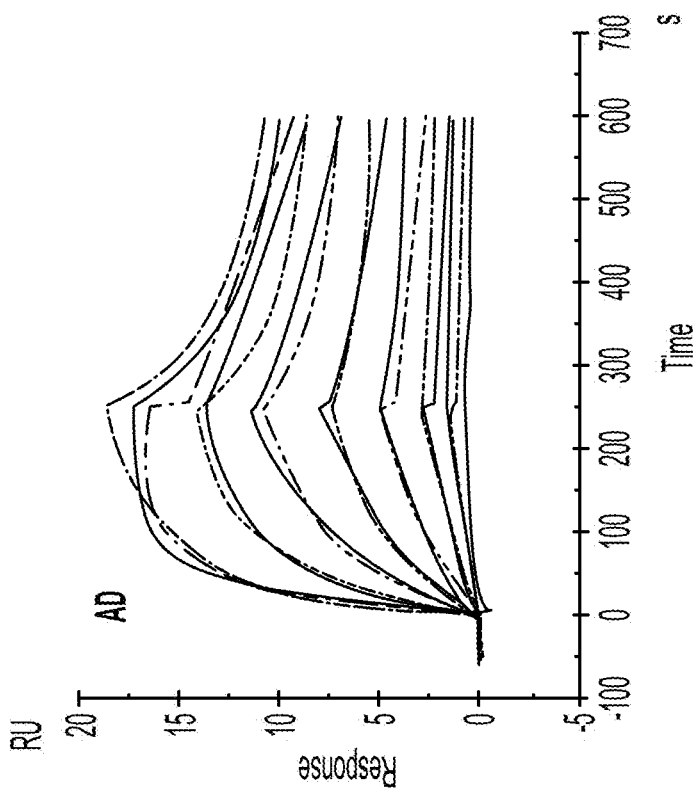
Figures 16A, 16B:
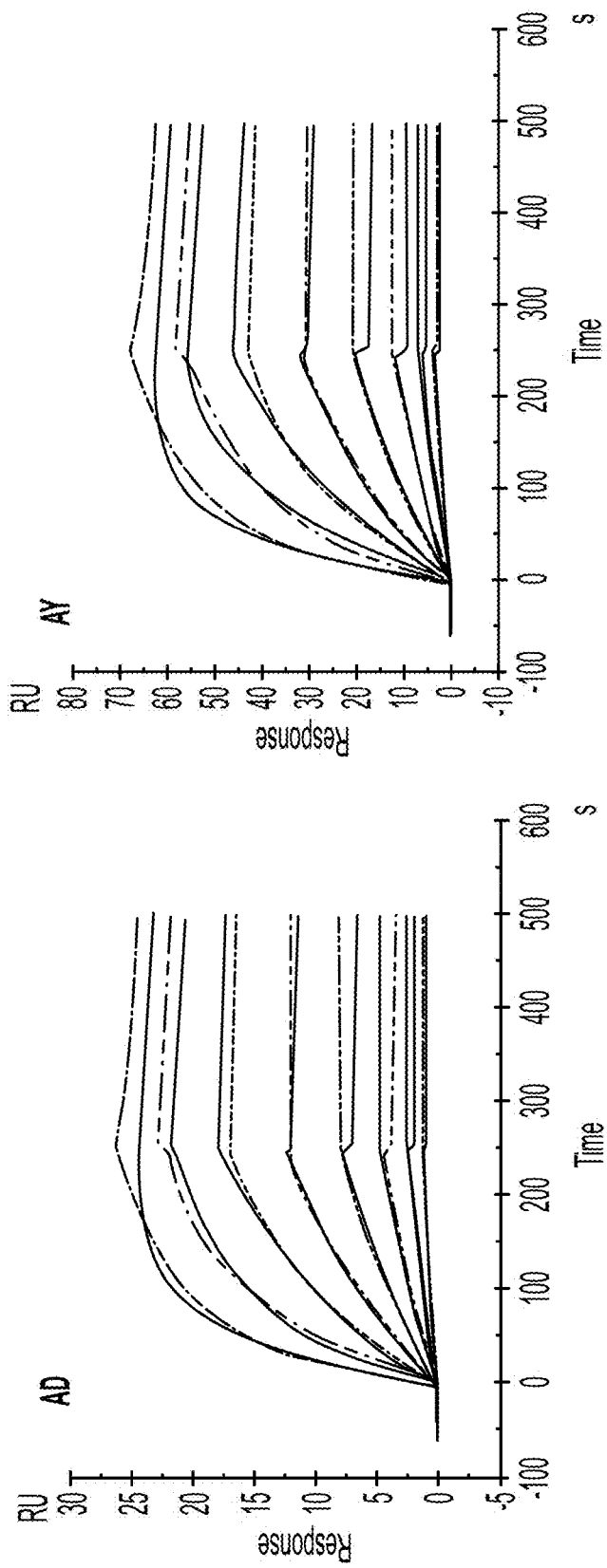
FIGS. 16A and 16B depict SPR/Biacore measurements of the NOV3842 antibody, showing the Kd for the AD and AY HBV serotypes.
Figure 17:
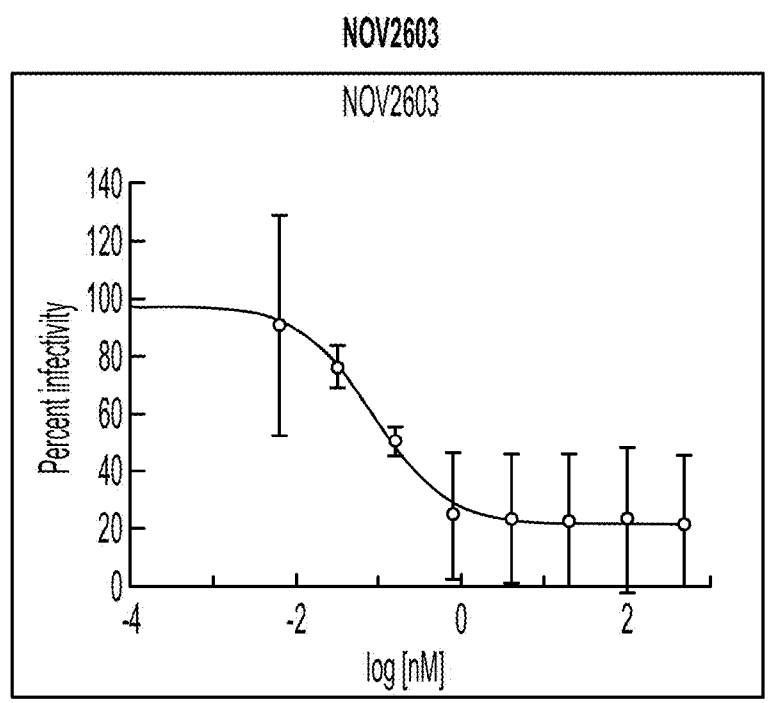
FIGS. 17-33 demonstrates that the antibodies neutralize HBV infection.
Figure 18:
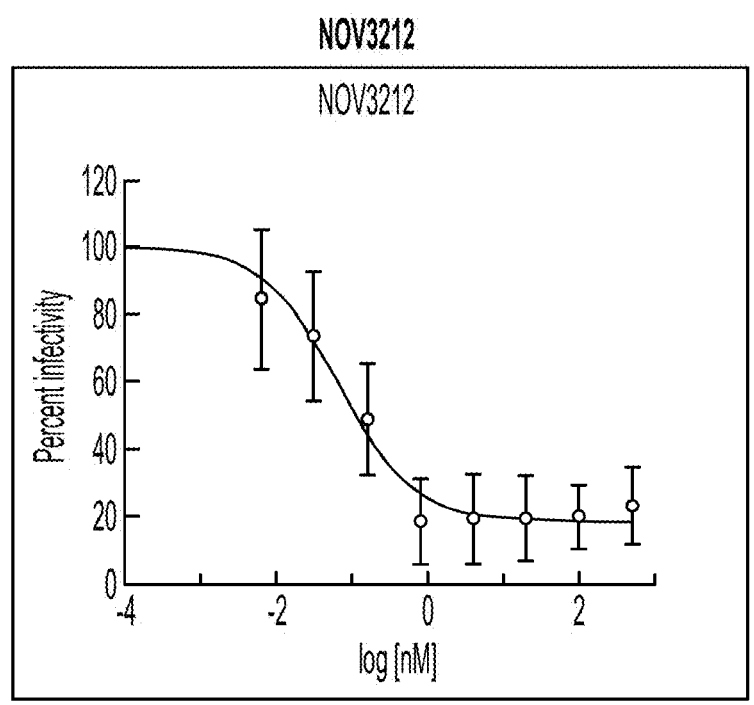
Figure 19:
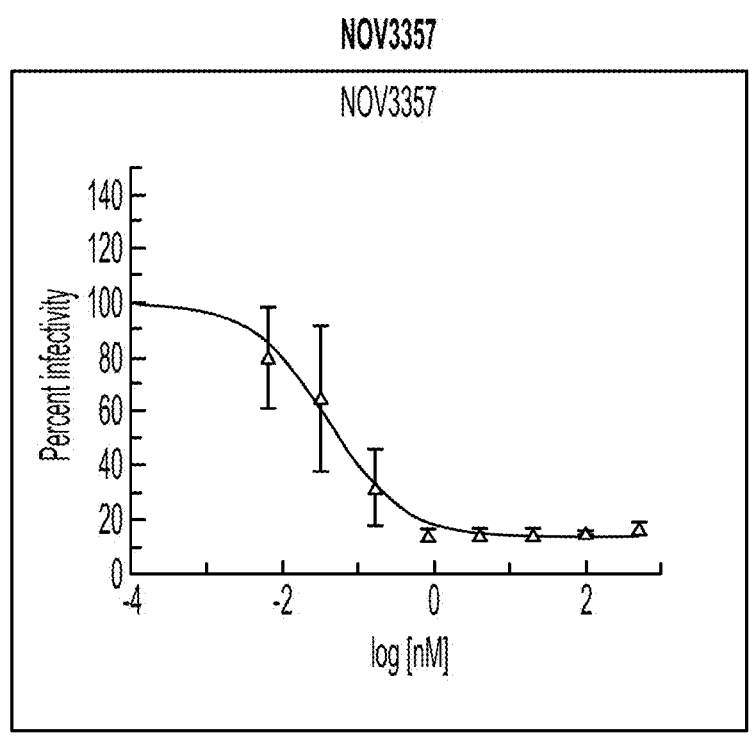
Figure 20:
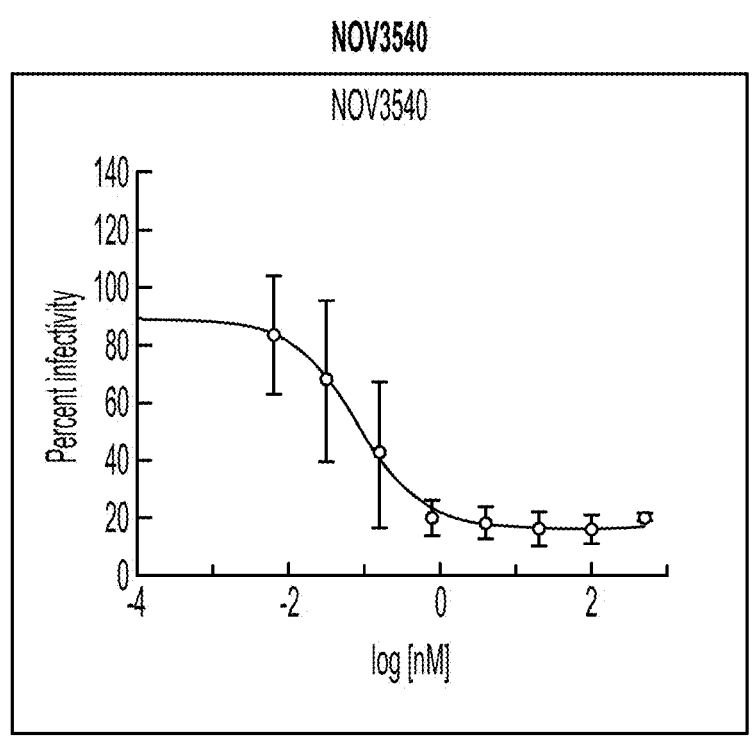
Figure 21:
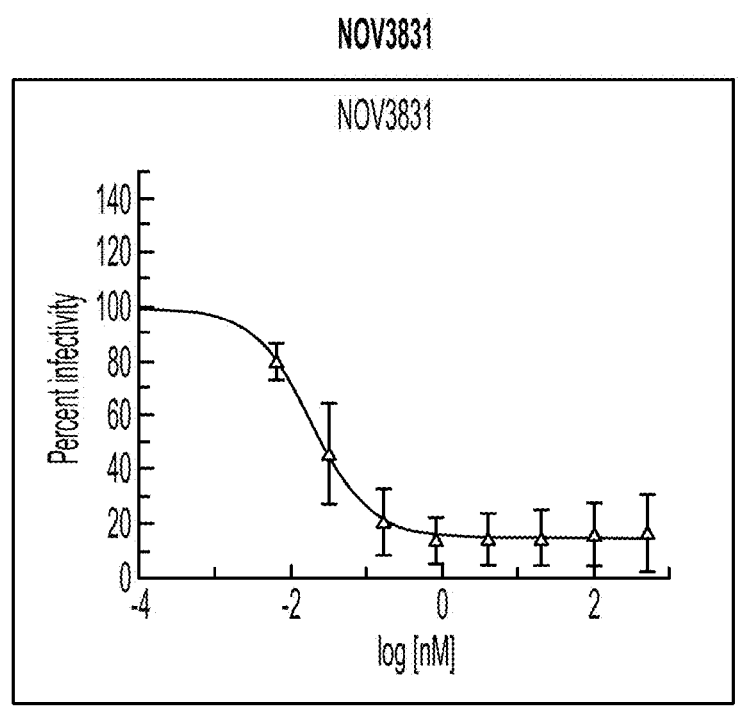
Figure 22:
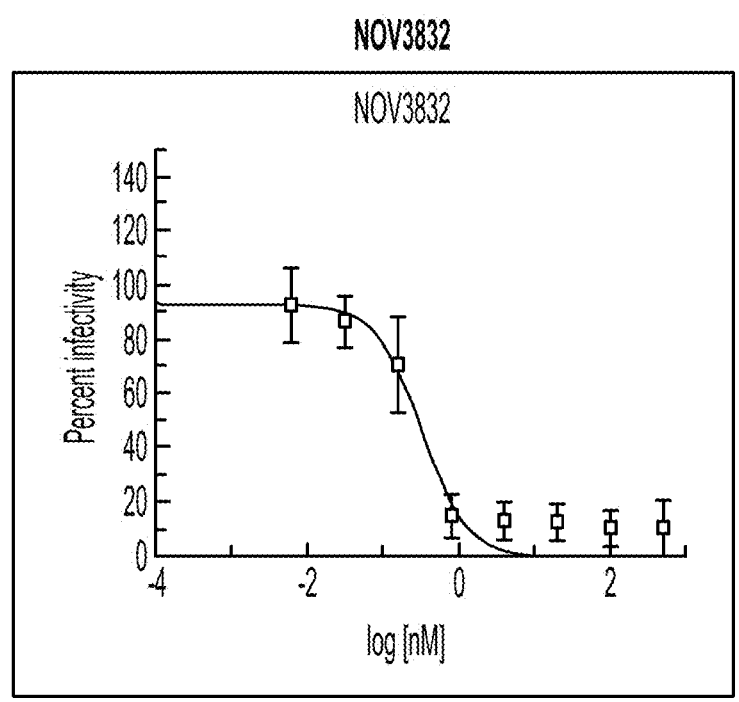
Figure 23:
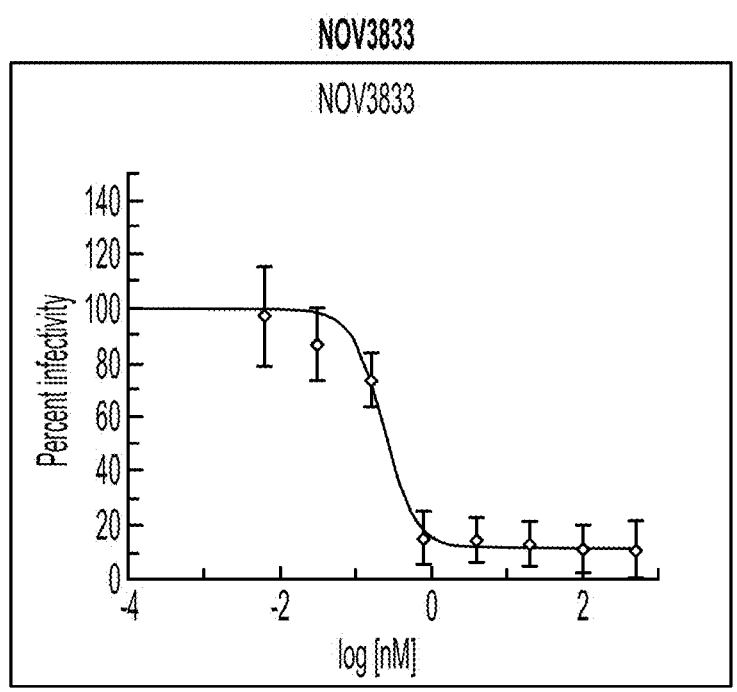
Figure 24:
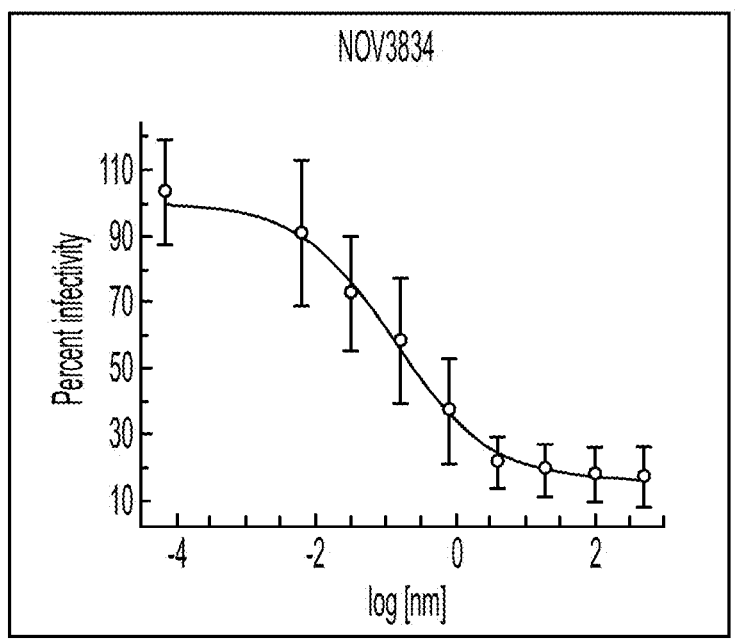
Figure 25:
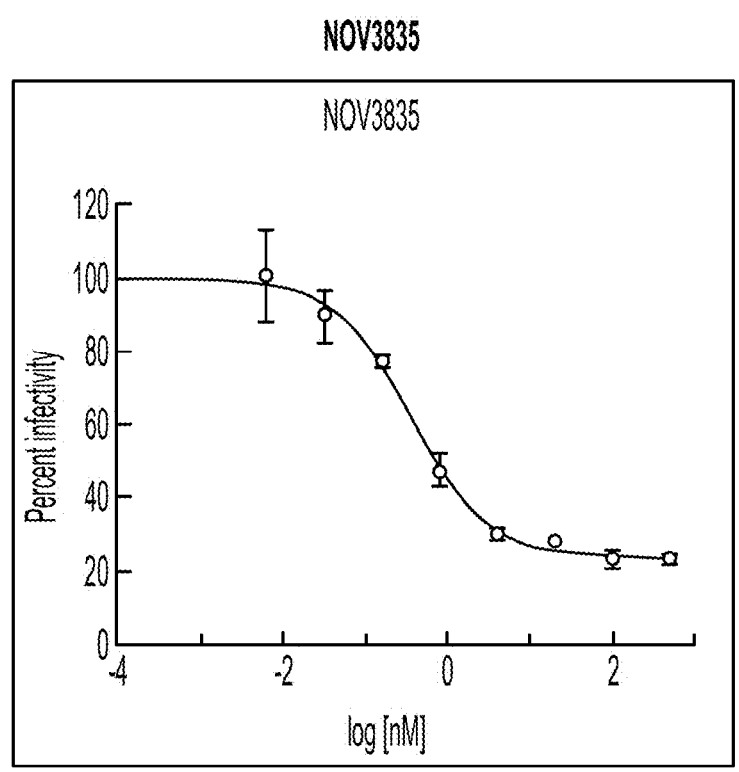
Figure 26:
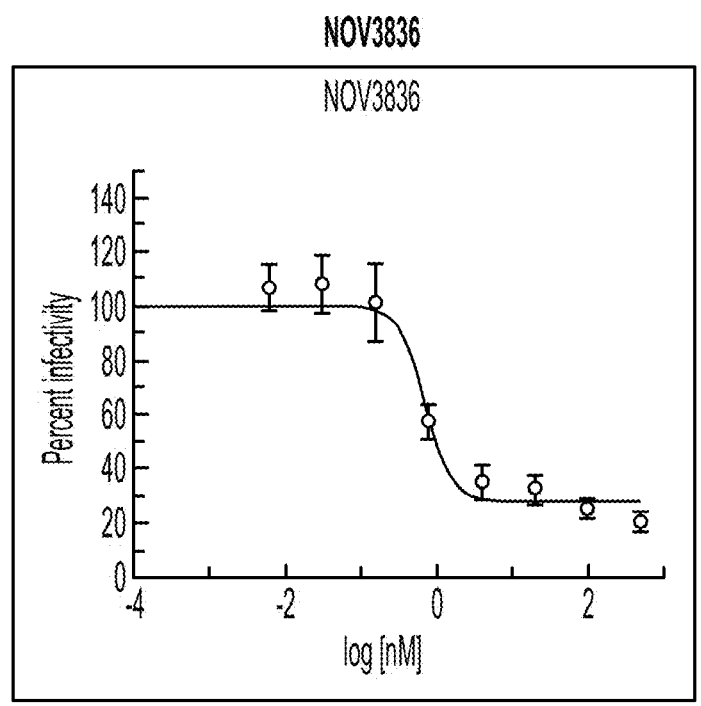
Figure 27:
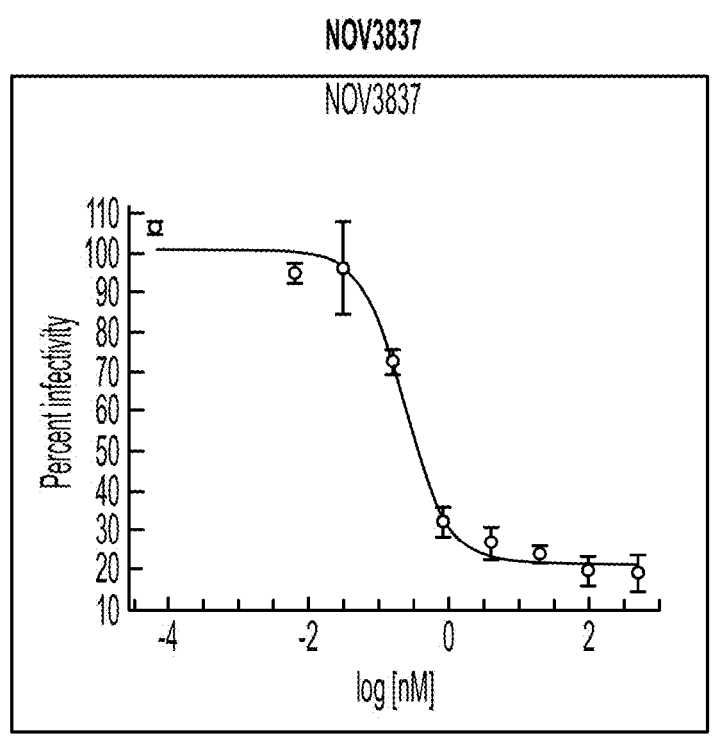
Figure 28:
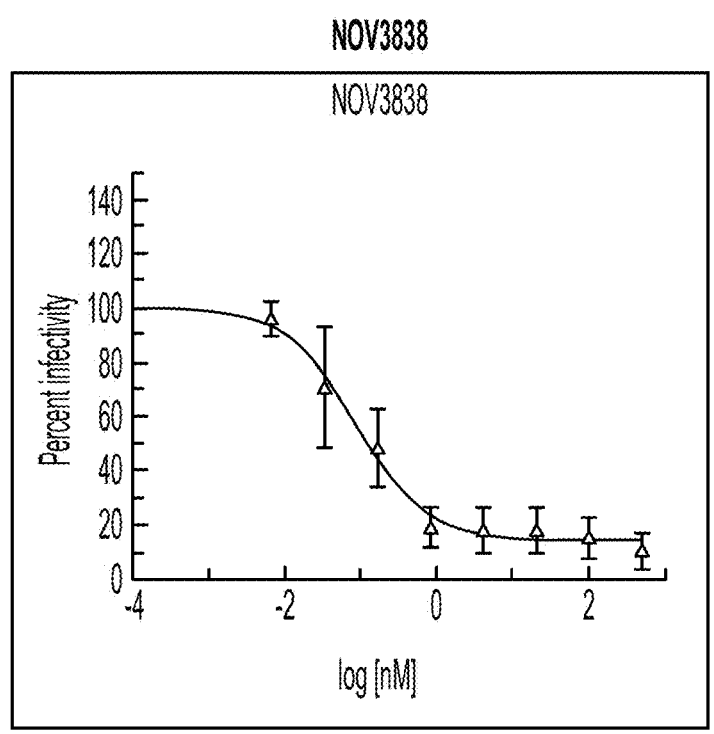
Figure 29:
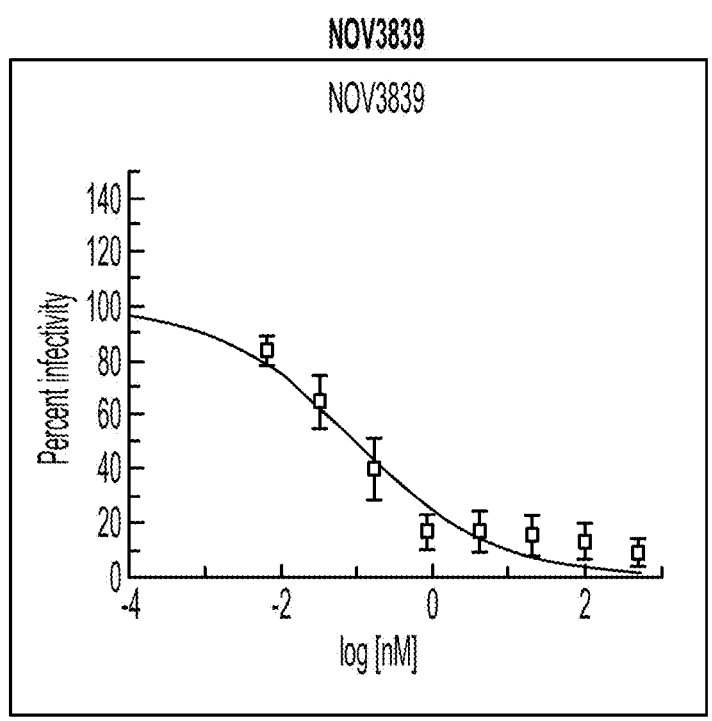
Figure 30:
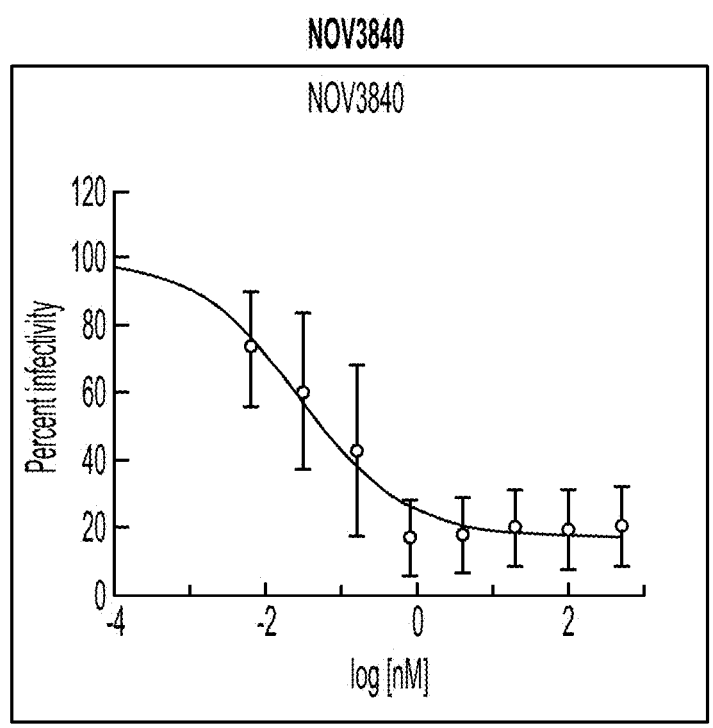
Figure 31:
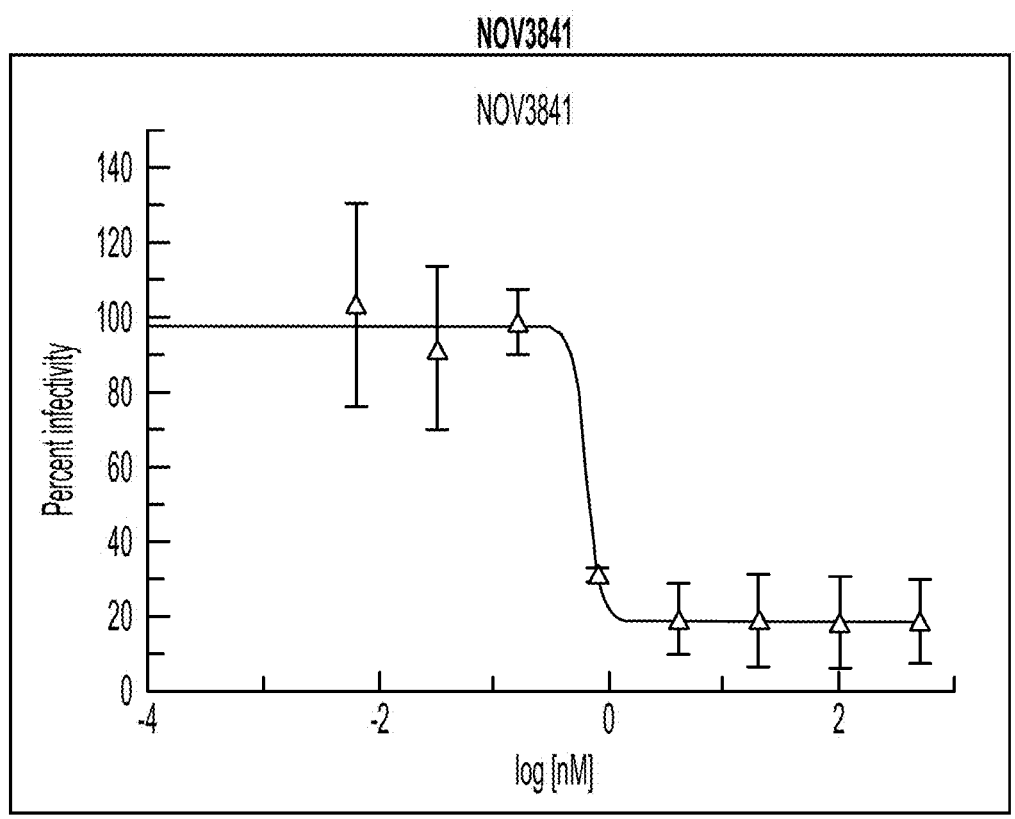
Figure 32:
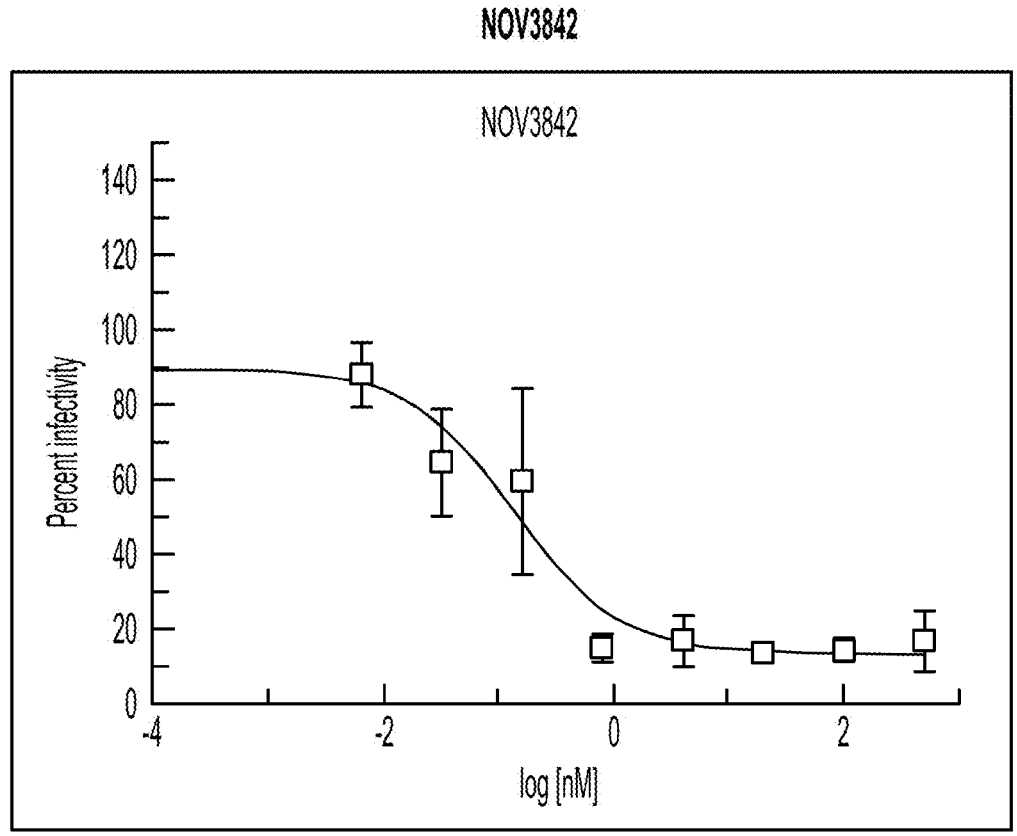
Figure 33:
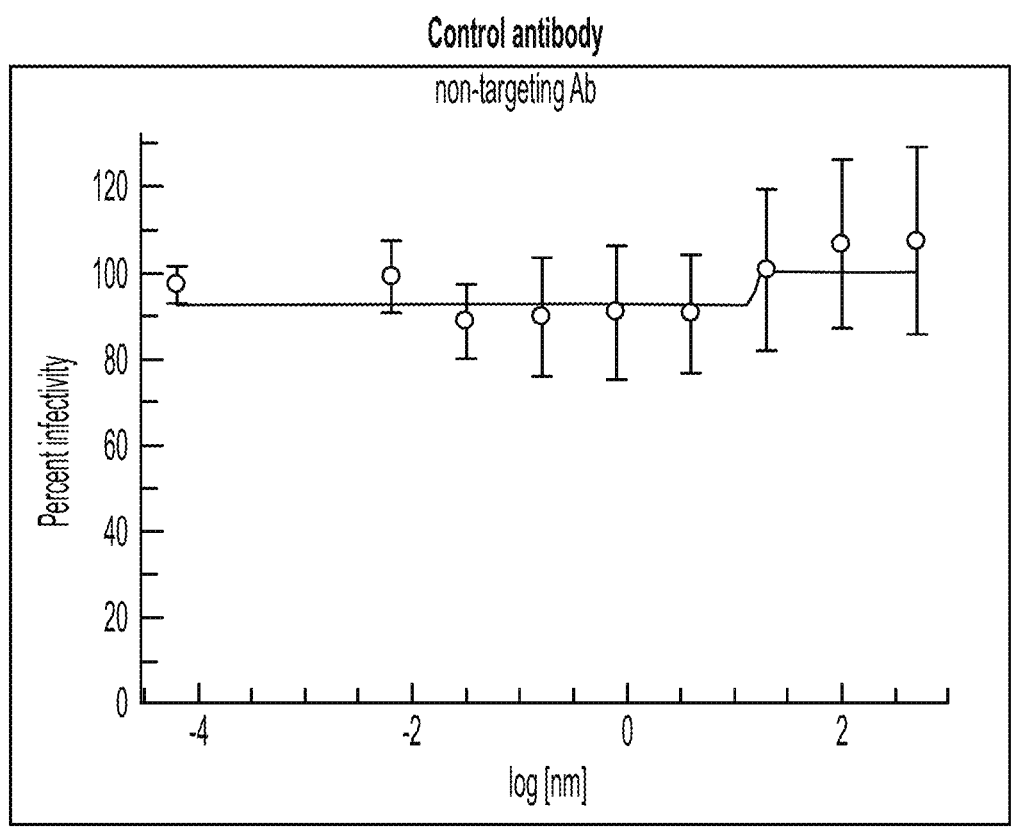
Figure 34:
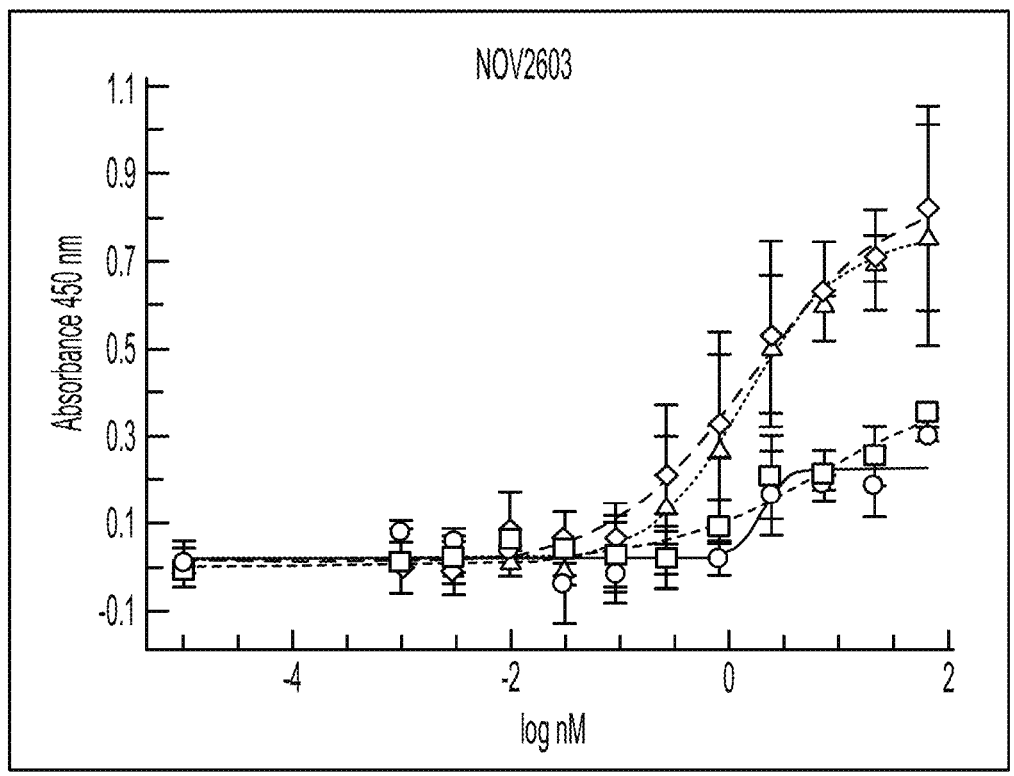
FIGS. 34-50 shows the $IC_{50}$ of the antibodies to four genotypes (A-D).
Figure 35:
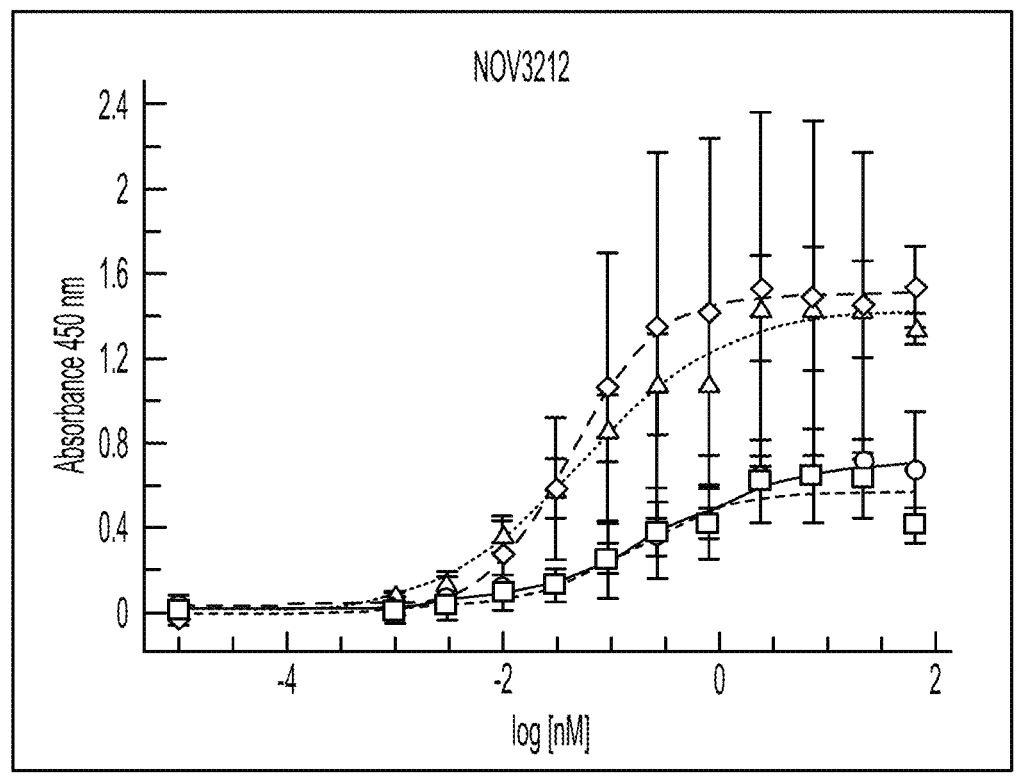
Figure 36:
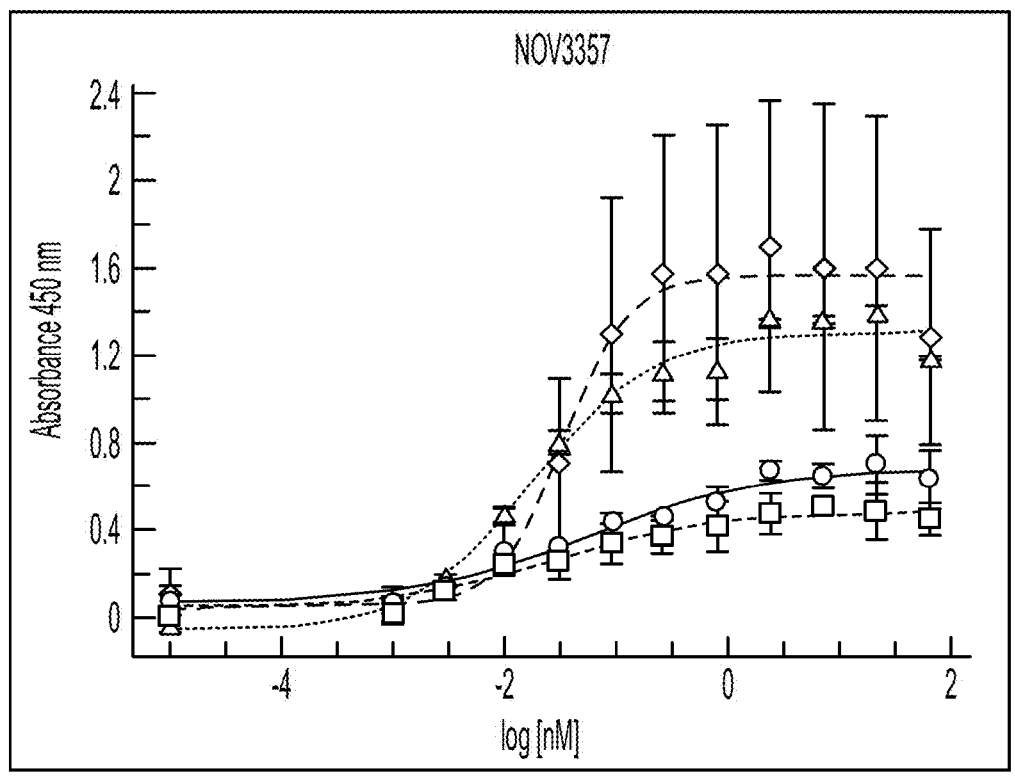
Figure 37:
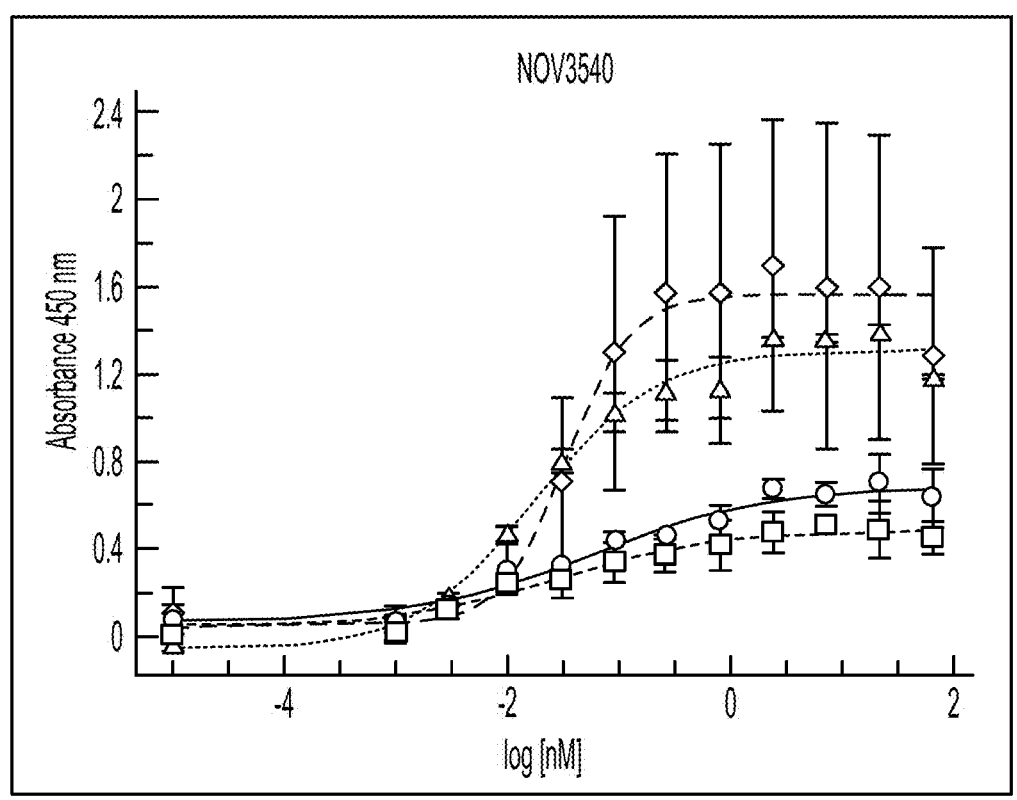
Figure 38:
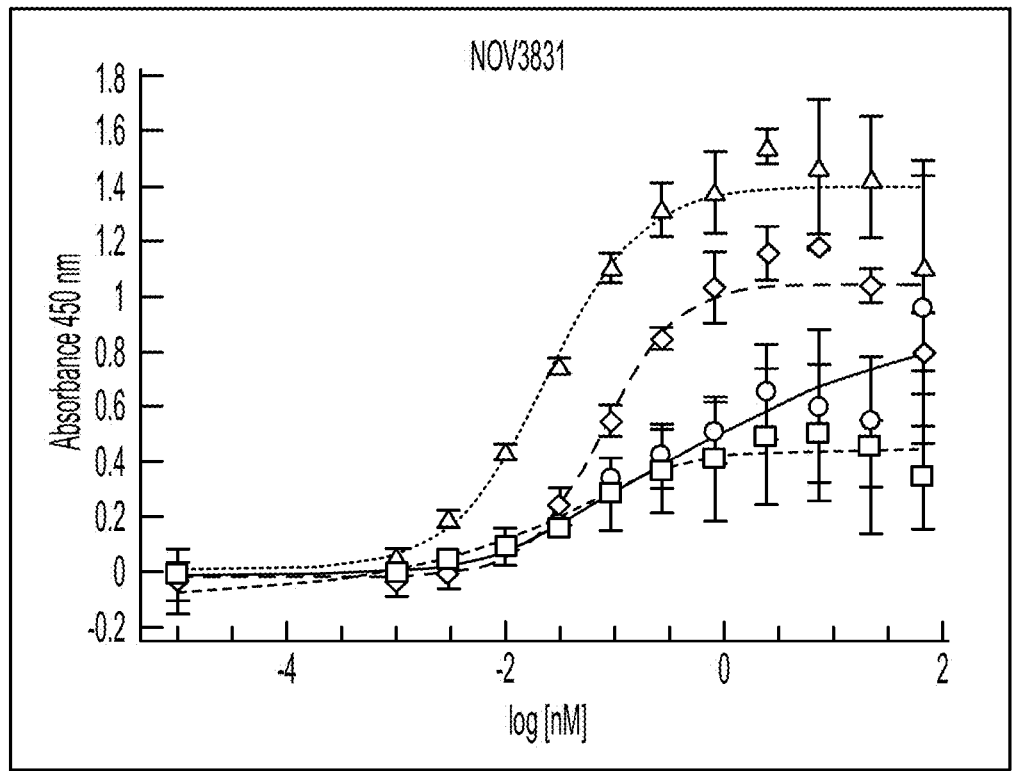
Figure 39:
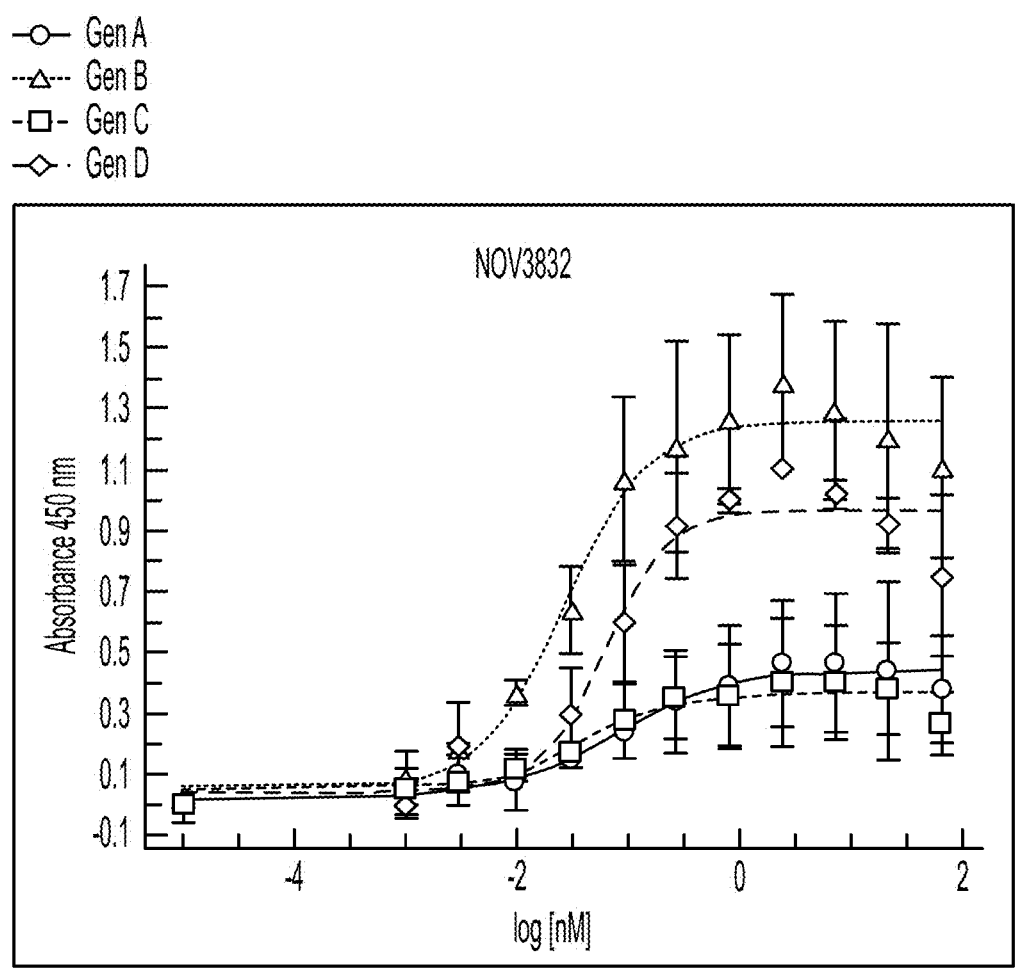
Figure 40:
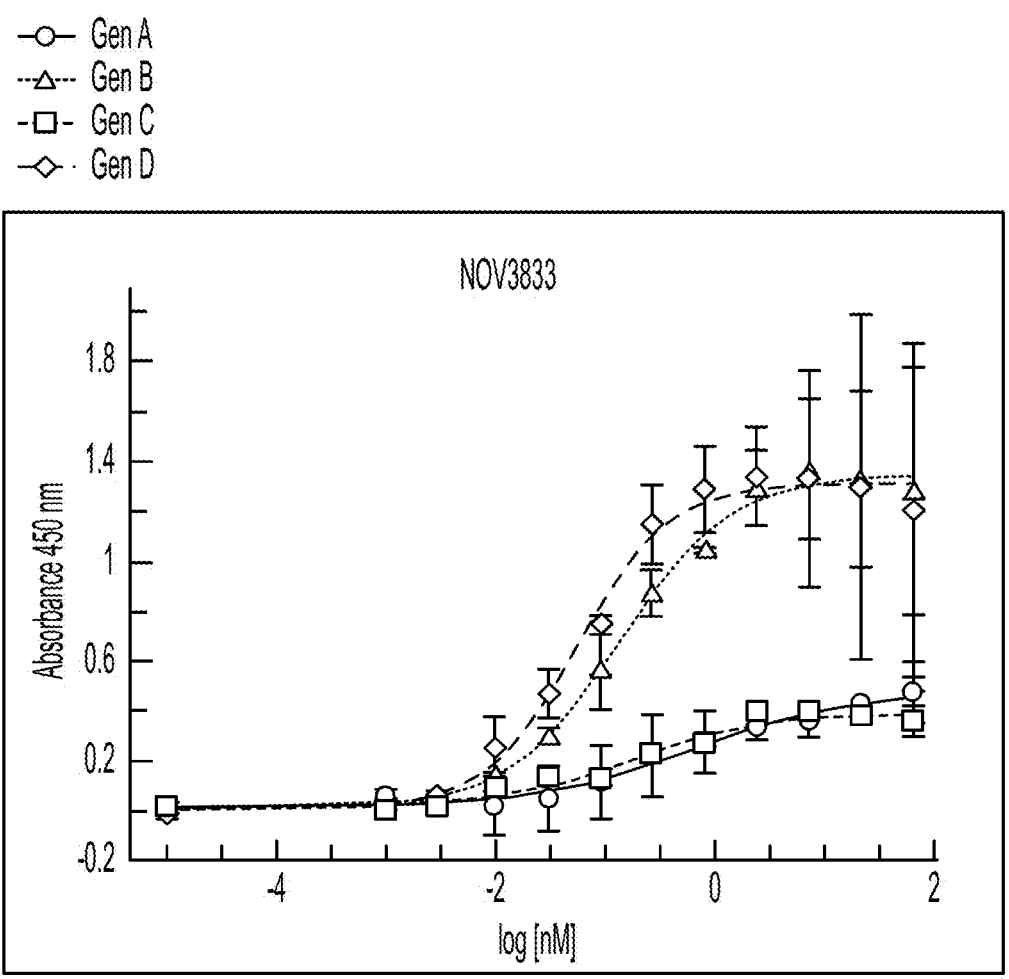
Figure 41:
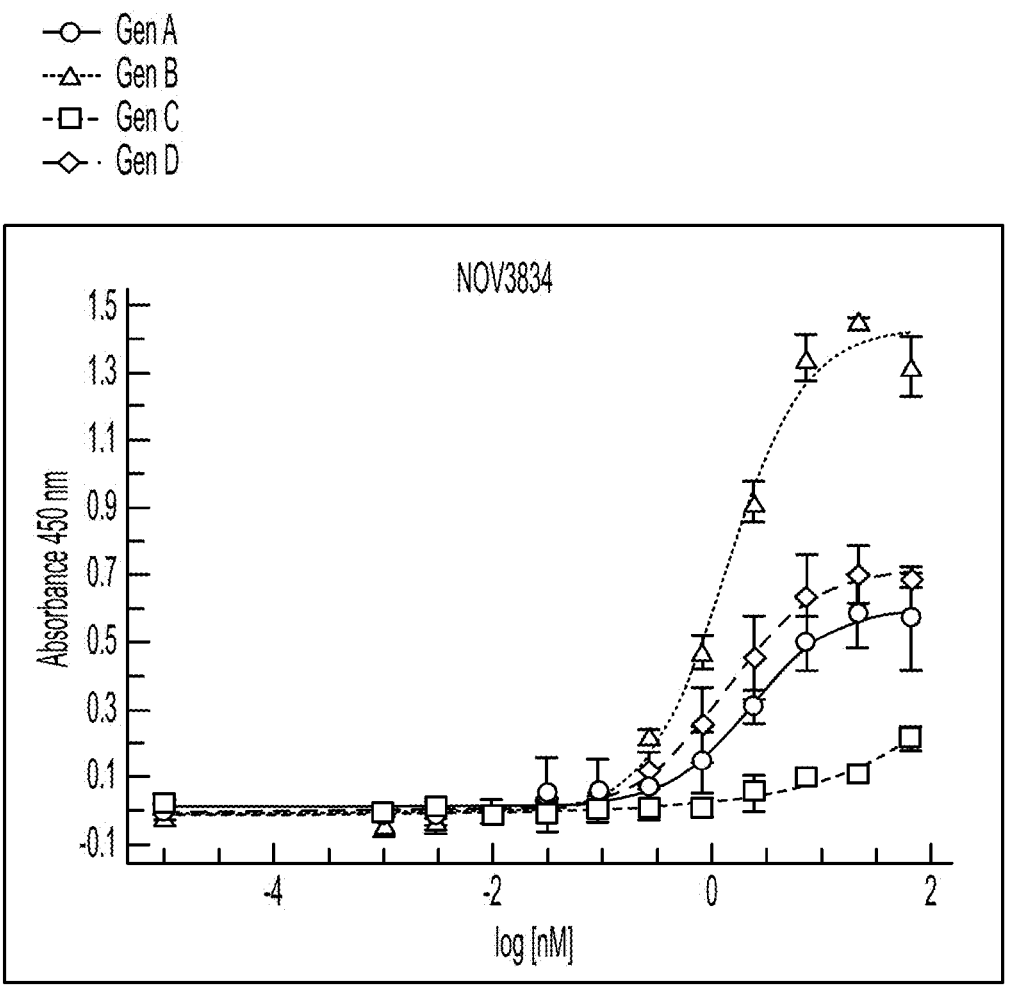
Figure 42:
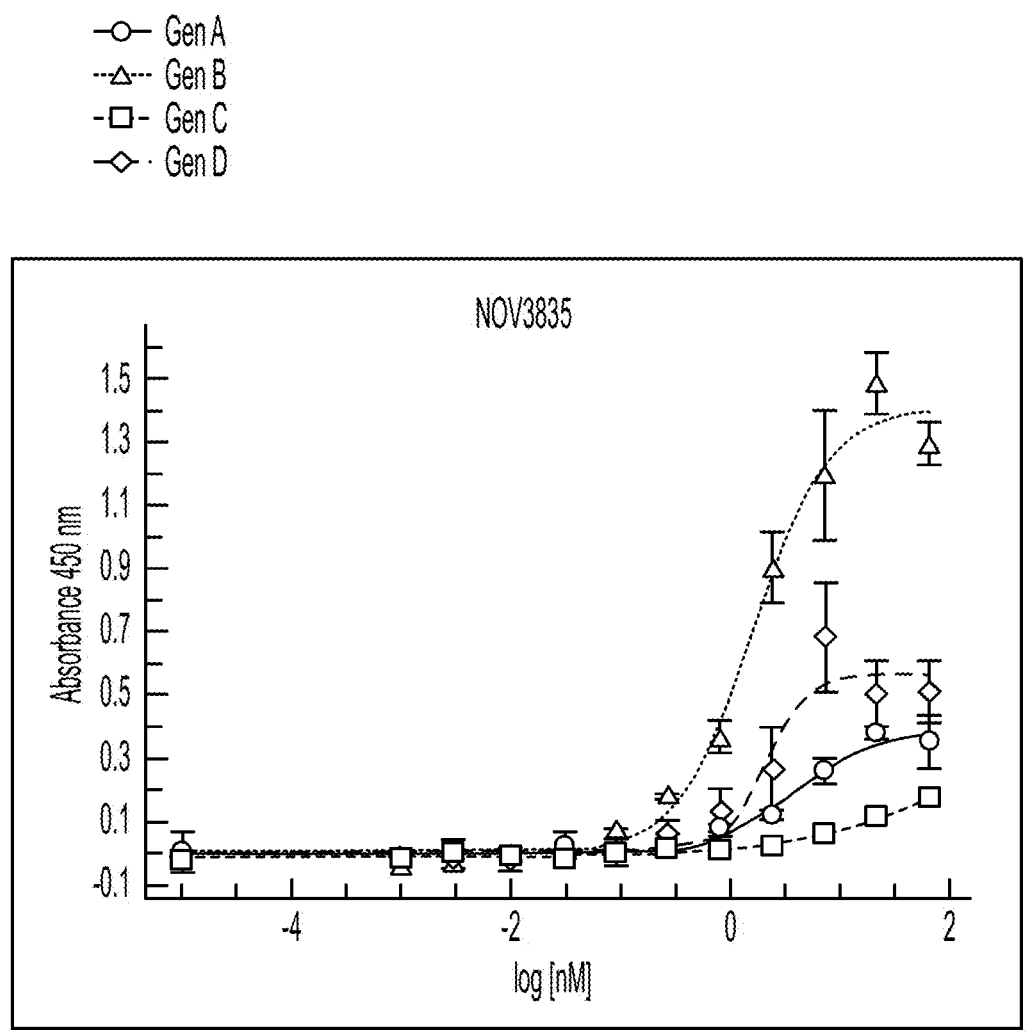
Figure 43:
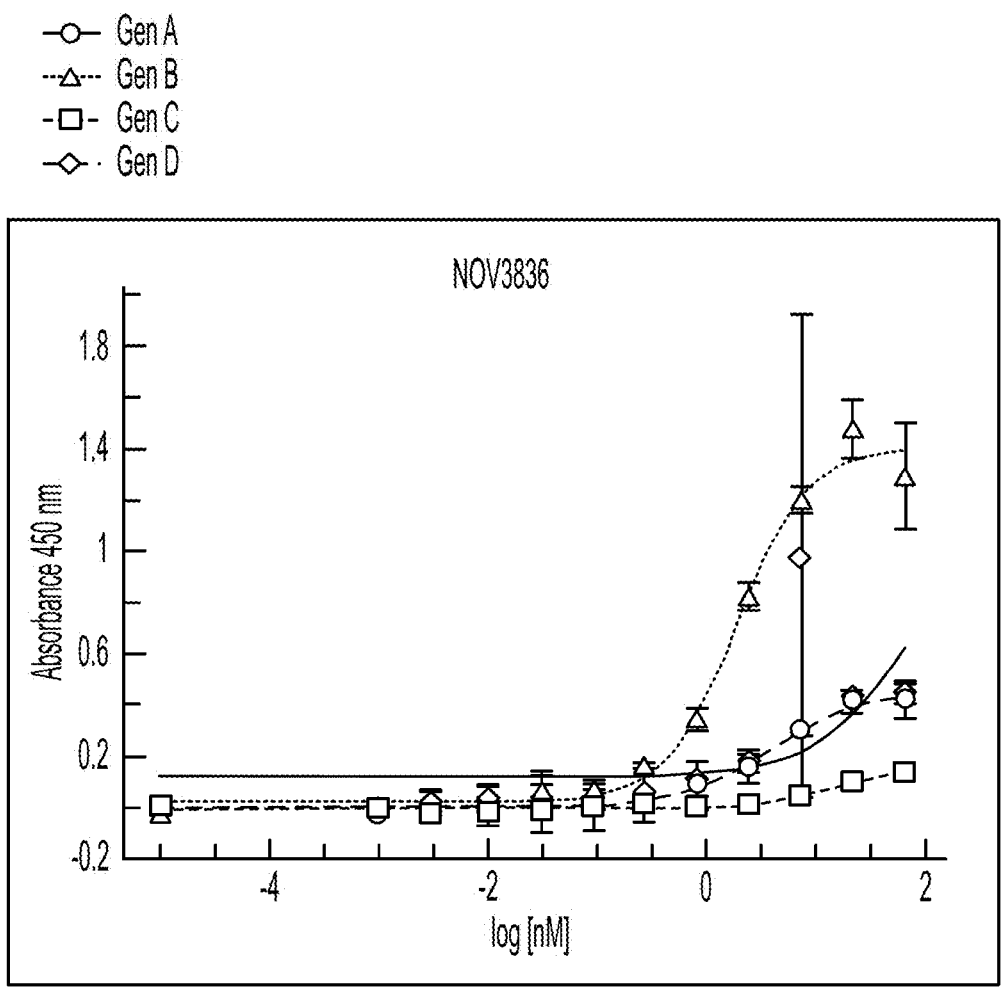
Figure 44:
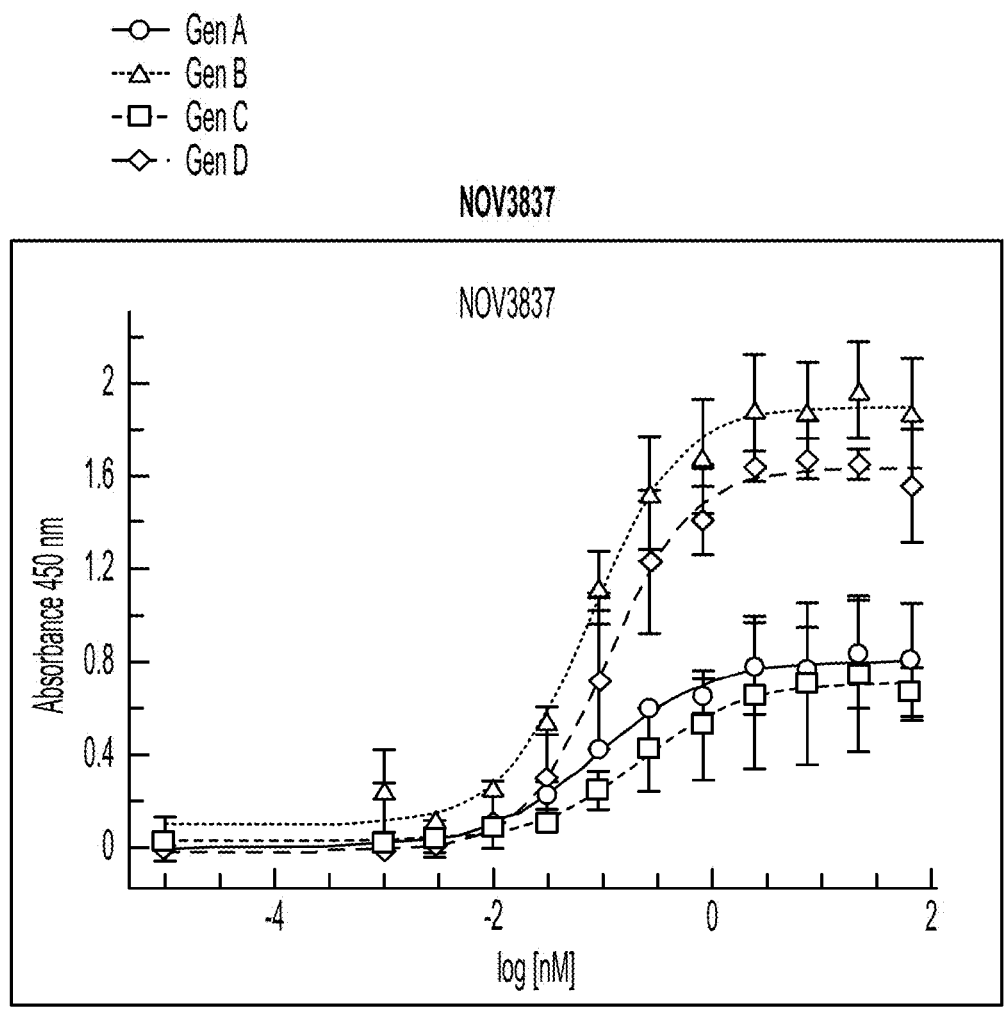
Figure 45:
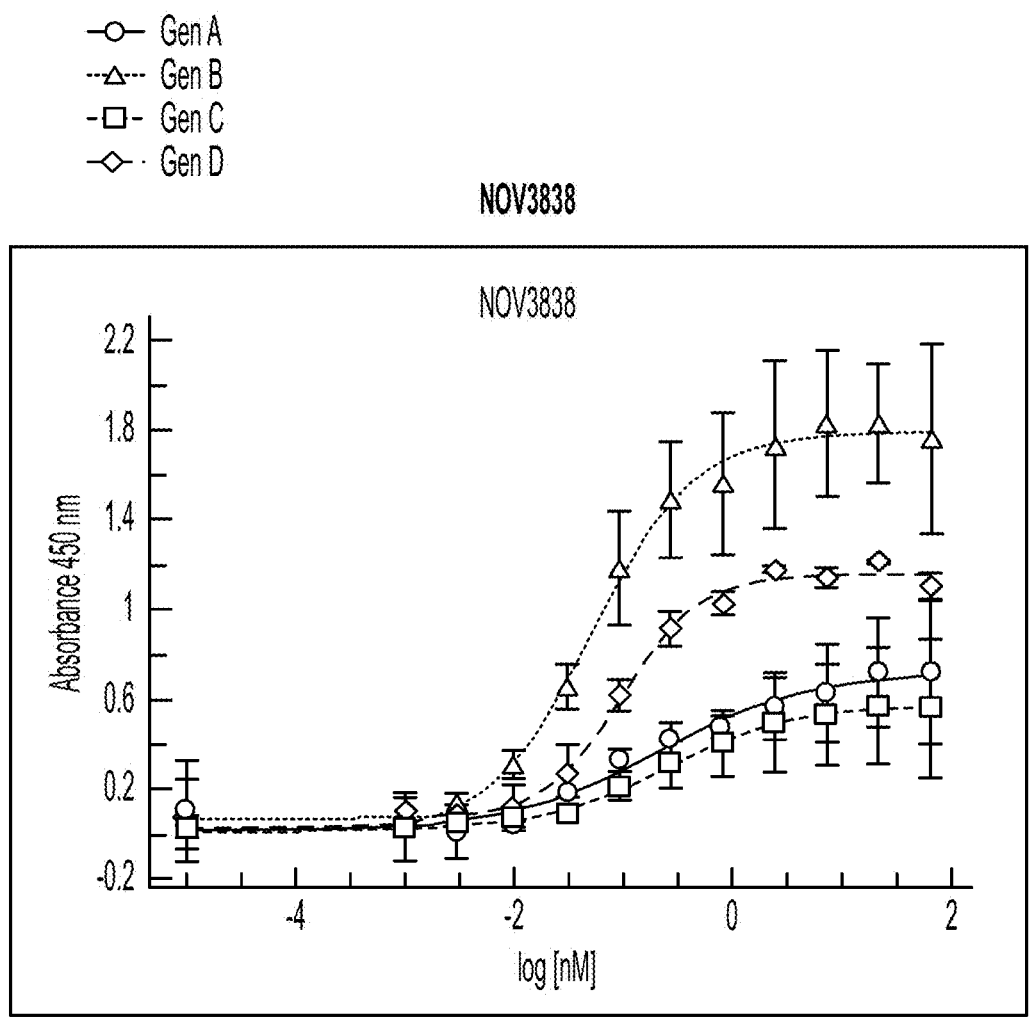
Figure 46:
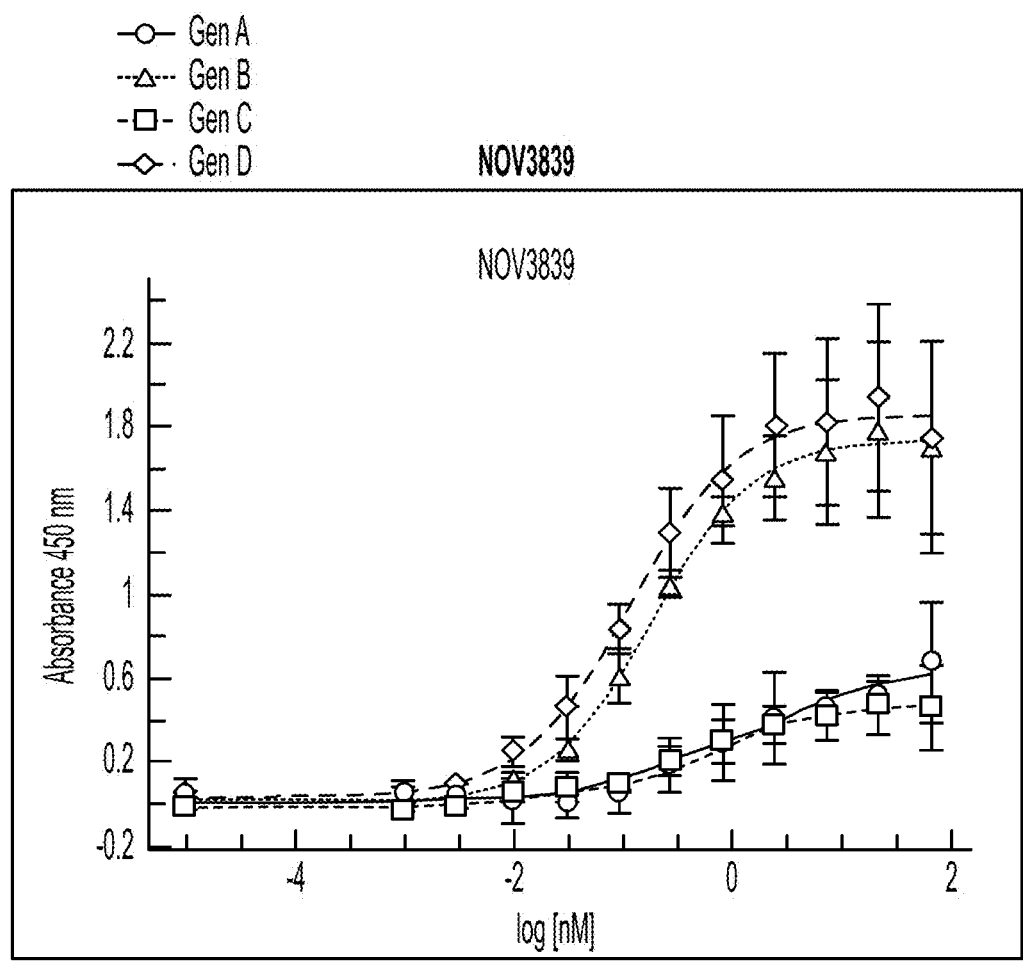
Figure 47:
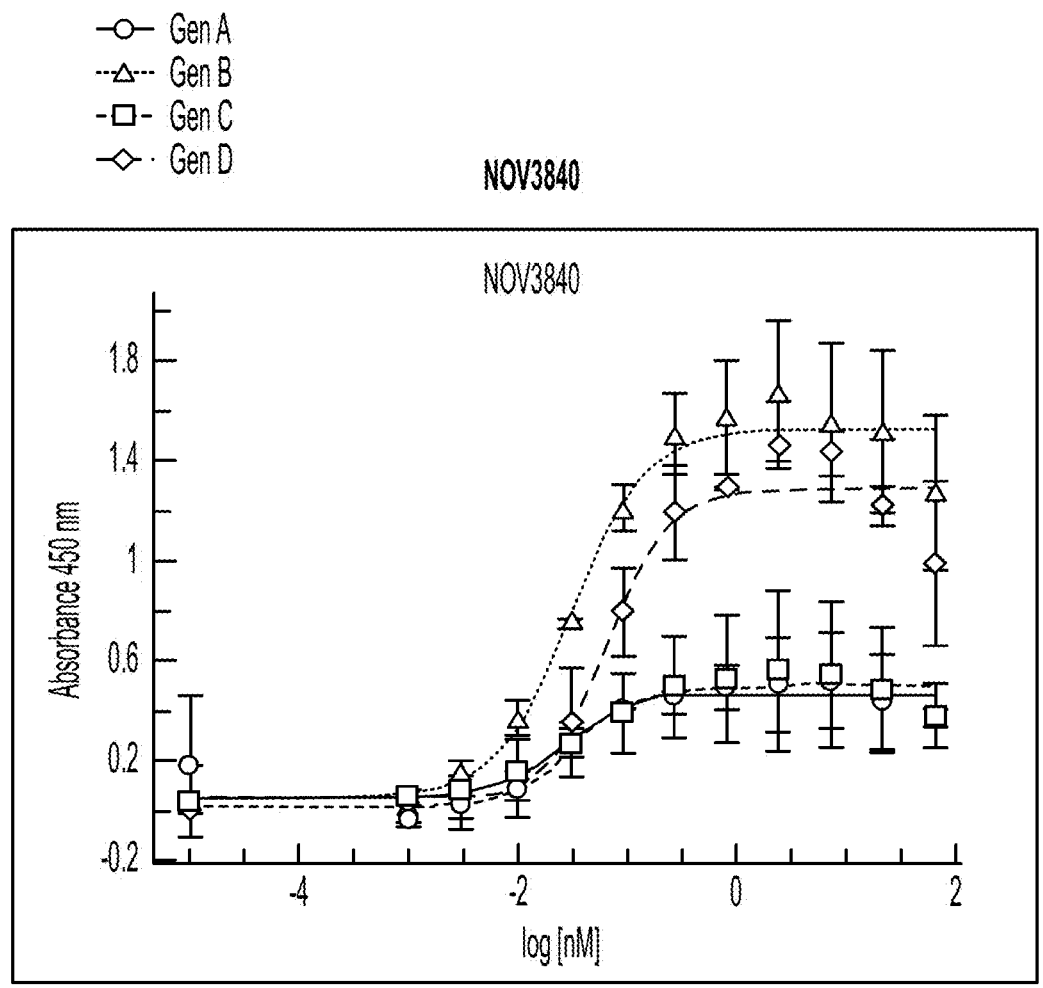
Figure 48:
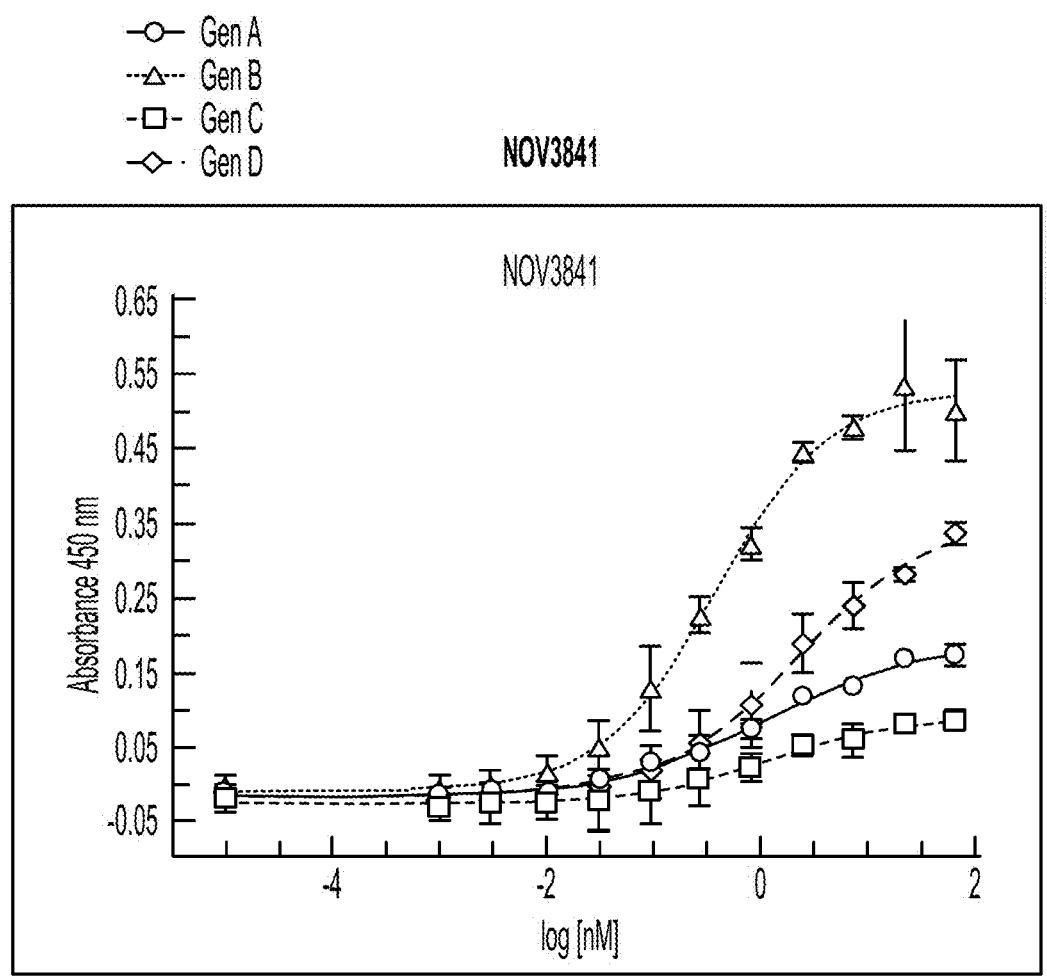
Figure 49:
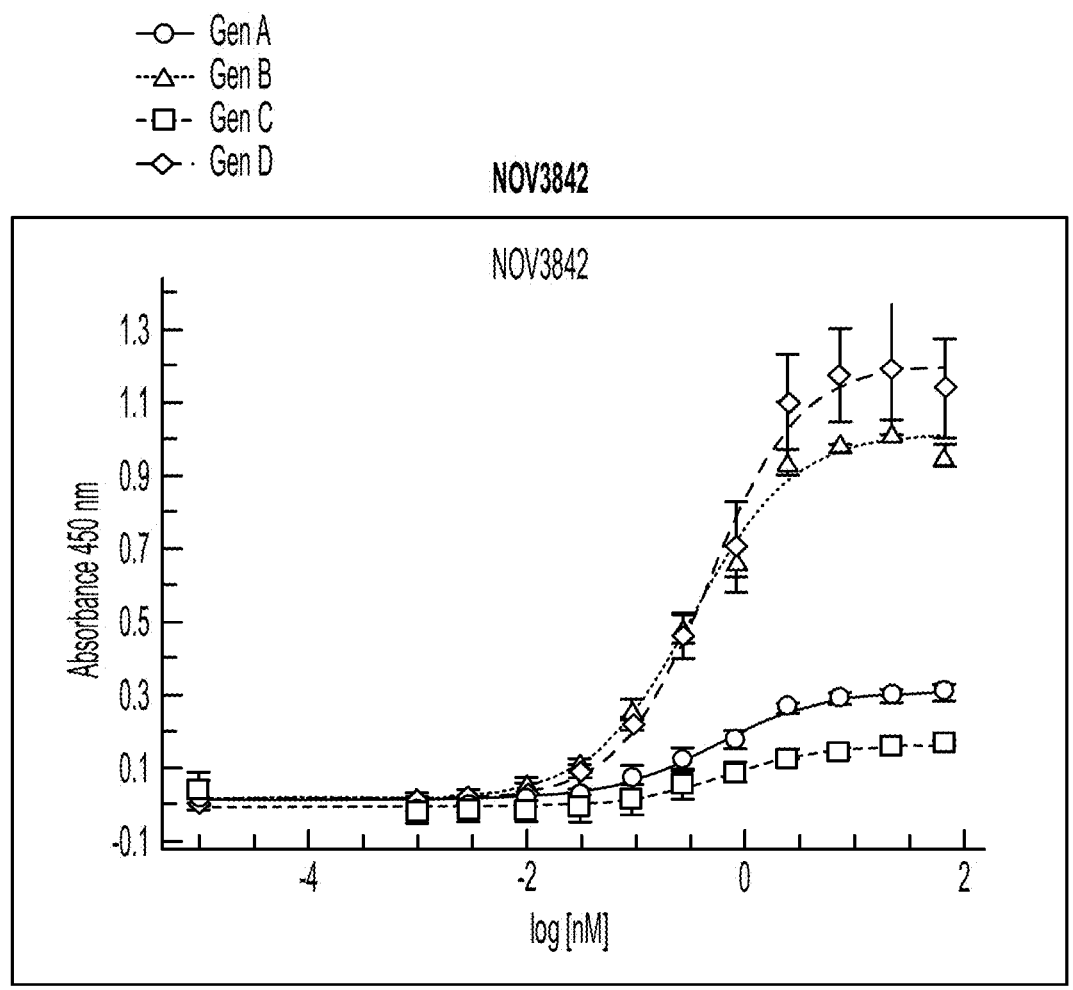
Figure 50:
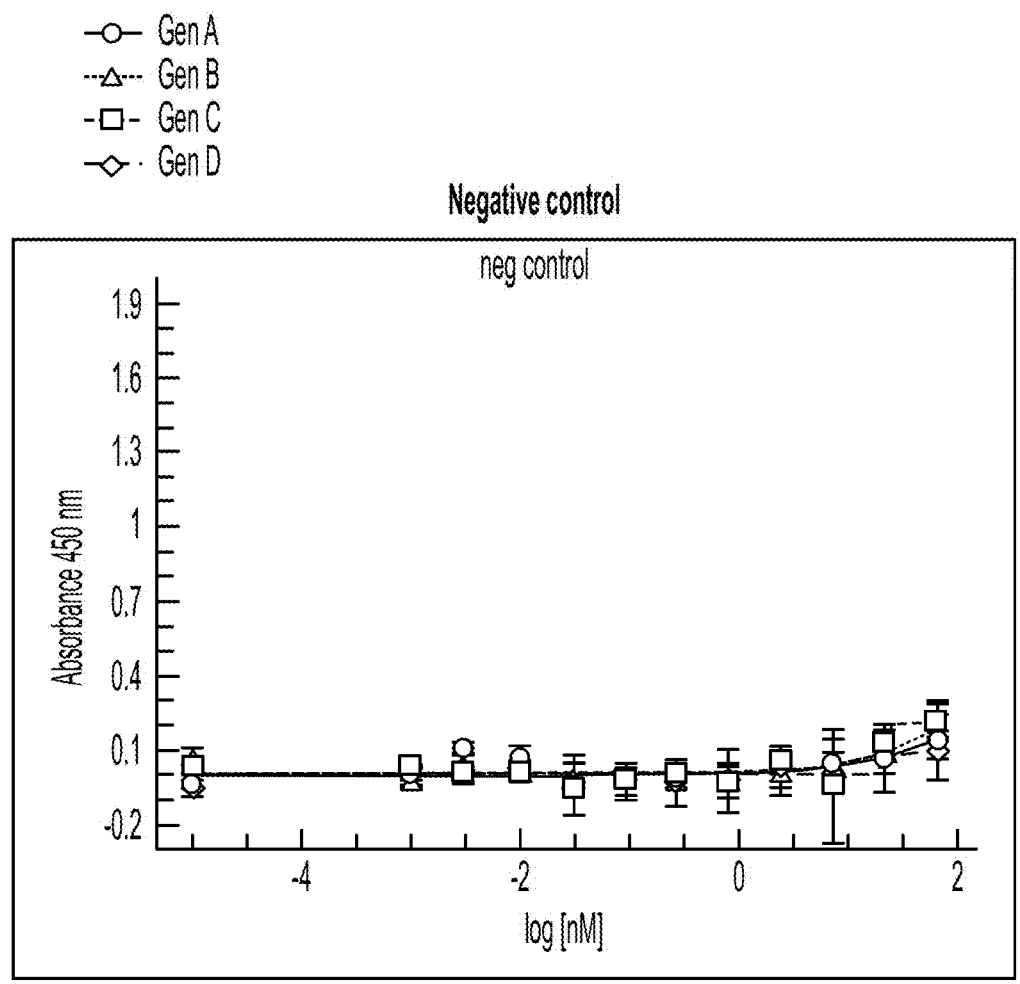
Figure 51:
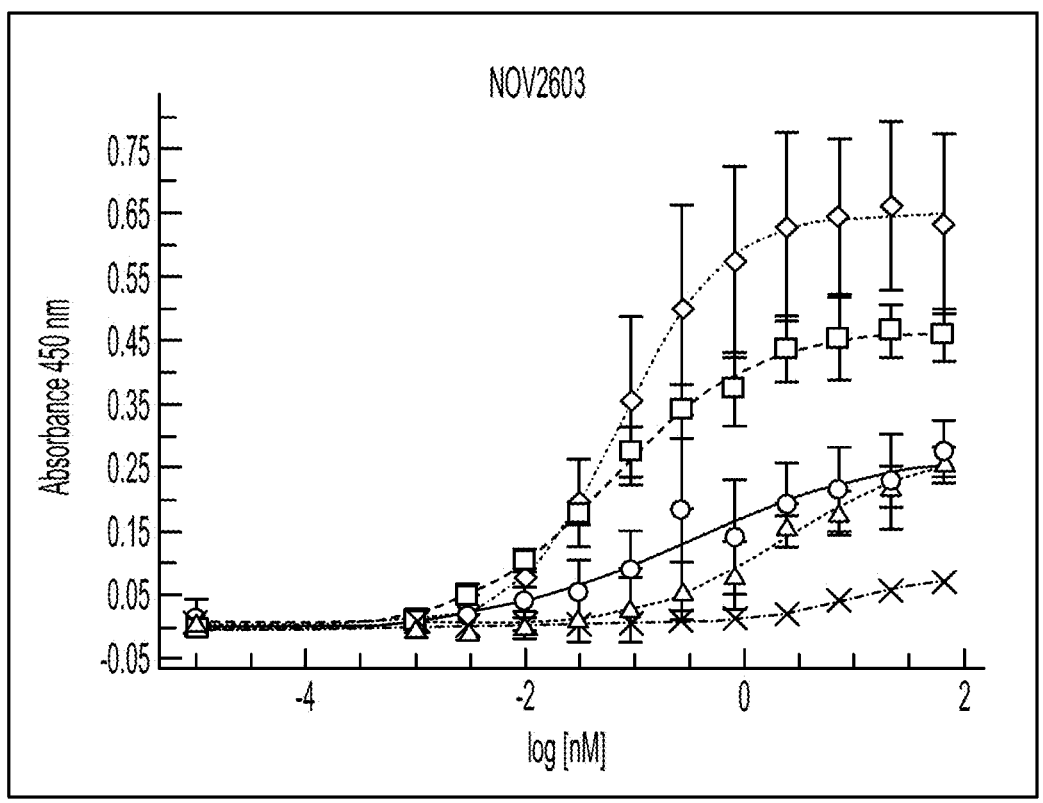
FIGS. 51-66 shows the $IC_{50}$ of the antibodies to four different clinical mutations.
Figure 52:
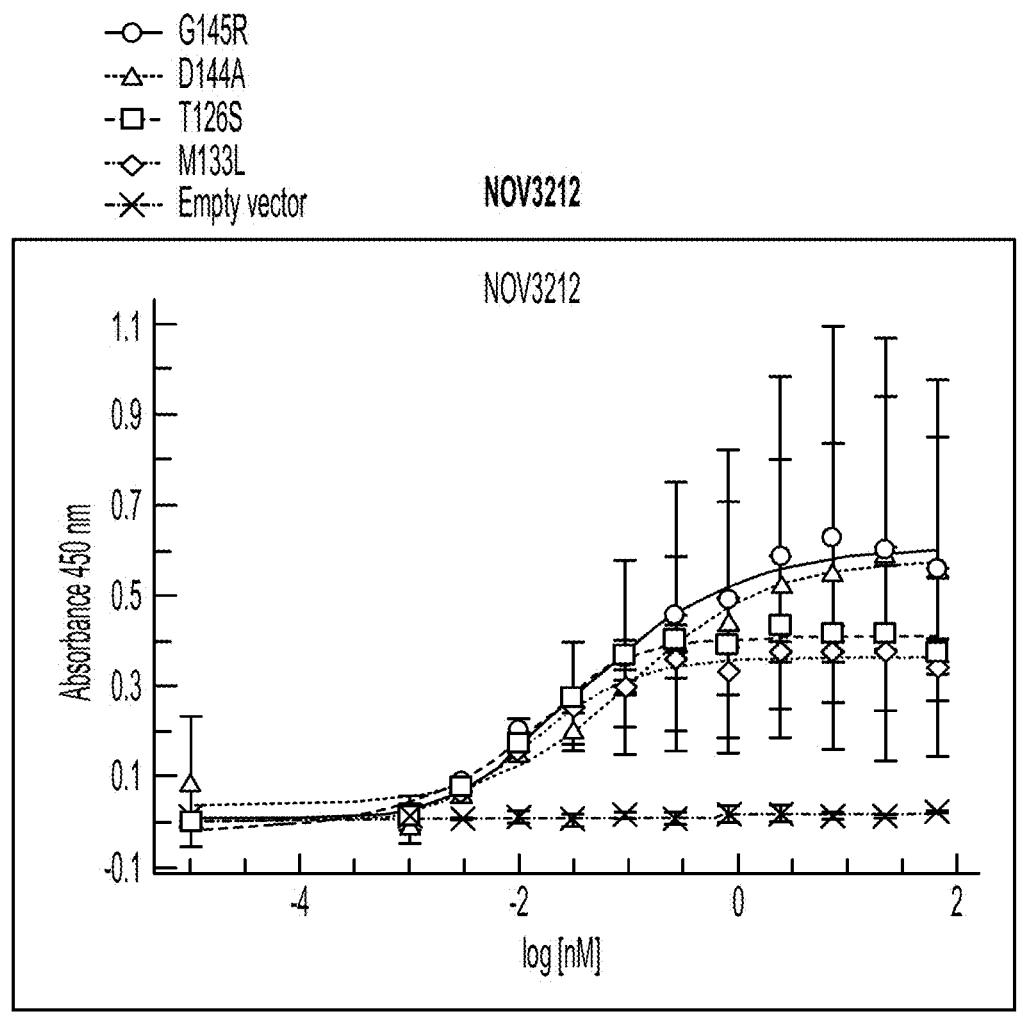
Figure 53:
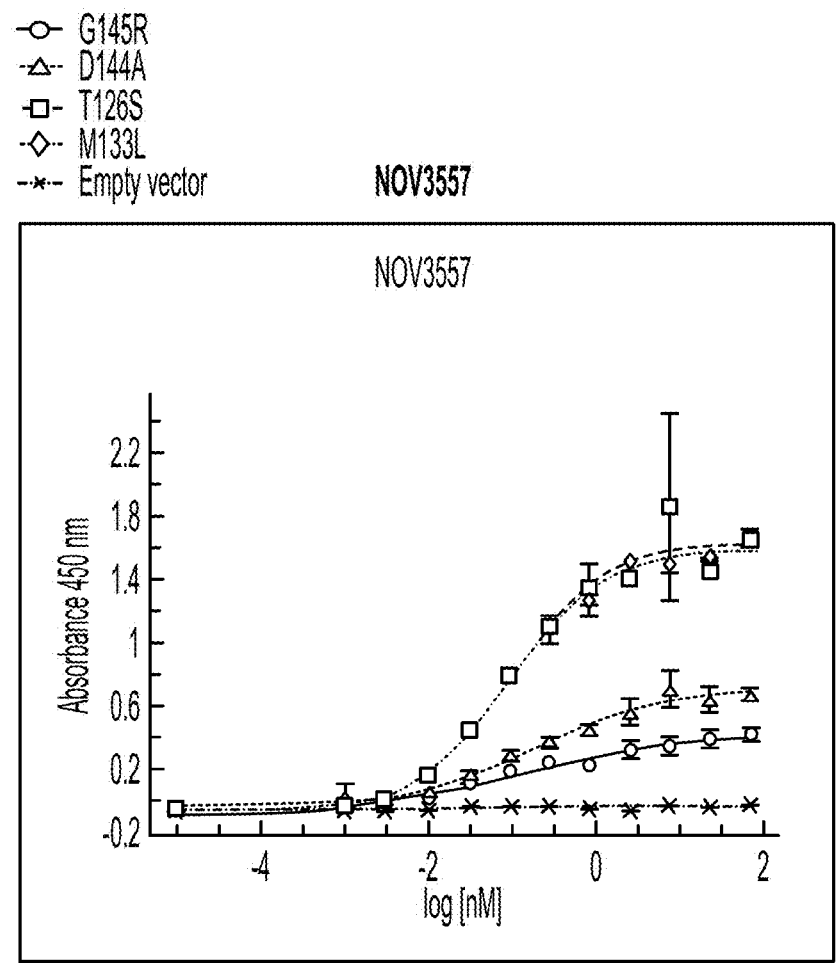
Figure 54:
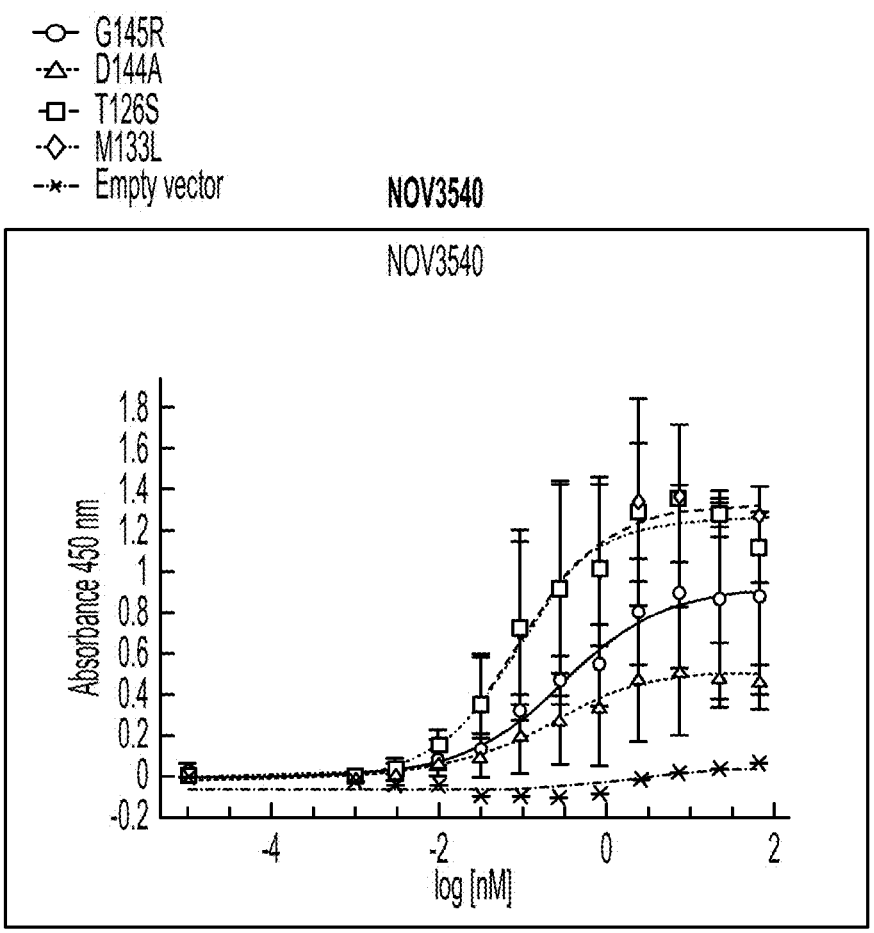
Figure 55:
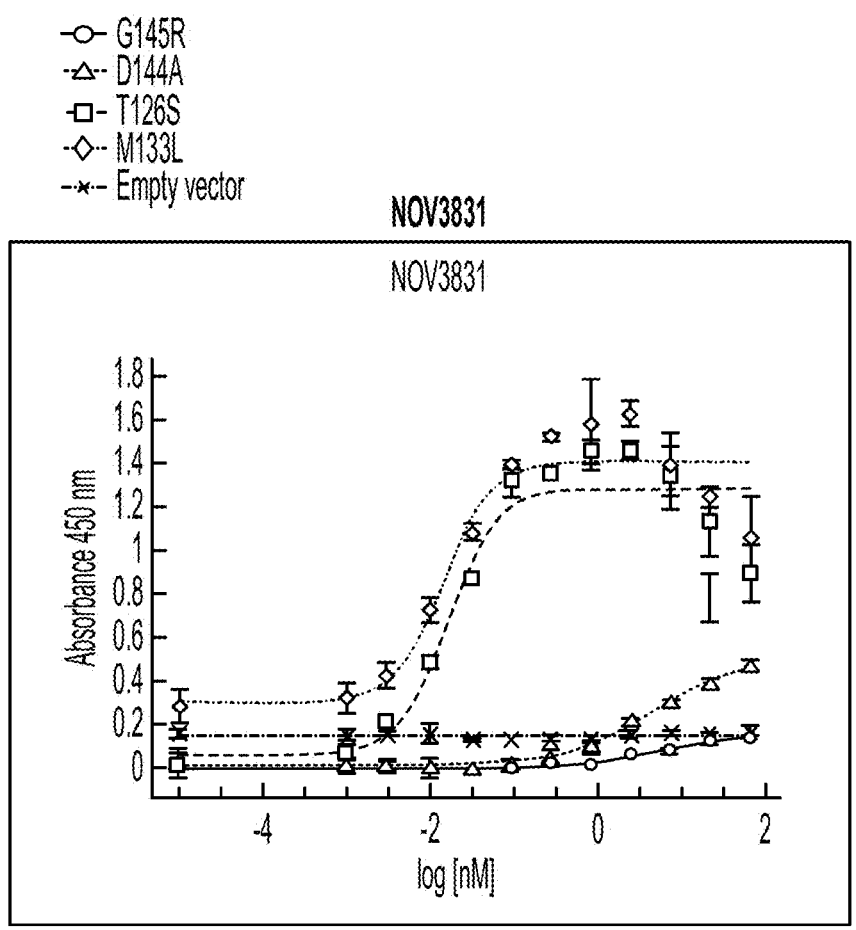
Figure 56:
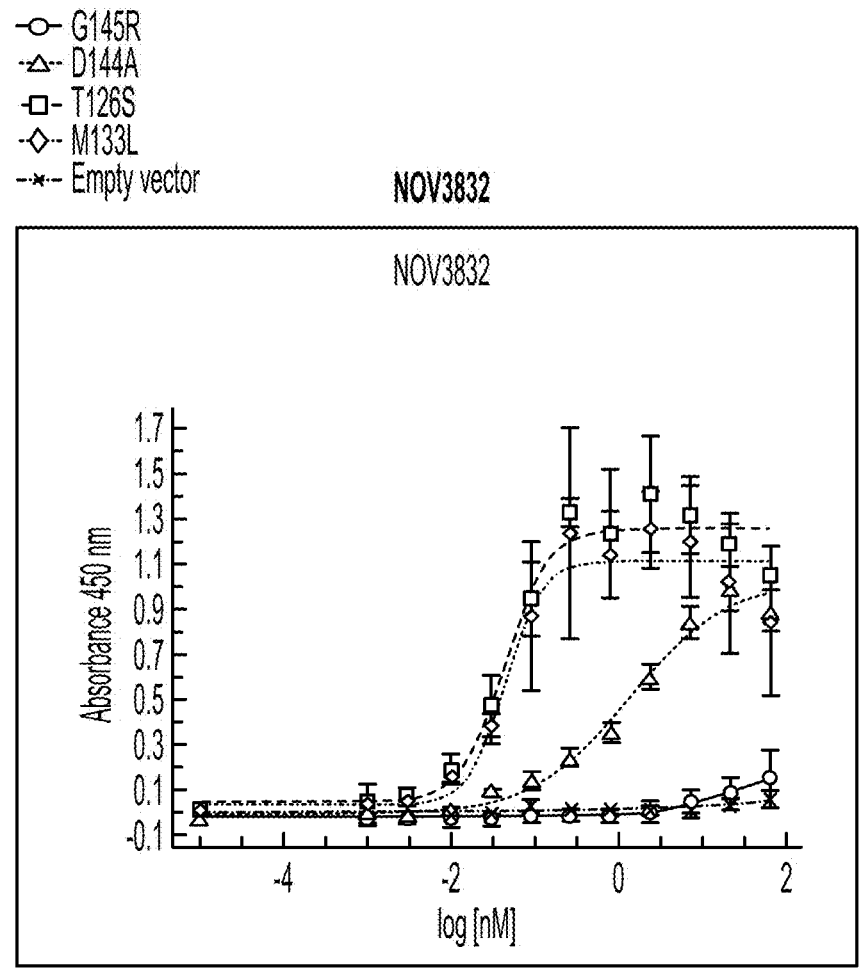
Figure 57:
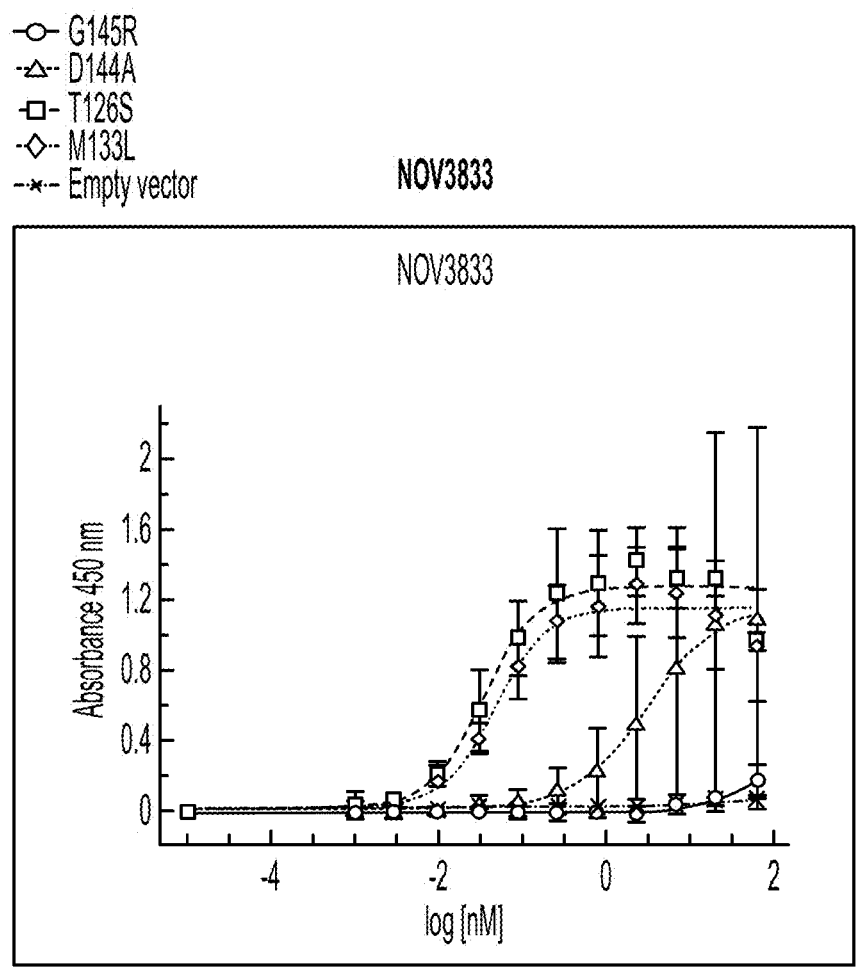
Figure 58:
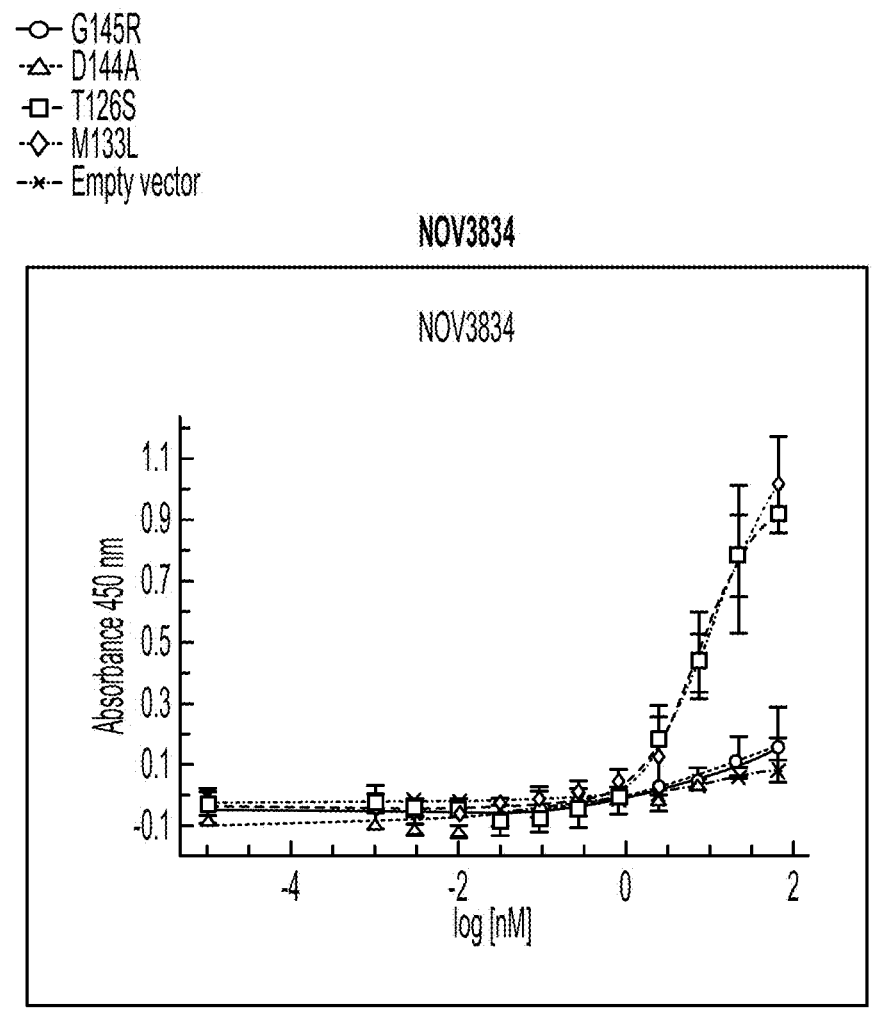
Figure 59:
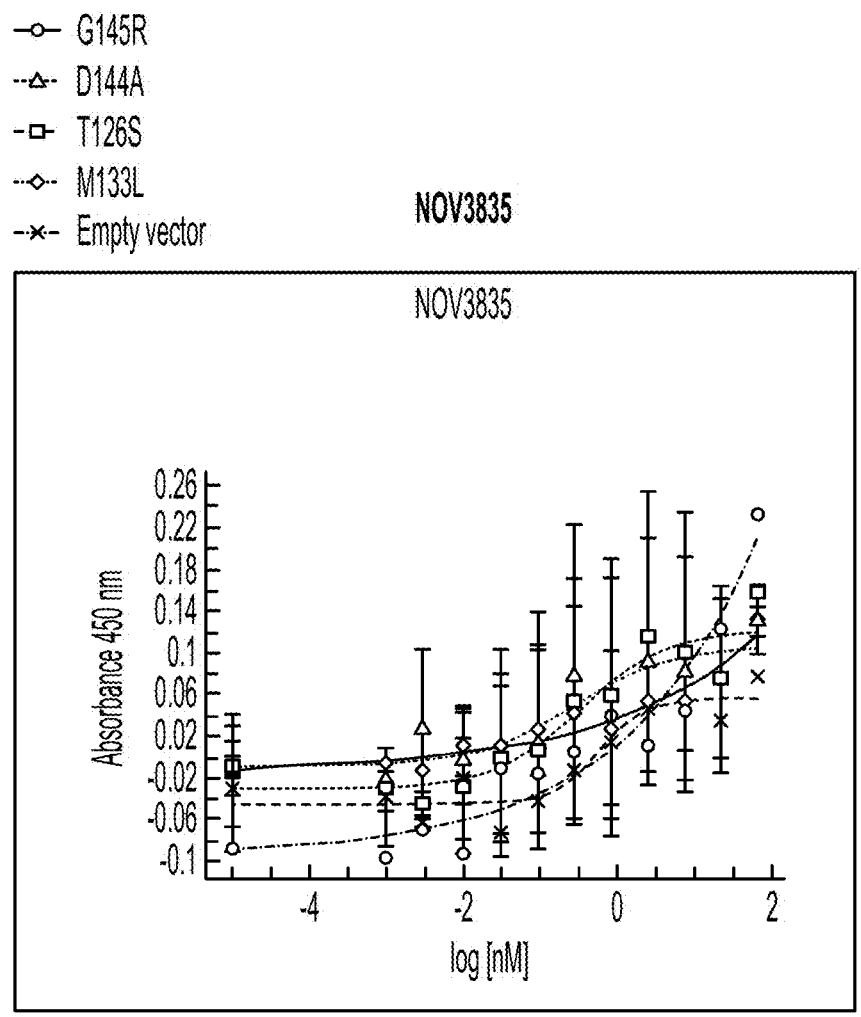
Figure 60:
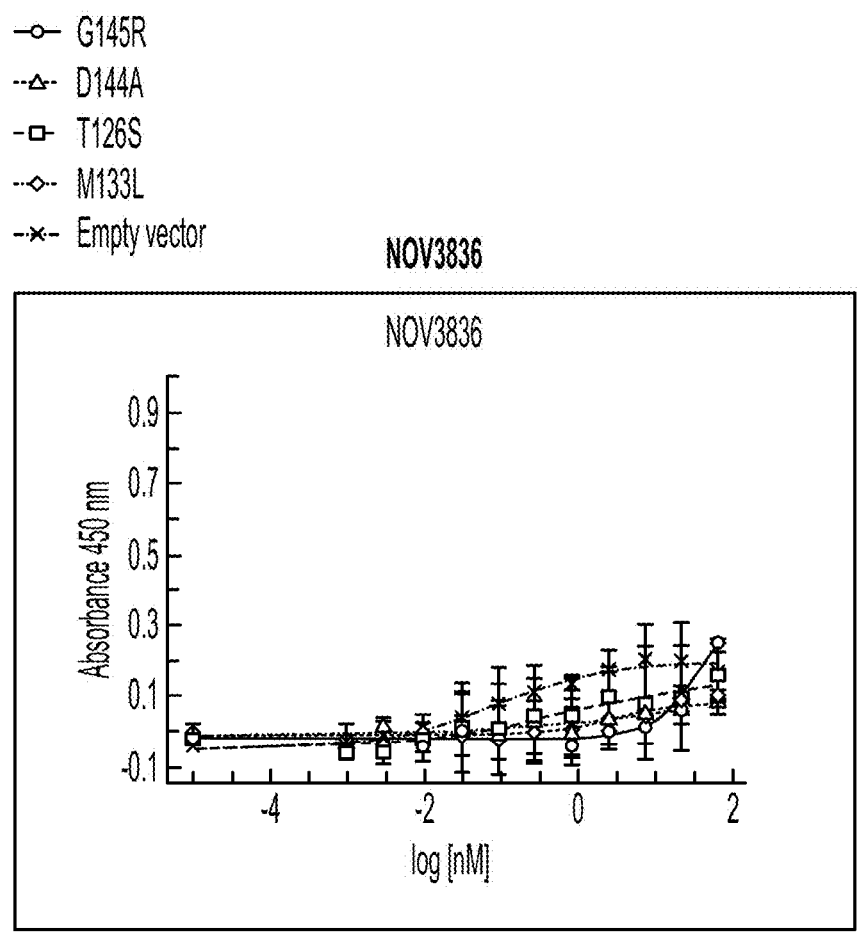
Figure 61:
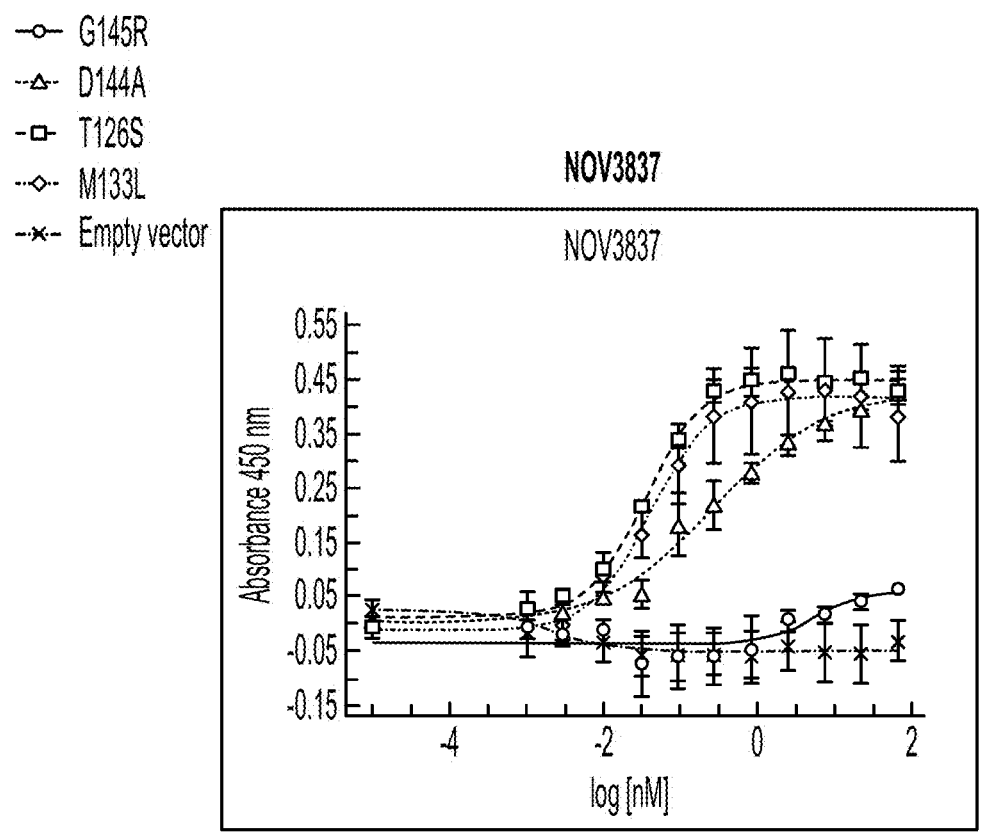
Figure 62:
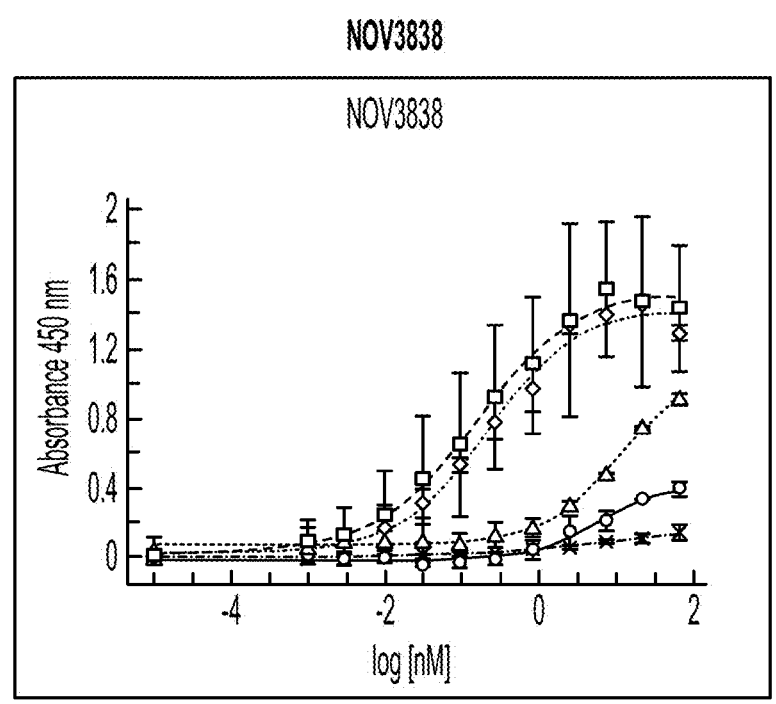
Figure 63:
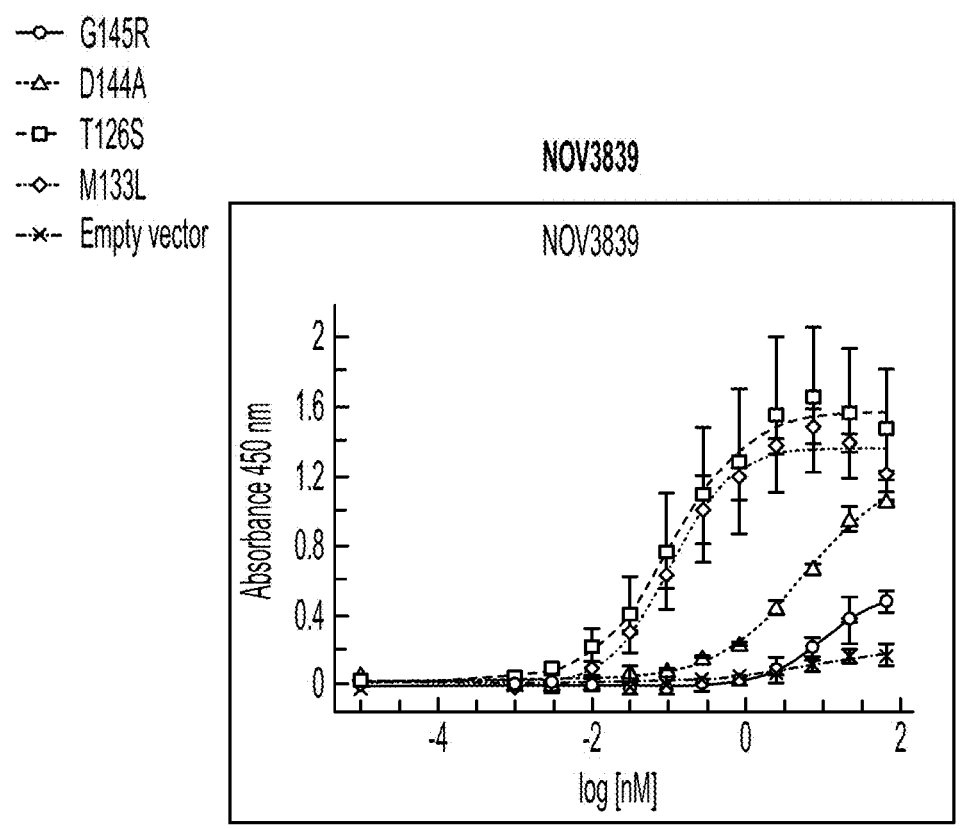
Figure 64:
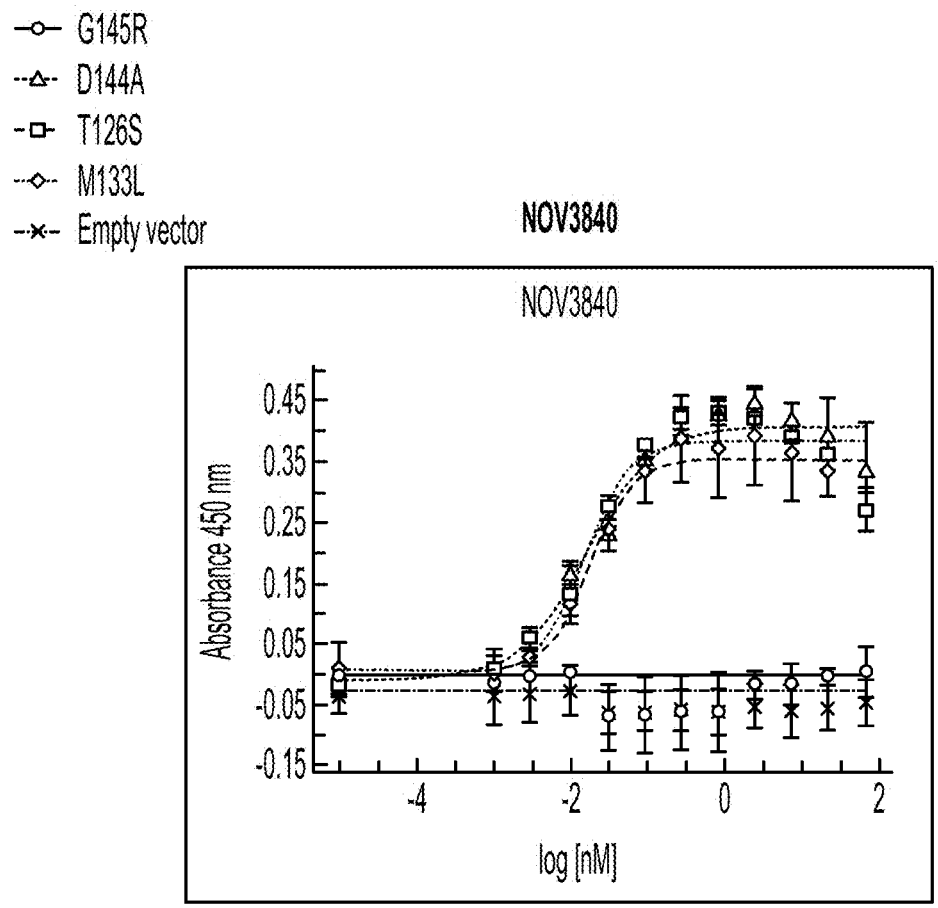
Figure 65:
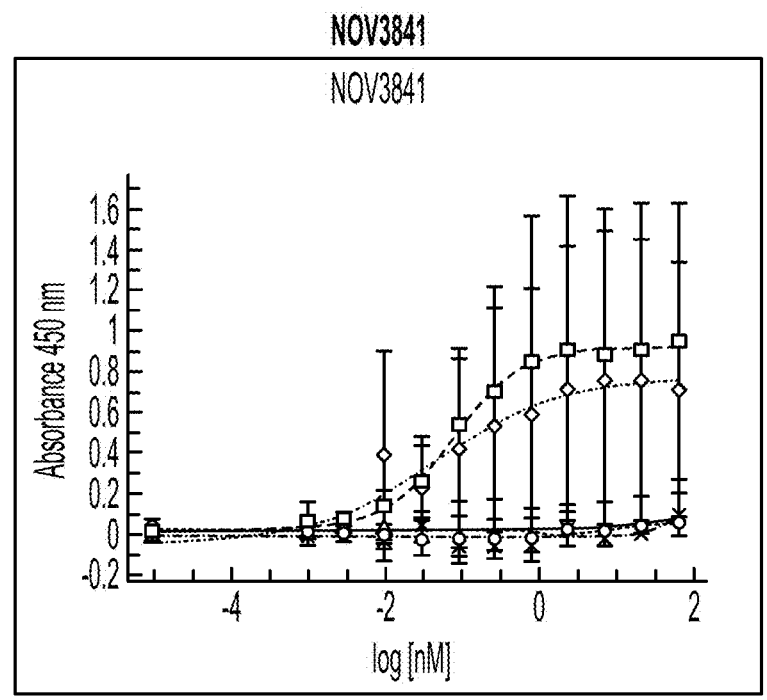
Figure 66:
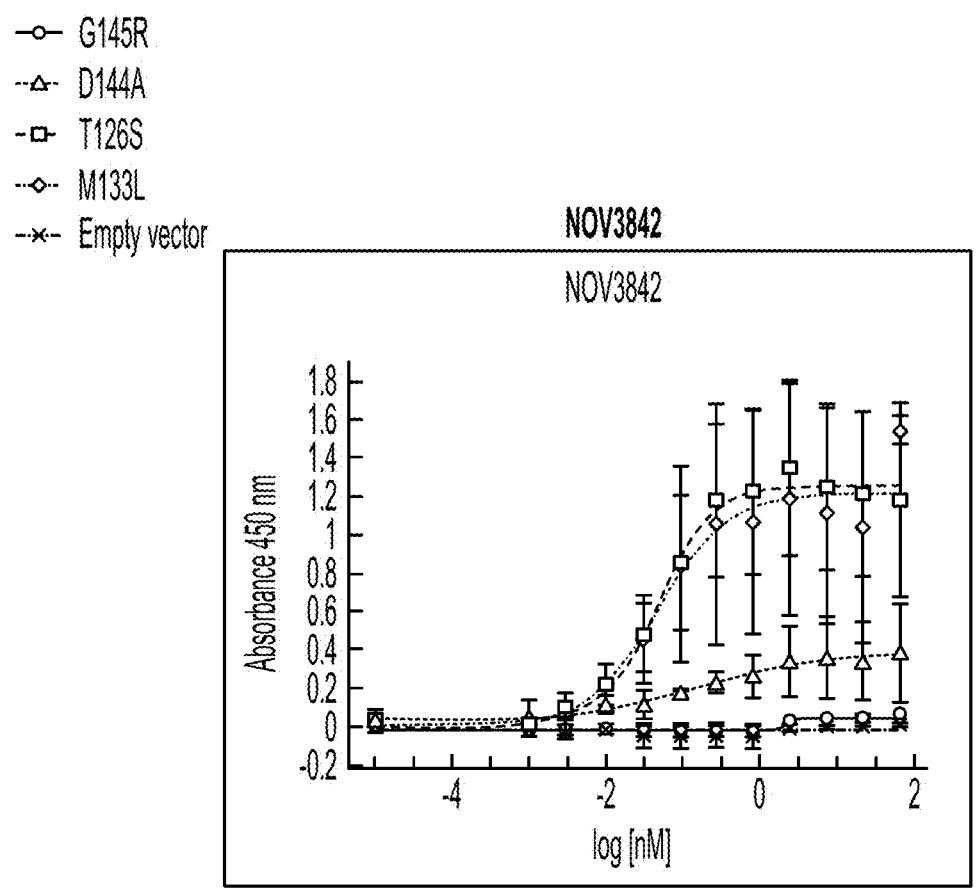

The present disclosure provides for antibodies, antibody fragments (e.g., antigen binding fragments), that bind and neutralize hepatitis B. Furthermore, the present disclosure provides antibodies that have desirable pharmacokinetic characteristics and other desirable attributes, and thus can be used for reducing the likelihood of or treating hepatitis B associate liver failure, liver cirrhosis or hepatocellular cancer. The present disclosure further provides pharmaceutical compositions comprising the antibodies and methods of making and using such pharmaceutical compositions for the prevention and treatment of hepatitis B infection and associated disorders.

Anti-HBsAg Antibodies

The present disclosure provides for antibodies or antibody fragments (e.g., antigen binding fragments) that specifically bind to HBsAg. Antibodies or antibody fragments (e.g., antigen binding fragments) of the present disclosure include, but are not limited to, the human monoclonal antibodies or fragments thereof, isolated as described, in the Examples below.

The present disclosure in certain aspects provides antibodies or antibody fragments (e.g., antigen binding fragments) that specifically bind to HBsAg, said antibodies or antibody fragments (e.g., antigen binding fragments) comprise a VH domain having an amino acid sequence of SEQ ID NO: 18, 50, 82, 114, 146, 178, 210, 242, 274, 306, 338, 370, 402, 434, 466, or 498 (Table 2). The present disclosure also provides antibodies or antibody fragments (e.g., antigen binding fragments) that specifically bind to HBsAg, said antibodies or antibody fragments (e.g., antigen binding fragments) comprise a VH CDR having an amino acid sequence of any one of the VH CDRs listed in Table 2. In particular aspects, the present disclosure provides antibodies or antibody fragments (e.g., antigen binding fragments) that specifically bind to HBsAg, said antibodies comprising (or alternatively, consist of) one, two, three, or more VH CDRs having an amino acid sequence of any of the VH CDRs listed in Table 2.

The present disclosure provides antibodies or antibody fragments (e.g., antigen binding fragments) that specifically bind to HBsAg, said antibodies or antibody fragments (e.g., antigen binding fragments) comprise a VL domain having an amino acid sequence of SEQ ID NO: 34, 66, 98, 130, 162, 194, 226, 258, 290, 322, 354, 386, 418, 450, 482 or 514 (Table 2). The present disclosure also provides antibodies or antibody fragments (e.g., antigen binding fragments) that specifically bind to HBsAg, said antibodies or antibody fragments (e.g., antigen binding fragments) comprise a VL CDR having an amino acid sequence of any one of the VL CDRs listed in Table 2. In particular, the disclosure provides antibodies or antibody fragments (e.g., antigen binding fragments) that specifically bind to HBsAg, said antibodies or antibody fragments (e.g., antigen binding fragments) comprise (or alternatively, consist of) one, two, three or more VL CDRs having an amino acid sequence of any of the VL CDRs listed in Table 2.

Other antibodies or antibody fragments (e.g., antigen binding fragments) of the present disclosure include amino acids that have been mutated, yet have at least 60, 70, 80, 90 or 95 percent identity in the CDR regions with the CDR regions depicted in the sequences described in Table 2. In some aspects, it includes mutant amino acid sequences wherein no more than 1, 2, 3, 4 or 5 amino acids have been mutated in the CDR regions when compared with the CDR regions depicted in the sequence described in Table 2.

The present disclosure also provides nucleic acid sequences that encode VH, VL, the full length heavy chain, and the full length light chain of the antibodies that specifically bind to HBsAg. Such nucleic acid sequences can be optimized for expression in mammalian cells.

TABLE 2 anti-HBV Antibodies

| NOV3832HC | | | |
|---|---|---|---|
| SEQ ID NO: 6 (Combined) | HCDR1 | GFTFDNYAMS | |
| SEQ ID NO: 7 (Combined) | HCDR2 | SISGSGGSTYYADSVKG | |
| SEQ ID NO: 8 (Combined) | HCDR3 | SSILSGGHARVYGIDV | |
| SEQ ID NO: 9 (Kabat) | HCDR1 | NYAMS | |

TABLE 2-continued anti-HBV Antibodies

| SEQ ID NO: 10 (Kabat) | HCDR2 | SISGSGGSTYYADSVKG |
|---|---|---|
| SEQ ID NO: 11 (Kabat) | HCDR3 | SSILSGGHARVYGIDV |
| SEQ ID NO: 12 (Chothia) | HCDR1 | GFTFDNY |
| SEQ ID NO: 13 (Chothia) | HCDR2 | SGSGGS |
| SEQ ID NO: 14 (Chothia) | HCDR3 | SSILSGGHARVYGIDV |
| SEQ ID NO: 15 (IMGT) | HCDR1 | GFTFDNYA |
| SEQ ID NO: 16 (IMGT) | HCDR2 | ISGSGGST |
| SEQ ID NO: 17 (IMGT) | HCDR3 | AKSSILSGGHARVYGIDV |
| SEQ ID NO: 18 | VH | EMQVLESGGGLVQPGGSLRLSCAASGFTFDNYAMSWV RQVPGKGLEWVSSISGSGGSTYYADSVKGQFTISRDN SKNTLYLQMNSLRAEDTAVYYCAKSSILSGGHARVYG IDVWGQGTTVTVSS |
| SEQ ID NO: 19 | DNA VH | GAGATGCAGGTCTTGGAATCTGGCGGAGGACTGGTTC AACCTGGCGGCTCTCTGAGACTGTCTTGTGCCGCCAG CGGCTTCACCTTCGATAACTACGCCATGTCCTGGGTC CGACAGGTGCCAGGCAAAGGACTGGAATGGGTGTCCT CTATCAGCGGCTCTGGCGGCAGCACATATTACGCCGA TAGCGTGAAGGGCCAGTTCACCATCAGCCGGGACAAC AGCAAGAACACCCTGTACCTCCAGATGAACAGCCTGA GAGCCGAGGATACCGCCGTGTACTACTGTGCCAAGAG CAGCATTCTGTCTGGCGGCCACGCCAGAGTGTATGGC ATTGATGTTTGGGGCCAGGGAACCACCGTGACCGTTA GTTCT |
| SEQ ID NO: 20 | Heavy Chain | EMQVLESGGGLVQPGGSLRLSCAASGFTFDNYAMSWV RQVPGKGLEWVSSISGSGGSTYYADSVKGQFTISRDN SKNTLYLQMNSLRAEDTAVYYCAKSSILSGGHARVYG IDVWGQGTTVTVSSASTKGPSVFPLAPSSKSTSGGTA ALGCLVKDYFPEPVTVSWNSGALTSGVHTFPAVLQSS GLYSLSSVVTVPSSSLGTQTYICNVNHKPSNTKVDKR VEPKSCDKTHTCPPCPAPELLGGPSVFLFPPKPKDTL MISRTPEVTCVVVDVSHEDPEVKFNWYVDGVEVHNAK TKPREEQYNSTYRVVSVLTVLHQDWLNGKEYKCKVSN KALPAPIEKTISKAKGQPREPQVYTLPPSREEMTKNQ VSLTCLVKGFYPSDIAVEWESNGQPENNYKTTPPVLD SDGSFFLYSKLTVDKSRWQQGNVFSCSVMHEALHNHY TQKSLSLSPGK |
| SEQ ID NO: 21 | DNA Heavy Chain | GAGATGCAGGTCTTGGAATCTGGCGGAGGACTGGTTC AACCTGGCGGCTCTCTGAGACTGTCTTGTGCCGCCAG CGGCTTCACCTTCGATAACTACGCCATGTCCTGGGTC CGACAGGTGCCAGGCAAAGGACTGGAATGGGTGTCCT CTATCAGCGGCTCTGGCGGCAGCACATATTACGCCGA TAGCGTGAAGGGCCAGTTCACCATCAGCCGGGACAAC AGCAAGAACACCCTGTACCTCCAGATGAACAGCCTGA GAGCCGAGGATACCGCCGTGTACTACTGTGCCAAGAG CAGCATTCTGTCTGGCGGCCACGCCAGAGTGTATGGC ATTGATGTTTGGGGCCAGGGAACCACCGTGACCGTTA GTTCTGCTAGCACCAAGGGCCCCAGCGTGTTCCCCCT GGCCCCCAGCAGCAAGAGCACCAGCGGCGGCACAGCC GCCCTGGGCTGCCTGGTGAAGGACTACTTCCCCGAGC CCGTGACCGTGTCCTGGAACAGCGGAGCCCTGACCTC CGGCGTGCACACCTTCCCCGCCGTGCTGCAGAGCAGC GGCCTGTACAGCCTGTCCAGCGTGGTGACAGTGCCCA GCAGCAGCCTGGGCACCCAGACCTACATCTGCAACGT GAACCACAAGCCCAGCAACACCAAGGTGGACAAGAGA GTGGAGCCCAAGAGCTGCGACAAGACCCACACATGCC CCCCTGCCCGGCGCCAGAGCTGCTGGGCGGACCCTC CGTGTTCCTGTTCCCCCCCAAGCCCAAGGACACCCTG ATGATCAGCAGGACCCCCGAGGTGACCTGCGTGGTGG |

TABLE 2-continued anti-HBV Antibodies

```
TGGACGTGAGCCACGAGGACCCAGAGGTGAAGTTCAA
CTGGTACGTGGACGGCGTGGAGGTGCACAACGCCAAG
ACCAAGCCCAGAGAGGAGCAGTACAACAGCACCTACA
GGGTGGTGTCCGTGCTGACCGTGCTGCACCAGGACTG
GCTGAACGGCAAGGAATACAAGTGCAAGGTCTCCAAC
AAGGCCCTGCCAGCCCCCATCGAAAAGACCATCAGCA
AGGCCAAGGGCCAGCCACGGGAGCCCCAGGTGTACAC
CCTGCCCCCTCCCGGGAGGAGATGACCAAGAACCAG
GTGTCCCTGACCTGTCTGGTGAAGGGCTTCTACCCCA
GCGACATCGCCGTGGAGTGGGAGAGCAACGGCCAGCC
CGAGAACAACTACAAGACCACCCCCCCAGTGCTGGAC
AGCGACGGCAGCTTCTTCCTGTACAGCAAGCTGACCG
TGGACAAGTCCAGGTGGCAGCAGGGCAACGTGTTCAG
CTGCAGCGTGATGCACGAGGCCCTGCACAACCACTAC
ACCCAGAAGAGCCTGAGCTTAAGCCCCGGCAAG
```

NOV3832 LC

| | | |
|---|---|---|
| SEQ ID NO: 22 (Combined) | LCDR1 | GGNNIGSQSVH |
| SEQ ID NO: 23 (Combined) | LCDR2 | DDTDRPS |
| SEQ ID NO: 24 (Combined) | LCDR3 | QVWDSSSDHVV |
| SEQ ID NO: 25 (Kabat) | LCDR1 | GGNNIGSQSVH |
| SEQ ID NO: 26 (Kabat) | LCDR2 | DDTDRPS |
| SEQ ID NO: 27 (Kabat) | LCDR3 | QVWDSSSDHVV |
| SEQ ID NO: 28 (Chothia) | LCDR1 | NNIGSQS |
| SEQ ID NO: 29 (Chothia) | LCDR2 | DDT |
| SEQ ID NO: 30 (Chothia) | LCDR3 | WDSSSDHV |
| SEQ ID NO: 31 (IMGT) | LCDR1 | NIGSQS |
| SEQ ID NO: 32 (IMGT) | LCDR2 | DDT |
| SEQ ID NO: 33 (IMGT) | LCDR3 | QVWDSSSDHVV |
| SEQ ID NO: 34 | VL | QSALTQPPSVSVAPGQTARITCGGNNIGSQSVHWYQQ KPGQAPILVVYDDTDRPSGIPARFSGSSSGSTATLTI GRVEAGDEADYYCQVWDSSSDHVVFGGGTKLTVL |
| SEQ ID NO: 35 | DNA VL | CAGTCTGCCCTGACTCAGCCACCCTCGGTGTCAGTGG CCCCAGGACAGACGGCCAGGATTACCTGTGGGGGAAA CAACATTGGAAGTCAAAGTGTGCACTGGTACCAGCAG AAGCCAGGCCAGGCCCCTATACTGGTCGTCTATGATG ATACCGACCGGCCCTCAGGGATCCCTGCGCGATTCTC TGGCTCCAGCTCTGGGAGCACGGCCACCCTGACCATC GGCAGGGTCGAAGCCGGGGATGAGGCCGACTATTACT GTCAGGTGTGGGATAGTAGTAGTGATCATGTGGTATT CGGCGGAGGGACCAAGCTGACCGTCTTA |
| SEQ ID NO: 36 | Light Chain | QSALTQPPSVSVAPGQTARITCGGNNIGSQSVHWYQQ KPGQAPILVVYDDTDRPSGIPARFSGSSSGSTATLTI GRVEAGDEADYYCQVWDSSSDHVVFGGGTKLTVLSQP KAAPSVTLFPPSSEELQANKATLVCLISDFYPGAVTV AWKADSSPVKAGVETTTPSKQSNNKYAASSYLSLTPE QWKSHRSYSCQVTHEGSTVEKTVAPTECS |

TABLE 2-continued anti-HBV Antibodies

| SEQ ID NO: 37 | DNA Light Chain | CAGTCTGCCCTGACTCAGCCACCCTCGGTGTCAGTGG<br>CCCCAGGACAGACGGCCAGGATTACCTGTGGGGGAAA<br>CAACATTGGAAGTCAAAGTGTGCACTGGTACCAGCAG<br>AAGCCAGGCCAGGCCCCTATACTGGTCGTCTATGATG<br>ATACCGACCGGCCCTCAGGGATCCCTGCGCGATTCTC<br>TGGCTCCAGCTCTGGGAGCACGGCCACCCTGACCATC<br>GGCAGGGTCGAAGCCGGGGATGAGGCCGACTATTACT<br>GTCAGGTGTGGGATAGTAGTAGTGATCATGTGGTATT<br>CGGCGGAGGGACCAAGCTGACCGTCTTAAGTCAGCCC<br>AAGGCTGCCCCCTCGGTCACTCTGTTCCCGCCCTCCT<br>CTGAGGAGCTTCAAGCCAACAAGGCCACACTGGTGTG<br>TCTCATAAGTGACTTCTACCCGGGAGCCGTGACAGTG<br>GCCTGGAAGGCAGATAGCAGCCCCGTCAAGGCGGGAG<br>TGGAGACCACCACACCCTCCAAACAAAGCAACAACAA<br>GTACGCCGCCAGCAGCTACCTGAGCCTGACCCCCGAG<br>CAGTGGAAGAGCCACAGAAGCTACAGCTGCCAGGTCA<br>CCCACGAGGGCAGCACCGTGGAGAAAACCGTGGCCCC<br>CACCGAGTGCAGC |

NOV3833 HC

| SEQ ID NO: 38<br>(Combined) | HCDR1 | GFTFHNYAMS |
| SEQ ID NO: 39<br>(Combined) | HCDR2 | SISGSGGSTYYADSVKG |
| SEQ ID NO: 40<br>(Combined) | HCDR3 | SSILSGGHARVYGIDV |
| SEQ ID NO: 41<br>(Kabat) | HCDR1 | NYAMS |
| SEQ ID NO: 42<br>(Kabat) | HCDR2 | SISGSGGSTYYADSVKG |
| SEQ ID NO: 43<br>(Kabat) | HCDR3 | SSILSGGHARVYGIDV |
| SEQ ID NO: 44<br>(Chothia) | HCDR1 | GFTFHNY |
| SEQ ID NO: 45<br>(Chothia) | HCDR2 | SGSGGS |
| SEQ ID NO: 46<br>(Chothia) | HCDR3 | SSILSGGHARVYGIDV |
| SEQ ID NO: 47<br>(IMGT) | HCDR1 | GFTFHNYA |
| SEQ ID NO: 48<br>(IMGT) | HCDR2 | ISGSGGST |
| SEQ ID NO: 49<br>(IMGT) | HCDR3 | AKSSILSGGHARVYGIDV |
| SEQ ID NO: 50 | VH | EMQVLESGGGLVQPGGSLRLSCAASGFTFHNYAMSWV<br>RQVPGKGLEWVSSISGSGGSTYYADSVKGQFTISRDN<br>SKNTLYLQMNSLRAEDTAVYYCAKSSILSGGHARVYG<br>IDVWGQGTTVTVSS |
| SEQ ID NO: 51 | DNA VH | GAGATGCAGGTCTTGGAATCTGGCGGAGGACTGGTTC<br>AACCTGGCGGCTCTCTGAGACTGTCTTGTGCCGCCAG<br>CGGCTTCACCTTCCATAACTACGCCATGTCCTGGGTC<br>CGACAGGTGCCAGGCAAAGGACTGGAATGGGTGTCCT<br>CTATCAGCGGCTCTGGCGGCAGCACATATTACGCCGA<br>TAGCGTGAAGGGCCAGTTCACCATCAGCCGGGACAAC<br>AGCAAGAACACCCTGTACCTCCAGATGAACAGCCTGA<br>GAGCCGAGGATACCGCCGTGTACTACTGTGCCAAGAG<br>CAGCATTCTGTCTGGCGGCCACGCCAGAGTGTATGGC<br>ATTGATGTTTGGGCCAGGGAACCACCGTGACCGTTA<br>GTTCT |

TABLE 2-continued

| anti-HBV Antibodies | | |
|---|---|---|
| SEQ ID NO: 52 | Heavy Chain | EMQVLESGGGLVQPGGSLRLSCAASGFTFHNYAMSWV RQVPGKGLEWVSSISGSGGSTYYADSVKGQFTISRDN SKNTLYLQMNSLRAEDTAVYYCAKSSILSGGHARVYG IDVWGQGTTVTVSSASTKGPSVFPLAPSSKSTSGGTA ALGCLVKDYFPEPVTVSWNSGALTSGVHTFPAVLQSS GLYSLSSVVTVPSSSLGTQTYICNVNHKPSNTKVDKR VEPKSCDKTHTCPPCPAPELLGGPSVFLFPPKPKDTL MISRTPEVTCVVVDVSHEDPEVKFNWYVDGVEVHNAK TKPREEQYNSTYRVVSVLTVLHQDWLNGKEYKCKVSN KALPAPIEKTISKAKGQPREPQVYTLPPSREEMTKNQ VSLTCLVKGFYPSDIAVEWESNGQPENNYKTTPPVLD SDGSFFLYSKLTVDKSRWQQGNVFSCSVMHEALHNHY TQKSLSLSPGK |
| SEQ ID NO: 53 | DNA Heavy Chain | GAGATGCAGGTCTTGGAATCTGGCGGAGGACTGGTTC AACCTGGCGGCTCTCTGAGACTGTCTTGTGCCGCCAG CGGCTTCACCTTCCATAACTACGCCATGTCCTGGGTC CGACAGGTGCCAGGCAAAGGACTGGAATGGGTGTCCT CTATCAGCGGCTCTGGCGGCAGCACATATTACGCCGA TAGCGTGAAGGGCCAGTTCACCATCAGCCGGGACAAC AGCAAGAACACCCTGTACCTCCAGATGAACAGCCTGA GAGCCGAGGATACCGCCGTGTACTACTGTGCCAAGAG CAGCATTCTGTCTGGCGGCCACGCCAGAGTGTATGGC ATTGATGTTTGGGGCCAGGGAACCACCGTGACCGTTA GTTCTGCTAGCACCAAGGGCCCCAGCGTGTTCCCCCT GGCCCCCAGCAGCAAGAGCACCAGCGGCGGCACAGCC GCCCTGGGCTGCCTGGTGAAGGACTACTTCCCCGAGC CCGTGACCGTGTCCTGGAACAGCGGAGCCCTGACCTC CGGCGTGCACACCTTCCCCGCCGTGCTGCAGAGCAGC GGCCTGTACAGCCTGTCCAGCGTGGTGACAGTGCCCA GCAGCAGCCTGGGCACCCAGACCTACATCTGCAACGT GAACCACAAGCCCAGCAACACCAAGGTGGACAAGAGA GTGGAGCCCAAGAGCTGCGACAAGACCCACACATGCC CCCCTGCCCGGCGCCAGAGCTGCTGGGCGGACCCTC CGTGTTCCTGTTCCCCCCCAAGCCCAAGGACACCCTG ATGATCAGCAGGACCCCCGAGGTGACCTGCGTGGTGG TGGACGTGAGCCACGAGGACCCAGAGGTGAAGTTCAA CTGGTACGTGGACGGCGTGGAGGTGCACAACGCCAAG ACCAAGCCCAGAGAGGAGCAGTACAACAGCACCTACA GGGTGGTGTCCGTGCTGACCGTGCTGCACCAGGACTG GCTGAACGGCAAGGAATACAAGTGCAAGGTCTCCAAC AAGGCCCTGCCAGCCCCCATCGAAAAGACCATCAGCA AGGCCAAGGGCCAGCCACGGGAGCCCCAGGTGTACAC CCTGCCCCCCTCCCGGGAGGAGATGACCAAGAACCAG GTGTCCCTGACCTGTCTGGTGAAGGGCTTCTACCCCA GCGACATCGCCGTGGAGTGGGAGAGCAACGGCCAGCC CGAGAACAACTACAAGACCACCCCCCCAGTGCTGGAC AGCGACGGCAGCTTCTTCCTGTACAGCAAGCTGACCG TGGACAAGTCCAGGTGGCAGCAGGGCAACGTGTTCAG CTGCAGCGTGATGCACGAGGCCCTGCACAACCACTAC ACCCAGAAGAGCCTGAGCTTAAGCCCCGGCAAG |
| NOV3833 LC | | |
| SEQ ID NO: 54 (Combined) | LCDR1 | GGNNIGSQSVH |
| SEQ ID NO: 55 (Combined) | LCDR2 | DDTDRPS |
| SEQ ID NO: 56 (Combined) | LCDR3 | QVWDSSSDHVV |
| SEQ ID NO: 57 (Kabat) | LCDR1 | GGNNIGSQSVH |
| SEQ ID NO: 58 (Kabat) | LCDR2 | DDTDRPS |
| SEQ ID NO: 59 (Kabat) | LCDR3 | QVWDSSSDHVV |
| SEQ ID NO: 60 (Chothia) | LCDR1 | NNIGSQS |
| SEQ ID NO: 61 (Chothia) | LCDR2 | DDT |

TABLE 2-continued anti-HBV Antibodies

| | | |
|---|---|---|
| SEQ ID NO: 62 (Chothia) | LCDR3 | WDSSSDHV |
| SEQ ID NO: 63 (IMGT) | LCDR1 | NIGSQS |
| SEQ ID NO: 64 (IMGT) | LCDR2 | DDT |
| SEQ ID NO: 65 (IMGT) | LCDR3 | QVWDSSSDHVV |
| SEQ ID NO: 66 | VL | QSALTQPPSVSVAPGQTARITCGGNNIGSQSVHWYQQ KPGQAPILVVYDDTDRPSGIPARFSGSSSGSTATLTI GRVEAGDEADYYCQVWDSSSDHVVFGGGTKLTVL |
| SEQ ID NO: 67 | DNA VL | CAGTCTGCCCTGACTCAGCCACCCTCGGTGTCAGTGG CCCCAGGACAGACGGCCAGGATTACCTGTGGGGGAAA CAACATTGGAAGTCAAAGTGTGCACTGGTACCAGCAG AAGCCAGGCCAGGCCCCTATACTGGTCGTCTATGATG ATACCGACCGGCCCTCAGGGATCCCTGCGCGATTCTC TGGCTCCAGCTCTGGGAGCACGGCCACCCTGACCATC GGCAGGGTCGAAGCCGGGGATGAGGCCGACTATTACT GTCAGGTGTGGGATAGTAGTAGTGATCATGTGGTATT CGGCGGAGGGACCAAGCTGACCGTCTTA |
| SEQ ID NO: 68 | Light Chain | QSALTQPPSVSVAPGQTARITCGGNNIGSQSVHWYQQ KPGQAPILVVYDDTDRPSGIPARFSGSSSGSTATLTI GRVEAGDEADYYCQVWDSSSDHVVFGGGTKLTVLSQP KAAPSVTLFPPSSEELQANKATLVCLISDFYPGAVTV AWKADSSPVKAGVETTTPSKQSNNKYAASSYLSLTPE QWKSHRSYSCQVTHEGSTVEKTVAPTECS |
| SEQ ID NO: 69 | DNA Light Chain | CAGTCTGCCCTGACTCAGCCACCCTCGGTGTCAGTGG CCCCAGGACAGACGGCCAGGATTACCTGTGGGGGAAA CAACATTGGAAGTCAAAGTGTGCACTGGTACCAGCAG AAGCCAGGCCAGGCCCCTATACTGGTCGTCTATGATG ATACCGACCGGCCCTCAGGGATCCCTGCGCGATTCTC TGGCTCCAGCTCTGGGAGCACGGCCACCCTGACCATC GGCAGGGTCGAAGCCGGGGATGAGGCCGACTATTACT GTCAGGTGTGGGATAGTAGTAGTGATCATGTGGTATT CGGCGGAGGGACCAAGCTGACCGTCTTAAGTCAGCCC AAGGCTGCCCCCTCGGTCACTCTGTTCCCGCCCTCCT CTGAGGAGCTTCAAGCCAACAAGGCCACACTGGTGTG TCTCATAAGTGACTTCTACCCGGGAGCCGTGACAGTG GCCTGGAAGGCAGATAGCAGCCCCGTCAAGGCGGGAG TGGAGACCACCACACCCTCCAAACAAAGCAACAACAA GTACGCCGCCAGCAGCTACCTGAGCCTGACCCCCGAG CAGTGGAAGAGCCACAGAAGCTACAGCTGCCAGGTCA CCCACGAGGGCAGCACCGTGGAGAAAACCGTGGCCCC CACCGAGTGCAGC |
| NOV3831 HC | | |
| SEQ ID NO: 70 (Combined) | HCDR1 | GFTFNNYAMS |
| SEQ ID NO: 71 (Combined) | HCDR2 | SISGSGGSTYYADSVKG |
| SEQ ID NO: 72 (Combined) | HCDR3 | SSILSGGHARVYGIDV |
| SEQ ID NO: 73 (Kabat) | HCDR1 | NYAMS |
| SEQ ID NO: 74 (Kabat) | HCDR2 | SISGSGGSTYYADSVKG |
| SEQ ID NO: 75 (Kabat) | HCDR3 | SSILSGGHARVYGIDV |
| SEQ ID NO: 76 (Chothia) | HCDR1 | GFTFNNY |
| SEQ ID NO: 77 (Chothia) | HCDR2 | SGSGGS |

TABLE 2-continued anti-HBV Antibodies

| SEQ ID NO: 78 (Chothia) | HCDR3 | SSILSGGHARVYGIDV |
|---|---|---|
| SEQ ID NO: 79 (IMGT) | HCDR1 | GFTFNNYA |
| SEQ ID NO: 80 (IMGT) | HCDR2 | ISGSGGST |
| SEQ ID NO: 81 (IMGT) | HCDR3 | AKSSILSGGHARVYGIDV |
| SEQ ID NO: 82 | VH | EMQVLESGGGLVQPGGSLRLSCAASGFTFNNYAMSWV<br>RQVPGKGLEWVSSISGSGGSTYYADSVKGQFTISRDN<br>SKNTLYLQMNSLRAEDTAVYYCAKSSILSGGHARVYG<br>IDVWGQGTTVTVSS |
| SEQ ID NO: 83 | DNA VH | GAAATGCAGGTGTTGGAGTCTGGGGGAGGCCTGGTAC<br>AGCCTGGGGGGTCCCTGAGACTCTCCTGTGCAGCCTC<br>TGGATTCACCTTTAACAACTATGCCATGAGCTGGGTC<br>CGCCAGGTTCCAGGGAAGGGGCTGGAGTGGGTCTCAA<br>GTATTAGTGGTAGTGGAGGTAGCACGTACTACGCAGA<br>CTCCGTGAAGGGCCAGTTCACCATCTCCAGAGACAAT<br>TCCAAGAATACGCTGTATCTGCAAATGAACAGCCTGA<br>GAGCCGAGGACACGGCCGTATATTACTGTGCAAATC<br>CTCTATCTTGAGTGGTGGTCACGCGCGGGTCTACGGC<br>ATAGACGTCTGGGGCCAAGGGACCACGGTCACCGTCT<br>CCTCA |
| SEQ ID NO: 84 | Heavy Chain | EMQVLESGGGLVQPGGSLRLSCAASGFTFNNYAMSWV<br>RQVPGKGLEWVSSISGSGGSTYYADSVKGQFTISRDN<br>SKNTLYLQMNSLRAEDTAVYYCAKSSILSGGHARVYG<br>IDVWGQGTTVTVSSASTKGPSVFPLAPSSKSTSGGTA<br>ALGCLVKDYFPEPVTVSWNSGALTSGVHTFPAVLQSS<br>GLYSLSSVVTVPSSSLGTQTYICNVNHKPSNTKVDKR<br>VEPKSCDKTHTCPPCPAPELLGGPSVFLFPPKPKDTL<br>MISRTPEVTCVVVDVSHEDPEVKFNWYVDGVEVHNAK<br>TKPREEQYNSTYRVVSVLTVLHQDWLNGKEYKCKVSN<br>KALPAPIEKTISKAKGQPREPQVYTLPPSREEMTKNQ<br>VSLTCLVKGFYPSDIAVEWESNGQPENNYKTTPPVLD<br>SDGSFFLYSKLTVDKSRWQQGNVFSCSVMHEALHNHY<br>TQKSLSLSPGK |
| SEQ ID NO: 85 | DNA Heavy Chain | GAAATGCAGGTGTTGGAGTCTGGGGGAGGCCTGGTAC<br>AGCCTGGGGGGTCCCTGAGACTCTCCTGTGCAGCCTC<br>TGGATTCACCTTTAACAACTATGCCATGAGCTGGGTC<br>CGCCAGGTTCCAGGGAAGGGGCTGGAGTGGGTCTCAA<br>GTATTAGTGGTAGTGGAGGTAGCACGTACTACGCAGA<br>CTCCGTGAAGGGCCAGTTCACCATCTCCAGAGACAAT<br>TCCAAGAATACGCTGTATCTGCAAATGAACAGCCTGA<br>GAGCCGAGGACACGGCCGTATATTACTGTGCAAATC<br>CTCTATCTTGAGTGGTGGTCACGCGCGGGTCTACGGC<br>ATAGACGTCTGGGGCCAAGGGACCACGGTCACCGTCT<br>CCTCAGCCTCCACCAAGGGCCCATCGGTCTTCCCCCT<br>GGCACCCTCCTCCAAGAGCACCTCTGGGGGCACAGCG<br>GCCCTGGGCTGCCTGGTCAAGGACTACTTCCCCGAAC<br>CGGTGACGGTGTCATGGAACTCAGGCGCCCTGACCAG<br>CGGCGTGCACACCTTCCCGGCTGTCCTACAGTCCTCA<br>GGACTCTACTCCCTCAGCAGCGTGGTGACCGTGCCCT<br>CCAGCAGCTTGGGCACCCAGACCTACATCTGCAACGT<br>GAACCACAAGCCCAGCAACACCAAGGTGGACAAGAGA<br>GTGGAGCCCAAGAGCTGCGACAAGACCCACACCTGCC<br>CCCCCTGCCCAGCCCCAGAGCTGCTGGGCGGACCCTC<br>CGTGTTCCTGTTCCCCCCCAAGCCCAAGGACACCCTG<br>ATGATCAGCAGGACCCCCGAGGTGACCTGCGTGGTGG<br>TGGACGTGAGCCACGAGGACCCAGAGGTGAAGTTCAA<br>CTGGTACGTGGACGGCGTGGAGGTGCACAACGCCAAG<br>ACCAAGCCCAGAGAGGAGCAGTACAACAGCACCTACA<br>GGGTGGTGTCCGTGCTGACCGTGCTGCACCAGGACTG<br>GCTGAACGGCAAGGAATACAAGTGCAAGGTCTCCAAC<br>AAGGCCCTGCCAGCCCCCATCGAAAAGACCATCAGCA<br>AGGCCAAGGGCCAGCCACGGGAGCCCCAGGTGTACAC<br>CCTGCCCCCTCCCGGGAGGAGATGACCAAGAACCAG<br>GTGTCCCTGACCTGTCTGGTGAAGGGCTTCTACCCCA<br>GCGACATCGCCGTGGAGTGGGAGAGCAACGGCCAGCC<br>CGAGAACAACTACAAGACCACCCCCCCAGTGCTGGAC<br>AGCGACGGCAGCTTCTTCCTGTACAGCAAGCTGACCG |

TABLE 2-continued anti-HBV Antibodies

```
                    TGGACAAGTCCAGGTGGCAGCAGGGCAACGTGTTCAG
                    CTGCAGCGTGATGCACGAGGCCCTGCACAACCACTAC
                    ACCCAGAAGAGCCTGAGCCTGTCCCCCGGCAAG
```

NOV3831 LC

| SEQ ID NO | Region | Sequence |
|---|---|---|
| SEQ ID NO: 86 (Combined) | LCDR1 | GGNNIGSQSVH |
| SEQ ID NO: 87 (Combined) | LCDR2 | DDTDRPS |
| SEQ ID NO: 88 (Combined) | LCDR3 | QVWDSSSDHVV |
| SEQ ID NO: 89 (Kabat) | LCDR1 | GGNNIGSQSVH |
| SEQ ID NO: 90 (Kabat) | LCDR2 | DDTDRPS |
| SEQ ID NO: 91 (Kabat) | LCDR3 | QVWDSSSDHVV |
| SEQ ID NO: 92 (Chothia) | LCDR1 | NNIGSQS |
| SEQ ID NO: 93 (Chothia) | LCDR2 | DDT |
| SEQ ID NO: 94 (Chothia) | LCDR3 | WDSSSDHV |
| SEQ ID NO: 95 (IMGT) | LCDR1 | NIGSQS |
| SEQ ID NO: 96 (IMGT) | LCDR2 | DDT |
| SEQ ID NO: 97 (IMGT) | LCDR3 | QVWDSSSDHVV |
| SEQ ID NO: 98 | VL | QSALTQPPSVSVAPGQTARITCGGNNIGSQSVHWYQQ KPGQAPILVVYDDTDRPSGIPARFSGSSSGSTATLTI GRVEAGDEADYYCQVWDSSSDHVVFGGGTKLTVL |
| SEQ ID NO: 99 | DNA VL | CAGTCTGCCCTGACTCAGCCACCCTCGGTGTCAGTGG CCCCAGGACAGACGGCCAGGATTACCTGTGGGGGAAA CAACATTGGAAGTCAAAGTGTGCACTGGTACCAGCAG AAGCCAGGCCAGGCCCCTATACTGGTCGTCTATGATG ATACCGACCGGCCCTCAGGGATCCCTGCGCGATTCTC TGGCTCCAGCTCTGGGAGCACGGCCACCCTGACCATC GGCAGGGTCGAAGCCGGGGATGAGGCCGACTATTACT GTCAGGTGTGGGATAGTAGTAGTGATCATGTGGTATT CGGCGGAGGGACCAAGCTGACCGTCTTA |
| SEQ ID NO: 100 | Light Chain | QSALTQPPSVSVAPGQTARITCGGNNIGSQSVHWYQQ KPGQAPILVVYDDTDRPSGIPARFSGSSSGSTATLTI GRVEAGDEADYYCQVWDSSSDHVVFGGGTKLTVLSQP KAAPSVTLFPPSSEELQANKATLVCLISDFYPGAVTV AWKADSSPVKAGVETTTPSKQSNNKYAASSYLSLTPE QWKSHRSYSCQVTHEGSTVEKTVAPTECS |
| SEQ ID NO: 101 | DNA Light Chain | CAGTCTGCCCTGACTCAGCCACCCTCGGTGTCAGTGG CCCCAGGACAGACGGCCAGGATTACCTGTGGGGGAAA CAACATTGGAAGTCAAAGTGTGCACTGGTACCAGCAG AAGCCAGGCCAGGCCCCTATACTGGTCGTCTATGATG ATACCGACCGGCCCTCAGGGATCCCTGCGCGATTCTC TGGCTCCAGCTCTGGGAGCACGGCCACCCTGACCATC GGCAGGGTCGAAGCCGGGGATGAGGCCGACTATTACT GTCAGGTGTGGGATAGTAGTAGTGATCATGTGGTATT CGGCGGAGGGACCAAGCTGACCGTCTTAAGTCAGCCC AAGGCTGCCCCCTCGGTCACTCTGTTCCCGCCCTCCT CTGAGGAGCTTCAAGCCAACAAGGCCACACTGGTGTG TCTCATAAGTGACTTCTACCCGGGAGCCGTGACAGTG GCCTGGAAGGCAGATAGCAGCCCCGTCAAGGCGGGAG TGGAGACCACCACACCCTCCAAACAAAGCAACAACAA GTACGCCGCCAGCAGCTACCTGAGCCTGACCCCCGAG |

TABLE 2-continued anti-HBV Antibodies

|  |  |  |
|---|---|---|
|  |  | CAGTGGAAGAGCCACAGAAGCTACAGCTGCCAGGTCA CCCACGAGGGCAGCACCGTGGAGAAAACCGTGGCCCC CACCGAGTGCAGC |
| NOV3540 HC |  |  |
| SEQ ID NO: 102 (Combined) | HCDR1 | GFTFSPHAMS |
| SEQ ID NO: 103 (Combined) | HCDR2 | AISDSGGSTHYADSVKG |
| SEQ ID NO: 104 (Combined) | HCDR3 | DDDAWSGYDYWFDY |
| SEQ ID NO: 105 (Kabat) | HCDR1 | PHAMS |
| SEQ ID NO: 106 (Kabat) | HCDR2 | AISDSGGSTHYADSVKG |
| SEQ ID NO: 107 (Kabat) | HCDR3 | DDDAWSGYDYWFDY |
| SEQ ID NO: 108 (Chothia) | HCDR1 | GFTFSPH |
| SEQ ID NO: 109 (Chothia) | HCDR2 | SDSGGS |
| SEQ ID NO: 110 (Chothia) | HCDR3 | DDDAWSGYDYWFDY |
| SEQ ID NO: 111 (IMGT) | HCDR1 | GFTFSPHA |
| SEQ ID NO: 112 (IMGT) | HCDR2 | ISDSGGST |
| SEQ ID NO: 113 (IMGT) | HCDR3 | ARDDDAWSGYDYWFDY |
| SEQ ID NO: 114 | VH | EVQLLESGGGLVQPGGSLRLSCAASGFTFSPHAMSWV RQAPGKGLEWVSAISDSGGSTHYADSVKGRFTISRDN SKNTLYLQMNSLRAEDTAVYYCARDDDAWSGYDYWFD YWGQGTLVTVSS |
| SEQ ID NO: 115 | DNA VH | GAGGTCCAATTGCTGGAATCTGGCGGAGGACTGGTTC AGCCTGGTGGCTCTCTGAGACTGTCTTGTGCCGCCAG CGGCTTCACCTTTAGCCCTCATGCCATGTCCTGGGTC CGACAGGCTCCTGGAAAAGGACTCGAGTGGGTGTCCG CCATTTCTGATTCTGGCGGCAGCACACACTACGCCGA TAGCGTGAAGGGCAGATTCACCATCAGCCGGGACAAC AGCAAGAACACCCTGTACCTGCAGATGAACAGCCTGA GAGCCGAGGACACAGCCGTGTACTATTGCGCGCGTGA CGATGATGCTTGGTCCGGCTACGACTATTGGTTCGAT TACTGGGGCCAGGGCACCCTGGTCACAGTTAGCTCA |
| SEQ ID NO: 116 | Heavy Chain | EVQLLESGGGLVQPGGSLRLSCAASGFTFSPHAMSWV RQAPGKGLEWVSAISDSGGSTHYADSVKGRFTISRDN SKNTLYLQMNSLRAEDTAVYYCARDDDAWSGYDYWFD YWGQGTLVTVSSASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKRVE PKSCDKTHTCPPCPAPELLGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |
| SEQ ID NO: 117 | DNA Heavy Chain | GAGGTCCAATTGCTGGAATCTGGCGGAGGACTGGT TCAGCCTGGTGGCTCTCTGAGACTGTCTTGTGCCGC CAGCGGCTTCACCTTTAGCCCTCATGCCATGTCCTG GGTCCGACAGGCTCCTGGAAAAGGACTCGAGTGGG TGTCCGCCATTTCTGATTCTGGCGGCAGCACACACT ACGCCGATAGCGTGAAGGGCAGATTCACCATCAGC |

TABLE 2-continued anti-HBV Antibodies

| | | |
|---|---|---|
| | | CGGGACAACAGCAAGAACACCCTGTACCTGCAGAT
GAACAGCCTGAGAGCCGAGGACACAGCCGTGTACT
ATTGCGCGCGTGACGATGATGCTTGGTCCGGCTAC
GACTATTGGTTCGATTACTGGGGCCAGGGCACCCT
GGTCACAGTTAGCTCAGCTAGCACCAAGGGCCCCA
GCGTGTTCCCCCTGGCCCCCAGCAGCAAGAGCACC
AGCGGCGGCACAGCCGCCCTGGGCTGCCTGGTGAA
GGACTACTTCCCCGAGCCCGTGACCGTGTCCTGGA
ACAGCGGAGCCCTGACCTCCGGCGTGCACACCTTC
CCCGCCGTGCTGCAGAGCAGCGGCCTGTACAGCCT
GTCCAGCGTGGTGACAGTGCCCAGCAGCAGCCTGG
GCACCCAGACCTACATCTGCAACGTGAACCACAAG
CCCAGCAACACCAAGGTGGACAAGAGAGTGGAGC
CCAAGAGCTGCGACAAGACCCACACATGCCCCCCC
TGCCCGGCGCCAGAGCTGCTGGGCGGACCCTCCGT
GTTCCTGTTCCCCCCCAAGCCCAAGGACACCCTGAT
GATCAGCAGGACCCCCGAGGTGACCTGCGTGGTGG
TGGACGTGAGCCACGAGGACCCAGAGGTGAAGTTC
AACTGGTACGTGGACGGCGTGGAGGTGCACAACGC
CAAGACCAAGCCCAGAGAGGAGCAGTACAACAGC
ACCTACAGGGTGGTGTCCGTGCTGACCGTGCTGCA
CCAGGACTGGCTGAACGGCAAGGAATACAAGTGCA
AGGTCTCCAACAAGGCCCTGCCAGCCCCCATCGAA
AAGACCATCAGCAAGGCCAAGGGCCAGCCACGGG
AGCCCCAGGTGTACACCCTGCCCCCCTCCCGGGAG
GAGATGACCAAGAACCAGGTGTCCCTGACCTGTCT
GGTGAAGGGCTTCTACCCCAGCGACATCGCCGTGG
AGTGGGAGAGCAACGGCCAGCCCGAGAACAACTA
CAAGACCACCCCCCCAGTGCTGGACAGCGACGGCA
GCTTCTTCCTGTACAGCAAGCTGACCGTGGACAAG
TCCAGGTGGCAGCAGGGCAACGTGTTCAGCTGCAG
CGTGATGCACGAGGCCCTGCACAACCACTACACCC
AGAAGAGCCTGAGCTTAAGCCCCGGCAAG |

NOV3540 LC

| | | |
|---|---|---|
| SEQ ID NO: 118 (Combined) | LCDR1 | RASQSISPYLN |
| SEQ ID NO: 119 (Combined) | LCDR2 | AADSLQS |
| SEQ ID NO: 120 (Combined) | LCDR3 | QQSYKIPLT |
| SEQ ID NO: 121 (Kabat) | LCDR1 | RASQSISPYLN |
| SEQ ID NO: 122 (Kabat) | LCDR2 | AADSLQS |
| SEQ ID NO: 123 (Kabat) | LCDR3 | QQSYKIPLT |
| SEQ ID NO: 124 (Chothia) | LCDR1 | SQSISPY |
| SEQ ID NO: 125 (Chothia) | LCDR2 | AAD |
| SEQ ID NO: 126 (Chothia) | LCDR3 | SYKIPL |
| SEQ ID NO: 127 (IMGT) | LCDR1 | QSISPY |
| SEQ ID NO: 128 (IMGT) | LCDR2 | AAD |
| SEQ ID NO: 129 (IMGT) | LCDR3 | QQSYKIPLT |
| SEQ ID NO: 130 | VL | DIQMTQSPSSLSASVGDRVTITCRASQSISPYLNWYQ
QKPGKAPKLLIYAADSLQSGVPSRFSGSGSGTDFTLT
ISSLQPEDFATYYCQQSYKIPLTFGQGTKVEIK |

TABLE 2-continued anti-HBV Antibodies

| SEQ ID NO: 131 | DNA VL | GATATCCAGATGACACAGAGCCCTAGCAGCCTGTC<br>TGCCTCTGTGGGCGATAGAGTGACCATCACCTGTA<br>GAGCCAGCCAGAGCATCAGCCCCTACCTGAATTGG<br>TACCAGCAGAAGCCTGGCAAGGCCCCTAAGCTGCT<br>GATCTATGCTGCCGACTCTCTGCAGTCTGGCGTGCC<br>AAGCAGATTTTCTGGCAGCGGCTCTGGCACCGACT<br>TCACCCTGACAATTAGCTCCCTGCAGCCTGAAGACT<br>TCGCCACCTACTACTGCCAGCAGAGCTACAAGATC<br>CCTCTGACCTTTGGCCAGGGCACCAAGGTGGAAAT<br>CAAG |
| --- | --- | --- |
| SEQ ID NO: 132 | Light Chain | DIQMTQSPSSLSASVGDRVTITCRASQSISPYLNWYQ<br>QKPGKAPKLLIYAADSLQSGVPSRFSGSGSGTDFTLT<br>ISSLQPEDFATYYCQQSYKIPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 133 | DNA Light Chain | GATATCCAGATGACACAGAGCCCTAGCAGCCTGTC<br>TGCCTCTGTGGGCGATAGAGTGACCATCACCTGTA<br>GAGCCAGCCAGAGCATCAGCCCCTACCTGAATTGG<br>TACCAGCAGAAGCCTGGCAAGGCCCCTAAGCTGCT<br>GATCTATGCTGCCGACTCTCTGCAGTCTGGCGTGCC<br>AAGCAGATTTTCTGGCAGCGGCTCTGGCACCGACT<br>TCACCCTGACAATTAGCTCCCTGCAGCCTGAAGACT<br>TCGCCACCTACTACTGCCAGCAGAGCTACAAGATC<br>CCTCTGACCTTTGGCCAGGGCACCAAGGTGGAAAT<br>CAAGCGTACGGTGGCCGCTCCCAGCGTGTTCATCTT<br>CCCCCCCAGCGACGAGCAGCTGAAGAGCGGCACCG<br>CCAGCGTGGTGTGCCTGCTGAACAACTTCTACCCCC<br>GGGAGGCCAAGGTGCAGTGGAAGGTGGACAACGC<br>CCTGCAGAGCGGCAACAGCCAGGAGAGCGTCACCG<br>AGCAGGACAGCAAGGACTCCACCTACAGCCTGAGC<br>AGCACCCTGACCCTGAGCAAGGCCGACTACGAGAA<br>GCATAAGGTGTACGCCTGCGAGGTGACCCACCAGG<br>GCCTGTCCAGCCCCGTGACCAAGAGCTTCAACAGG<br>GGCGAGTGC |

NOV3357 HC

| SEQ ID NO: 134 (Combined) | HCDR1 | GFTFSPHAMS |
| --- | --- | --- |
| SEQ ID NO: 135 (Combined) | HCDR2 | AISDSGGSTHYADSVKG |
| SEQ ID NO: 136 (Combined) | HCDR3 | DDDGWSGYDYWFDY |
| SEQ ID NO: 137 (Kabat) | HCDR1 | PHAMS |
| SEQ ID NO: 138 (Kabat) | HCDR2 | AISDSGGSTHYADSVKG |
| SEQ ID NO: 139 (Kabat) | HCDR3 | DDDGWSGYDYWFDY |
| SEQ ID NO: 140 (Chothia) | HCDR1 | GFTFSPH |
| SEQ ID NO: 141 (Chothia) | HCDR2 | SDSGGS |
| SEQ ID NO: 142 (Chothia) | HCDR3 | DDDGWSGYDYWFDY |
| SEQ ID NO: 143 (IMGT) | HCDR1 | GFTFSPHA |
| SEQ ID NO: 144 (IMGT) | HCDR2 | ISDSGGST |
| SEQ ID NO: 145 (IMGT) | HCDR3 | ARDDDGWSGYDYWFDY |

TABLE 2-continued anti-HBV Antibodies

| SEQ ID NO: 146 | VH | EVQLLESGGGLVQPGGSLRLSCAASGFTFSPHAMSWV
RQAPGKGLEWVSAISDSGGSTHYADSVKGRFTISRDN
SKNTLYLQMNSLRAEDTAVYYCARDDDGWSGYDYWFD
YWGQGTLVTVSS |
|---|---|---|
| SEQ ID NO: 147 | DNA VH | GAGGTCCAATTGCTGGAATCTGGCGGAGGACTGGT
TCAGCCTGGTGGCTCTCTGAGACTGTCTTGTGCCGC
CAGCGGCTTCACATTCAGCCCTCATGCCATGTCCTG
GGTCCGACAGGCTCCTGGAAAAGGACTCGAGTGGG
TGTCCGCCATTTCTGATTCTGGCGGCAGCACACACT
ACGCCGATAGCGTGAAGGGCAGATTCACCATCAGC
CGGGACAACAGCAAGAACACCCTGTACCTGCAGAT
GAACAGCCTGAGAGCCGAGGACACAGCCGTGTACT
ATTGCGCGCGTGACGATGATGGATGGTCCGGCTAC
GACTATTGGTTCGATTACTGGGGCCAGGGCACCCT
GGTCACAGTTAGCTCA |
| SEQ ID NO: 148 | Heavy Chain | EVQLLESGGGLVQPGGSLRLSCAASGFTFSPHAMSWV
RQAPGKGLEWVSAISDSGGSTHYADSVKGRFTISRDN
SKNTLYLQMNSLRAEDTAVYYCARDDDGWSGYDYWFD
YWGQGTLVTVSSASTKGPSVFPLAPSSKSTSGGTAAL
GCLVKDYFPEPVTVSWNSGALTSGVHTFPAVLQSSGL
YSLSSVVTVPSSSLGTQTYICNVNHKPSNTKVDKRVE
PKSCDKTHTCPPCPAPELLGGPSVFLFPPKPKDTLMI
SRTPEVTCVVVDVSHEDPEVKFNWYVDGVEVHNAKTK
PREEQYNSTYRVVSVLTVLHQDWLNGKEYKCKVSNKA
LPAPIEKTISKAKGQPREPQVYTLPPSREEMTKNQVS
LTCLVKGFYPSDIAVEWESNGQPENNYKTTPPVLDSD
GSFFLYSKLTVDKSRWQQGNVFSCSVMHEALHNHYTQ
KSLSLSPGK |
| SEQ ID NO: 149 | DNA Heavy Chain | GAGGTCCAATTGCTGGAATCTGGCGGAGGACTGGT
TCAGCCTGGTGGCTCTCTGAGACTGTCTTGTGCCGC
CAGCGGCTTCACATTCAGCCCTCATGCCATGTCCTG
GGTCCGACAGGCTCCTGGAAAAGGACTCGAGTGGG
TGTCCGCCATTTCTGATTCTGGCGGCAGCACACACT
ACGCCGATAGCGTGAAGGGCAGATTCACCATCAGC
CGGGACAACAGCAAGAACACCCTGTACCTGCAGAT
GAACAGCCTGAGAGCCGAGGACACAGCCGTGTACT
ATTGCGCGCGTGACGATGATGGATGGTCCGGCTAC
GACTATTGGTTCGATTACTGGGGCCAGGGCACCCT
GGTCACAGTTAGCTCAGCTAGCACCAAGGGCCCCA
GCGTGTTCCCCCTGGCCCCCAGCAGCAAGAGCACC
AGCGGCGGCACAGCCGCCCTGGGCTGCCTGGTGAA
GGACTACTTCCCCGAGCCCGTGACCGTGTCCTGGA
ACAGCGGAGCCCTGACCTCCGGCGTGCACACCTTC
CCCGCCGTGCTGCAGAGCAGCGGCCTGTACAGCCT
GTCCAGCGTGGTGACAGTGCCCAGCAGCAGCCTGG
GCACCCAGACCTACATCTGCAACGTGAACCACAAG
CCCAGCAACACCAAGGTGGACAAGAGAGTGGAGC
CCAAGAGCTGCGACAAGACCCACACATGCCCCCCC
TGCCCGGCGCCAGAGCTGCTGGGCGGACCCTCCGT
GTTCCTGTTCCCCCCCAAGCCCAAGGACACCCTGAT
GATCAGCAGGACCCCCGAGGTGACCTGCGTGGTGG
TGGACGTGAGCCACGAGGACCCAGAGGTGAAGTTC
AACTGGTACGTGGACGGCGTGGAGGTGCACAACGC
CAAGACCAAGCCCAGAGAGGAGCAGTACAACAGC
ACCTACAGGGTGGTGTCCGTGCTGACCGTGCTGCA
CCAGGACTGGCTGAACGGCAAGGAATACAAGTGCA
AGGTCTCCAACAAGGCCCTGCCAGCCCCCATCGAA
AAGACCATCAGCAAGGCCAAGGGCCAGCCACGGG
AGCCCCAGGTGTACACCCTGCCCCCCTCCCGGGAG
GAGATGACCAAGAACCAGGTGTCCCTGACCTGTCT
GGTGAAGGGCTTCTACCCCAGCGACATCGCCGTGG
AGTGGGAGAGCAACGGCCAGCCCGAGAACAACTA
CAAGACCACCCCCCCAGTGCTGGACAGCGACGGCA
GCTTCTTCCTGTACAGCAAGCTGACCGTGGACAAG
TCCAGGTGGCAGCAGGGCAACGTGTTCAGCTGCAG
CGTGATGCACGAGGCCCTGCACAACCACTACACCC
AGAAAGAGCCTGAGCTTAAGCCCCGGCAAG |

NOV3357LC

| SEQ ID NO: 150 (Combined) | LCDR1 | RASQSISPYLN |
|---|---|---|

TABLE 2-continued

| anti-HBV Antibodies | | | |
|---|---|---|---|
| SEQ ID NO: 151 (Combined) | LCDR2 | | AADSLQS |
| SEQ ID NO: 152 (Combined) | LCDR3 | | QQSYKIPLT |
| SEQ ID NO: 153 (Kabat) | LCDR1 | | RASQSISPYLN |
| SEQ ID NO: 154 (Kabat) | LCDR2 | | AADSLQS |
| SEQ ID NO: 155 (Kabat) | LCDR3 | | QQSYKIPLT |
| SEQ ID NO: 156 (Chothia) | LCDR1 | | SQSISPY |
| SEQ ID NO: 157 (Chothia) | LCDR2 | | AAD |
| SEQ ID NO: 158 (Chothia) | LCDR3 | | SYKIPL |
| SEQ ID NO: 159 (IMGT) | LCDR1 | | QSISPY |
| SEQ ID NO: 160 (IMGT) | LCDR2 | | AAD |
| SEQ ID NO: 161 (IMGT) | LCDR3 | | QQSYKIPLT |
| SEQ ID NO: 162 | VL | | DIQMTQSPSSLSASVGDRVTITCRASQSISPYLNWYQ<br>QKPGKAPKLLIYAADSLQSGVPSRFSGSGSGTDFTLT<br>ISSLQPEDFATYYCQQSYKIPLTFGQGTKVEIK |
| SEQ ID NO: 163 | DNA VL | | GATATCCAGATGACACAGAGCCCTAGCAGCCTGTC<br>TGCCTCTGTGGGCGATAGAGTGACCATCACCTGTA<br>GAGCCAGCCAGAGCATCAGCCCCTACCTGAATTGG<br>TACCAGCAGAAGCCTGGCAAGGCCCCTAAGCTGCT<br>GATCTATGCTGCCGACTCTCTGCAGTCTGGCGTGCC<br>AAGCAGATTTTCTGGCAGCGGCTCTGGCACCGACT<br>TCACCCTGACAATTAGCTCCCTGCAGCCTGAAGACT<br>TCGCCACCTACTACTGCCAGCAGAGCTACAAGATC<br>CCTCTGACCTTTGGCCAGGGCACCAAGGTGGAAAT<br>CAAG |
| SEQ ID NO: 164 | Light Chain | | DIQMTQSPSSLSASVGDRVTITCRASQSISPYLNWYQ<br>QKPGKAPKLLIYAADSLQSGVPSRFSGSGSGTDFTLT<br>ISSLQPEDFATYYCQQSYKIPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 165 | DNA Light Chain | | GATATCCAGATGACACAGAGCCCTAGCAGCCTGTC<br>TGCCTCTGTGGGCGATAGAGTGACCATCACCTGTA<br>GAGCCAGCCAGAGCATCAGCCCCTACCTGAATTGG<br>TACCAGCAGAAGCCTGGCAAGGCCCCTAAGCTGCT<br>GATCTATGCTGCCGACTCTCTGCAGTCTGGCGTGCC<br>AAGCAGATTTTCTGGCAGCGGCTCTGGCACCGACT<br>TCACCCTGACAATTAGCTCCCTGCAGCCTGAAGACT<br>TCGCCACCTACTACTGCCAGCAGAGCTACAAGATC<br>CCTCTGACCTTTGGCCAGGGCACCAAGGTGGAAAT<br>CAAGCGTACGGTGGCCGCTCCCAGCGTGTTCATCTT<br>CCCCCCCAGCGACGAGCAGCTGAAGAGCGGCACCG<br>CCAGCGTGGTGTGCCTGCTGAACAACTTCTACCCCC<br>GGGAGGCCAAGGTGCAGTGGAAGGTGGACAACGC<br>CCTGCAGAGCGGCAACAGCCAGGAGAGCGTCACCG<br>AGCAGGACAGCAAGGACTCCACCTACAGCCTGAGC<br>AGCACCCTGACCCTGAGCAAGGCCGACTACGAGAA<br>GCATAAGGTGTACGCCTGCGAGGTGACCCACCAGG<br>GCCTGTCCAGCCCCGTGACCAAGAGCTTCAACAGG<br>GGCGAGTGC |

TABLE 2-continued anti-HBV Antibodies

NOV3834HC

| SEQ ID NO: 166 (Combined) | HCDR1 | GFTFNRYGMH |
| --- | --- | --- |
| SEQ ID NO: 167 (Combined) | HCDR2 | GIWHDGSHKYYADSLRG |
| SEQ ID NO: 168 (Combined) | HCDR3 | QTNRGRLDDAFDI |
| SEQ ID NO: 169 (Kabat) | HCDR1 | RYGMH |
| SEQ ID NO: 170 (Kabat) | HCDR2 | GIWHDGSHKYYADSLRG |
| SEQ ID NO: 171 (Kabat) | HCDR3 | QTNRGRLDDAFDI |
| SEQ ID NO: 172 (Chothia) | HCDR1 | GFTFNRY |
| SEQ ID NO: 173 (Chothia) | HCDR2 | WHDGSH |
| SEQ ID NO: 174 (Chothia) | HCDR3 | QTNRGRLDDAFDI |
| SEQ ID NO: 175 (IMGT) | HCDR1 | GFTFNRYG |
| SEQ ID NO: 176 (IMGT) | HCDR2 | IWHDGSHK |
| SEQ ID NO: 177 (IMGT) | HCDR3 | VRQTNRGRLDDAFDI |
| SEQ ID NO: 178 | VH | QVQLVESGGGVVQPGRSLRLSCAASGFTFNRYGMHWV RQAPGKGLEWVAGIWHDGSHKYYADSLRGRFTISRDN AKNTLDLQLNRLRAEDTSVYYCVRQTNRGRLDDAFDI WGQGTMVTVSS |
| SEQ ID NO: 179 | DNA VH | CAGGTGCAGCTGGTGGAGTCTGGGGGAGGCGTGGT CCAGCCTGGGAGGTCCCTGAGACTCTCCTGTGCAG CGTCAGGATTCACATTCAATAGATATGGCATGCAC TGGGTCCGCCAGGCTCCAGGCAAGGGGTTGGAGTG GGTGGCTGGTATATGGCATGATGGAAGTCATAAAT ACTATGCAGACTCTCTGAGGGGCCGATTCACCATCT CCAGAGACAATGCCAAGAACACGCTGGATCTGCAA TTGAACAGGCTGAGAGCCGAAGACACGTCTGTGTA TTATTGTGTGAGGCAAACCAACAGGGGACGTCTCG ATGATGCTTTTGACATCTGGGGCCAAGGGACAATG GTCACCGTTAGCTCA |
| SEQ ID NO: 180 | Heavy Chain | QVQLVESGGGVVQPGRSLRLSCAASGFTFNRYGMHWV RQAPGKGLEWVAGIWHDGSHKYYADSLRGRFTISRDN AKNTLDLQLNRLRAEDTSVYYCVRQTNRGRLDDAFDI WGQGTMVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEP KSCDKTHTCPPCPAPELLGGPSVFLFPPKPKDTLMIS RTPEVTCVVVDVSHEDPEVKFNWYVDGVEVHNAKTKP REEQYNSTYRVVSVLTVLHQDWLNGKEYKCKVSNKAL PAPIEKTISKAKGQPREPQVYTLPPSREEMTKNQVSL TCLVKGFYPSDIAVEWESNGQPENNYKTTPPVLDSDG SFFLYSKLTVDKSRWQQGNVFSCSVMHEALHNHYTQK SLSLSPGK |
| SEQ ID NO: 181 | DNA Heavy Chain | CAGGTGCAGCTGGTGGAGTCTGGGGGAGGCGTGGT CCAGCCTGGGAGGTCCCTGAGACTCTCCTGTGCAG CGTCAGGATTCACATTCAATAGATATGGCATGCAC TGGGTCCGCCAGGCTCCAGGCAAGGGGTTGGAGTG GGTGGCTGGTATATGGCATGATGGAAGTCATAAAT ACTATGCAGACTCTCTGAGGGGCCGATTCACCATCT CCAGAGACAATGCCAAGAACACGCTGGATCTGCAA TTGAACAGGCTGAGAGCCGAAGACACGTCTGTGTA |

TABLE 2-continued anti-HBV Antibodies

|  |  |  |
|---|---|---|
|  |  | TTATTGTGTGAGGCAAACCAACAGGGGACGTCTCG<br>ATGATGCTTTTGACATCTGGGGCCAAGGGACAATG<br>GTCACCGTTAGCTCAGCTAGCACCAAGGGCCCCAG<br>CGTGTTCCCCCTGGCCCCCAGCAGCAAGAGCACCA<br>GCGGCGGCACAGCCGCCCTGGGCTGCCTGGTGAAG<br>GACTACTTCCCCGAGCCCGTGACCGTGTCCTGGAA<br>CAGCGGAGCCCTGACCTCCGGCGTGCACACCTTCC<br>CCGCCGTGCTGCAGAGCAGCGGCCTGTACAGCCTG<br>TCCAGCGTGGTGACAGTGCCCAGCAGCAGCCTGGG<br>CACCCAGACCTACATCTGCAACGTGAACCACAAGC<br>CCAGCAACACCAAGGTGGACAAGAGAGTGGAGCC<br>CAAGAGCTGCGACAAGACCCACACCTGCCCCCCCT<br>GCCCAGCCCCAGAGCTGCTGGGCGGACCCTCCGTG<br>TTCCTGTTCCCCCCCAAGCCCAAGGACACCCTGATG<br>ATCAGCAGGACCCCCGAGGTGACCTGCGTGGTGGT<br>GGACGTGAGCCACGAGGACCCAGAGGTGAAGTTCA<br>ACTGGTACGTGGACGGCGTGGAGGTGCACAACGCC<br>AAGACCAAGCCCAGAGAGGAGCAGTACAACAGCA<br>CCTACAGGGTGGTGTCCGTGCTGACCGTGCTGCAC<br>CAGGACTGGCTGAACGGCAAGGAATACAAGTGCA<br>AGGTCTCCAACAAGGCCCTGCCAGCCCCCATCGAA<br>AAGACCATCAGCAAGGCCAAGGGCCAGCCACGGG<br>AGCCCCAGGTGTACACCCTGCCCCCCTCCCGGGAG<br>GAGATGACCAAGAACCAGGTGTCCCTGACCTGTCT<br>GGTGAAGGGCTTCTACCCCAGCGACATCGCCGTGG<br>AGTGGGAGAGCAACGGCCAGCCCGAGAACAACTA<br>CAAGACCACCCCCCCCAGTGCTGGACAGCGACGGCA<br>GCTTCTTCCTGTACAGCAAGCTGACCGTGGACAAG<br>TCCAGGTGGCAGCAGGGCAACGTGTTCAGCTGCAG<br>CGTGATGCACGAGGCCCTGCACAACCACTACACCC<br>AGAAGAGCCTGAGCCTGTCCCCCGGCAAG |
| NOV3834LC |  |  |
| SEQ ID NO: 182<br>(Combined) | LCDR1 | RASQTISSYLN |
| SEQ ID NO: 183<br>(Combined) | LCDR2 | AASTLQS |
| SEQ ID NO: 184<br>(Combined) | LCDR3 | QQNYDTLWT |
| SEQ ID NO: 185<br>(Kabat) | LCDR1 | RASQTISSYLN |
| SEQ ID NO: 186<br>(Kabat) | LCDR2 | AASTLQS |
| SEQ ID NO: 187<br>(Kabat) | LCDR3 | QQNYDTLWT |
| SEQ ID NO: 188<br>(Chothia) | LCDR1 | SQTISSY |
| SEQ ID NO: 189<br>(Chothia) | LCDR2 | AAS |
| SEQ ID NO: 190<br>(Chothia) | LCDR3 | NYDTLW |
| SEQ ID NO: 191<br>(IMGT) | LCDR1 | QTISSY |
| SEQ ID NO: 192<br>(IMGT) | LCDR2 | AAS |
| SEQ ID NO: 193<br>(IMGT) | LCDR3 | QQNYDTLWT |
| SEQ ID NO: 194 | VL | DIQMTQSPSSLSAAVGDRVTISCRASQTISSYLNWYQ<br>QKPGEAPKLLIYAASTLQSGVPSRFGGSGSGTDFTLT<br>ISSLQPEDSATYYCQQNYDTLWTFGQGTKVEIK |
| SEQ ID NO: 195 | DNA VL | GATATCCAGATGACCCAGTCTCCATCCTCCCTGTCT<br>GCAGCTGTAGGAGACAGAGTCACCATCTCTTGCCG<br>GGCAAGTCAGACCATTAGTAGTTATTTAAATTGGT<br>ATCAGCAGAAACCAGGGGAAGCCCCTAAGCTCCTG |

TABLE 2-continued anti-HBV Antibodies

|  |  |  |
|---|---|---|
|  |  | ATCTATGCTGCCTCCACCTTGCAAAGTGGGGTCCCT<br>TCAAGGTTCGGTGGCAGTGGATCTGGGACAGATTT<br>CACTCTCACCATCAGCAGTCTGCAACCTGAAGATTC<br>TGCAACTTACTACTGTCAACAGAATTACGATACTTT<br>GTGGACGTTCGGCCAAGGGACCAAGGTGGAAATCA<br>AA |
| SEQ ID NO: 196 | Light Chain | DIQMTQSPSSLSAAVGDRVTISCRASQTISSYLNWYQ<br>QKPGEAPKLLIYAASTLQSGVPSRFGGSGSGTDFTLT<br>ISSLQPEDSATYYCQQNYDTLWTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 197 | DNA Light<br>Chain | GATATCCAGATGACCCAGTCTCCATCCTCCCTGTCT<br>GCAGCTGTAGGAGACAGAGTCACCATCTCTTGCCG<br>GGCAAGTCAGACCATTAGTAGTTATTTAAATTGGT<br>ATCAGCAGAAACCAGGGGAAGCCCCTAAGCTCCTG<br>ATCTATGCTGCCTCCACCTTGCAAAGTGGGGTCCCT<br>TCAAGGTTCGGTGGCAGTGGATCTGGGACAGATTT<br>CACTCTCACCATCAGCAGTCTGCAACCTGAAGATTC<br>TGCAACTTACTACTGTCAACAGAATTACGATACTTT<br>GTGGACGTTCGGCCAAGGGACCAAGGTGGAAATCA<br>AACGTACGGTGGCCGCTCCCAGCGTGTTCATCTTCC<br>CCCCAGCGACGAGCAGCTGAAGAGCGGCACCGCC<br>AGCGTGGTGTGCCTGCTGAACAACTTCTACCCCCG<br>GGAGGCCAAGGTGCAGTGGAAGGTGGACAACGCC<br>CTGCAGAGCGGCAACAGCCAGGAGAGCGTCACCG<br>AGCAGGACAGCAAGGACTCCACCTACAGCCTGAGC<br>AGCACCCTGACCCTGAGCAAGGCCGACTACGAGAA<br>GCATAAGGTGTACGCCTGCGAGGTGACCCACCAGG<br>GCCTGTCCAGCCCCGTGACCAAGAGCTTCAACAGG<br>GGCGAGTGC |

NOV3835 HC

| SEQ ID NO: 198<br>(Combined) | HCDR1 | GFTFDRYGMH |
| SEQ ID NO: 199<br>(Combined) | HCDR2 | GIWHEGSHKYYADSLRG |
| SEQ ID NO: 200<br>(Combined) | HCDR3 | QTNRGRLDDAFDI |
| SEQ ID NO: 201<br>(Kabat) | HCDR1 | RYGMH |
| SEQ ID NO: 202<br>(Kabat) | HCDR2 | GIWHEGSHKYYADSLRG |
| SEQ ID NO: 203<br>(Kabat) | HCDR3 | QTNRGRLDDAFDI |
| SEQ ID NO: 204<br>(Chothia) | HCDR1 | GFTFDRY |
| SEQ ID NO: 205<br>(Chothia) | HCDR2 | WHEGSH |
| SEQ ID NO: 206<br>(Chothia) | HCDR3 | QTNRGRLDDAFDI |
| SEQ ID NO: 207<br>(IMGT) | HCDR1 | GFTFDRYG |
| SEQ ID NO: 208<br>(IMGT) | HCDR2 | IWHEGSHK |
| SEQ ID NO: 209<br>(IMGT) | HCDR3 | VRQTNRGRLDDAFDI |
| SEQ ID NO: 210 | VH | QVQLVESGGGVVQPGRSLRLSCAASGFTFDRYGMHWV<br>RQAPGKGLEWVAGIWHEGSHKYYADSLRGRFTISRDN<br>AKNTLDLQLNRLRAEDTSVYYCVRQTNRGRLDDAFDI<br>WGQGTMVTVSS |

TABLE 2-continued anti-HBV Antibodies

| SEQ ID NO: 211 | DNA VH | CAGGTGCAGCTGGTTGAATCTGGTGGCGGAGTGGT
GCAGCCTGGCAGATCTCTGAGACTGTCTTGTGCCGC
AGCGGCTTCACCTTCGACAGATATGGCATGCACT
GGGTCCGACAGGCCCCTGGAAAAGGACTTGAATGG
GTGGCCGGAATCTGGCACGAAGGCAGCCACAAGTA
CTACGCCGATAGCCTGAGAGGCCGGTTCACCATCA
GCAGAGACAACGCCAAGAACACCCTGGACCTCCAG
CTGAACAGACTGAGAGCCGAGGATACCAGCGTGTA
CTACTGCGTGCGGCAGACCAACAGAGGCAGACTGG
ACGATGCCTTCGATATCTGGGGCCAAGGGACAATG
GTCACCGTTAGCTCA |
|---|---|---|
| SEQ ID NO: 212 | Heavy Chain | QVQLVESGGGVVQPGRSLRLSCAASGFTFDRYGMHWV
RQAPGKGLEWVAGIWHEGSHKYYADSLRGRFTISRDN
AKNTLDLQLNRLRAEDTSVYYCVRQTNRGRLDDAFDI
WGQGTMVTVSSASTKGPSVFPLAPSSKSTSGGTAALG
CLVKDYFPEPVTVSWNSGALTSGVHTFPAVLQSSGLY
SLSSVVTVPSSSLGTQTYICNVNHKPSNTKVDKRVEP
KSCDKTHTCPPCPAPELLGGPSVFLFPPKPKDTLMIS
RTPEVTCVVVDVSHEDPEVKFNWYVDGVEVHNAKTKP
REEQYNSTYRVVSVLTVLHQDWLNGKEYKCKVSNKAL
PAPIEKTISKAKGQPREPQVYTLPPSREEMTKNQVSL
TCLVKGFYPSDIAVEWESNGQPENNYKTTPPVLDSDG
SFFLYSKLTVDKSRWQQGNVFSCSVMHEALHNHYTQK
SLSLSPGK |
| SEQ ID NO: 213 | DNA Heavy Chain | CAGGTGCAGCTGGTTGAATCTGGTGGCGGAGTGGT
GCAGCCTGGCAGATCTCTGAGACTGTCTTGTGCCGC
AGCGGCTTCACCTTCGACAGATATGGCATGCACT
GGGTCCGACAGGCCCCTGGAAAAGGACTTGAATGG
GTGGCCGGAATCTGGCACGAAGGCAGCCACAAGTA
CTACGCCGATAGCCTGAGAGGCCGGTTCACCATCA
GCAGAGACAACGCCAAGAACACCCTGGACCTCCAG
CTGAACAGACTGAGAGCCGAGGATACCAGCGTGTA
CTACTGCGTGCGGCAGACCAACAGAGGCAGACTGG
ACGATGCCTTCGATATCTGGGGCCAAGGGACAATG
GTCACCGTTAGCTCAGCTAGCACCAAGGGCCCCAG
CGTGTTCCCCCTGGCCCCCAGCAGCAAGAGCACCA
GCGGCGGCACAGCCGCCCTGGGCTGCCTGGTGAAG
GACTACTTCCCCGAGCCCGTGACCGTGTCCTGGAA
CAGCGGAGCCCTGACCTCCGGCGTGCACACCTTCC
CCGCCGTGCTGCAGAGCAGCGGCCTGTACAGCCTG
TCCAGCGTGGTGACAGTGCCCAGCAGCAGCCTGGG
CACCCAGACCTACATCTGCAACGTGAACCACAAGC
CCAGCAACACCAAGGTGGACAAGAGAGTGGAGCC
CAAGAGCTGCGACAAGACCCACACCTGCCCCCCCT
GCCCAGCCCCAGAGCTGCTGGGCGGACCCTCCGTG
TTCCTGTTCCCCCCCAAGCCCAAGGACACCCTGATG
ATCAGCAGGACCCCCGAGGTGACCTGCGTGGTGGT
GGACGTGAGCCACGAGGACCCAGAGGTGAAGTTCA
ACTGGTACGTGGACGGCGTGGAGGTGCACAACGCC
AAGACCAAGCCCAGAGAGGAGCAGTACAACAGCA
CCTACAGGGTGGTGTCCGTGCTGACCGTGCTGCAC
CAGGACTGGCTGAACGGCAAGGAATACAAGTGCA
AGGTCTCCAACAAGGCCCTGCCAGCCCCCATCGAA
AAGACCATCAGCAAGGCCAAGGGCCAGCCACGGG
AGCCCCAGGTGTACACCCTGCCCCCCTCCCGGGAG
GAGATGACCAAGAACCAGGTGTCCCTGACCTGTCT
GGTGAAGGGCTTCTACCCCAGCGACATCGCCGTGG
AGTGGGAGAGCAACGGCCAGCCCGAGAACAACTA
CAAGACCACCCCCCCAGTGCTGGACAGCGACGGCA
GCTTCTTCCTGTACAGCAAGCTGACCGTGGACAAG
TCCAGGTGGCAGCAGGGCAACGTGTTCAGCTGCAG
CGTGATGCACGAGGCCCTGCACAACCACTACACCC
AGAAGAGCCTGAGCCTGTCCCCCGGCAAG |

NOV3835LC

| SEQ ID NO: 214 (Combined) | LCDR1 | RASQTISSYLN |
|---|---|---|
| SEQ ID NO: 215 (Combined) | LCDR2 | AASTLQS |
| SEQ ID NO: 216 (Combined) | LCDR3 | QQNYDTLWT |

TABLE 2-continued anti-HBV Antibodies

| | | |
|---|---|---|
| SEQ ID NO: 217 (Kabat) | LCDR1 | RASQTISSYLN |
| SEQ ID NO: 218 (Kabat) | LCDR2 | AASTLQS |
| SEQ ID NO: 219 (Kabat) | LCDR3 | QQNYDTLWT |
| SEQ ID NO: 220 (Chothia) | LCDR1 | SQTISSY |
| SEQ ID NO: 221 (Chothia) | LCDR2 | AAS |
| SEQ ID NO: 222 (Chothia) | LCDR3 | NYDTLW |
| SEQ ID NO: 223 (IMGT) | LCDR1 | QTISSY |
| SEQ ID NO: 224 (IMGT) | LCDR2 | AAS |
| SEQ ID NO: 225 (IMGT) | LCDR3 | QQNYDTLWT |
| SEQ ID NO: 226 | VL | DIQMTQSPSSLSAAVGDRVTISCRASQTISSYLNWYQ QKPGEAPKLLIYAASTLQSGVPSRFGGSGSGTDFTLT ISSLQPEDSATYYCQQNYDTLWTFGQGTKVEIK |
| SEQ ID NO: 227 | DNA VL | GATATCCAGATGACCCAGTCTCCATCCTCCCTGTCT GCAGCTGTAGGAGACAGAGTCACCATCTCTTGCCG GGCAAGTCAGACCATTAGTAGTTATTTAAATTGGT ATCAGCAGAAACCAGGGGAAGCCCCTAAGCTCCTG ATCTATGCTGCCTCCACCTTGCAAAGTGGGGTCCCT TCAAGGTTCGGTGGCAGTGGATCTGGGACAGATTT CACTCTCACCATCAGCAGTCTGCAACCTGAAGATTC TGCAACTTACTACTGTCAACAGAATTACGATACTTT GTGGACGTTCGGCCAAGGGACCAAGGTGGAAATCA AA |
| SEQ ID NO: 228 | Light Chain | DIQMTQSPSSLSAAVGDRVTISCRASQTISSYLNWYQ QKPGEAPKLLIYAASTLQSGVPSRFGGSGSGTDFTLT ISSLQPEDSATYYCQQNYDTLWTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 229 | DNA Light Chain | GATATCCAGATGACCCAGTCTCCATCCTCCCTGTCT GCAGCTGTAGGAGACAGAGTCACCATCTCTTGCCG GGCAAGTCAGACCATTAGTAGTTATTTAAATTGGT ATCAGCAGAAACCAGGGGAAGCCCCTAAGCTCCTG ATCTATGCTGCCTCCACCTTGCAAAGTGGGGTCCCT TCAAGGTTCGGTGGCAGTGGATCTGGGACAGATTT CACTCTCACCATCAGCAGTCTGCAACCTGAAGATTC TGCAACTTACTACTGTCAACAGAATTACGATACTTT GTGGACGTTCGGCCAAGGGACCAAGGTGGAAATCA AACGTACGGTGGCCGCTCCCAGCGTGTTCATCTTCC CCCCAGCGACGAGCAGCTGAAGAGCGGCACCGCC AGCGTGGTGTGCCTGCTGAACAACTTCTACCCCCG GGAGGCCAAGGTGCAGTGGAAGGTGGACAACGCC CTGCAGAGCGGCAACAGCCAGGAGAGCGTCACCG AGCAGGACAGCAAGGACTCCACCTACAGCCTGAGC AGCACCCTGACCCTGAGCAAGGCCGACTACGAGAA GCATAAGGTGTACGCCTGCGAGGTGACCCACCAGG GCCTGTCCAGCCCCGTGACCAAGAGCTTCAACAGG GGCGAGTGC |

NOV3836HC

| | | |
|---|---|---|
| SEQ ID NO: 230 (Combined) | HCDR1 | GFTFERYGMH |
| SEQ ID NO: 231 (Combined) | HCDR2 | GIWHEGSHKYYADSLRG |

TABLE 2-continued anti-HBV Antibodies

| | | |
|---|---|---|
| SEQ ID NO: 232 (Combined) | HCDR3 | QTNRGRLDDAFDI |
| SEQ ID NO: 233 (Kabat) | HCDR1 | RYGMH |
| SEQ ID NO: 234 (Kabat) | HCDR2 | GIWHEGSHKYYADSLRG |
| SEQ ID NO: 235 (Kabat) | HCDR3 | QTNRGRLDDAFDI |
| SEQ ID NO: 236 (Chothia) | HCDR1 | GFTFERY |
| SEQ ID NO: 237 (Chothia) | HCDR2 | WHEGSH |
| SEQ ID NO: 238 (Chothia) | HCDR3 | QTNRGRLDDAFDI |
| SEQ ID NO: 239 (IMGT) | HCDR1 | GFTFERYG |
| SEQ ID NO: 240 (IMGT) | HCDR2 | IWHEGSHK |
| SEQ ID NO: 241 (IMGT) | HCDR3 | VRQTNRGRLDDAFDI |
| SEQ ID NO: 242 | VH | QVQLVESGGGVVQPGRSLRLSCAASGFTFERYGMHWV RQAPGKGLEWVAGIWHEGSHKYYADSLRGRFTISRDN AKNTLDLQLNRLRAEDTSVYYCVRQTNRGRLDDAFDI WGQGTMVTVSS |
| SEQ ID NO: 243 | DNA VH | CAGGTGCAGCTGGTTGAATCTGGTGGCGGAGTGGT GCAGCCTGGCAGATCTCTGAGACTGTCTTGTGCCGC CAGCGGCTTCACCTTCGAGAGATATGGCATGCACT GGGTCCGACAGGCCCCTGGAAAAGGACTTGAATGG GTGGCCGGAATCTGGCACGAAGGCAGCCACAAGTA CTACGCCGATAGCCTGAGAGGCCGGTTCACCATCA GCAGAGACAACGCCAAGAACACCCTGGACCTCCAG CTGAACAGACTGAGAGCCGAGGATACCAGCGTGTA CTACTGCGTGCGGCAGACCAACAGAGGCAGACTGG ACGATGCCTTCGATATCTGGGGCCAAGGGACAATG GTCACCGTTAGCTCA |
| SEQ ID NO: 244 | Heavy Chain | QVQLVESGGGVVQPGRSLRLSCAASGFTFERYGMHWV RQAPGKGLEWVAGIWHEGSHKYYADSLRGRFTISRDN AKNTLDLQLNRLRAEDTSVYYCVRQTNRGRLDDAFDI WGQGTMVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKRVEP KSCDKTHTCPPCPAPELLGGPSVFLFPPKPKDTLMIS RTPEVTCVVVDVSHEDPEVKFNWYVDGVEVHNAKTKP REEQYNSTYRVVSVLTVLHQDWLNGKEYKCKVSNKAL PAPIEKTISKAKGQPREPQVYTLPPSREEMTKNQVSL TCLVKGFYPSDIAVEWESNGQPENNYKTTPPVLDSDG SFFLYSKLTVDKSRWQQGNVFSCSVMHEALHNHYTQK SLSLSPGK |
| SEQ ID NO: 245 | DNA Heavy Chain | CAGGTGCAGCTGGTTGAATCTGGTGGCGGAGTGGT GCAGCCTGGCAGATCTCTGAGACTGTCTTGTGCCGC CAGCGGCTTCACCTTCGAGAGATATGGCATGCACT GGGTCCGACAGGCCCCTGGAAAAGGACTTGAATGG GTGGCCGGAATCTGGCACGAAGGCAGCCACAAGTA CTACGCCGATAGCCTGAGAGGCCGGTTCACCATCA GCAGAGACAACGCCAAGAACACCCTGGACCTCCAG CTGAACAGACTGAGAGCCGAGGATACCAGCGTGTA CTACTGCGTGCGGCAGACCAACAGAGGCAGACTGG ACGATGCCTTCGATATCTGGGGCCAAGGGACAATG GTCACCGTTAGCTCAGCTAGCACCAAGGGCCCCA CGTGTTCCCCCTGGCCCCAGCAGCAAGAGCACCA GCGGCGGCACAGCCGCCCTGGGCTGCCTGGTGAAG GACTACTTCCCCGAGCCCGTGACCGTGTCCTGGAA CAGCGGAGCCCTGACCTCCGGCGTGCACACCTTCC CCGCCGTGCTGCAGAGCAGCGGCCTGTACAGCCTG |

TABLE 2-continued anti-HBV Antibodies

|  |  |  | |
|---|---|---|---|
|  |  |  | TCCAGCGTGGTGACAGTGCCCAGCAGCAGCCTGGG<br>CACCCAGACCTACATCTGCAACGTGAACCACAAGC<br>CCAGCAACACCAAGGTGGACAAGAGAGTGGAGCC<br>CAAGAGCTGCGACAAGACCCACACCTGCCCCCCCT<br>GCCCAGCCCCAGAGCTGCTGGGCGGACCCTCCGTG<br>TTCCTGTTCCCCCCCAAGCCCAAGGACACCCTGATG<br>ATCAGCAGGACCCCCGAGGTGACCTGCGTGGTGGT<br>GGACGTGAGCCACGAGGACCCAGAGGTGAAGTTCA<br>ACTGGTACGTGGACGGCGTGGAGGTGCACAACGCC<br>AAGACCAAGCCCAGAGAGGAGCAGTACAACAGCA<br>CCTACAGGGTGGTGTCCGTGCTGACCGTGCTGCAC<br>CAGGACTGGCTGAACGGCAAGGAATACAAGTGCA<br>AGGTCTCCAACAAGGCCCTGCCAGCCCCCATCGAA<br>AAGACCATCAGCAAGGCCAAGGGCCAGCCACGGG<br>AGCCCCAGGTGTACACCCTGCCCCCCTCCCGGGAG<br>GAGATGACCAAGAACCAGGTGTCCCTGACCTGTCT<br>GGTGAAGGGCTTCTACCCCAGCGACATCGCCGTGG<br>AGTGGGAGAGCAACGGCCAGCCCGAGAACAACTA<br>CAAGACCACCCCCCCAGTGCTGGACAGCGACGGCA<br>GCTTCTTCCTGTACAGCAAGCTGACCGTGGACAAG<br>TCCAGGTGGCAGCAGGGCAACGTGTTCAGCTGCAG<br>CGTGATGCACGAGGCCCTGCACAACCACTACACCC<br>AGAAGAGCCTGAGCCTGTCCCCCGGCAAG |

NOV3836LC

| SEQ ID NO: 246 (Combined) | LCDR1 | RASQTISSYLN |
| SEQ ID NO: 247 (Combined) | LCDR2 | AASTLQS |
| SEQ ID NO: 248 (Combined) | LCDR3 | QQNYDTLWT |
| SEQ ID NO: 249 (Kabat) | LCDR1 | RASQTISSYLN |
| SEQ ID NO: 250 (Kabat) | LCDR2 | AASTLQS |
| SEQ ID NO: 251 (Kabat) | LCDR3 | QQNYDTLWT |
| SEQ ID NO: 252 (Chothia) | LCDR1 | SQTISSY |
| SEQ ID NO: 253 (Chothia) | LCDR2 | AAS |
| SEQ ID NO: 254 (Chothia) | LCDR3 | NYDTLW |
| SEQ ID NO: 255 (IMGT) | LCDR1 | QTISSY |
| SEQ ID NO: 256 (IMGT) | LCDR2 | AAS |
| SEQ ID NO: 257 (IMGT) | LCDR3 | QQNYDTLWT |
| SEQ ID NO: 258 | VL | DIQMTQSPSSLSAAVGDRVTISCRASQTISSYLNWYQ<br>QKPGEAPKLLIYAASTLQSGVPSRFGGSGSGTDFTLT<br>ISSLQPEDSATYYCQQNYDTLWTFGQGTKVEIK |
| SEQ ID NO: 259 | DNA VL | GATATCCAGATGACCCAGTCTCCATCCTCCCTGTCT<br>GCAGCTGTAGGAGACAGAGTCACCATCTCTTGCCG<br>GGCAAGTCAGACCATTAGTAGTTATTTAAATTGGT<br>ATCAGCAGAAACCAGGGGAAGCCCCTAAGCTCCTG<br>ATCTATGCTGCCTCCACCTTGCAAAGTGGGGTCCCT<br>TCAAGGTTCGGTGGCAGTGGATCTGGGACAGATTT<br>CACTCTCACCATCAGCAGTCTGCAACCTGAAGATTC<br>TGCAACTTACTACTGTCAACAGAATTACGATACTTT<br>GTGGACGTTCGGCCAAGGGACCAAGGTGGAAATCA<br>AA |

TABLE 2-continued anti-HBV Antibodies

| SEQ ID NO: 260 | Light Chain | DIQMTQSPSSLSAAVGDRVTISCRASQTISSYLNWYQ
QKPGEAPKLLIYAASTLQSGVPSRFGGSGSGTDFTLT
ISSLQPEDSATYYCQQNYDTLWTFGQGTKVEIKRTVA
APSVFIFPPSDEQLKSGTASVVCLLNNFYPREAKVQW
KVDNALQSGNSQESVTEQDSKDSTYSLSSTLTLSKAD
YEKHKVYACEVTHQGLSSPVTKSFNRGEC |
| SEQ ID NO: 261 | DNA Light Chain | GATATCCAGATGACCCAGTCTCCATCCTCCCTGTCT
GCAGCTGTAGGAGACAGAGTCACCATCTCTTGCCG
GGCAAGTCAGACCATTAGTAGTTATTTAAATTGGT
ATCAGCAGAAACCAGGGGAAGCCCCTAAGCTCCTG
ATCTATGCTGCCTCCACCTTGCAAAGTGGGGTCCCT
TCAAGGTTCGGTGGCAGTGGATCTGGGACAGATTT
CACTCTCACCATCAGCAGTCTGCAACCTGAAGATTC
TGCAACTTACTACTGTCAACAGAATTACGATACTTT
GTGGACGTTCGGCCAAGGGACCAAGGTGGAAATCA
AACGTACGGTGGCCGCTCCCAGCGTGTTCATCTTCC
CCCCCAGCGACGAGCAGCTGAAGAGCGGCACCGCC
AGCGTGGTGTGCCTGCTGAACAACTTCTACCCCCG
GGAGGCCAAGGTGCAGTGGAAGGTGGACAACGCC
CTGCAGAGCGGCAACAGCCAGGAGAGCGTCACCG
AGCAGGACAGCAAGGACTCCACCTACAGCCTGAGC
AGCACCCTGACCCTGAGCAAGGCCGACTACGAGAA
GCATAAGGTGTACGCCTGCGAGGTGACCCACCAGG
GCCTGTCCAGCCCCGTGACCAAGAGCTTCAACAGG
GGCGAGTGC |

NOV3837HC

| SEQ ID NO: 262 (Combined) | HCDR1 | GFIFTDYYMT |
| SEQ ID NO: 263 (Combined) | HCDR2 | FITSGGETTYYADSVKG |
| SEQ ID NO: 264 (Combined) | HCDR3 | AHFDGYQYDTRGDFTYYFDN |
| SEQ ID NO: 265 (Kabat) | HCDR1 | DYYMT |
| SEQ ID NO: 266 (Kabat) | HCDR2 | FITSGGETTYYADSVKG |
| SEQ ID NO: 267 (Kabat) | HCDR3 | AHFDGYQYDTRGDFTYYFDN |
| SEQ ID NO: 268 (Chothia) | HCDR1 | GFIFTDY |
| SEQ ID NO: 269 (Chothia) | HCDR2 | TSGGET |
| SEQ ID NO: 270 (Chothia) | HCDR3 | AHFDGYQYDTRGDFTYYFDN |
| SEQ ID NO: 271 (IMGT) | HCDR1 | GFIFTDYY |
| SEQ ID NO: 272 (IMGT) | HCDR2 | ITSGGETT |
| SEQ ID NO: 273 (IMGT) | HCDR3 | VRAHFDGYQYDTRGDFTYYFDN |
| SEQ ID NO: 274 | VH | QVQLQESGGRLVRPGGSLRLSCAASGFIFTDYYMTWI
RQAPGKGPEWIAFITSGGETTYYADSVKGRFTISRDN
AKKSLFLQMYSLRADDTAVYYCVRAHFDGYQYDTRGD
FTYYFDNWGLGTLVSVSS |
| SEQ ID NO: 275 | DNA VH | CAGGTGCAGCTGCAGGAGTCGGGGGGACGCTTGGT
CAGGCCTGGAGGGTCCCTGAGACTCTCCTGTGCAG
CCTCCGGATTCATCTTCACTGACTACTACATGACCT
GGATCCGCCAGGCTCCAGGGAAGGGGCCGGAGTG
GATTGCATTTATCACAAGTGGGGGCGAGACCACAT
ACTACGCAGACTCTGTGAAGGGCCGCTTCACCATTT
CCAGGGACAACGCCAAGAAGTCACTCTTTCTGCAA |

TABLE 2-continued anti-HBV Antibodies

| | | |
|---|---|---|
| | | ATGTACAGCCTGAGAGCCGACGACACGGCCGTGTA<br>TTATTGTGTGAGAGCCCACTTTGATGGTTATCAGTA<br>TGATACTCGTGGTGACTTCACTTATTACTTTGACAA<br>CTGGGGCCTGGGAACCCTGGTCAGCGTCTCCTCA |
| SEQ ID NO: 276 | Heavy<br>Chain | QVQLQESGGRLVRPGGSLRLSCAASGFIFTDYYMTWI<br>RQAPGKGPEWIAFITSGGETTYYADSVKGRFTISRDN<br>AKKSLFLQMYSLRADDTAVYYCVRAHFDGYQYDTRGD<br>FTYYFDNWGLGTLVSVSSASTKGPSVFPLAPSSKSTS<br>GGTAALGCLVKDYFPEPVTVSWNSGALTSGVHTFPAV<br>LQSSGLYSLSSVVTVPSSSLGTQTYICNVNHKPSNTK<br>VDKRVEPKSCDKTHTCPPCPAPELLGGPSVFLFPPKP<br>KDTLMISRTPEVTCVVVDVSHEDPEVKFNWYVDGVEV<br>HNAKTKPREEQYNSTYRVVSVLTVLHQDWLNGKEYKC<br>KVSNKALPAPIEKTISKAKGQPREPQVYTLPPSREEM<br>TKNQVSLTCLVKGFYPSDIAVEWESNGQPENNYKTTP<br>PVLDSDGSFFLYSKLTVDKSRWQQGNVFSCSVMHEAL<br>HNHYTQKSLSLSPGK |
| SEQ ID NO: 277 | DNA Heavy<br>Chain | CAGGTGCAGCTGCAGGAGTCGGGGGGACGCTTGGT<br>CAGGCCTGGAGGGTCCCTGAGACTCTCCTGTGCAG<br>CCTCCGGATTCATCTTCACTGACTACTACATGACCT<br>GGATCCGCCAGGCTCCAGGGAAGGGGCCGGAGTG<br>GATTGCATTTATCACAAGTGGGGGCGAGACCACAT<br>ACTACGCAGACTCTGTGAAGGGCCGCTTCACCATTT<br>CCAGGGACAACGCCAAGAAGTCACTCTTTCTGCAA<br>ATGTACAGCCTGAGAGCCGACGACACGGCCGTGTA<br>TTATTGTGTGAGAGCCCACTTTGATGGTTATCAGTA<br>TGATACTCGTGGTGACTTCACTTATTACTTTGACAA<br>CTGGGGCCTGGGAACCCTGGTCAGCGTCTCCTCAG<br>CTAGCACCAAGGGCCCCAGCGTGTTCCCCCTGGCC<br>CCCAGCAGCAAGAGCACCAGCGGCGGCACAGCCG<br>CCCTGGGCTGCCTGGTGAAGGACTACTTCCCCGAG<br>CCCGTGACCGTGTCCTGGAACAGCGGAGCCCTGAC<br>CTCCGGCGTGCACACCTTCCCCGCCGTGCTGCAGA<br>GCAGCGGCCTGTACAGCCTGTCCAGCGTGGTGACA<br>GTGCCCAGCAGCAGCCTGGGCACCCAGACCTACAT<br>CTGCAACGTGAACCACAAGCCCAGCAACACCAAGG<br>TGGACAAGAGAGTGGAGCCCAAGAGCTGCGACAA<br>GACCCACACCTGCCCCCCCTGCCCAGCCCCAGAGC<br>TGCTGGGCGGACCCTCCGTGTTCCTGTTCCCCCCA<br>AGCCCAAGGACACCCTGATGATCAGCAGGACCCCC<br>GAGGTGACCTGCGTGGTGGTGGACGTGAGCCACGA<br>GGACCCAGAGGTGAAGTTCAACTGGTACGTGGACG<br>GCGTGGAGGTGCACAACGCCAAGACCAAGCCCAG<br>AGAGGAGCAGTACAACAGCACCTACAGGGTGGTGT<br>CCGTGCTGACCGTGCTGCACCAGGACTGGCTGAAC<br>GGCAAGGAATACAAGTGCAAGGTCTCCAACAAGGC<br>CCTGCCAGCCCCCATCGAAAAGACCATCAGCAAGG<br>CCAAGGGCCAGCCACGGGAGCCCCAGGTGTACACC<br>CTGCCCCCCTCCCGGGAGGAGATGACCAAGAACCA<br>GGTGTCCCTGACCTGTCTGGTGAAGGGCTTCTACCC<br>CAGCGACATCGCCGTGGAGTGGGAGAGCAACGGCC<br>AGCCCGAGAACAACTACAAGACCACCCCCCCAGTG<br>CTGGACAGCGACGGCAGCTTCTTCCTGTACAGCAA<br>GCTGACCGTGGACAAGTCCAGGTGGCAGCAGGGCA<br>ACGTGTTCAGCTGCAGCGTGATGCACGAGGCCCTG<br>CACAACCACTACACCCAGAAGAGCCTGAGCCTGTC<br>CCCCGGCAAG |

NOV3837LC

| | | |
|---|---|---|
| SEQ ID NO: 278<br>(Combined) | LCDR1 | RASQSVSSSLA |
| SEQ ID NO: 279<br>(Combined) | LCDR2 | GASTRAT |
| SEQ ID NO: 280<br>(Combined) | LCDR3 | HQYINWPPGDT |
| SEQ ID NO: 281<br>(Kabat) | LCDR1 | RASQSVSSSLA |
| SEQ ID NO: 282<br>(Kabat) | LCDR2 | GASTRAT |

TABLE 2-continued anti-HBV Antibodies

| SEQ ID NO: 283 (Kabat) | LCDR3 | HQYINWPPGDT |
|---|---|---|
| SEQ ID NO: 284 (Chothia) | LCDR1 | SQSVSSS |
| SEQ ID NO: 285 (Chothia) | LCDR2 | GAS |
| SEQ ID NO: 286 (Chothia) | LCDR3 | YINWPPGD |
| SEQ ID NO: 287 (IMGT) | LCDR1 | QSVSSS |
| SEQ ID NO: 288 (IMGT) | LCDR2 | GAS |
| SEQ ID NO: 289 (IMGT) | LCDR3 | HQYINWPPGDT |
| SEQ ID NO: 290 | VL | EIVMTQSPATLSVSPGERVTLSCRASQSVSSSLAWYQ QKPGRAPRLLIYGASTRATGVPARFSGGGSGTDFTLT ISSLQSEDFAVYYCHQYINWPPGDTFGQGTRLDIK |
| SEQ ID NO: 291 | DNA VL | GAAATAGTGATGACTCAGTCTCCAGCCACCCTGTCT GTGTCTCCAGGGGAAAGAGTCACCCTCTCCTGCAG GGCCAGTCAGAGTGTTAGTAGCAGCTTAGCCTGGT ACCAGCAGAAACCTGGCCGGGCTCCCAGGCTCCTC ATTTATGGAGCATCCACCAGGGCCACTGGTGTCCC AGCCAGGTTCAGTGGCGGTGGGTCTGGGACAGACT TCACTCTCACCATCAGCAGCCTGCAGTCTGAAGATT TTGCAGTTTATTACTGTCACCAGTATATTAATTGGC CTCCGGGGGACACTTTTGGCCAGGGGACGAGGCTG GATATCAAA |
| SEQ ID NO: 292 | Light Chain | EIVMTQSPATLSVSPGERVTLSCRASQSVSSSLAWYQ QKPGRAPRLLIYGASTRATGVPARFSGGGSGTDFTLT ISSLQSEDFAVYYCHQYINWPPGDTFGQGTRLDIKRT VAAPSVFIFPPSDEQLKSGTASVVCLLNNFYPREAKV QWKVDNALQSGNSQESVTEQDSKDSTYSLSSTLTLSK ADYEKHKVYACEVTHQGLSSPVTKSFNRGEC |
| SEQ ID NO: 293 | DNA Light Chain | GAAATAGTGATGACTCAGTCTCCAGCCACCCTGTCT GTGTCTCCAGGGGAAAGAGTCACCCTCTCCTGCAG GGCCAGTCAGAGTGTTAGTAGCAGCTTAGCCTGGT ACCAGCAGAAACCTGGCCGGGCTCCCAGGCTCCTC ATTTATGGAGCATCCACCAGGGCCACTGGTGTCCC AGCCAGGTTCAGTGGCGGTGGGTCTGGGACAGACT TCACTCTCACCATCAGCAGCCTGCAGTCTGAAGATT TTGCAGTTTATTACTGTCACCAGTATATTAATTGGC CTCCGGGGGACACTTTTGGCCAGGGGACGAGGCTG GATATCAAACGTACGGTGGCCGCTCCCAGCGTGTT CATCTTCCCCCCCAGCGACGAGCAGCTGAAGAGCG GCACCGCCAGCGTGGTGTGCCTGCTGAACAACTTC TACCCCCGGGAGGCCAAGGTGCAGTGGAAGGTGGA CAACGCCCTGCAGAGCGGCAACAGCCAGGAGAGC GTCACCGAGCAGGACAGCAAGGACTCCACCTACAG CCTGAGCAGCACCCTGACCCTGAGCAAGGCCGACT ACGAGAAGCATAAGGTGTACGCCTGCGAGGTGACC CACCAGGGCCTGTCCAGCCCCGTGACCAAGAGCTT CAACAGGGGCGAGTGC |

NOV3838HC

| SEQ ID NO: 294 (Combined) | HCDR1 | GFIFTDYYMT |
|---|---|---|
| SEQ ID NO: 295 (Combined) | HCDR2 | FITSGGETTYYADSVKG |
| SEQ ID NO: 296 (Combined) | HCDR3 | AHFDLYQYDTRGDFTYYFDN |
| SEQ ID NO: 297 (Kabat) | HCDR1 | DYYMT |

TABLE 2-continued anti-HBV Antibodies

| | | |
|---|---|---|
| SEQ ID NO: 298 (Kabat) | HCDR2 | FITSGGETTYYADSVKG |
| SEQ ID NO: 299 (Kabat) | HCDR3 | AHFDLYQYDTRGDFTYYFDN |
| SEQ ID NO: 300 (Chothia) | HCDR1 | GFIFTDY |
| SEQ ID NO: 301 (Chothia) | HCDR2 | TSGGET |
| SEQ ID NO: 302 (Chothia) | HCDR3 | AHFDLYQYDTRGDFTYYFDN |
| SEQ ID NO: 303 (IMGT) | HCDR1 | GFIFTDYY |
| SEQ ID NO: 304 (IMGT) | HCDR2 | ITSGGETT |
| SEQ ID NO: 305 (IMGT) | HCDR3 | VRAHFDLYQYDTRGDFTYYFDN |
| SEQ ID NO: 306 | VH | QVQLQESGGRLVRPGGSLRLSCAASGFIFTDYYMTWI RQAPGKGPEWIAFITSGGETTYYADSVKGRFTISRDN AKKSLFLQMYSLRADDTAVYYCVRAHFDLYQYDTRGD FTYYFDNWGLGTLVSVSS |
| SEQ ID NO: 307 | DNA VH | CAGGTTCAGCTGCAAGAATCTGGCGGCAGACTCGT TAGACCTGGCGGCTCTCTGAGACTGTCTTGTGCCGC CAGCGGCTTCATCTTCACCGACTACTACATGACCTG GATCAGACAGGCCCCTGGCAAGGGACCTGAGTGGA TCGCCTTTATCACAAGCGGCGGAGAGACAACCTAC TACGCCGATAGCGTGAAGGGCAGATTCACCATCAG CCGGGACAACGCCAAGAAGTCCCTGTTCCTCCAGA TGTACAGCCTGAGAGCCGACGATACCGCCGTGTAT TATTGCGTGCGGGCCCACTTTGACCTGTACCAGTAC GATACCAGAGGCGATTTCACCTACTACTTCGACAA CTGGGGCCTGGGAACCCTGGTGTCTGTCTCTTCT |
| SEQ ID NO: 308 | Heavy Chain | QVQLQESGGRLVRPGGSLRLSCAASGFIFTDYYMTWI RQAPGKGPEWIAFITSGGETTYYADSVKGRFTISRDN AKKSLFLQMYSLRADDTAVYYCVRAHFDLYQYDTRGD FTYYFDNWGLGTLVSVSSASTKGPSVFPLAPSSKSTS GGTAALGCLVKDYFPEPVTVSWNSGALTSGVHTFPAV LQSSGLYSLSSVVTVPSSSLGTQTYICNVNHKPSNKT VDKRVEPKSCDKTHTCPPCPAPELLGGPSVFLFPPKP KDTLMISRTPEVTCVVVDVSHEDPEVKFNWYVDGVEV HNAKTKPREEQYNSTYRVVSVLTVLHQDWLNGKEYKC KVSNKALPAPIEKTISKAKGQPREPQVYTLPPSREEM TKNQVSLTCLVKGFYPSDIAVEWESNGQPENNYKTTP PVLDSDGSFFLYSKLTVDKSRWQQGNVFSCSVMHEAL HNHYTQKSLSLSPGK |
| SEQ ID NO: 309 | DNA Heavy Chain | CAGGTTCAGCTGCAAGAATCTGGCGGCAGACTCGT TAGACCTGGCGGCTCTCTGAGACTGTCTTGTGCCGC CAGCGGCTTCATCTTCACCGACTACTACATGACCTG GATCAGACAGGCCCCTGGCAAGGGACCTGAGTGGA TCGCCTTTATCACAAGCGGCGGAGAGACAACCTAC TACGCCGATAGCGTGAAGGGCAGATTCACCATCAG CCGGGACAACGCCAAGAAGTCCCTGTTCCTCCAGA TGTACAGCCTGAGAGCCGACGATACCGCCGTGTAT TATTGCGTGCGGGCCCACTTTGACCTGTACCAGTAC GATACCAGAGGCGATTTCACCTACTACTTCGACAA CTGGGGCCTGGGAACCCTGGTGTCTGTCTCTTCTGC TAGCACCAAGGGCCCCAGCGTGTTCCCCCTGGCCC CCAGCAGCAAGAGCACCAGCGGCGGCACAGCCGC CCTGGGCTGCCTGGTGAAGGACTACTTCCCCGAGC CCGTGACCGTGTCCTGGAACAGCGGAGCCCTGACC TCCGGCGTGCACACCTTCCCCGCCGTGCTGCAGAG CAGCGGCCTGTACAGCCTGTCAGCGTGGTGACAG TGCCCAGCAGCAGCCTGGCACCCAGACCTACATC TGCAACGTGAACCACAAGCCCAGCAACACCAAGGT GGACAAGAGAGTGGAGCCCAAGAGCTGCGACAAG ACCCACACATGCCCCCCTGCCCGGCGCCAGAGCT GCTGGGCGGACCCTCCGTGTTCCTGTTCCCCCCAA GCCCAAGGACACCCTGATGATCAGCAGGACCCCCG |

TABLE 2-continued anti-HBV Antibodies

```
                        AGGTGACCTGCGTGGTGGTGGACGTGAGCCACGAG
                        GACCCAGAGGTGAAGTTCAACTGGTACGTGGACGG
                        CGTGGAGGTGCACAACGCCAAGACCAAGCCCAGA
                        GAGGAGCAGTACAACAGCACCTACAGGGTGGTGTC
                        CGTGCTGACCGTGCTGCACCAGGACTGGCTGAACG
                        GCAAGGAATACAAGTGCAAGGTCTCCAACAAGGCC
                        CTGCCAGCCCCCATCGAAAAGACCATCAGCAAGGC
                        CAAGGGCCAGCCACGGGAGCCCCAGGTGTACACCC
                        TGCCCCCCTCCCGGGAGGAGATGACCAAGAACCAG
                        GTGTCCCTGACCTGTCTGGTGAAGGGCTTCTACCCC
                        AGCGACATCGCCGTGGAGTGGGAGAGCAACGGCC
                        AGCCCGAGAACAACTACAAGACCACCCCCCCAGTG
                        CTGGACAGCGACGGCAGCTTCTTCCTGTACAGCAA
                        GCTGACCGTGGACAAGTCCAGGTGGCAGCAGGGCA
                        ACGTGTTCAGCTGCAGCGTGATGCACGAGGCCCTG
                        CACAACCACTACACCCAGAAGAGCCTGAGCTTAAG
                        CCCCGGCAAG
```

NOV3838LC

| SEQ ID NO: 310 (Combined) | LCDR1 | RASQSVSSSLA |
| SEQ ID NO: 311 (Combined) | LCDR2 | GASTRAT |
| SEQ ID NO: 312 (Combined) | LCDR3 | HQYINWPPGDT |
| SEQ ID NO: 313 (Kabat) | LCDR1 | RASQSVSSSLA |
| SEQ ID NO: 314 (Kabat) | LCDR2 | GASTRAT |
| SEQ ID NO: 315 (Kabat) | LCDR3 | HQYINWPPGDT |
| SEQ ID NO: 316 (Chothia) | LCDR1 | SQSVSSS |
| SEQ ID NO: 317 (Chothia) | LCDR2 | GAS |
| SEQ ID NO: 318 (Chothia) | LCDR3 | YINWPPGD |
| SEQ ID NO: 319 (IMGT) | LCDR1 | QSVSSS |
| SEQ ID NO: 320 (IMGT) | LCDR2 | GAS |
| SEQ ID NO: 321 (IMGT) | LCDR3 | HQYINWPPGDT |
| SEQ ID NO: 322 | VL | EIVMTQSPATLSVSPGERVTLSCRASQSVSSSLAWYQ QKPGRAPRLLIYGASTRATGVPARFSGGGSGTDFTLT ISSLQSEDFAVYYCHQYINWPPGDTFGQGTRLDIK |
| SEQ ID NO: 323 | DNA VL | GAAATAGTGATGACTCAGTCTCCAGCCACCCTGTCT GTGTCTCCAGGGGAAAGAGTCACCCTCTCCTGCAG GGCCAGTCAGAGTGTTAGTAGCAGCTTAGCCTGGT ACCAGCAGAAACCTGGCCGGGCTCCCAGGCTCCTC ATTTATGGAGCATCCACCAGGGCCACTGGTGTCCC AGCCAGGTTCAGTGGCGGTGGGTCTGGGACAGACT TCACTCTCACCATCAGCAGCCTGCAGTCTGAAGATT TTGCAGTTTATTACTGTCACCAGTATATTAATTGGC CTCCGGGGGACACTTTTGGCCAGGGGACGAGGCTG GATATCAAA |
| SEQ ID NO: 324 | Light Chain | EIVMTQSPATLSVSPGERVTLSCRASQSVSSSLAWYQ QKPGRAPRLLIYGASTRATGVPARFSGGGSGTDFTLT ISSLQSEDFAVYYCHQYINWPPGDTFGQGTRLDIKRT VAAPSVFIFPPSDEQLKSGTASVVCLLNNFYPREAKV QWKVDNALQSGNSQESVTEQDSKDSTYSLSSTLTLSK ADYEKHKVYACEVTHQGLSSPVTKSFNRGEC |

TABLE 2-continued anti-HBV Antibodies

| SEQ ID NO: 325 | DNA Light Chain | GAAATAGTGATGACTCAGTCTCCAGCCACCCTGTCTG
TGTCTCCAGGGGAAAGAGTCACCCTCTCCTGCAGGGC
CAGTCAGAGTGTTAGTAGCAGCTTAGCCTGGTACCAG
CAGAAACCTGGCCGGGCTCCCAGGCTCCTCATTTATG
GAGCATCCACCAGGGCCACTGGTGTCCCAGCCAGGTT
CAGTGGCGGTGGGTCTGGGACAGACTTCACTCTCACC
ATCAGCAGCCTGCAGTCTGAAGATTTTGCAGTTTATT
ACTGTCACCAGTATATTAATTGGCCTCCGGGGGACAC
TTTTGGCCAGGGGACGAGGCTGGATATCAAACGTACG
GTGGCCGCTCCCAGCGTGTTCATCTTCCCCCCCAGCG
ACGAGCAGCTGAAGAGCGGCACCGCCAGCGTGGTGTG
CCTGCTGAACAACTTCTACCCCGGGAGGCCAAGGTG
CAGTGGAAGGTGGACAACGCCCTGCAGAGCGGCAACA
GCCAGGAGAGCGTCACCGAGCAGGACAGCAAGGACTC
CACCTACAGCCTGAGCAGCACCCTGACCCTGAGCAAG
GCCGACTACGAGAAGCATAAGGTGTACGCCTGCGAGG
TGACCCACCAGGGCCTGTCCAGCCCCGTGACCAAGAG
CTTCAACAGGGGCGAGTGC |

NOV3839HC

| SEQ ID NO: 326 (Combined) | HCDR1 | GFIFTDYYMT |
| SEQ ID NO: 327 (Combined) | HCDR2 | FITSGGETTYYADSVKG |
| SEQ ID NO: 328 (Combined) | HCDR3 | AHFDIYQYDTRGDFTYYFDN |
| SEQ ID NO: 329 (Kabat) | HCDR1 | DYYMT |
| SEQ ID NO: 330 (Kabat) | HCDR2 | FITSGGETTYYADSVKG |
| SEQ ID NO: 331 (Kabat) | HCDR3 | AHFDIYQYDTRGDFTYYFDN |
| SEQ ID NO: 332 (Chothia) | HCDR1 | GFIFTDY |
| SEQ ID NO: 333 (Chothia) | HCDR2 | TSGGET |
| SEQ ID NO: 334 (Chothia) | HCDR3 | AHFDIYQYDTRGDFTYYFDN |
| SEQ ID NO: 335 (IMGT) | HCDR1 | GFIFTDYY |
| SEQ ID NO: 336 (IMGT) | HCDR2 | ITSGGETT |
| SEQ ID NO: 337 (IMGT) | HCDR3 | VRAHFDIYQYDTRGDFTYYFDN |
| SEQ ID NO: 338 | VH | QVQLQESGGRLVRPGGSLRLSCAASGFIFTDYYMTWI
RQAPGKGPEWIAFITSGGETTYYADSVKGRFTISRDN
AKKSLFLQMYSLRADDTAVYYCVRAHFDIYQYDTRGD
FTYYFDNWGLGTLVSVSS |
| SEQ ID NO: 339 | DNA VH | CAGGTTCAGCTGCAAGAATCTGGCGGCAGACTCGT
TAGACCTGGCGGCTCTCTGAGACTGTCTTGTGCCGC
CAGCGGCTTCATCTTCACCGACTACTACATGACCTG
GATCAGACAGGCCCCTGGCAAGGGACCTGAGTGGA
TCGCCTTTATCACAAGCGGCGGAGAGACAACCTAC
TACGCCGATAGCGTGAAGGGCAGATTCACCATCAG
CCGGGACAACGCCAAGAAGTCCCTGTTCCTCCAGA
TGTACAGCCTGAGAGCCGACGATACCGCCGTGTAT
TATTGCGTGCGGGCCCACTTTGACATCTACCAGTAC
GATACCAGAGGCGATTTCACCTACTACTTCGACAA
CTGGGGCCTGGGAACCCTGGTGTCTGTCTCTTCT |
| SEQ ID NO: 340 | Heavy Chain | QVQLQESGGRLVRPGGSLRLSCAASGFIFTDYYMTWI
RQAPGKGPEWIAFITSGGETTYYADSVKGRFTISRDN
AKKSLFLQMYSLRADDTAVYYCVRAHFDIYQYDTRGD
FTYYFDNWGLGTLVSVSSASTKGPSVFPLAPSSKSTS |

TABLE 2-continued anti-HBV Antibodies

| | | |
|---|---|---|
| | | GGTAALGCLVKDYFPEPVTVSWNSGALTSGVHTFPAV
LQSSGLYSLSSVVTVPSSSLGTQTYICNVNHKPSNTK
VDKRVEPKSCDKTHTCPPCPAPELLGGPSVFLFPPKP
KDTLMISRTPEVTCVVVDVSHEDPEVKFNWYVDGVEV
HNAKTKPREEQYNSTYRVVSVLTVLHQDWLNGKEYKC
KVSNKALPAPIEKTISKAKGQPREPQVYTLPPSREEM
TKNQVSLTCLVKGFYPSDIAVEWESNGQPENNYKTTP
PVLDSDGSFFLYSKLTVDKSRWQQGNVFSCSVMHEAL
HNHYTQKSLSLSPGK |
| SEQ ID NO: 341 | DNA Heavy Chain | CAGGTTCAGCTGCAAGAATCTGGCGGCAGACTCGT
TAGACCTGGCGGCTCTCTGAGACTGTCTTGTGCCGC
CAGCGGCTTCATCTTCACCGACTACTACATGACCTG
GATCAGACAGGCCCCTGGCAAGGGACCTGAGTGGA
TCGCCTTTATCACAAGCGGCGGAGAGACAACCTAC
TACGCCGATAGCGTGAAGGGCAGATTCACCATCAG
CCGGGACAACGCCAAGAAGTCCCTGTTCCTCCAGA
TGTACAGCCTGAGAGCCGACGATACCGCCGTGTAT
TATTGCGTGCGGGCCCACTTTGACATCTACCAGTAC
GATACCAGAGGCGATTTCACCTACTACTTCGACAA
CTGGGGCCTGGGAACCCTGGTGTCTGTCTCTTCTGC
TAGCACCAAGGGCCCCAGCGTGTTCCCCCTGGCCC
CCAGCAGCAAGAGCACCAGCGGCGGCACAGCCGC
CCTGGGCTGCCTGGTGAAGGACTACTTCCCCGAGC
CCGTGACCGTGTCCTGGAACAGCGGAGCCCTGACC
TCCGGCGTGCACACCTTCCCCGCCGTGCTGCAGAG
CAGCGGCCTGTACAGCCTGTCCAGCGTGGTGACAG
TGCCCAGCAGCAGCCTGGGCACCCAGACCTACATC
TGCAACGTGAACCACAAGCCCAGCAACACCAAGGT
GGACAAGAGAGTGGAGCCCAAGAGCTGCGACAAG
ACCCACACATGCCCCCCCTGCCCGGCGCCAGAGCT
GCTGGGCGGACCCTCCGTGTTCCTGTTCCCCCCCAA
GCCCAAGGACACCCTGATGATCAGCAGGACCCCCG
AGGTGACCTGCGTGGTGGTGGACGTGAGCCACGAG
GACCCAGAGGTGAAGTTCAACTGGTACGTGGACGG
CGTGGAGGTGCACAACGCCAAGACCAAGCCCAGA
GAGGAGCAGTACAACAGCACCTACAGGGTGGTGTC
CGTGCTGACCGTGCTGCACCAGGACTGGCTGAACG
GCAAGGAATACAAGTGCAAGGTCTCCAACAAGGCC
CTGCCAGCCCCCATCGAAAAGACCATCAGCAAGGC
CAAGGGCCAGCCACGGGAGCCCCAGGTGTACACCC
TGCCCCCCTCCCGGGAGGAGATGACCAAGAACCAG
GTGTCCCTGACCTGTCTGGTGAAGGGCTTCTACCCC
AGCGACATCGCCGTGGAGTGGGAGAGCAACGGCC
AGCCCGAGAACAACTACAAGACCACCCCCCCAGTG
CTGGACAGCGACGGCAGCTTCTTCCTGTACAGCAA
GCTGACCGTGGACAAGTCCAGGTGGCAGCAGGGCA
ACGTGTTCAGCTGCAGCGTGATGCACGAGGCCCTG
CACAACCACTACACCCAGAAGAGCCTGAGCTTAAG
CCCCGGCAAG |

NOV3839LC

| | | |
|---|---|---|
| SEQ ID NO: 342 (Combined) | LCDR1 | RASQSVSSSLA |
| SEQ ID NO: 343 (Combined) | LCDR2 | GASTRAT |
| SEQ ID NO: 344 (Combined) | LCDR3 | HQYINWPPGDT |
| SEQ ID NO: 345 (Kabat) | LCDR1 | RASQSVSSSLA |
| SEQ ID NO: 346 (Kabat) | LCDR2 | GASTRAT |
| SEQ ID NO: 347 (Kabat) | LCDR3 | HQYINWPPGDT |
| SEQ ID NO: 348 (Chothia) | LCDR1 | SQSVSSS |
| SEQ ID NO: 349 (Chothia) | LCDR2 | GAS |

TABLE 2-continued anti-HBV Antibodies

| | | |
|---|---|---|
| SEQ ID NO: 350 (Chothia) | LCDR3 | YINWPPGD |
| SEQ ID NO: 351 (IMGT) | LCDR1 | QSVSSS |
| SEQ ID NO: 352 (IMGT) | LCDR2 | GAS |
| SEQ ID NO: 353 (IMGT) | LCDR3 | HQYINWPPGDT |
| SEQ ID NO: 354 | VL | EIVMTQSPATLSVSPGERVTLSCRASQSVSSSLAWYQ QKPGRAPRLLIYGASTRATGVPARFSGGGSGTDFTLT ISSLQSEDFAVYYCHQYINWPPGDTFGQGTRLDIK |
| SEQ ID NO: 355 | DNA VL | GAAATAGTGATGACTCAGTCTCCAGCCACCCTGTCT GTGTCTCCAGGGGAAAGAGTCACCCTCTCCTGCAG GGCCAGTCAGAGTGTTAGTAGCAGCTTAGCCTGGT ACCAGCAGAAACCTGGCCGGGCTCCCAGGCTCCTC ATTTATGGAGCATCCACCAGGGCCACTGGTGTCCC AGCCAGGTTCAGTGGCGGTGGGTCTGGGACAGACT TCACTCTCACCATCAGCAGCCTGCAGTCTGAAGATT TTGCAGTTTATTACTGTCACCAGTATATTAATTGGC CTCCGGGGGACACTTTTGGCCAGGGGACGAGGCTG GATATCAAA |
| SEQ ID NO: 356 | Light Chain | EIVMTQSPATLSVSPGERVTLSCRASQSVSSSLAWYQ QKPGRAPRLLIYGASTRATGVPARFSGGGSGTDFTLT ISSLQSEDFAVYYCHQYINWPPGDTFGQGTRLDIKRT VAAPSVFIFPPSDEQLKSGTASVVCLLNNFYPREAKV QWKVDNALQSGNSQESVTEQDSKDSTYSLSSTLTLSK ADYEKHKVYACEVTHQGLSSPVTKSFNRGEC |
| SEQ ID NO: 357 | DNA Light Chain | GAAATAGTGATGACTCAGTCTCCAGCCACCCTGTCT GTGTCTCCAGGGGAAAGAGTCACCCTCTCCTGCAG GGCCAGTCAGAGTGTTAGTAGCAGCTTAGCCTGGT ACCAGCAGAAACCTGGCCGGGCTCCCAGGCTCCTC ATTTATGGAGCATCCACCAGGGCCACTGGTGTCCC AGCCAGGTTCAGTGGCGGTGGGTCTGGGACAGACT TCACTCTCACCATCAGCAGCCTGCAGTCTGAAGATT TTGCAGTTTATTACTGTCACCAGTATATTAATTGGC CTCCGGGGGACACTTTTGGCCAGGGGACGAGGCTG GATATCAAACGTACGGTGGCCGCTCCCAGCGTGTT CATCTTCCCCCCCAGCGACGAGCAGCTGAAGAGCG GCACCGCCAGCGTGGTGTGCCTGCTGAACAACTTC TACCCCCGGGAGGCCAAGGTGCAGTGGAAGGTGGA CAACGCCCTGCAGAGCGGCAACAGCCAGGAGAGC GTCACCGAGCAGGACAGCAAGGACTCCACCTACAG CCTGAGCAGCACCCTGACCCTGAGCAAGGCCGACT ACGAGAAGCATAAGGTGTACGCCTGCGAGGTGACC CACCAGGGCCTGTCCAGCCCCGTGACCAAGAGCTT CAACAGGGGCGAGTGC |

NOV3840HC

| | | |
|---|---|---|
| SEQ ID NO: 358 (Combined) | HCDR1 | GFTFSYYGMN |
| SEQ ID NO: 359 (Combined) | HCDR2 | GITNSGSITYYADSVKG |
| SEQ ID NO: 360 (Combined) | HCDR3 | VGVRSSSGMWDLDY |
| SEQ ID NO: 361 (Kabat) | HCDR1 | YYGMN |
| SEQ ID NO: 362 (Kabat) | HCDR2 | GITNSGSITYYADSVKG |
| SEQ ID NO: 363 (Kabat) | HCDR3 | VGVRSSSGMWDLDY |
| SEQ ID NO: 364 (Chothia) | HCDR1 | GFTFSYY |

TABLE 2-continued anti-HBV Antibodies

| SEQ ID NO: 365 (Chothia) | HCDR2 | TNSGSI |
|---|---|---|
| SEQ ID NO: 366 (Chothia) | HCDR3 | VGVRSSSGMWDLDY |
| SEQ ID NO: 367 (IMGT) | HCDR1 | GFTFSYYG |
| SEQ ID NO: 368 (IMGT) | HCDR2 | ITNSGSIT |
| SEQ ID NO: 369 (IMGT) | HCDR3 | AKVGVRSSSGMWDLDY |
| SEQ ID NO: 370 | VH | EVQLLESGGGLVQPGGSRRLSCAASGFTFSYYGMNWV RQAPGKGLEWVSGITNSGSITYYADSVKGRFSISRDN SKNTLFLQMNSLRAEDTAVYYCAKVGVRSSSGMWDLD YWGQGTLVTVSS |
| SEQ ID NO: 371 | DNA VH | GAGGTTCAATTGTTGGAGTCTGGGGGAGGCCTGGT ACAGCCGGGGGGTCCCGGAGACTGTCCTGTGCAG CCTCTGGATTCACCTTTAGCTACTATGGCATGAACT GGGTCCGCCAGGCTCCAGGGAAGGGACTGGAATGG GTCTCAGGTATTACTAATAGTGGTAGTATCACATAC TACGCAGACTCCGTGAAGGGCCGGTTCAGCATCTC CAGAGACAATTCCAAGAACACGTTGTTTCTGCAAA TGAACAGCCTGAGAGCCGAGGACACGGCCGTATAT TACTGTGCGAAGGTGGGAGTGCGCAGTTCGTCCGG GATGTGGGACCTTGACTACTGGGGCCAGGGAACCC TGGTCACCGTCAGCTCA |
| SEQ ID NO: 372 | Heavy Chain | EVQLLESGGGLVQPGGSRRLSCAASGFTFSYYGMNWV RQAPGKGLEWVSGITNSGSITYYADSVKGRFSISRDN SKNTLFLQMNSLRAEDTAVYYCAKVGVRSSSGMWDLD YWGQGTLVTVSSASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKRVE PKSCDKTHTCPPCPAPELLGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |
| SEQ ID NO: 373 | DNA Heavy Chain | GAGGTTCAATTGTTGGAGTCTGGGGGAGGCCTGGT ACAGCCGGGGGGTCCCGGAGACTGTCCTGTGCAG CCTCTGGATTCACCTTTAGCTACTATGGCATGAACT GGGTCCGCCAGGCTCCAGGGAAGGGACTGGAATGG GTCTCAGGTATTACTAATAGTGGTAGTATCACATAC TACGCAGACTCCGTGAAGGGCCGGTTCAGCATCTC CAGAGACAATTCCAAGAACACGTTGTTTCTGCAAA TGAACAGCCTGAGAGCCGAGGACACGGCCGTATAT TACTGTGCGAAGGTGGGAGTGCGCAGTTCGTCCGG GATGTGGGACCTTGACTACTGGGGCCAGGGAACCC TGGTCACCGTCAGCTCAGCTAGCACCAAGGGCCCC AGCGTGTTCCCCCTGGCCCCCAGCAGCAAGAGCAC CAGCGGCGGCACAGCCGCCCTGGGCTGCCTGGTGA AGGACTACTTCCCCGAGCCCGTGACCGTGTCCTGG AACAGCGGAGCCCTGACCTCCGGCGTGCACACCTT CCCCGCCGTGCTGCAGAGCAGCGGCCTGTACAGCC TGTCCAGCGTGGTGACAGTGCCCAGCAGCAGCCTG GGCACCCAGACCTACATCTGCAACGTGAACCACAA GCCCAGCAACACCAAGGTGGACAAGAGAGTGGAG CCCAAGAGCTGCGACAAGACCCACACCTGCCCCCC CTGCCCAGCCCCAGAGCTGCTGGGCGGACCCTCCG TGTTCCTGTTCCCCCCCAAGCCCAAGGACACCCTGA TGATCAGCAGGACCCCCGAGGTGACCTGCGTGGTG GTGGACGTGAGCCACGAGGACCCAGAGGTGAAGTT CAACTGGTACGTGGACGGCGTGGAGGTGCACAACG CCAAGACCAAGCCCAGAGAGGAGCAGTACAACAG CACCTACAGGGTGGTGTCCGTGCTGACCGTGCTGC ACCAGGACTGGCTGAACGGCAAGGAATACAAGTGC AAGGTCTCCAACAAGGCCCTGCCAGCCCCCATCGA AAAGACCATCAGCAAGGCCAAGGGCCAGCCACGG GAGCCCCAGGTGTACACCCTGCCCCCCTCCCGGGA GGAGATGACCAAGAACCAGGTGTCCCTGACCTGTC |

TABLE 2-continued anti-HBV Antibodies

|  |  |  |
|---|---|---|
|  |  | TGGTGAAGGGCTTCTACCCCAGCGACATCGCCGTG<br>GAGTGGGAGAGCAACGGCCAGCCCGAGAACAACT<br>ACAAGACCACCCCCCCAGTGCTGGACAGCGACGGC<br>AGCTTCTTCCTGTACAGCAAGCTGACCGTGGACAA<br>GTCCAGGTGGCAGCAGGGCAACGTGTTCAGCTGCA<br>GCGTGATGCACGAGGCCCTGCACAACCACTACACC<br>CAGAAGAGCCTGAGCCTGTCCCCCGGCAAG |
| NOV3840LC |  |  |
| SEQ ID NO: 374<br>(Combined) | LCDR1 | GGNNIGSKSLQ |
| SEQ ID NO: 375<br>(Combined) | LCDR2 | DDSDRPS |
| SEQ ID NO: 376<br>(Combined) | LCDR3 | QVWDTSSDHVV |
| SEQ ID NO: 377<br>(Kabat) | LCDR1 | GGNNIGSKSLQ |
| SEQ ID NO: 378<br>(Kabat) | LCDR2 | DDSDRPS |
| SEQ ID NO: 379<br>(Kabat) | LCDR3 | QVWDTSSDHVV |
| SEQ ID NO: 380<br>(Chothia) | LCDR1 | NNIGSKS |
| SEQ ID NO: 381<br>(Chothia) | LCDR2 | DDS |
| SEQ ID NO: 382<br>(Chothia) | LCDR3 | WDTSSDHV |
| SEQ ID NO: 383<br>(IMGT) | LCDR1 | NIGSKS |
| SEQ ID NO: 384<br>(IMGT) | LCDR2 | DDS |
| SEQ ID NO: 385<br>(IMGT) | LCDR3 | QVWDTSSDHVV |
| SEQ ID NO: 386 | VL | SYVLTQPPSVSVAPGQTARLSCGGNNIGSKSLQWYQQ<br>KPGQAPVLVVNDDSDRPSGIPERFSGSNSGNTATLTI<br>SRVEAGDEADYYCQVWDTSSDHVVFGGGTKLTVL |
| SEQ ID NO: 387 | DNA VL | TCCTATGTGCTGACTCAGCCACCCTCGGTGTCAGTG<br>GCCCCAGGACAGACGGCCAGACTTTCCTGTGGGGG<br>AAACAACATTGGAAGTAAAAGTCTGCAGTGGTACC<br>AGCAGAAGCCAGGCCAGGCCCCTGTGCTGGTCGTC<br>AATGATGATAGCGACCGGCCCTCAGGGATCCCTGA<br>GCGATTCTCTGGCTCCAACTCTGGGAACACGGCCA<br>CCCTGACCATCAGCAGGGTCGAAGCCGGGGATGAG<br>GCCGACTATTACTGTCAGGTGTGGGATACTAGTAG<br>TGATCATGTGGTCTTCGGCGGAGGGACCAAGCTGA<br>CCGTCCTA |
| SEQ ID NO: 388 | Light Chain | SYVLTQPPSVSVAPGQTARLSCGGNNIGSKSLQWYQQ<br>KPGQAPVLVVNDDSDRPSGIPERFSGSNSGNTATLTI<br>SRVEAGDEADYYCQVWDTSSDHVVFGGGTKLTVLGQP<br>KAAPSVTLFPPSSEELQANKATLVCLISDFYPGAVTV<br>AWKADSSPVKAGVETTTPSKQSNNKYAASSYLSLTPE<br>QWKSHRSYSCQVTHEGSTVEKTVAPTECS |
| SEQ ID NO: 389 | DNA Light<br>Chain | TCCTATGTGCTGACTCAGCCACCCTCGGTGTCAGTG<br>GCCCCAGGACAGACGGCCAGACTTTCCTGTGGGG<br>AAACAACATTGGAAGTAAAAGTCTGCAGTGGTACC<br>AGCAGAAGCCAGGCCAGGCCCCTGTGCTGGTCGTC<br>AATGATGATAGCGACCGGCCCTCAGGGATCCCTGA<br>GCGATTCTCTGGCTCCAACTCTGGGAACACGGCCA<br>CCCTGACCATCAGCAGGGTCGAAGCCGGGGATGAG<br>GCCGACTATTACTGTCAGGTGTGGGATACTAGTAG<br>TGATCATGTGGTCTTCGGCGGAGGGACCAAGCTGA<br>CCGTCCTAGGCCAGCCTAAGGCCGCTCCCTCCGTG |

TABLE 2-continued anti-HBV Antibodies

ACCCTGTTCCCCCCAGCTCCGAGGAACTGCAGGC
CAACAAGGCCACCCTGGTGTGCCTGATCAGCGACT
TCTACCCTGGCGCCGTGACCGTGGCCTGGAAGGCC
GACAGCAGCCCCGTGAAGGCCGGCGTGGAGACAA
CCACCCCCAGCAAGCAGAGCAACAACAAGTACGCC
GCCAGCAGCTACCTGAGCCTGACCCCCGAGCAGTG
GAAGAGCCACAGAAGCTACAGCTGCCAGGTCACCC
ACGAGGGCAGCACCGTGGAGAAAACCGTGGCCCCC
ACCGAGTGCAGC

NOV3841HC

| | | |
|---|---|---|
| SEQ ID NO: 390 (Combined) | HCDR1 | GFTFSYYGMN |
| SEQ ID NO: 391 (Combined) | HCDR2 | GITQSGSITYYADTVKG |
| SEQ ID NO: 392 (Combined) | HCDR3 | VGVRSSSGMWDLDY |
| SEQ ID NO: 393 (Kabat) | HCDR1 | YYGMN |
| SEQ ID NO: 394 (Kabat) | HCDR2 | GITQSGSITYYADTVKG |
| SEQ ID NO: 395 (Kabat) | HCDR3 | VGVRSSSGMWDLDY |
| SEQ ID NO: 396 (Chothia) | HCDR1 | GFTFSYY |
| SEQ ID NO: 397 (Chothia) | HCDR2 | TQSGSI |
| SEQ ID NO: 398 (Chothia) | HCDR3 | VGVRSSSGMWDLDY |
| SEQ ID NO: 399 (IMGT) | HCDR1 | GFTFSYYG |
| SEQ ID NO: 400 (IMGT) | HCDR2 | ITQSGSIT |
| SEQ ID NO: 401 (IMGT) | HCDR3 | AKVGVRSSSGMWDLDY |
| SEQ ID NO: 402 | VH | EVQLLESGGGLVQPGGSRRLSCAASGFTFSYYGMNWV RQAPGKGLEWVSGITQSGSITYYADTVKGRFSISRDN SKNTLFLQMNSLRAEDTAVYYCAKVGVRSSSGMWDLD YWGQGTLVTVSS |
| SEQ ID NO: 403 | DNA VH | GAGGTTCAATTGTTGGAGTCTGGGGGAGGCCTGGT ACAGCCGGGGGGGTCCCGGAGACTGTCCTGTGCAG CCTCTGGATTCACCTTTAGCTACTATGGCATGAACT GGGTCCGCCAGGCTCCAGGGAAGGGACTGGAATGG GTCTCAGGTATTACTCAGAGTGGTAGTATCACATAC TACGCAGACACCGTGAAGGGCCGGTTCAGCATCTC CAGAGACAATTCCAAGAACACGTTGTTTCTGCAAA TGAACAGCCTGAGAGCCGAGGACACGGCCGTATAT TACTGTGCGAAGGTGGGAGTGCGCAGTTCGTCCGG GATGTGGGACCTTGACTACTGGGGCCAGGGAACCC TGGTCACCGTCAGCTCA |
| SEQ ID NO: 404 | Heavy Chain | EVQLLESGGGLVQPGGSRRLSCAASGFTFSYYGMNWV RQAPGKGLEWVSGITQSGSITYYADTVKGRFSISRDN SKNTLFLQMNSLRAEDTAVYYCAKVGVRSSSGMWDLD YWGQGTLVTVSSASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKRVE PKSCDKTHTCPPCPAPELLGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |

TABLE 2-continued anti-HBV Antibodies

| SEQ ID NO: 405 | DNA Heavy Chain | GAGGTTCAATTGTTGGAGTCTGGGGGAGGCCTGGT
ACAGCCGGGGGGTCCCCGGAGACTGTCCTGTGCAG
CCTCTGGATTCACCTTTAGCTACTATGGCATGAACT
GGGTCCGCCAGGCTCCAGGGAAGGGACTGGAATGG
GTCTCAGGTATTACTCAGAGTGGTAGTATCACATAC
TACGCAGACACCGTGAAGGGCCGGTTCAGCATCTC
CAGAGACAATTCCAAGAACACGTTGTTTCTGCAAA
TGAACAGCCTGAGAGCCGAGGACACGGCCGTATAT
TACTGTGCGAAGGTGGGAGTGCGCAGTTCGTCCGG
GATGTGGGACCTTGACTACTGGGGCCAGGGAACCC
TGGTCACCGTCAGCTCAGCTAGCACCAAGGGCCCC
AGCGTGTTCCCCCTGGCCCCCAGCAGCAAGAGCAC
CAGCGGCGGCACAGCCGCCCTGGGCTGCCTGGTGA
AGGACTACTTCCCCGAGCCCGTGACCGTGTCCTGG
AACAGCGGAGCCCTGACCTCCGGCGTGCACACCTT
CCCCGCCGTGCTGCAGAGCAGCGGCCTGTACAGCC
TGTCCAGCGTGGTGACAGTGCCCAGCAGCAGCCTG
GGCACCCAGACCTACATCTGCAACGTGAACCACAA
GCCCAGCAACACCAAGGTGGACAAGAGAGTGGAG
CCCAAGAGCTGCGACAAGACCCACACCTGCCCCCC
CTGCCCAGCCCCAGAGCTGCTGGGCGGACCCTCCG
TGTTCCTGTTCCCCCCCAAGCCCAAGGACACCCTGA
TGATCAGCAGGACCCCCGAGGTGACCTGCGTGGTG
GTGGACGTGAGCCACGAGGACCCAGAGGTGAAGTT
CAACTGGTACGTGGACGGCGTGGAGGTGCACAACG
CCAAGACCAAGCCCAGAGAGGAGCAGTACAACAG
CACCTACAGGGTGGTGTCCGTGCTGACCGTGCTGC
ACCAGGACTGGCTGAACGGCAAGGAATACAAGTGC
AAGGTCTCCAACAAGGCCCTGCCAGCCCCCATCGA
AAAGACCATCAGCAAGGCCAAGGGCCAGCCACGG
GAGCCCCAGGTGTACACCCTGCCCCCCTCCCGGGA
GGAGATGACCAAGAACCAGGTGTCCCTGACCTGTC
TGGTGAAGGGCTTCTACCCCAGCGACATCGCCGTG
GAGTGGGAGAGCAACGGCCAGCCCGAGAACAACT
ACAAGACCACCCCCCCAGTGCTGGACAGCGACGGC
AGCTTCTTCCTGTACAGCAAGCTGACCGTGGACAA
GTCCAGGTGGCAGCAGGGCAACGTGTTCAGCTGCA
GCGTGATGCACGAGGCCCTGCACAACCACTACACC
CAGAAGAGCCTGAGCCTGTCCCCCGGCAAG |

NOV3841LC

| SEQ ID NO: 406 (Combined) | LCDR1 | GGNNIGSKSLQ |
| SEQ ID NO: 407 (Combined) | LCDR2 | DESDRPS |
| SEQ ID NO: 408 (Combined) | LCDR3 | QVWDTSSDHVV |
| SEQ ID NO: 409 (Kabat) | LCDR1 | GGNNIGSKSLQ |
| SEQ ID NO: 410 (Kabat) | LCDR2 | DESDRPS |
| SEQ ID NO: 411 (Kabat) | LCDR3 | QVWDTSSDHVV |
| SEQ ID NO: 412 (Chothia) | LCDR1 | NNIGSKS |
| SEQ ID NO: 413 (Chothia) | LCDR2 | DES |
| SEQ ID NO: 414 (Chothia) | LCDR3 | WDTSSDHV |
| SEQ ID NO: 415 (IMGT) | LCDR1 | NIGSKS |
| SEQ ID NO: 416 (IMGT) | LCDR2 | DES |
| SEQ ID NO: 417 (IMGT) | LCDR3 | QVWDTSSDHVV |

TABLE 2-continued anti-HBV Antibodies

| SEQ ID NO: 418 | VL | SYVLTQPPSVSVAPGQTARLSCGGNNIGSKSLQWYQQ
KPGQAPVLVVNDESDRPSGIPERFSGSNSGNTATLTI
SRVEAGDEADYYCQVWDTSSDHVVFGGGTKLTVL |
|---|---|---|
| SEQ ID NO: 419 | DNA VL | TCCTATGTGCTGACTCAGCCACCCTCGGTGTCAGTG
GCCCCAGGACAGACGGCCAGACTTTCCTGTGGGGG
AAACAACATTGGAAGTAAAAGTCTGCAGTGGTACC
AGCAGAAGCCAGGCCAGGCCCCTGTGCTGGTCGTC
AATGATGAGAGCGACCGGCCCTCAGGGATCCCTGA
GCGATTCTCTGGCTCCAACTCTGGGAACACGGCCA
CCCTGACCATCAGCAGGGTCGAAGCCGGGGATGAG
GCCGACTATTACTGTCAGGTGTGGGATACTAGTAG
TGATCATGTGGTCTTCGGCGGAGGGACCAAGCTGA
CCGTCCTA |
| SEQ ID NO: 420 | Light Chain | SYVLTQPPSVSVAPGQTARLSCGGNNIGSKSLQWYQQ
KPGQAPVLVVNDESDRPSGIPERFSGSNSGNTATLTI
SRVEAGDEADYYCQVWDTSSDHVVFGGGTKLTVLGQP
KAAPSVTLFPPSSEELQANKATLVCLISDFYPGAVTV
AWKADSSPVKAGVETTTPSKQSNNKYAASSYLSLTPE
QWKSHRSYSCQVTHEGSTVEKTVAPTECS |
| SEQ ID NO: 421 | DNA Light Chain | TCCTATGTGCTGACTCAGCCACCCTCGGTGTCAGTG
GCCCCAGGACAGACGGCCAGACTTTCCTGTGGGGG
AAACAACATTGGAAGTAAAAGTCTGCAGTGGTACC
AGCAGAAGCCAGGCCAGGCCCCTGTGCTGGTCGTC
AATGATGAGAGCGACCGGCCCTCAGGGATCCCTGA
GCGATTCTCTGGCTCCAACTCTGGGAACACGGCCA
CCCTGACCATCAGCAGGGTCGAAGCCGGGGATGAG
GCCGACTATTACTGTCAGGTGTGGGATACTAGTAG
TGATCATGTGGTCTTCGGCGGAGGGACCAAGCTGA
CCGTCCTAGGCCAGCCTAAGGCCGCTCCCTCCGTG
ACCCTGTTCCCCCCCAGCTCCGAGGAACTGCAGGC
CAACAAGGCCACCCTGGTGTGCCTGATCAGCGACT
TCTACCCTGGCGCCGTGACCGTGGCCTGGAAGGCC
GACAGCAGCCCCGTGAAGGCCGGCGTGGAGACAA
CCACCCCCAGCAAGCAGAGCAACAACAAGTACGCC
GCCAGCAGCTACCTGAGCCTGACCCCCGAGCAGTG
GAAGAGCCACAGAAGCTACAGCTGCCAGGTCACCC
ACGAGGGCAGCACCGTGGAGAAAACCGTGGCCCCC
ACCGAGTGCAGC |

NOV3842HC

| SEQ ID NO: 422 (Combined) | HCDR1 | GFTFSYYGMN |
|---|---|---|
| SEQ ID NO: 423 (Combined) | HCDR2 | GITNVGSITYYADTVKG |
| SEQ ID NO: 424 (Combined) | HCDR3 | VGVRSSSGMWDLDY |
| SEQ ID NO: 425 (Kabat) | HCDR1 | YYGMN |
| SEQ ID NO: 426 (Kabat) | HCDR2 | GITNVGSITYYADTVKG |
| SEQ ID NO: 427 (Kabat) | HCDR3 | VGVRSSSGMWDLDY |
| SEQ ID NO: 428 (Chothia) | HCDR1 | GFTFSYY |
| SEQ ID NO: 429 (Chothia) | HCDR2 | TNVGSI |
| SEQ ID NO: 430 (Chothia) | HCDR3 | VGVRSSSGMWDLDY |
| SEQ ID NO: 431 (IMGT) | HCDR1 | GFTFSYYG |
| SEQ ID NO: 432 (IMGT) | HCDR2 | ITNVGSIT |

TABLE 2-continued

| | | anti-HBV Antibodies |
|---|---|---|
| SEQ ID NO: 433 (IMGT) | HCDR3 | AKVGVRSSSGMWDLDY |
| SEQ ID NO: 434 | VH | EVQLLESGGGLVQPGGSRRLSCAASGFTFSYYGMNWV RQAPGKGLEWVSGITNVGSITYYADTVKGRFSISRDN SKNTLFLQMNSLRAEDTAVYYCAKVGVRSSSGMWDLD YWGQGTLVTVSS |
| SEQ ID NO: 435 | DNA VH | GAGGTTCAATTGTTGGAGTCTGGGGGAGGCCTGGT ACAGCCGGGGGGGTCCCGGAGACTGTCCTGTGCAG CCTCTGGATTCACCTTTAGCTACTATGGCATGAACT GGGTCCGCCAGGCTCCAGGGAAGGGACTGGAATGG GTCTCAGGTATTACTAATGTGGGTAGTATCACATAC TACGCAGACACCGTGAAGGGCCGGTTCAGCATCTC CAGAGACAATTCCAAGAACACGTTGTTTCTGCAAA TGAACAGCCTGAGAGCCGAGGACACGGCCGTATAT TACTGTGCGAAGGTGGGAGTGCGCAGTTCGTCCGG GATGTGGGACCTTGACTACTGGGGCCAGGGAACCC TGGTCACCGTCAGCTCA |
| SEQ ID NO: 436 | Heavy Chain | EVQLLESGGGLVQPGGSRRLSCAASGFTFSYYGMNWV RQAPGKGLEWVSGITNVGSITYYADTVKGRFSISRDN SKNTLFLQMNSLRAEDTAVYYCAKVGVRSSSGMWDLD YWGQGTLVTVSSASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKRVE PKSCDKTHTCPPCPAPELLGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |
| SEQ ID NO: 437 | DNA Heavy Chain | GAGGTTCAATTGTTGGAGTCTGGGGGAGGCCTGGT ACAGCCGGGGGGGTCCCGGAGACTGTCCTGTGCAG CCTCTGGATTCACCTTTAGCTACTATGGCATGAACT GGGTCCGCCAGGCTCCAGGGAAGGGACTGGAATGG GTCTCAGGTATTACTAATGTGGGTAGTATCACATAC TACGCAGACACCGTGAAGGGCCGGTTCAGCATCTC CAGAGACAATTCCAAGAACACGTTGTTTCTGCAAA TGAACAGCCTGAGAGCCGAGGACACGGCCGTATAT TACTGTGCGAAGGTGGGAGTGCGCAGTTCGTCCGG GATGTGGGACCTTGACTACTGGGGCCAGGGAACCC TGGTCACCGTCAGCTCAGCTAGCACCAAGGGCCCC AGCGTGTTCCCCCTGGCCCCCAGCAGCAAGAGCAC CAGCGGCGGCACAGCCGCCCTGGGCTGCCTGGTGA AGGACTACTTCCCCGAGCCCGTGACCGTGTCCTGG AACAGCGGAGCCCTGACCTCCGGCGTGCACACCTT CCCCGCCGTGCTGCAGAGCAGCGGCCTGTACAGCC TGTCCAGCGTGGTGACAGTGCCCAGCAGCAGCCTG GGCACCCAGACCTACATCTGCAACGTGAACCACAA GCCCAGCAACACCAAGGTGGACAAGAGAGTGGAG CCCAAGAGCTGCGACAAGACCCACACCTGCCCCCC CTGCCCAGCCCCAGAGCTGCTGGGCGGACCCTCCG TGTTCCTGTTCCCCCCCAAGCCCAAGGACACCCTGA TGATCAGCAGGACCCCCGAGGTGACCTGCGTGGTG GTGGACGTGAGCCACGAGGACCCAGAGGTGAAGTT CAACTGGTACGTGGACGGCGTGGAGGTGCACAACG CCAAGACCAAGCCCAGAGAGGAGCAGTACAACAG CACCTACAGGGTGGTGTCCGTGCTGACCGTGCTGC ACCAGGACTGGCTGAACGGCAAGGAATACAAGTGC AAGGTCTCCAACAAGGCCCTGCCAGCCCCCATCGA AAAGACCATCAGCAAGGCCAAGGGCCAGCCACGG GAGCCCCAGGTGTACACCCTGCCCCCCTCCCGGGA GGAGATGACCAAGAACCAGGTGTCCCTGACCTGTC TGGTGAAGGGCTTCTACCCCAGCGACATCGCCGTG GAGTGGGAGAGCAACGGCCAGCCCGAGAACAACT ACAAGACCACCCCCCCAGTGCTGGACAGCGACGGC AGCTTCTTCCTGTACAGCAAGCTGACCGTGGACAA GTCCAGGTGGCAGCAGGGCAACGTGTTCAGCTGCA GCGTGATGCACGAGGCCCTGCACAACCACTACACC CAGAAGAGCCTGAGCCTGTCCCCCGGCAAG |

NOV3842LC

| SEQ ID NO: 438 (Combined) | LCDR1 | GGNNIGSKSLQ |

TABLE 2-continued anti-HBV Antibodies

| SEQ ID NO: 439 (Combined) | LCDR2 | DESDRPS |
|---|---|---|
| SEQ ID NO: 440 (Combined) | LCDR3 | QVWDTSSDHVV |
| SEQ ID NO: 441 (Kabat) | LCDR1 | GGNNIGSKSLQ |
| SEQ ID NO: 442 (Kabat) | LCDR2 | DESDRPS |
| SEQ ID NO: 443 (Kabat) | LCDR3 | QVWDTSSDHVV |
| SEQ ID NO: 444 (Chothia) | LCDR1 | NNIGSKS |
| SEQ ID NO: 445 (Chothia) | LCDR2 | DES |
| SEQ ID NO: 446 (Chothia) | LCDR3 | WDTSSDHV |
| SEQ ID NO: 447 (IMGT) | LCDR1 | NIGSKS |
| SEQ ID NO: 448 (IMGT) | LCDR2 | DES |
| SEQ ID NO: 449 (IMGT) | LCDR3 | QVWDTSSDHVV |
| SEQ ID NO: 450 | VL | SYVLTQPPSVSVAPGQTARLSCGGNNIGSKSLQWYQQ KPGQAPVLVVNDESDRPSGIPERFSGSNSGNTATLTI SRVEAGDEADYYCQVWDTSSDHVVFGGGTKLTVL |
| SEQ ID NO: 451 | DNA VL | TCCTATGTGCTGACTCAGCCACCCTCGGTGTCAGTG GCCCCAGGACAGACGGCCAGACTTTCCTGTGGGGG AAACAACATTGGAAGTAAAAGTCTGCAGTGGTACC AGCAGAAGCCAGGCCAGGCCCCTGTGCTGGTCGTC AATGATGAGAGCGACCGGCCCTCAGGGATCCCTGA GCGATTCTCTGGCTCCAACTCTGGGAACACGGCCA CCCTGACCATCAGCAGGGTCGAAGCCGGGGATGAG GCCGACTATTACTGTCAGGTGTGGGATACTAGTAG TGATCATGTGGTCTTCGGCGGAGGGACCAAGCTGA CCGTCCTA |
| SEQ ID NO: 452 | Light Chain | SYVLTQPPSVSVAPGQTARLSCGGNNIGSKSLQWYQQ KPGQAPVLVVNDESDRPSGIPERFSGSNSGNTATLTI SRVEAGDEADYYCQVWDTSSDHVVFGGGTKLTVLGQP KAAPSVTLFPPSSEELQANKATLVCLISDFYPGAVTV AWKADSSPVKAGVETTTPSKQSNNKYAASSYLSLTPE QWKSHRSYSCQVTHEGSTVEKTVAPTECS |
| SEQ ID NO: 453 | DNA Light Chain | TCCTATGTGCTGACTCAGCCACCCTCGGTGTCAGTG GCCCCAGGACAGACGGCCAGACTTTCCTGTGGGGG AAACAACATTGGAAGTAAAAGTCTGCAGTGGTACC AGCAGAAGCCAGGCCAGGCCCCTGTGCTGGTCGTC AATGATGAGAGCGACCGGCCCTCAGGGATCCCTGA GCGATTCTCTGGCTCCAACTCTGGGAACACGGCCA CCCTGACCATCAGCAGGGTCGAAGCCGGGGATGAG GCCGACTATTACTGTCAGGTGTGGGATACTAGTAG TGATCATGTGGTCTTCGGCGGAGGGACCAAGCTGA CCGTCCTAGGCCAGCCTAAGGCCGCTCCCTCCGTG ACCCTGTTCCCCCCCAGCTCCGAGGAACTGCAGGC CAACAAGGCCACCCTGGTGTGCCTGATCAGCGACT TCTACCCTGGCGCCGTGACCGTGGCCTGGAAGGCC GACAGCAGCCCCGTGAAGGCCGGCGTGGAGACAA CCACCCCCAGCAAGCAGAGCAACAACAAGTACGCC GCCAGCAGCTACCTGAGCCTGACCCCCGAGCAGTG GAAGAGCCACAGAAGCTACAGCTGCCAGGTCACCC ACGAGGGCAGCACCGTGGAGAAAACCGTGGCCCCC ACCGAGTGCAGC |

TABLE 2-continued anti-HBV Antibodies

NOV2603 HC

| SEQ ID NO: 454 (Combined) | HCDR1 | GYTFTSYYMH |
| --- | --- | --- |
| SEQ ID NO: 455 (Combined) | HCDR2 | IISPSGGSTSYAQKFQG |
| SEQ ID NO: 456 (Combined) | HCDR3 | DWEGGDPYGYYYAFDY |
| SEQ ID NO: 457 (Kabat) | HCDR1 | SYYMH |
| SEQ ID NO: 458 (Kabat) | HCDR2 | IISPSGGSTSYAQKFQG |
| SEQ ID NO: 459 (Kabat) | HCDR3 | DWEGGDPYGYYYAFDY |
| SEQ ID NO: 460 (Chothia) | HCDR1 | GYTFTSY |
| SEQ ID NO: 461 (Chothia) | HCDR2 | SPSGGS |
| SEQ ID NO: 462 (Chothia) | HCDR3 | DWEGGDPYGYYYAFDY |
| SEQ ID NO: 463 (IMGT) | HCDR1 | GYTFTSYY |
| SEQ ID NO: 464 (IMGT) | HCDR2 | ISPSGGST |
| SEQ ID NO: 465 (IMGT) | HCDR3 | ARDWEGGDPYGYYYAFDY |
| SEQ ID NO: 466 | VH | QVQLVQSGAEVKKPGASVKVSCKASGYTFTSYYMHWV RQAPGQGLEWMGIISPSGGSTSYAQKFQGRVTMTRDT STSTVYMELSSLRSEDTAVYYCARDWEGGDPYGYYYA FDYWGQGTLVTVSS |
| SEQ ID NO: 467 | DNA VH | CAGGTGCAATTGGTGCAGAGCGGAGCCGAAGTGAA AAAACCTGGGGCCAGCGTGAAAGTGTCCTGCAAAG CCTCCGGATACACCTTCACCAGCTACTACATGCACT GGGTCCGCCAGGCCCCAGGCCAGGGACTCGAGTGG ATGGGCATCATCAGCCCTAGCGGCGGCAGCACCAG CTACGCCCAGAAATTCCAGGGCCGGGTGACCATGA CCCGCGACACCAGCACCAGCACCGTGTACATGGAA CTGAGCAGCCTGCGCAGCGAGGACACCGCCGTGTA TTATTGCGCGCGTGACTGGGAAGGTGGTGACCCGT ACGGTTACTACTACGCTTTCGACTACTGGGGTCAAG GCACCCTGGTTACAGTCAGCTCA |
| SEQ ID NO: 468 | Heavy Chain | QVQLVQSGAEVKKPGASVKVSCKASGYTFTSYYMHWV RQAPGQGLEWMGIISPSGGSTSYAQKFQGRVTMTRDT STSTVYMELSSLRSEDTAVYYCARDWEGGDPYGYYYA FDYWGQGTLVTVSSASTKGPSVFPLAPSSKSTSGGTA ALGCLVKDYFPEPVTVSWNSGALTSGVHTFPAVLQSS GLYSLSSVVTVPSSSLGTQTYICNVNHKPSNTKVDKR VEPKSCDKTHTCPPCPAPELLGGPSVFLFPPKPKDTL MISRTPEVTCVVVDVSHEDPEVKFNWYVDGVEVHNAK TKPREEQYNSTYRVVSVLTVLHQDWLNGKEYKCKVSN KALPAPIEKTISKAKGQPREPQVYTLPPSREEMTKNQ VSLTCLVKGFYPSDIAVEWESNGQPENNYKTTPPVLD SDGSFFLYSKLTVDKSRWQQGNVFSCSVMHEALHNHY TQKSLSLSPGK |
| SEQ ID NO: 469 | DNA Heavy Chain | CAGGTGCAATTGGTGCAGAGCGGAGCCGAAGTGAA AAAACCTGGGGCCAGCGTGAAAGTGTCCTGCAAAG CCTCCGGATACACCTTCACCAGCTACTACATGCACT GGGTCCGCCAGGCCCCAGGCCAGGGACTCGAGTGG ATGGGCATCATCAGCCCTAGCGGCGGCAGCACCAG CTACGCCCAGAAATTCCAGGGCCGGGTGACCATGA CCCGCGACACCAGCACCAGCACCGTGTACATGGAA CTGAGCAGCCTGCGCAGCGAGGACACCGCCGTGTA |

TABLE 2-continued anti-HBV Antibodies

TTATTGCGCGCGTGACTGGGAAGGTGGTGACCCGT
ACGGTTACTACTACGCTTTCGACTACTGGGGTCAAG
GCACCCTGGTTACAGTCAGCTCAGCTAGCACCAAG
GGCCCCAGCGTGTTCCCCCTGGCCCCCAGCAGCAA
GAGCACCAGCGGCGGCACAGCCGCCCTGGGCTGCC
TGGTGAAGGACTACTTCCCCGAGCCCGTGACCGTG
TCCTGGAACAGCGGAGCCCTGACCTCCGGCGTGCA
CACCTTCCCCGCCGTGCTGCAGAGCAGCGGCCTGT
ACAGCCTGTCCAGCGTGGTGACAGTGCCCAGCAGC
AGCCTGGGCACCCAGACCTACATCTGCAACGTGAA
CCACAAGCCCAGCAACACCAAGGTGGACAAGAGA
GTGGAGCCCAAGAGCTGCGACAAGACCCACACCTG
CCCCCCCTGCCCAGCCCCAGAGCTGCTGGGCGGAC
CCTCCGTGTTCCTGTTCCCCCCCAAGCCCAAGGACA
CCCTGATGATCAGCAGGACCCCCGAGGTGACCTGC
GTGGTGGTGGACGTGAGCCACGAGGACCCAGAGGT
GAAGTTCAACTGGTACGTGGACGGCGTGGAGGTGC
ACAACGCCAAGACCAAGCCCAGAGAGGAGCAGTA
CAACAGCACCTACAGGGTGGTGTCCGTGCTGACCG
TGCTGCACCAGGACTGGCTGAACGGCAAGGAATAC
AAGTGCAAGGTCTCCAACAAGGGCCTGCCAGCCCC
CATCGAAAAGACCATCAGCAAGGCCAAGGGCCAG
CCACGGGAGCCCCAGGTGTACACCCTGCCCCCCCTC
CCGGGAGGAGATGACCAAGAACCAGGTGTCCCTGA
CCTGTCTGGTGAAGGGCTTCTACCCCAGCGACATC
GCCGTGGAGTGGGAGAGCAACGGCCAGCCCGAGA
ACAACTACAAGACCACCCCCCCAGTGCTGGACAGC
GACGGCAGCTTCTTCCTGTACAGCAAGCTGACCGT
GGACAAGTCCAGGTGGCAGCAGGGCAACGTGTTCA
GCTGCAGCGTGATGCACGAGGCCCTGCACAACCAC
TACACCCAGAAGAGCCTGAGCCTGTCCCCCGGCAA
G

NOV2603 LC

| SEQ ID NO: 470 (Combined) | LCDR1 | RASQSISSYLN |
| SEQ ID NO: 471 (Combined) | LCDR2 | AASSLQS |
| SEQ ID NO: 472 (Combined) | LCDR3 | QQSYSTPLT |
| SEQ ID NO: 473 (Kabat) | LCDR1 | RASQSISSYLN |
| SEQ ID NO: 474 (Kabat) | LCDR2 | AASSLQS |
| SEQ ID NO: 475 (Kabat) | LCDR3 | QQSYSTPLT |
| SEQ ID NO: 476 (Chothia) | LCDR1 | SQSISSY |
| SEQ ID NO: 477 (Chothia) | LCDR2 | AAS |
| SEQ ID NO: 478 (Chothia) | LCDR3 | SYSTPL |
| SEQ ID NO: 479 (IMGT) | LCDR1 | QSISSY |
| SEQ ID NO: 480 (IMGT) | LCDR2 | AAS |
| SEQ ID NO: 481 (IMGT) | LCDR3 | QQSYSTPLT |
| SEQ ID NO: 482 | VL | DIQMTQSPSSLSASVGDRVTITCRASQSISSYLNWYQ QKPGKAPKLLIYAASSLQSGVPSRFSGSGSGTDFTLT ISSLQPEDFATYYCQQSYSTPLTFGQGTKVEIK |
| SEQ ID NO: 483 | DNA VL | GATATCCAGATGACCCAGAGCCCTAGCAGCCTGAG CGCCAGCGTGGGCGACCGCGTGACCATTACCTGCA GAGCCAGCCAGAGCATCAGCAGCTACCTGAACTGG |

TABLE 2-continued anti-HBV Antibodies

|  |  |  |
|---|---|---|
|  |  | TACCAGCAGAAACCTGGCAAGGCGCCCAAACTATT<br>AATCTACGCCGCCAGCAGCCTTCAGAGCGGCGTGC<br>CAAGCCGCTTTAGCGGATCCGGCAGCGGCACCGAC<br>TTCACCCTGACCATCAGCTCCCTTCAGCCTGAAGAC<br>TTCGCCACCTACTACTGCCAGCAGAGCTACAGCAC<br>CCCTCTGACCTTTGGCCAGGGCACCAAAGTGGAAA<br>TCAAA |
| SEQ ID NO: 484 | Light Chain | DIQMTQSPSSLSASVGDRVTITCRASQSISSYLNWYQ<br>QKPGKAPKLLIYAASSLQSGVPSRFSGSGSGTDFTLT<br>ISSLQPEDFATYYCQQSYSTPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 485 | DNA Light<br>Chain | GATATCCAGATGACCCAGAGCCCTAGCAGCCTGAG<br>CGCCAGCGTGGGCGACCGCGTGACCATTACCTGCA<br>GAGCCAGCCAGAGCATCAGCAGCTACCTGAACTGG<br>TACCAGCAGAAACCTGGCAAGGCGCCCAAACTATT<br>AATCTACGCCGCCAGCAGCCTTCAGAGCGGCGTGC<br>CAAGCCGCTTTAGCGGATCCGGCAGCGGCACCGAC<br>TTCACCCTGACCATCAGCTCCCTTCAGCCTGAAGAC<br>TTCGCCACCTACTACTGCCAGCAGAGCTACAGCAC<br>CCCTCTGACCTTTGGCCAGGGCACCAAAGTGGAAA<br>TCAAACGTACGGTGGCCGCTCCCAGCGTGTTCATCT<br>TCCCCCCCAGCGACGAGCAGCTGAAGAGCGGCACC<br>GCCAGCGTGGTGTGCCTGCTGAACAACTTCTACCCC<br>CGGGAGGCCAAGGTGCAGTGGAAGGTGGACAACG<br>CCCTGCAGAGCGGCAACAGCCAGGAGAGCGTCACC<br>GAGCAGGACAGCAAGGACTCCACCTACAGCCTGAG<br>CAGCACCCTGACCCTGAGCAAGGCCGACTACGAGA<br>AGCATAAGGTGTACGCCTGCGAGGTGACCCACCAG<br>GGCCTGTCCAGCCCCGTGACCAAGAGCTTCAACAG<br>GGGCGAGTGC |

NOV3212 HC

| SEQ ID NO: 486<br>(Combined) | HCDR1 | GYTFTSLEMH |
|---|---|---|
| SEQ ID NO: 487<br>(Combined) | HCDR2 | IIEPSGGSTSYAQKFQG |
| SEQ ID NO: 488<br>(Combined) | HCDR3 | DWEGGDPYGYYYAFDY |
| SEQ ID NO: 489<br>(Kabat) | HCDR1 | SLEMH |
| SEQ ID NO: 490<br>(Kabat) | HCDR2 | IIEPSGGSTSYAQKFQG |
| SEQ ID NO: 491<br>(Kabat) | HCDR3 | DWEGGDPYGYYYAFDY |
| SEQ ID NO: 492<br>(Chothia) | HCDR1 | GYTFTSL |
| SEQ ID NO: 493<br>(Chothia) | HCDR2 | EPSGGS |
| SEQ ID NO: 494<br>(Chothia) | HCDR3 | DWEGGDPYGYYYAFDY |
| SEQ ID NO: 495<br>(IMGT) | HCDR1 | GYTFTSLE |
| SEQ ID NO: 496<br>(IMGT) | HCDR2 | IEPSGGST |
| SEQ ID NO: 497<br>(IMGT) | HCDR3 | ARDWEGGDPYGYYYAFDY |
| SEQ ID NO: 498 | VH | QVQLVQSGAEVKKPGASVKVSCKASGYTFTSLEMHWV<br>RQAPGQGLEWMGIIEPSGGSTSYAQKFQGRVTMTRDT<br>STSTVYMELSSLRSEDTAVYYCARDWEGGDPYGYYYA<br>FDYWGQGTLVTVSS |

TABLE 2-continued anti-HBV Antibodies

| SEQ ID NO: 499 | DNA VH | CAGGTCCAATTGGTGCAGTCTGGCGCCGAAGTGAA
GAAACCAGGCGCCAGCGTGAAGGTGTCCTGTAAAG
CCAGCGGCTACACCTTTACCAGCCTGGAAATGCAT
TGGGTCCGACAGGCTCCAGGACAGGGACTCGAGTG
GATGGGAATTATCGAGCCTAGCGGCGGCAGCACAA
GCTACGCCCAGAAATTCCAGGGCAGAGTGACCATG
ACCAGAGACACCAGCACCTCCACCGTGTACATGGA
ACTGAGCAGCCTGAGAAGCGAGGACACCGCCGTGT
ATTATTGCGCGCGTGATTGGGAAGGCGGCGACCCT
TATGGCTACTACTACGCCTTTGATTACTGGGGCCAG
GGCACCCTGGTCACAGTTAGCTCA |
|---|---|---|
| SEQ ID NO: 500 | Heavy Chain | QVQLVQSGAEVKKPGASVKVSCKASGYTFTSLEMHWV
RQAPGQGLEWMGIIEPSGGSTSYAQKFQGRVTMTRDT
STSTVYMELSSLRSEDTAVYYCARDWEGGDPYGYYYA
FDYWGQGTLVTVSSASTKGPSVFPLAPSSKSTSGGTA
ALGCLVKDYFPEPVTVSWNSGALTSGVHTFPAVLQSS
GLYSLSSVVTVPSSSLGTQTYICNVNHKPSNTKVDKR
VEPKSCDKTHTCPPCPAPELLGGPSVFLFPPKPKDTL
MISRTPEVTCVVVDVSHEDPEVKFNWYVDGVEVHNAK
TKPREEQYNSTYRVVSVLTVLHQDWLNGKEYKCKVSN
KALPAPIEKTISKAKGQPREPQVYTLPPSREEMTKNQ
VSLTCLVKGFYPSDIAVEWESNGQPENNYKTTPPVLD
SDGSFFLYSKLTVDKSRWQQGNVFSCSVMHEALHNHY
TQKSLSLSPGK |
| SEQ ID NO: 501 | DNA Heavy Chain | CAGGTCCAATTGGTGCAGTCTGGCGCCGAAGTGAA
GAAACCAGGCGCCAGCGTGAAGGTGTCCTGTAAAG
CCAGCGGCTACACCTTTACCAGCCTGGAAATGCAT
TGGGTCCGACAGGCTCCAGGACAGGGACTCGAGTG
GATGGGAATTATCGAGCCTAGCGGCGGCAGCACAA
GCTACGCCCAGAAATTCCAGGGCAGAGTGACCATG
ACCAGAGACACCAGCACCTCCACCGTGTACATGGA
ACTGAGCAGCCTGAGAAGCGAGGACACCGCCGTGT
ATTATTGCGCGCGTGATTGGGAAGGCGGCGACCCT
TATGGCTACTACTACGCCTTTGATTACTGGGGCCAG
GGCACCCTGGTCACAGTTAGCTCAGCTAGCACCAA
GGGCCCCAGCGTGTTCCCCCTGGCCCCCAGCAGCA
AGAGCACCAGCGGCGGCACAGCCGCCCTGGGCTGC
CTGGTGAAGGACTACTTCCCCGAGCCCGTGACCGT
GTCCTGGAACAGCGGAGCCCTGACCTCCGGCGTGC
ACACCTTCCCCGCCGTGCTGCAGAGCAGCGGCCTG
TACAGCCTGTCCAGCGTGGTGACAGTGCCCAGCAG
CAGCCTGGGCACCCAGACCTACATCTGCAACGTGA
ACCACAAGCCCAGCAACACCAAGGTGGACAAGAG
AGTGGAGCCCAAGAGCTGCGACAAGACCCACACAT
GCCCCCCCTGCCCGGCGCCAGAGCTGCTGGGCGGA
CCCTCCGTGTTCCTGTTCCCCCCCAAGCCCAAGGAC
ACCCTGATGATCAGCAGGACCCCCGAGGTGACCTG
CGTGGTGGTGGACGTGAGCCACGAGGACCCAGAGG
TGAAGTTCAACTGGTACGTGGACGGCGTGGAGGTG
CACAACGCCAAGACCAAGCCCAGAGAGGAGCAGT
ACAACAGCACCTACAGGGTGGTGTCCGTGCTGACC
GTGCTGCACCAGGACTGGCTGAACGGCAAGGAATA
CAAGTGCAAGGTCTCCAACAAGGCCCTGCCAGCCC
CCATCGAAAAGACCATCAGCAAGGCCAAGGGCCA
GCCACGGGAGCCCCAGGTGTACACCCTGCCCCCCT
CCCGGGAGGAGATGACCAAGAACCAGGTGTCCCTG
ACCTGTCTGGTGAAGGGCTTCTACCCCAGCGACAT
CGCCGTGGAGTGGGAGAGCAACGGCCAGCCCGAG
AACAACTACAAGACCACCCCCCCAGTGCTGGACAG
CGACGGCAGCTTCTTCCTGTACAGCAAGCTGACCG
TGGACAAGTCCAGGTGGCAGCAGGGCAACGTGTTC
AGCTGCAGCGTGATGCACGAGGCCCTGCACAACCA
CTACACCCAGAAGAGCCTGAGCTTAAGCCCCGGCA
AG |

NOV3212 LC

| SEQ ID NO: 502 (Combined) | LCDR1 | RASQSISSYLN |
|---|---|---|
| SEQ ID NO: 503 (Combined) | LCDR2 | AASSLQS |
| SEQ ID NO: 504 (Combined) | LCDR3 | QQSYSTPLT |

TABLE 2-continued anti-HBV Antibodies

| | | |
|---|---|---|
| SEQ ID NO: 505 (Kabat) | LCDR1 | RASQSISSYLN |
| SEQ ID NO: 506 (Kabat) | LCDR2 | AASSLQS |
| SEQ ID NO: 507 (Kabat) | LCDR3 | QQSYSTPLT |
| SEQ ID NO: 508 (Chothia) | LCDR1 | SQSISSY |
| SEQ ID NO: 509 (Chothia) | LCDR2 | AAS |
| SEQ ID NO: 510 (Chothia) | LCDR3 | SYSTPL |
| SEQ ID NO: 511 (IMGT) | LCDR1 | QSISSY |
| SEQ ID NO: 512 (IMGT) | LCDR2 | AAS |
| SEQ ID NO: 513 (IMGT) | LCDR3 | QQSYSTPLT |
| SEQ ID NO: 514 | VL | DIQMTQSPSSLSASVGDRVTITCRASQSISSYLNWYQ QKPGKAPKLLIYAASSLQSGVPSRFSGSGSGTDFTLT ISSLQPEDFATYYCQQSYSTPLTFGQGTKVEIK |
| SEQ ID NO: 515 | DNA VL | GATATCCAGATGACCCAGAGCCCTAGCAGCCTGAG CGCCAGCGTGGGCGACCGCGTGACCATTACCTGCA GAGCCAGCCAGAGCATCAGCAGCTACCTGAACTGG TACCAGCAGAAACCTGGCAAGGCGCCCAAACTATT AATCTACGCCGCCAGCAGCCTTCAGAGCGGCGTGC CAAGCCGCTTTAGCGGATCCGGCAGCGGCACCGAC TTCACCCTGACCATCAGCTCCCTTCAGCCTGAAGAC TTCGCCACCTACTACTGCCAGCAGAGCTACAGCAC CCCTCTGACCTTTGGCCAGGGCACCAAAGTGGAAA TCAAA |
| SEQ ID NO: 516 | Light Chain | DIQMTQSPSSLSASVGDRVTITCRASQSISSYLNWYQ QKPGKAPKLLIYAASSLQSGVPSRFSGSGSGTDFTLT ISSLQPEDFATYYCQQSYSTPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 517 | DNA Light Chain | GATATCCAGATGACCCAGAGCCCTAGCAGCCTGAG CGCCAGCGTGGGCGACCGCGTGACCATTACCTGCA GAGCCAGCCAGAGCATCAGCAGCTACCTGAACTGG TACCAGCAGAAACCTGGCAAGGCGCCCAAACTATT AATCTACGCCGCCAGCAGCCTTCAGAGCGGCGTGC CAAGCCGCTTTAGCGGATCCGGCAGCGGCACCGAC TTCACCCTGACCATCAGCTCCCTTCAGCCTGAAGAC TTCGCCACCTACTACTGCCAGCAGAGCTACAGCAC CCCTCTGACCTTTGGCCAGGGCACCAAAGTGGAAA TCAAACGTACGGTGGCCGCTCCCAGCGTGTTCATCT TCCCCCCCAGCGACGAGCAGCTGAAGAGCGGCACC GCCAGCGTGGTGTGCCTGCTGAACAACTTCTACCCC CGGGAGGCCAAGGTGCAGTGGAAGGTGGACAACG CCCTGCAGAGCGGCAACAGCCAGGAGAGCGTCACC GAGCAGGACAGCAAGGACTCCACCTACAGCCTGAG CAGCACCCTGACCCTGAGCAAGGCCGACTACGAGA AGCATAAGGTGTACGCCTGCGAGGTGACCCACCAG GGCCTGTCCAGCCCCGTGACCAAGAGCTTCAACAG GGGCGAGTGC |

Other antibodies of the present disclosure include those where the amino acids or nucleic acids encoding the amino acids have been mutated; yet have at least 60, 70, 80, 90 or 95 percent identity to the sequences described in Table 2. In some aspects, it includes mutant amino acid sequences wherein no more than 1, 2, 3, 4 or 5 amino acids have been mutated in the variable regions when compared with the variable regions depicted in the sequence described in Table 2, while retaining substantially the same therapeutic activity.

Since these antibodies can bind to HBsAg, the VH, VL, full length light chain, and full length heavy chain sequences (amino acid sequences and the nucleotide sequences encoding the amino acid sequences) can be "mixed and matched" to create other HBsAg-binding antibodies. Such "mixed and matched" HBsAg-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise, a full length light chain sequence from a particular full length heavy chain/full length light chain pairing should be replaced with a structurally similar full length light chain sequence. Accordingly, in one aspect, the disclosure provides for an isolated monoclonal antibody or antigen binding region thereof having: a heavy chain variable region comprising an amino acid sequence selected from the group consisting of SEQ ID NO: 18, 50, 82, 114, 146, 178, 210, 242, 274, 306, 338, 370, 402, 434, 466, or 498 (Table 2); and a light chain variable region comprising an amino acid sequence selected from the group consisting of SEQ ID NO: 34, 66, 98, 130, 162, 194, 226, 258, 290, 322, 354, 386, 418, 450, 482 or 514 (Table 2); wherein the antibody specifically binds to HBsAg.

In another aspect, the disclosure provides (i) an isolated monoclonal antibody having: a full length heavy chain comprising an amino acid sequence that has been optimized for expression in the cell of a mammalian selected from the group consisting of SEQ ID NOS: 20, 52, 84, 116, 148, 180, 212, 244, 276, 308, 340, 372, 404, 436, 468, or 500 (Table 2) and a full length light chain comprising an amino acid sequence that has been optimized for expression in the cell of a mammalian selected from the group consisting of SEQ ID NOs: 36, 68, 100, 132, 164, 196, 228, 260, 292, 324, 356, 388, 420, 452, 484 or 516 (Table 2) or (ii) a functional protein comprising an antigen binding portion thereof.

In another aspect, the present disclosure provides HBsAg binding antibodies that comprise the heavy chain and light chain CDR1s, CDR2s and CDR3s as described in Table 2, or combinations thereof. The amino acid sequences of the VH CDR1s of the antibodies are shown in SEQ ID NOs 9, 41, 73, 105, 137, 169, 201, 233, 265, 297, 329, 361, 393, 425, 457 or 489. The amino acid sequences of the VH CDR2s of the antibodies and are shown in SEQ ID NOs: 10, 42, 74, 106, 138, 170, 202, 234, 266, 298, 330, 362, 394, 426, 458 or 490. The amino acid sequences of the VH CDR3s of the antibodies are shown in SEQ ID NOs: 11, 43, 75, 107, 139, 171, 203, 235, 267, 299, 331, 363, 395, 427, 459 or 491. The amino acid sequences of the VL CDR1s of the antibodies are shown in SEQ ID NOs: 25, 57, 89, 121, 153, 185, 217, 249, 281, 313, 345, 377, 409, 441, 473 or 505. The amino acid sequences of the VL CDR2s of the antibodies are shown in SEQ ID NOs 26, 58, 90, 122, 154, 186, 218, 250, 282, 314, 346, 378, 410, 442, 474 or 506. The amino acid sequences of the VL CDR3s of the antibodies are shown in SEQ ID NOs: 27, 59, 91, 123, 155, 187, 219, 251, 283, 315, 347, 379, 411, 443, 475 or 507.

Given that each of these antibodies can bind to HBsAg and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody must contain a VH CDR1, 2 and 3 and a VL CDR1, 2 and 3 to create other HBsAg-binding binding molecules. Such "mixed and matched" HBsAg-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present disclosure.

Accordingly, the present disclosure provides an isolated monoclonal antibody or antigen binding region thereof comprising a heavy chain CDR1 comprising an amino acid sequence selected from the group consisting of SEQ ID NOs: 9, 41, 73, 105, 137, 169, 201, 233, 265, 297, 329, 361, 393, 425, 457 or 489; a heavy chain CDR2 comprising an amino acid sequence selected from the group consisting of SEQ ID NOs: 10, 42, 74, 106, 138, 170, 202, 234, 266, 298, 330, 362, 394, 426, 458 or 490; a heavy chain CDR3 comprising an amino acid sequence selected from the group consisting of SEQ ID NOs: 11, 43, 75, 107, 139, 171, 203, 235, 267, 299, 331, 363, 395, 427, 459 or 491; a light chain CDR1 comprising an amino acid sequence selected from the group consisting of SEQ ID NOs: 25, 57, 89, 121, 153, 185, 217, 249, 281, 313, 345, 377, 409, 441, 473 or 505; a light chain CDR2 comprising an amino acid sequence selected from the group consisting of SEQ ID NOs: 26, 58, 90, 122, 154, 186, 218, 250, 282, 314, 346, 378, 410, 442, 474 or 506; and a light chain CDR3 comprising an amino acid sequence selected from the group consisting of SEQ ID NOs: 27, 59, 91, 123, 155, 187, 219, 251, 283, 315, 347, 379, 411, 443, 475 or 507; wherein the antibody specifically binds to HBsAg.

In certain aspects, an antibody that specifically binds to HBsAg is an antibody or antibody fragment (e.g., antigen binding fragment) that is described in Table 2.

1. Identification of Antibodies

The present disclosure provides antibodies and antibody fragments (e.g., antigen binding fragments) that bind to HBsAg. In certain aspects the antibodies and antibody fragments can bind to the same epitope within all four hepatitis B serotypes.

The present disclosure also provides antibodies and antibody fragments (e.g., antigen binding fragments) that bind to the same epitope as do the HBsAg antibodies described in Table 2. Additional antibodies and antibody fragments (e.g., antigen binding fragments) can therefore be identified based on their ability to cross-compete (e.g., to competitively inhibit the binding of, in a statistically significant manner) with other antibodies in binding assays. The ability of a test antibody to inhibit the binding of antibodies and antibody fragments (e.g., antigen binding fragments) of the present disclosure to HBsAg demonstrates that the test antibody can compete with that antibody or antibody fragment (e.g., antigen binding fragments) for binding to HBsAg; such an antibody may, according to non-limiting theory, bind to the same or a related (e.g., a structurally similar or spatially proximal) epitope on HBsAg as the antibody or antibody fragment (e.g., antigen binding fragments) with which it competes. In a certain aspect, the antibody that binds to the same epitope on HBsAg as the antibodies or antibody fragments (e.g., antigen binding fragments) of the present disclosure is a human or humanized monoclonal antibody.

Such human or humanized monoclonal antibodies can be prepared and isolated as described herein.

2. Further Alteration of the Framework of Fc Region

The present disclosure disclosed specific HBsAg antibodies. These antibodies comprise modified antibodies or antigen binding fragments thereof that further comprise modifications to framework residues within VH and/or VL, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies can be engineered to include modifications within the Fc region, typically to alter one or more functional properties of the antibody, such as serum half-life, complement fixation, Fc receptor binding, and/or antigen-dependent cellular cytotoxicity. Furthermore, an antibody can be chemically modified (e.g., one or more chemical moieties can be attached to the antibody) or be modified to alter its glycosylation, again to alter one or more functional properties of the antibody. Each of these aspects is described in further detail below.

In one aspect, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another aspect, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other aspects, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another aspect, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another aspect, one or more amino acid residues are altered to thereby alter the ability of the antibody to fix complement. This approach is described in, e.g., the PCT Publication WO 94/29351 by Bodmer et al. In a specific aspect, one or more amino acids of an antibody or antigen binding fragment thereof of the present disclosure are replaced by one or more allotypic amino acid residues, for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another aspect, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγRI, FcγRII, FcγRIII and FcRn have been mapped and variants with improved binding have been described (see Shields et al., J. Biol. Chem. 276:6591-6604, 2001).

In still another aspect, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta (1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another aspect, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In order to minimize the ADCC activity of an antibody, specific mutations in the Fc region result in "Fc silent" antibodies that have minimal interaction with effector cells. In general, the "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody.

Silenced effector functions can be obtained by mutation in the Fc region of the antibodies and have been described in the art: LALA and N297A (Strohl, W., 2009, Curr. Opin. Biotechnol. vol. 20 (6): 685-691); and D265A (Baudino et al., 2008, J. Immunol. 181:6664-69) see also Heusser et al., WO2012065950. Examples of silent Fc IgG1 antibodies are the LALA mutant comprising L234A and L235A mutation in the IgG1 Fc amino acid sequence. Another example of a silent IgG1 antibody is the DAPA (D265A, P329A) mutation (U.S. Pat. No. 6,737,056). Another silent IgG1 antibody comprises the N297A mutation, which results in aglycosylated/non-glycosylated antibodies.

Fc silent antibodies result in no or low ADCC activity, meaning that an Fc silent antibody exhibits an ADCC activity that is below 50% specific cell lysis (low ADCC activity), or that is below 1% specific cell lysis (no ADCC activity).

3. Production of the Antibodies

Anti-HBsAg antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The disclosure further provides polynucleotides encoding the antibodies described herein, e.g., polynucleotides encoding heavy or light chain variable regions or segments comprising the complementarity determining regions as described herein. In some aspects, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 19, 51, 83, 115, 147, 179, 211, 243, 275, 307, 339, 371, 403, 435, 467 or 499. In some aspects, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 35, 67, 99, 131, 163, 195, 227, 259, 291, 323, 355, 387, 419, 451, 483 or 515.

In some aspects, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 21, 53, 85, 117, 149, 181, 213, 245, 277, 309, 341, 373, 405, 437, 469 or 501. In some aspects, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:37, 69, 101, 133, 165, 197, 229, 261, 293, 325, 357, 389, 421, 453, 485, or 517

The polynucleotides of the present disclosure can encode only the variable region sequence of an anti-HBsAg antibody. They can also encode both a variable region and a constant region of the antibody. Some of the polynucleotide sequences encode a polypeptide that comprises variable regions of both the heavy chain and the light chain of one of an exemplified anti-HBsAg antibody. Some other polynucleotides encode two polypeptide segments that respectively are substantially identical to the variable regions of the heavy chain and the light chain of one of the antibodies.

The polynucleotide sequences can be produced by de novo solid-phase DNA synthesis or by PCR mutagenesis of an existing sequence encoding an anti-HBsAg antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, C A, 1990; Mattila et al., Nucleic Acids Res. 19:967, 1991; and Eckert et al., PCR Methods and Applications 1:17, 1991.

Also provided in the present disclosure are expression vectors and host cells for producing the anti-HBsAg antibodies described above. Various expression vectors can be employed to express the polynucleotides encoding the anti-HBsAg antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-HBsAg polynucleotides and polypeptides in mammalian (e.g., human) cells include pThioHis A, B & C, pcDNA3.1/His, pEBVHis A, B & C (Invitrogen, San Diego, CA), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-HBsAg antibody chain or fragment. In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements may also be required or desired for efficient expression of an anti-HBsAg antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-HBsAg antibody sequences. More often, the inserted anti-HBsAg antibody sequences are linked to a signal sequences before inclusion in the vector. Vectors to be used to receive sequences encoding anti-HBsAg antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-HBsAg antibody chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-HBsAg antibodies. Insect cells in combination with baculovirus vectors can also be used.

In other aspects, mammalian host cells are used to express and produce the anti-HBsAg antibodies of the present disclosure. For example, they can be either a hybridoma cell line expressing endogenous immunoglobulin genes (e.g., the myeloma hybridoma clones as described in the Examples) or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various COS cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP pollll promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation: nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-HBsAg antibody chains or binding fragments can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic and Diagnostic Uses

The antibodies, antibody fragments (e.g., antigen binding fragments) of the present disclosure are useful in a variety of applications including, but not limited to, hepatitis B viral infection and disease. In certain aspects, the antibodies, antibody fragments (e.g., antigen binding fragments), and are useful for neutralizing hepatitis B infection and the prevention or treatment of liver cirrhosis or liver cancer). The methods of use can be in vitro, ex vivo, or in vivo methods.

In one aspect, the antibodies, antibody fragments (e.g., antigen binding fragments), are useful for detecting the presence of HBsAg in a biological sample. The term "detecting" as used herein encompasses quantitative or qualitative detection. In certain aspects, a biological sample comprises a cell or tissue. In certain aspects, such tissues include normal and/or cancerous tissues that express HBsAg at higher levels relative to other tissues.

In one aspect, the present disclosure provides a method of detecting the presence of HBsAg or hepatitis B in a biological sample. In certain aspects, the method comprises contacting the biological sample with an anti-HBsAg antibody under conditions permissive for binding of the antibody to the antigen, and detecting whether a complex is formed between the antibody and the antigen. The biological sample can include, without limitation, urine or blood samples.

Also included is a method of diagnosing a disorder associated with expression of HBsAg. In certain aspects, the method comprises contacting a test cell with an anti-HBsAg antibody; determining the level of expression (either quantitatively or qualitatively) of HBsAg in the test cell by detecting binding of the antibody to HBsAg; and comparing the level of infection in the test cell with the level of infection of hepatitis B virus in a control cell (e.g., a normal cell of the same tissue origin as the test cell or a non-virus infected cell), wherein a higher level of presence of HBsAg in the test cell as compared to the control cell indicates the presence of a disorder associated with infection with hepatitis B. In certain aspects, the test cell is obtained from an individual suspected of having a hepatitis B virus infection.

In certain aspects, a method of diagnosis or detection, such as those described above, comprises detecting binding of a HBsAg antibody to a hepatitis B virus infected cell. An exemplary assay for detecting binding of an anti-HBsAg antibody to a hepatitis B infected cell is a "FACS" assay.

Certain other methods can be used to detect binding of anti-HBsAg antibodies. Such methods include, but are not limited to, antigen-binding assays that are well known in the art, such as Western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain aspects, the anti-HBsAg antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain aspects, the anti-HBsAg antibodies are immobilized on an insoluble matrix. Immobilization entails separating the anti-HBsAg antibody from any hepatitis B proteins that remain free in solution. This conventionally is accomplished by either insolubilizing the anti-HBsAg antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-HBsAg antibody after formation of a complex between the anti-HBsAg antibody and HBsAg protein, e.g., by immunoprecipitation.

Any of the above aspects of diagnosis or detection can be carried out using an anti-HBsAg antibody of the present disclosure in place of or in addition to another anti-HBsAg antibody.

In one aspect, the disclosure provides for a method of treating, reducing the likelihood of or ameliorating a disease comprising administering the antibodies, antibody fragments (e.g., antigen binding fragments), to a patient, thereby treating the disease. In certain aspects, the disease treated with the antibodies, antibody fragments (e.g., antigen binding fragments), is a hepatitis B viral infection. Examples of hepatitis B diseases which can be treated and/or prevented include, but are not limited to; liver failure, cirrhosis, and hepatocellular carcinoma. In certain aspects, the infection is characterized by HBsAg expressing cells to which the anti-HBsAg antibodies, antibody fragments (e.g., antigen binding fragments) can specifically bind.

The present disclosure provides for methods of treating hepatitis B viral infection and liver failure, cirrhosis, and/or hepatocellular carcinoma comprising administering a therapeutically effective amount of the antibodies, antibody fragments (e.g., antigen binding fragments). In certain aspects, the subject is a human.

In certain aspects, the method of reducing hepatitis B viral infection comprises administering to a subject a therapeutically effective amount of antibodies or antibody fragments (e.g., antigen binding fragments). In certain aspects, the subject is a human. In certain aspects, the subject is immunosuppressed, immunocompromised or has reduced immune function. For immunosuppresed subjects, the amount of immunosuppression can be increased or decreased due to the therapeutic effects of the anti-HBsAg antibodies.

For the treatment of hepatitis B viral infection, the appropriate dosage of the HBsAg antibodies, or antibody fragments (e.g., antigen binding fragments), depend on various factors, such as the type of infection to be treated, the severity and course of the infection, the responsiveness of the infection, the generation of viral resistance to therapy, previous therapy, patient's clinical history, and so on. The antibody can be administered one time or over a series of treatments lasting from several days to several months, or until a cure is effected or a diminution of the infection is achieved (e.g., reduction in viruria or viral damage to the liver). Optimal dosing schedules can be calculated from measurements of drug accumulation in the body of the patient and will vary depending on the relative potency of an individual antibody or antibody fragment (e.g., antigen binding fragment). In certain aspects, dosage is from 0.01 mg to 100 mg (e.g., 0.01 mg, 0.05 mg, 0.1 mg, 0.5 mg, 1 mg, 2 mg, 3 mg, 4 mg, 5 mg, 7 mg, 8 mg, 9 mg, 10 mg, 20 mg, 30 mg, 40 mg, 50 mg, 60 mg, 70 mg, 80 mg. 90 mg or 100 mg) per kg of body weight, and can be given once or more daily, weekly, monthly or yearly. In certain aspects, the antibody or antibody fragment (e.g., antigen binding fragment), of the present disclosure is given once every two weeks or once every three weeks. The treating physician can estimate repetition rates for dosing based on measured half-life and concentrations of the antibody in bodily fluids or tissues.

Combination Therapy

In certain instances, the antibody or antibody fragment (e.g., antigen binding fragment), of the present disclosure is combined with other therapeutic agents, such as other antiviral agents, anti-allergic agents, anti-nausea agents (or anti-emetics), pain relievers, cytoprotective agents, immunosuppressants and combinations thereof.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or infection described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the individual components separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the individual components are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present disclosure provides a method of treating hepatitis B infection by administering to a subject in need thereof anti-HBsAg antibody in together with immunosuppressant therapies. The anti-HBsAg antibodies will reduce the amount of HBsAg in the circulation and allow the immune system to mount a response to the hepatitis B viral infection resulting from the immunosuppressant therapy prior to or post administration. Examples of immunosuppressant therapy include, but are not limited to; a monophosphate dehydrogenase inhibitor, a purine synthesis inhibitor, a calcineurin inhibitor or an mTOR inhibitor. Specific examples of immunosuppressive therapeutics include but are not limited to; mycophenolate mofetil (MMF), mycophenolate sodium, azathioprine, tacrolimus, sirolimus and cyclosporine.

In one embodiment, an anti-HBsAg antibody combination is used with a PD-1 inhibitor, e.g., as described in WO2015/026684 or WO2016/057846. In some embodiments, the PD-1 inhibitor is an anti-PD-1 antibody chosen from Nivolumab, Pembrolizumab or Pidilizumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. In one embodiment, the inhibitor of PD-1 is Nivolumab, and having a sequence disclosed therein (or a sequence substantially identical or similar thereto, e.g., a sequence at least 85%, 90%, 95% identical or higher to the sequence specified).

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) New England Journal of Medicine 369 (2): 134-44, U.S. Pat. No. 8,354,509 and WO2009/114335.

In one embodiment, the inhibitor of PD-1 is Pembrolizumab, disclosed in, e.g., U.S. Pat. No. 8,354,509 and WO 2009/114335, and having a sequence disclosed therein (or a sequence substantially identical or similar thereto, e.g., a sequence at least 85%, 90%, 95% identical or higher to the sequence specified).

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in WO2009/101611. Other anti-PD1 antibodies include AMP 514 (Amplimmune), among others, e.g., anti-PD1 antibodies disclosed in U.S. Pat. No. 8,609,089, US2010028330, and/or US20120114649.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224 (B7-DClg; Amplimmune; e.g., disclosed in WO2010/027827 and WO2011/066342), is a PD-L2 Fc fusion soluble receptor that blocks the interaction between PD-1 and B7-H1.

In one embodiment, an anti-HBsAg antibody combination is used with an anti-PD-L1 antibody, e.g., as described in WO2016/061142. In some embodiments, the anti-PD-L1 antibody is Atezolizumab, Avelumab or Durvalumab. In some embodiments, the anti-PD-L1 antibody is Atezolizumab, disclosed in WO2010/077634. In some embodiments, the anti-PD-L1 antibody is Durvalumab, disclosed in WO2011/066389. Other anti-PD-L1 antibodies include BMS-936559 also known as MDX-1105, as disclosed in WO2007/005874 and AMP-224 also known as GSK2661380 disclosed in WO2010/027423.

Pharmaceutical Compositions

To prepare pharmaceutical or sterile compositions including anti-HBsAg antibodies, the antibodies of the present disclosure are mixed with a pharmaceutically acceptable carrier or excipient. The compositions can additionally contain one or more other therapeutic agents that are suitable for neutralizing hepatitis B infection.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, et al. (eds.), Pharmaceutical Dosage Forms: Tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

In a specific aspect, the anti-HBsAg antibody is a lyophilisate in a vial containing the antibody. The lyophilisate can be reconstituted with water or a pharmaceutical carrier suitable for injection. For subsequent intravenous administration, the obtained solution will usually be further diluted into a carrier solution.

The antibodies disclosed herein are useful in the neutralization of hepatitis B in patients suffering from liver failure, cirrhosis, and/or hepatocellular carcinoma, so a pharmaceutical carrier of sucrose and human albumin as used previously in bone marrow transplant patients receiving CytoGam® can be used (DeRienzo et al. Pharmacotherapy 2000; 20:1175-8). Alternatively, the anti-HBsAg antibodies can be introduced into transplant patients via a pharmaceutical carrier as described for another anti-viral antibody, Synagis®, as described in WO2003/105894. In this publication, the pharmaceutical carrier was comprised of histidine and/or glycine, a saccharide (e.g. sucrose) and a polyol (e.g. polysorbate).

Selecting an administration regimen for a therapeutic depends on several factors, including the severity of the infection, the level of symptoms, and the accessibility of the target cells in the biological matrix. In certain aspects, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., infusion reactions.

Actual dosage levels of the active ingredients in the pharmaceutical compositions with the anti-HBsAg antibodies can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the neutralizing activity of the antibodies, the route of administration, the time of administration, the half-life of the antibody in the patient, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof can be provided by continuous infusion, or by doses at intervals of, e.g., one day, one week, or 1-7 times per week. Doses can be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the antibodies described herein, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof can be calculated using the patient's weight in kilograms (kg) multiplied by the dose to be administered in mg/kg.

Doses of the antibodies then can be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present disclosure can also be administered via one or more routes of administration using one or more of a variety of methods known in the art. As will be appreciated by the skilled artisan, the route and/or mode of administration will vary depending upon the desired results. Selected routes of administration for the antibodies include intravenous, intramuscular, intradermal, intraperitoneal, subcutaneous, spinal or other parenteral routes of administration, for example by injection or infusion. Parenteral administration can represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the present disclosure can be administered via a non-parenteral route, such as a topical, epidermal or mucosal route of administration, for example, intranasally, orally, vaginally, rectally, sublingually or topically. In one aspect, the antibodies of the present disclosure are administered by infusion. In another aspect, the antibodies are administered subcutaneously.

If the antibodies of the present disclosure are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the antibodies (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one aspect, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more antibodies of the present disclosure. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, each of which is incorporated herein by reference in their entirety.

If the antibodies of the disclosure are administered topically, they can be formulated in the form of an ointment, cream, transdermal patch, lotion, gel, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the antibodies are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., an immunosuppressant, a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the anti-HBsAg antibodies may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the anti-HBsAg antibodies of the present disclosure. The two or more therapies may be administered within one same patient visit.

In certain aspects, anti-HBsAg antibodies can be formulated to ensure proper distribution in vivo. For example, the blood-brain barrier (BBB) excludes many highly hydrophilic compounds. To ensure that the anti-HBsAg antibodies cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The present disclosure provides protocols for the administration of pharmaceutical composition comprising antibodies alone or in combination with other therapies to a subject in need thereof. The combination therapies (e.g., prophylactic or therapeutic agents) can be administered concomitantly or sequentially to a subject. The therapy (e.g., prophylactic or therapeutic agents) of the combination therapies can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof are administered to a subject in a sequence and within a time interval such that the antibodies can act together with the other therapy (ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various aspects, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other aspects, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Generation of Anti-HBsAg Virus Antibodies

Human memory B cells from HBV vaccinated donors were in vitro expanded and selected for their capacity to secrete IgG antibodies against HBsAg. Specific B cells were lysed and the VH (heavy) and VL (light) chains were amplified by RT-PCR and subsequently sequenced and analyzed to identify critical post translational modification (PTM) sites. Plasmids of the VH and VL chains were then transfected in a CHO mammalian cell line in an IgG1 backbone vector for expression of the full IgG1 antibodies.

Methods for generation of monoclonal antibodies using phage display technology are known in the art (Antibody Methods and Protocols, Methods in Molecular Biology vol. 901, 2012, Chapter 3:33). Briefly, a synthetic human germline framework antibody library in Fab format randomized in CDR-H3 was screened for anti-HBsAg antibodies by solution panning with streptavidin-coupled magnetic beads complexed with biotinylated recombinant HBsAg (TRINA Bioreactives AG, Cat #C028-3001994774 (AD serotype), C028-3001994774 (AY serotype) or Biorbyte, Cat #orb82536 (AD isotype)) over 3 rounds of selection with increasing stringency. Isolates were first expressed as Fab and screened for binding to both HBsAg serotype AD and serotype AY by ELISA. Selected isolates were then cloned and expressed as IgG1, reanalyzed for binding to HBsAg (serotype AD and AY) by ELISA and for functional activity in neutralization assays, and finally transfected in a CHO mammalian cell line for expression of the full IgG1. antibodies. Anti-HBsAg antibodies were affinity matured by CDR-directed mutagenesis. Beneficial mutations have been identified by comparing enrichment after two rounds of phage display in relation to the initial mutagenesis library by deep sequencing. Selected beneficial mutations alone and in combination were then cloned and expressed as IgG1, reanalyzed for binding to HBsAg (serotype AD and AY) by ELISA and for functional activity in neutralization assays, and finally transfected in a CHO mammalian cell line for expression of the full IgG1.

Changes to the anti-HBsAg antibodies are provided in Table 3.

TABLE 3

| Antibody | Changes |
|---|---|
| NOV2603 | No change |
| NOV3212 | Affinity maturation |
| NOV3357 | Affinity maturation |
| NOV3540 | NOV3357 change to remove post-translational modification: DDDGWSGYDYWFDY (SEQ ID NO: 139) to DDDAWSGYDYWFDY in HCDR3 (Kabat) (SEQ ID NO: 107) resulted in no significant change in affinity or activity |

TABLE 3-continued

| Antibody | Changes |
|---|---|
| NOV3831 | No change |
| NOV3832 | NOV3831 change to remove post-translational modification: FNN to FDN resulted in no significant change in affinity or activity |
| NOV3833 | NOV3831 change to remove post-translational modification: FNN to FHN resulted in no significant change in affinity or activity |
| NOV3834 | No change |
| NOV3835 | NOV3834 change to remove post-translational modification: FNR to FDR resulted in no significant change in affinity or activity |
| NOV3836 | NOV3834 change to remove post-translational modification: FNR to FER resulted in no significant change in affinity or activity |
| NOV3837 | No change |
| NOV3838 | NOV3837 change to remove post-translational modification: DGY to DLY resulted in no significant change in affinity or activity |
| NOV3839 | NOV3837 change to remove post-translational modification: DGY to DIY resulted in no significant change in affinity or activity |
| NOV3840 | No change |
| NOV3841 | NOV3840 change to remove post-translational modification: TNS to TQS and DS to DT for VH, and DDS to DES for VL resulted in no significant change in affinity or activity |
| NOV3842 | NOV3840 change to remove post-translational modification: TNS to TNV and DS to DT for VH, and DDS to DES for VL resulted in no significant change in affinity or activity |

Example 2: Binding of Anti-HBsAg Antibodies to HBsAg

Binding affinity interaction ($K_D$) of the anti-HBsAg antibodies with the two major serotypes of HBsAg, AY and AD, was determined utilizing surface plasma resonance (SPR) technology. HBsAg particles were immobilized at about 800 RU onto a Series S CM5 sensor chip and anti-HBsAg antibody flowed over in 2 fold serial dilutions starting at 128 nM to assess binding utilizing the Biacore T200 instrument (GE Healthcare, Cat #28975001, Pittsburgh, PA). The $K_D$ was determined by fitting the plot with a 1:1 fit model (O'Shannessy et al. Anal. Biochem 1993; 212:457-468; Karlsson, Fält J. Immunol. Methods. 1997; 200:121-133).

Biacore measured $K_D$ values range from 110 pM to 40 nM of the anti-HBsAg antibodies and were comparable across the two major serotypes for each of the antibodies tested (AD and AY). A summary of Biacore affinity data for the anti-HBsAg antibodies is found in Table 4, and the SPR tracings are found in FIGS. 1A/B-16A/B.

TABLE 4

| Antibody | Kd AD (nM) | Kd AY (nM) |
|---|---|---|
| NOV2603 | 15.5 | 3.1 |
| NOV3212 | 1.1 | 0.6 |
| NOV3357 | 0.18 | 0.11 |
| NOV3540 | 0.39 | 0.25 |
| NOV3831 | 0.67 | 0.59 |
| NOV3832 | 0.22 | 0.40 |
| NOV3833 | 0.33 | 0.26 |
| NOV3834 | 40.0 | 5.3 |
| NOV3835 | 33.0 | 11.0 |
| NOV3836 | 29.0 | 10.0 |
| NOV3837 | 0.67 | 0.75 |
| NOV3838 | 0.68 | 0.6 |
| NOV3839 | 0.59 | 2.4 |
| NOV3840 | 0.45 | 0.38 |
| NOV3841 | 0.91 | 0.61 |
| NOV3842 | 0.13 | 0.15 |

Example 3: Neutralization of Hepatitis B Viral Infection by Anti-HBsAg Antibodies Infectious HBV virus was purified from genotype D, serotype ayw cell culture-derived HBV as described (Meier et al., J. Virol Hepat. 2017; 24:662-671). Anti-HBsAg antibodies were pre-incubated with the virus for 1 hour at 37° C. to allow for binding and neutralization. HepG2-hNTCP1 cells, generated in house as described (Tropberger et al., Proc. Natl. Acad. Sci. U. S. A 2015; 112: E5715-E5724), were then exposed to the virus-antibody mixture for 24 hrs, replaced with fresh medium, and incubated for 6 additional days to allow for viral entry, cccDNA establishment, and viral protein expression. Supernatant was recovered and HBeAg levels were analyzed by a custom made in-house eAg AlphaScreen assay (Perkin Elmer, Bridgeville PA). Data was analyzed using the Envision Plate Reader (Perkin Elmer, Cat #2105-0010, Bridgeville PA) and presented as percent of infection relative to untreated control wells.

All antibodies were able to neutralize the infection by HBV with EC50 values ranging from 17 pM to 740 pM and this is shown in Table 5 and is show graphically in FIGS. 17-33.

TABLE 5

| Antibody | Virus neutralization $EC_{50}$ (nM) |
|---|---|
| NOV2603 | 0.14 |
| NOV3212 | 0.11 |
| NOV3357 | 0.056 |
| NOV3540 | 0.085 |
| NOV3831 | 0.026 |
| NOV3832 | 0.26 |
| NOV3833 | 0.27 |
| NOV3834 | 0.24 |
| NOV3835 | 0.72 |
| NOV3836 | 0.017 |
| NOV3837 | 0.049 |
| NOV3838 | 0.12 |
| NOV3839 | 0.09 |
| NOV3840 | 0.056 |

TABLE 5-continued

| Antibody | Virus neutralization EC$_{50}$ (nM) |
|---|---|
| NOV3841 | 0.74 |
| NOV3842 | 0.23 |
| Neg. Control | >500 |

Example 4: Hepatitis B Genotype Binding

The binding of anti-HBsAg antibodies to the 4 major genotypes (A-D) of HBV were analyzed by sandwich ELISA. Briefly, ELISA plates (Thermo Scientific, Cat #15031) were coated with 5 µg/ml horse polyclonal-HBsAg capture antibody (MyBiosource, Cat #MBS315002) for 2 hours at 37° C., then blocked overnight at 4° C. with 5% milk. Supernatant collected from HBV cell-culture derived genotypes in pcDNA3.1 backbone (Genotype A: AY934772, Genotype B: AF 121245, Genotype C: DQ087960, Genotype D: DQ219811.1) was allowed to bind antibody coated plates for 1 hour. Plates were washed (Alpha diagnostics wash buffer, Cat #80080) and incubated with serial dilutions of anti-HBsAg antibodies in LowCross buffer (Candor, Cat #100500) for 1 hour at room temperature. Following anti-HBsAg antibody incubation plates were washed and incubated with secondary antibody (HRP-conjugated goat anti-human IgG Fab fragment, Jackson ImmunoResearch Inc, Cat #109-035-097) diluted 1:2000 in dilution buffer (LowCross buffer, Candor, Cat #100500) for 1 hour at room temperature. Plates were washed and tetramethylbenzidine (TMB) microwell peroxidase substrate (Alpha Diagnostics, Cat #80091) was used to develop the reactions.

The anti-HBsAg antibodies NOV3834-36 showed similar binding to genotypes A (IC$_{50}$ ranging from 2 to 3.3 nM), genotype B (IC$_{50}$ ranging from 1.2 to 1.7 nM), and genotype D (IC$_{50}$ ranging from 1.3 to 8.2 nM), but showed reduced binding to genotype C (IC$_{50}$ ranging from 12-16 nM). In contrast, the remainder of the anti-HBsAg antibodies showed similar binding across the 4 major genotypes (IC$_{50}$ for genotype A ranging from 0.023 to 2.3 nM, genotype B ranging from 0.017 to 1.5 nM, genotype C ranging from 0.015 to 3.6 nM, and genotype D ranging from 0.026 to 1.3 nM). For example, NOV3832 had IC$_{50}$ of 0.05 nM for genotype A, 0.02 nM for genotype B, 0.015 nM for genotype C and 0.043 nM for genotype D. The IC$_{50}$ for all of the antibodies in Table 6 are shown graphically in FIGS. 34-50.

TABLE 6

| Antibody | IC$_{50}$ nM A | IC$_{50}$ nM B | IC$_{50}$ nM C | IC$_{50}$ nM D |
|---|---|---|---|---|
| NOV2603 | 2.3 | 1.5 | 3.6 | 1.3 |
| NOV3212 | 0.23 | 0.045 | 0.068 | 0.045 |
| NOV3357 | 0.03 | 0.017 | 0.016 | 0.026 |
| NOV3540 | 0.1 | 0.059 | 0.1 | 0.1 |
| NOV3831 | 0.69 | 0.015 | 0.031 | 0.056 |
| NOV3832 | 0.05 | 0.02 | 0.015 | 0.043 |
| NOV3833 | 0.56 | 0.12 | 0.12 | 0.047 |
| NOV3834 | 2 | 1.2 | 16 | 1.3 |
| NOV3835 | 3.3 | 1.4 | 14 | 2 |
| NOV3836 | 3.3 | 1.7 | 12 | 8.2 |
| NOV3837 | 0.093 | 0.069 | 0.17 | 0.1 |
| NOV3838 | 0.2 | 0.05 | 0.21 | 0.081 |
| NOV3839 | 1.6 | 0.17 | 0.37 | 0.097 |
| NOV3840 | 0.023 | 0.022 | 0.016 | 0.045 |
| NOV3841 | 1.1 | 0.35 | 2 | 2.1 |
| NOV3842 | 0.46 | 0.28 | 0.75 | 0.41 |
| Neg. Control | >67 | >67 | >67 | >67 |

Example 5: Anti-HBsAg Recognition of Hepatitis B Clinical Mutations

The binding of anti-HBsAg antibodies to 4 well characterized vaccine and/or HBsAg clinical mutations of HBsAg (G145R, D144A, T126S, M133L) were analyzed by sandwich ELISA. Mutations were generated by Q5 site directed mutagenesis (New England Biolabs, Cat #E0554S) along the HBV Genotype D, (ayw serotype) and the HBsAg sequence cloned into the pCl-neo vector (Promega, Cat #E1841) for generation of stable cell lines. Briefly, ELISA plates (Thermo Scientific, Cat #15031) were coated with 5 µg/ml horse polyclonal-HBsAg capture antibody (MyBiosource, Cat #MBS315002) for 2 hours at 37° C., then blocked overnight at 4° C. with 5% milk. Supernatant collected from HBsAg cell-culture derived clinical mutation stables (G145R, D144A, T126S, M133L) was allowed to bind antibody coated plates for 1 hour. Plates were washed (Alpha diagnostics wash buffer, Cat #80080) and incubated with serial dilutions of anti-HBsAg antibodies in LowCross buffer (Candor, Cat #100500) for 1 hour at room temperature. Following anti-HBsAg antibody incubation plates were washed and incubated with secondary antibody (HRP-conjugated goat anti-human IgG Fab fragment, Jackson ImmunoResearch Inc, Cat #109-035-097) diluted 1:2000 in dilution buffer (LowCross buffer, Candor, Cat #100500) for 1 hour at room temperature. Plates were washed and tetramethylbenzidine (TMB) microwell peroxidase substrate (Alpha Diagnostics, Cat #80091) was used to develop the reactions.

As shown in Table 7, the anti-HBsAg antibodies NOV2603, NOV3212, NOV3357, and NOV3540 are able to bind all 4 clinical mutations (G145R IC$_{50}$ values ranging from 0.033 to 5.5 nM, D144A ranging from 0.079 to 2.1 nM, T126S ranging from 0.06 to 0.22 nM, and M133L ranging from 0.012 to 0.67 nM). The antibodies NOV3831, NOV3832, NOV3833, NOV3838, NOV3839, NOV3841 and NOV3842 show loss of binding to the G145R mutation but retain binding to the other 3 clinical mutations (D144A IC$_{50}$ values ranging from 0.012 to 7.8 nM, T126S ranging from 0.01 to 0.11 nM, and M133L ranging from 0.013 to 0.15 nM). In contrast, the anti-HBsAg antibodies NOV3834-36 show either no binding to any of the 4 mutations (NOV3835, NOV3836) or very reduced binding (NOV3835) to just 2 (T126S, M133L) of the clinical mutation panel (T126S IC$_{50}$ value 7.4 nM, M133L IC$_{50}$ value 9.2 nM). The results shown in Table 7 are also represented graphically in FIGS. 51-66.

TABLE 7

| Antibody | IC$_{50}$ nM Clinical mutation G145R | IC$_{50}$ nM Clinical mutation D144A | IC$_{50}$ nM Clinical mutation T126S | IC$_{50}$ nM Clinical mutation M133L | Control Empty Vector |
|---|---|---|---|---|---|
| NOV2603 | 0.33 | 1.34 | 0.06 | 0.072 | >67 |
| NOV3212 | 0.033 | 0.079 | 0.012 | 0.012 | >67 |
| NOV3357 | 5.5 | 2.1 | 0.22 | 0.67 | >67 |
| NOV3540 | 0.25 | 0.16 | 0.063 | 0.091 | >67 |

TABLE 7-continued

| Antibody | IC$_{50}$ nM Clinical mutation G145R | IC$_{50}$ nM Clinical mutation D144A | IC$_{50}$ nM Clinical mutation T126S | IC$_{50}$ nM Clinical mutation M133L | Control Empty Vector |
|---|---|---|---|---|---|
| NOV3831 | >67 | 3.6 | 0.0093 | 0.0058 | >67 |
| NOV3832 | >67 | 0.99 | 0.034 | 0.034 | >67 |
| NOV3833 | >67 | 2.8 | 0.025 | 0.036 | >67 |
| NOV3834 | >67 | >67 | 7.4 | 9.2 | >67 |
| NOV3835 | >67 | >67 | >67 | >67 | >67 |
| NOV3836 | >67 | >67 | >67 | >67 | >67 |
| NOV3837 | >67 | 0.27 | 0.03 | 0.035 | >67 |
| NOV3838 | 5.2 | 6.1 | 0.11 | 0.15 | >67 |
| NOV3839 | 8.6 | 3.6 | 0.088 | 0.085 | >67 |
| NOV3840 | >67 | 0.012 | 0.01 | 0.013 | >67 |
| NOV3841 | >67 | 7.8 | 0.079 | 0.044 | >67 |
| NOV3842 | >67 | 0.12 | 0.042 | 0.084 | >67 |

Example 6: Anti-HBsAg Antibodies Show Efficacy in a FRGN Mouse Model

In vivo efficacy for the anti-HBsAg antibodies was determined in a HBV-infected FRGN mouse model by monitoring loss of HBsAg following antibody administration. Human liver populated FRGN mice were purchased from Yecuris (FRGN KO on NOD, Cat #10-0013) and infected with 1.7×10$^7$ copies HBV (Genotype C). Following stable infection, mice were treated with 20 mg/ml anti-HBsAg antibodies (n=2 per group) at day 0 and day 21 with serum collected at timepoints 0, 0.02, 0.3, 1, 3, 7, 14, 21, 24, and 28 days post initial antibody treatment. Free HBsAg levels were monitored through a protocol from Zhang et. al., Gut 2016; (4) 65:658-671. Briefly, serum was diluted 1:5 in sample diluent (provided in Alpha Diagnostic International, Cat #4110), 0.5 volumes lysis buffer added (15% sodium dodecyl sulphate in 20 mM Tris HCL buffer-pH 8.0) and samples incubated for 1 hour at 37° C. Samples were neutralized with the addition of 5 volumes 4% CHAPS dissolved in 20 mM Tris HCL buffer-pH 8.0 and HBsAg levels monitored utilizing an HBsAg commercial ELISA kit (Alpha Diagnostic International, Cat #4110) following the manufacturers protocol. HBsAg levels graphed as log fold change from prebleed levels collected at timepoint 0. Maximum log fold change for this model was −3.9.

Figure 67:
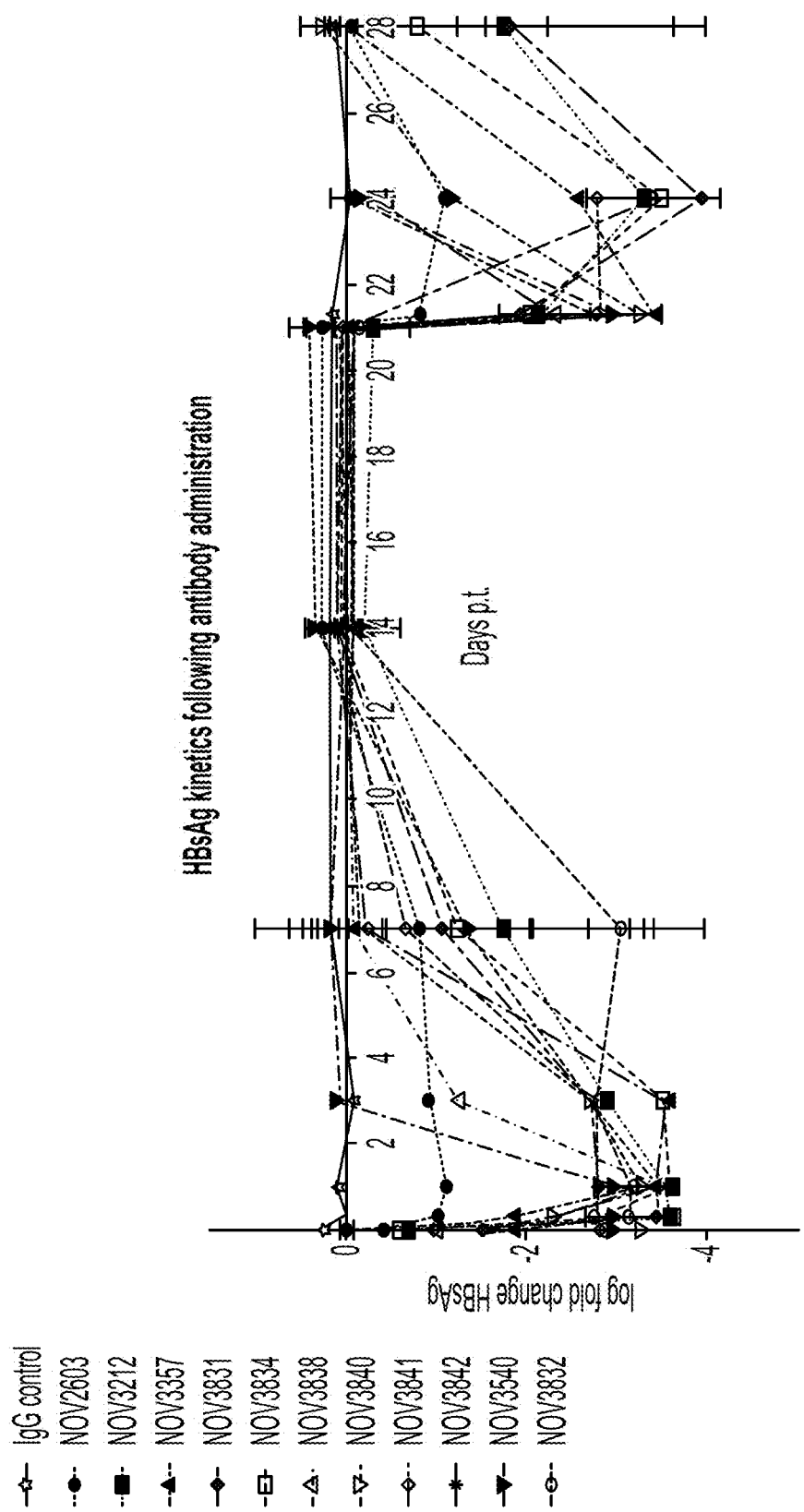
FIG. 67 shows the efficacy of the antibodies, reducing the amount of HBsAg in an FRGN mouse model.

Anti-HBsAg antibodies NOV3212, NOV3357, NOV3540, NOV3831, NOV3832, NOV3834, NOV3838, NOV3841 and NOV3842 all significantly dropped the levels of HBsAg with the max log drop ranging from −3.9 to −2.8, as shown in Table 8. In contrast, NOV2603 showed only a moderate log drop of HBsAg (−1.1). For example, in FIG. 67, NOV3832 greatly reduced HBsAg at the 0.3 day time point and kept the HBsAg level reduced for 7 days, with only a slow increase in HBsAg levels to day 14. After the second administration of NOV3832 at day 21, HBsAg levels were again reduced, and remained reduced until the end of the study on day 28. Thus, this study demonstrated that the anti-HBsAg antibodies of the disclosure can greatly reduce HBsAg in the serum in vivo.

TABLE 8

| Antibody | Max ΔHBsAg log reduction |
|---|---|
| NOV2603 | −1.1 |
| NOV3212 | −3.6 |
| NOV3357 | −3.6 |

TABLE 8-continued

| Antibody | Max ΔHBsAg log reduction |
|---|---|
| NOV3540 | −2.8 |
| NOV3831 | −3.9 |
| NOV3832 | −3.6 |
| NOV3834 | −3.6 |
| NOV3838 | −3.6 |
| NOV3840 | −3.3 |
| NOV3841 | −2.8 |
| NOV3842 | −2.8 |
| Neg. Control | 0 |

Example 7: Anti-HBsAg Cytotoxicity

Cytotoxicity of the anti-HBsAg antibodies on both de novo HBV infected and non-infected HepG2-hNTCP1 cells (Tropberger et al. Proc. Natl. Acad. Sci. U. S. A 2015; 112: E5715-E5724) was measured utilizing CellTiter-Glo (Promega, Cat #G7570), which monitors metabolic activity of cells through ATP concentration. In brief, HepG2-hNTCP1 cells were infected with either purified virus from genotype D (serotype ayw) cell culture-derived HBV or mock virus as described (Meier et al. J. Virol Hepat. 2017; 24:662-671). Cells were cultured for 4 days following infection to allow for viral entry, cccDNA establishment, and viral protein expression, media removed and replaced with fresh media containing serial dilutions of anti-HBsAg antibodies starting at 3.3 µM. Cells incubated with antibody mixture for an additional 4 days and then assayed with CellTiter-Glo reagent per manufactor protocol. Luminescence readout was performed using a PHERAstar microplate reader (BMG Labtech, Cary NC) and percent viability was presented relative to the negative (no antibody) control.

All of the anti-HBsAg antibodies of the disclosure show no effect on cell viability in the presence or absence of virus. In brief, the anti-HBsAg antibodies of the disclosure show no toxicity. This is in contrast to two published antibodies, CR8097 and HB48-59, which show cytotoxicity (CC50s ranging from 2.24 to 2.86 µM for uninfected HepG2-NTCP1, and 2.09 to 2.11 µM for HBV infected HepG2-NTCP1). As the CR8097 and HB48-59 antibodies show toxicity to uninfected cells at the same level as infected cells, this indicates that these antibodies are binding to off-target, normal cell proteins.

TABLE 9

| Antibody | CC50 (no virus) (µM) | CC50 (HBV infected) (µM) |
|---|---|---|
| NOV2603 | >3.3 | >3.3 |
| NOV3212 | >3.3 | >3.3 |
| NOV3357 | >3.3 | >3.3 |
| NOV3540 | >3.3 | >3.3 |
| NOV3831 | >3.3 | >3.3 |
| NOV3832 | >3.3 | >3.3 |
| NOV3833 | >3.3 | >3.3 |
| NOV3834 | >3.3 | >3.3 |
| NOV3835 | >3.3 | >3.3 |
| NOV3836 | >3.3 | >3.3 |
| NOV3837 | >3.3 | >3.3 |
| NOV3838 | >3.3 | >3.3 |
| NOV3839 | >3.3 | >3.3 |
| NOV3840 | >3.3 | >3.3 |
| NOV3841 | >3.3 | >3.3 |
| NOV3842 | >3.3 | >3.3 |

TABLE 9-continued

|  | CC50 (no virus) (µM) | CC50 (HBV infected) (µM) |
|---|---|---|
| Pos Control (puromycin) | 0.0003 nM | 0.0006 nM |
| Published antibodies |  |  |
| HBC34 | >3.3 | >3.3 |
| CR8097 | 2.86 | 2.11 |
| Green27 | >3.3 | >3.3 |
| HB48-33 | >3.3 | >3.3 |
| HB48-35 | >3.3 | >3.3 |
| HB48-59 | 2.24 | 2.09 |

Example 8: Eptiope Binning by SPR for Anti-HBsAg Antibodies

Epitope binning of anti-HBsAg antibodies with the two major serotypes of HBsAg, AY and AD, was performed utilizing surface plasmon resonance (SPR) technology. Antigens HBsAg AD and AY (TRINA Bioreactives AG, Cat #0824 [AD serotype], #0823 [AY serotype], Naenikon, Switzerland) were immobilized at about 800 RU in separate cells on the surface of a CM5 chip by amine coupling. Each pair of antibodies was tested for blocking one another's binding to their epitope on the antigen by subsequently applying one antibody as first (saturating) followed by the other as second (competing) antibody and vice versa. Saturating antibodies were applied at 500 nM for 120s. Competing antibodies utilized the same conditions but were supplemented with the first antibody at 500 nM to maintain saturation. Binding signals were corrected by subtracting the reference cell signal. Specific binding of the competing antibody in presence of the saturating antibody was calculated by subtracting a saturating antibody plus buffer reference signal. All signals were normalized to 100 RU of immobilized ligand. The specific binding signal obtained from the application as competing antibody was expressed as percentage of the binding signal obtained from the application of the same antibody as saturating (first) antibody, the signal of which was regarded 100% binding. Binding values less than 40% indicate that the first and second antibody cover the same region, and values greater than 60% represent different epitopes. The results indicate that the antibodies NOV3540, NOV3832, NOV3841 and NOV3842 do not compete with either CR8087 or HBC34 antibodies. Thus NOV3540, NOV3832, NOV3841 and NOV3842 bind different epitopes than CR8087 or HBC34. Results are show below in Table 10.

TABLE 10

| HBsAg AD serotype | | | | | | | |
|---|---|---|---|---|---|---|---|
| | CR8087 | | | | HBC34 | | |
| 2nd Ab | 1st Ab | 2nd Ab | 1st Ab | 2nd Ab | 1st Ab | 2nd Ab | 1st Ab |
| NOV3540 | 254 | 105 | NOV3540 | NOV3540 | 111 | 121 | NOV3540 |
| NOV3832 | 223 | 103 | NOV3832 | NOV3832 | 176 | 126 | NOV3832 |
| NOV3841 | 282 | 104 | NOV3841 | NOV3841 | 145 | 124 | NOV3841 |
| NOV3842 | 216 | 106 | NOV3842 | NOV3842 | 115 | 121 | NOV3842 |
| HBC34 | 146 | 98 | HBC34 | HBC34 | 0 | 0 | HBC34 |
| CR8087 | 0 | 0 | CR8087 | CR8087 | 98 | 146 | CR8087 |

| HBsAg AY serotype | | | | | | | |
|---|---|---|---|---|---|---|---|
| | CR8087 | | | | HBC34 | | |
| 2nd Ab | 1st Ab | 2nd Ab | 1st Ab | 2nd Ab | 1st Ab | 2nd Ab | 1st Ab |
| NOV3540 | 118 | 107 | NOV3540 | NOV3540 | 102 | 131 | NOV3540 |
| NOV3832 | 117 | 113 | NOV3832 | NOV3832 | 113 | 257 | NOV3832 |
| NOV3841 | 129 | 105 | NOV3841 | NOV3841 | 107 | 151 | NOV3841 |
| NOV3842 | 118 | 109 | NOV3842 | NOV3842 | 103 | 134 | NOV3842 |
| HBC34 | 166 | 107 | HBC34 | HBC34 | 0 | 0 | HBC34 |
| CR8087 | 0 | 0 | CR8087 | CR8087 | 107 | 166 | CR8087 |

Binding of second antibody < 40: First and second antibody cover the same region
Binding of second antibody > 60: First and second antibody have different epitopes

Example 9: Formulation

The anti-HBsAg virus antibodies described herein are monoclonal antibodies, IgG1 isotype with kappa or lambda light chains, and can be lyophilized. For subsequent intravenous administration, the obtained solution will usually be further diluted into a carrier solution to the ready-to-use antibody solution for infusion. Important stability-indicating analytical methods to select the most stable formulation encompassed, amongst others, size-exclusion chromatography to determine aggregation levels, subvisible particulate matter testing, and potency testing.

It is understood that the examples and aspects described herein are for illustrative purposes only and that various modifications or changes in light thereof will be suggested to persons skilled in the art and are to be included within the spirit and purview of this application and scope of the appended claims.

What is claimed is:

1. A method of treating a hepatitis B infection in a subject in need thereof, the method comprising administering to the subject an antibody comprising:

(i) a heavy chain variable region that comprises (a) a HCDR1 (CDR-Complementarity Determining Region) of SEQ ID NO: 9, (b) a HCDR2 of SEQ ID NO: 10, (c) a HCDR3 of SEQ ID NO: 11 and a light chain variable region that comprises: (d) a LCDR1 of SEQ ID NO:25, (e) a LCDR2 of SEQ ID NO:26, and (f) a LCDR3 of SEQ ID NO:27;

(ii) a heavy chain variable region that comprises (a) a HCDR1 of SEQ ID NO:41, (b) a HCDR2 of SEQ ID NO:42, (c) a HCDR3 of SEQ ID NO:43; and a light chain variable region that comprises: (d) a LCDR1 of SEQ ID NO:57, (e) a LCDR2 of SEQ ID NO:58, and (f) a LCDR3 of SEQ ID NO:59;

(iii) a heavy chain variable region that comprises (a) a HCDR1 of SEQ ID NO:73, (b) a HCDR2 of SEQ ID NO:74, (c) a HCDR3 of SEQ ID NO:75; and a light chain variable region that comprises: (d) a LCDR1 of SEQ ID NO:89, (e) a LCDR2 of SEQ ID NO:90, and (f) a LCDR3 of SEQ ID NO:91;

(iv) a heavy chain variable region that comprises: (a) a HCDR1 of SEQ ID NO: 105, (b) a HCDR2 of SEQ ID NO: 106, (c) a HCDR3 of SEQ ID NO: 107; and a light chain variable region that comprises: (d) a LCDR1 of SEQ ID NO: 121, (e) a LCDR2 of SEQ ID NO: 122, and (f) a LCDR3 of SEQ ID NO:123;

(v) a heavy chain variable region that comprises: (a) a HCDR1 of SEQ ID NO:137, (b) a HCDR2 of SEQ ID NO: 138, (c) a HCDR3 of SEQ ID NO: 139; and a light chain variable region that comprises: (d) a LCDR1 of SEQ ID NO: 153, (e) a LCDR2 of SEQ ID NO:154, and (f) a LCDR3 of SEQ ID NO:155;

(vi) a heavy chain variable region that comprises: (a) a HCDR1 of SEQ ID NO: 169, (b) a HCDR2 of SEQ ID NO: 170, (c) a HCDR3 of SEQ ID NO: 171; and a light chain variable region that comprises: (d) a LCDR1 of SEQ ID NO: 185, (e) a LCDR2 of SEQ ID NO: 186, and (f) a LCDR3 of SEQ ID NO: 187;

(vii) a heavy chain variable region that comprises: (a) a HCDR1 of SEQ ID NO:201, (b) a HCDR2 of SEQ ID NO: 202, (c) a HCDR3 of SEQ ID NO:203; and a light chain variable region that comprises: (d) a LCDR1 of SEQ ID NO:217, (e) a LCDR2 of SEQ ID NO:218, and (f) a LCDR3 of SEQ ID NO:219;

(viii) a heavy chain variable region that comprises: (a) a HCDR1 of SEQ ID NO:233, (b) a HCDR2 of SEQ ID NO:234, (c) a HCDR3 of SEQ ID NO:235; and a light chain variable region that comprises: (d) a LCDR1 of SEQ ID NO:249, (e) a LCDR2 of SEQ ID NO:250, and (f) a LCDR3 of SEQ ID NO:251;

(ix) a heavy chain variable region that comprises: (a) a HCDR1 of SEQ ID NO:265, (b) a HCDR2 of SEQ ID NO: 266, (c) a HCDR3 of SEQ ID NO:267; and a light chain variable region that comprises: (d) a LCDR1 of SEQ ID NO:281, (e) a LCDR2 of SEQ ID NO:282, and (f) a LCDR3 of SEQ ID NO: 283;

(x) a heavy chain variable region that comprises: (a) a HCDR1 of SEQ ID NO:297, (b) a HCDR2 of SEQ ID NO: 298, (c) a HCDR3 of SEQ ID NO:299; and a light chain variable region that comprises: (d) a LCDR1 of SEQ ID NO:313, (e) a LCDR2 of SEQ ID NO:314, and (f) a LCDR3 of SEQ ID NO: 315;

(xi) a heavy chain variable region that comprises: (a) a HCDR1 of SEQ ID NO:329, (b) a HCDR2 of SEQ ID NO:330, (c) a HCDR3 of SEQ ID NO:331; and a light chain variable region that comprises: (d) a LCDR1 of SEQ ID NO:345, (e) a LCDR2 of SEQ ID NO:346, and (f) a LCDR3 of SEQ ID NO: 347;

(xii) a heavy chain variable region that comprises: (a) a HCDR1 of SEQ ID NO:361, (b) a HCDR2 of SEQ ID NO:362, (c) a HCDR3 of SEQ ID NO:363; and a light chain variable region that comprises: (d) a LCDR1 of SEQ ID NO:377, (e) a LCDR2 of SEQ ID NO:378, and (f) a LCDR3 of SEQ ID NO: 379;

(xiii) a heavy chain variable region that comprises: (a) a HCDR1 of SEQ ID NO:393, (b) a HCDR2 of SEQ ID NO:394, (c) a HCDR3 of SEQ ID NO:395; and a light chain variable region that comprises: (d) a LCDR1 of SEQ ID NO:409, (e) a LCDR2 of SEQ ID NO:410, and (f) a LCDR3 of SEQ ID NO:411;

(xiv) a heavy chain variable region that comprises: (a) a HCDR1 of SEQ ID NO:425, (b) a HCDR2 of SEQ ID NO:426, (c) a HCDR3 of SEQ ID NO:427; and a light chain variable region that comprises: (d) a LCDR1 of SEQ ID NO:441, (e) a LCDR2 of SEQ ID NO:442, and (f) a LCDR3 of SEQ ID NO: 443;

(xv) a heavy chain variable region that comprises: (a) a HCDR1 of SEQ ID NO:457, (b) a HCDR2 of SEQ ID NO:458, (c) a HCDR3 of SEQ ID NO:459; and a light chain variable region that comprises: (d) a LCDR1 of SEQ ID NO:473, (e) a LCDR2 of SEQ ID NO:474, and (f) a LCDR3 of SEQ ID NO:475; or (xvi) a heavy chain variable region that comprises: (a) a HCDR1 of SEQ ID NO:489, (b) a HCDR2 of SEQ ID NO:490, (c) a HCDR3 of SEQ ID NO:491; and a light chain variable region that comprises: (d) a LCDR1 of SEQ ID NO:505, (e) a LCDR2 of SEQ ID NO:506, and (f) a LCDR3 of SEQ ID NO: 507.

2. The method of claim 1, wherein the antibody is a monoclonal antibody, a chimeric antibody, a humanized antibody, a human engineered antibody, a human antibody, a single chain antibody (scFv) or an antibody fragment.

3. The method of claim 1 wherein the antibody or fragment thereof has reduced glycosylation or no glycosylation or is hypofucosylated.

4. The method of claim 1, wherein the antibody is administered in combination with another therapeutic agent.

5. The method of claim 4, wherein the therapeutic agent is an anti-viral agent.

6. The method of claim 5, wherein the anti-viral agent is selected from lamivudine, entecavir, tenofovir, and alpha-interferon.

7. The method of claim 4, wherein the therapeutic agent is an immune checkpoint inhibitor.

8. The method of claim 7, wherein the immune checkpoint inhibitor is selected from PD-1, PD-L1, PD-L2, TIM3, CTLA-4, LAG-3, CEACAM-1, CEACAM-5, VISTA, BTLA, TIGIT, LAIR1, CD160, 2B4, and TGFR.

9. The method of claim 8, wherein the immune checkpoint inhibitor is an anti-PD-L1 antibody.

10. The method of claim 4, wherein the therapeutic agent is an additional anti-HBsAg antibody.

\* \* \* \* \*